(12) United States Patent
Kim et al.

(10) Patent No.: US 8,404,677 B2
(45) Date of Patent: Mar. 26, 2013

(54) KINASE INHIBITORS

(75) Inventors: Hong Woo Kim, Cambridge, MA (US); Jong Sung Koh, Seoul (KR); Jaekyoo Lee, North Andover, MA (US); Ho-Juhn Song, Andover, MA (US); Youngsam Kim, Seoul (KR); Hee Kyu Lee, Gunpo Si (KR); Jang-Sik Choi, Cheonan-si (KR); Sun-Hee Lim, Cheonan-si (KR); Sunhwa Chang, Cheonan-si (KR)

(73) Assignees: Genosco, Buena Park, CA (US); Oscotec, Inc., Cheonan (KR)

( * ) Notice: Subject to any disclaimer, the term of this patent is extended or adjusted under 35 U.S.C. 154(b) by 107 days.

(21) Appl. No.: 12/916,368

(22) Filed: Oct. 29, 2010

(65) Prior Publication Data

US 2011/0269739 A1    Nov. 3, 2011

Related U.S. Application Data

(60) Provisional application No. 61/256,222, filed on Oct. 29, 2009.

(51) Int. Cl.
*C07D 471/04* (2006.01)
*C07D 211/86* (2006.01)
*A61K 31/519* (2006.01)
*A61K 31/4375* (2006.01)

(52) U.S. Cl. ............ 514/218; 514/228.5; 514/234.2; 514/249; 514/264.1; 514/264.11; 540/575

(58) Field of Classification Search ............ 514/218, 514/228.5, 234.2, 249, 264.1, 264.11; 540/575; 544/58.1, 58.2, 61, 117, 279

See application file for complete search history.

(56) References Cited

U.S. PATENT DOCUMENTS

| | | | |
|---|---|---|---|
| 6,174,889 | B1 | 1/2001 | Cockerill et al. |
| 6,420,375 | B1 | 7/2002 | Aono et al. |
| 7,593,820 | B2 | 9/2009 | Wilks et al. |

FOREIGN PATENT DOCUMENTS

| | | |
|---|---|---|
| WO | WO 2007/041362 A1 | 4/2007 |
| WO | WO 2009/097287 A1 | 8/2009 |
| WO | WO 2010/019637 A1 | 2/2010 |

OTHER PUBLICATIONS

Notification of Transmittal of the International Search Report and the Written Opinion of the International Searching Authority, or the Declaration, International Search Report and Written Opinion in International Application No. PCT/US10/54853, 17 pages, mailed Jan. 11, 2011.

*Primary Examiner* — Bruck Kifle

(74) *Attorney, Agent, or Firm* — Edwards Wildman Palmer LLP; Mark D. Russett; Kongsik Kim

(57) ABSTRACT

The present invention provides a new group of protein kinase inhibitors, pyrido[4,3,-d]pyrimidin-5-one derivatives, and pharmaceutically acceptable salts thereof that are useful for intreating cell proliferative disease and disorder such as cancer, autoimmune diseases, infection, cardiovascular disease and neurodegenerative disease and disorder. The present invention provides methods for synthesizing and administering the protein kinase inhibitor compounds. The present invention also provides pharmaceutical formulations comprising at least one of the protein kinase inhibitor compounds together with a pharmaceutically acceptable carrier, diluent or excipient therefor. The invention also provides useful intermediates generated during the syntheses of the pyrido[4,3,-d]pyrimidin-5-one derivatives.

63 Claims, No Drawings

KINASE INHIBITORS

RELATED APPLICATION

This application claims the benefit of U.S. Provisional Application No. 61/256,222, filed on Oct. 29, 2009. The entire teachings of the above application are incorporated herein by reference.

BACKGROUND OF THE INVENTION

Protein kinases include a large set of structurally related phosphoryl transferases which catalyze the transfer of the terminal phosphate from ATP to the hydroxyl group of tyrosine, serine and/or threonine residues of proteins. Protein kinases are categorized into families by the substrates they phosphorylate, for example, protein tyrosine kinases (PTK) and protein serine/threonine kinases.

Phosphorylation via protein kinase(s) results in a functional change of the target protein (substrate) by changing enzyme activity, cellular location or association with other proteins. Protein kinases play vital role, not only in controlling cell growth and differentiation, but also in regulating a wide variety of cellular signal transduction pathways in which protein kinases effectively regulate production of growth factors and various cytokines such as tumor necrosis factor (TNF)-α. Examples of protein-tyrosine kinases include SYK, PYK2, FAK, ALK, AXL, CSF1R, FLT3, JAK2 (JH1domain-catalytic), JAK3 (JH1domain-catalytic), KIT, KIT (D816V), KIT (V559D, T670I), PDGFRB, RET, TYK2 and ZAP70. Examples of protein-serine/threonine kinases include PIM1, AURKA, AURKB, BMPR2, JNK1, JNK2, JNK3, LKB1, LRRK2, LRRK2(G2019S), MLK1, PAK4, PLK4, RSK2 (Kin.Dom.1-N-terminal), SNARK, SRPK3 and TAK1.

Misregulation of these protein kinases has been implicated in numerous diseases and disorders such as central nervous system disorders (e.g., Alzheimer's disease), inflammatory and autoimmune disorders (e.g., asthma, rheumatoid arthritis, Crohn's disease, and inflammatory bowel syndrome, and psoriasis), bone diseases (e.g., osteoporosis), metabolic disorders (e.g., diabetes), blood vessel proliferative disorders, ocular diseases, cardiovascular disease, cancer, restenosis, pain sensation, transplant rejection and infectious diseases. Although biological and clinical importance of protein kinases has been recognized in the field, a continuing need exists for compounds which inhibit protein kinases to provide an effective and safe clinical therapy for the diseases associated with or mediated by protein kinases. A need also exists for methods of administering such compounds, pharmaceutical formulations and medicaments to patients or subjects in need thereof.

SUMMARY OF THE INVENTION

The present invention provides compounds having Formula (I), and pharmaceutical acceptable salts, N-oxide derivatives, prodrug derivatives, protected derivatives, individual isomers and mixture of isomers thereof.

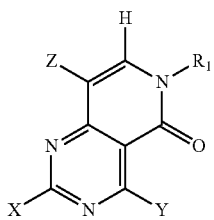

Formula (I)

$R^1$, X, Y, and Z are described in detail below.

The compounds of Formula (I) are useful for inhibiting one or more protein kinases and for treating diseases and disorders that are mediated by the protein kinases, such as cancer, autoimmune diseases, infection, cardiovascular disease, and neurodegenerative diseases.

In one aspect, the present invention provides pharmaceutical compositions comprising a compound of Formula (I) and a pharmaceutically acceptable carrier. In certain embodiments, such pharmaceutical compositions are formulated for intravenous administration, subcutaneous administration, inhalation, oral administration, rectal administration, parenteral, intravitreal administration, intramuscular administration, intranasal administration, dermal administration, topical administration, otic administration, ophthalmic administration, buccal administration, tracheal administration, bronchial administration, or sublingual administration. In other embodiments, such pharmaceutical composition are formulated as tablets, a pills, capsules, a liquid, an inhalant, a nasal spray solution, a suppository, a solution, a gel, an emulsion, an ointment, eye drops or ear drops.

In one aspect, the present invention provides methods of inhibiting SYK, PYK2, FAK, ZAP70, PIM1, FLT3, RET, JAK2, JAK3, LRRK2, LRRK2(G2019S), ALK, AURKA, AXL, BMPR2, CSF1R, JNK1, JNK2, JNK3, KIT, KIT (D816V), LKB1, MLK1, PAK4, PDGFRB, PLK4, RSK2, SNARK, SRPK3, TAK1, or TYK2 signaling in vivo or in vitro, comprising administering to said subject an effective amount of the compound of claim 1.

In one aspect, the present invention provides methods for treating a cell-proliferative disease or condition, such as cancer, comprising administering to a subject in need of such treatment a therapeutically effective amount of the compound of Formula (I) or pharmaceutically acceptable salts, pharmaceutical compositions or medicaments thereof, wherein the cell proliferative disease or condition include, for example, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer or gastrointestinal cancer. In one aspect, the present invention provides methods of inhibiting growth of cancer cells with the compound of claim 1 or a pharmaceutically acceptable salt thereof.

In another aspect, the present invention provides a medicament for treating a SYK, PYK2, FAK, ZAP70, PIM1, FLT3, RET, JAK2, JAK3, LRRK2, LRRK2(G2019S), ALK, AURKA, AXL, BMPR2, CSF1R, JNK1, JNK2, JNK3, KIT, KIT(D816V), LKB1, MLK1, PAK4, PDGFRB, PLK4, RSK2, SNARK, SRPK3, TAK1, or TYK2-mediated disease, disorder or condition in a patient comprising a therapeutically effective amount of the compound of Formula (I).

In another aspect, the present invention provides the use of the compound of Formula (I) in the manufacture of a medicament for treating a SYK, PYK2, FAK, ZAP70, PIM1, FLT3, RET, JAK2, JAK3, LRRK2, LRRK2(G2019S), ALK, AURKA, AXL, BMPR2, CSF1R, JNK1, JNK2, JNK3, KIT, KIT(D816V), LKB1, MLK1, PAK4, PDGFRB, PLK4, RSK2, SNARK, SRPK3, TAK1, or TYK2-mediated disease, disorder or condition.

In another aspect, the present invention provides methods for inhibiting a protein kinase, comprising administering to a subject in need thereof, a therapeutically effective amount of the compound of Formula (I) or a pharmaceutically acceptable salt or pharmaceutical composition thereof. The protein kinase includes, but is not limited to, SYK, PYK2, FAK, ZAP70, PIM1, FLT3, RET, JAK2, JAK3, LRRK2, LRRK2 (G2019S), ALK, AURKA, AXL, BMPR2, CSF1R, JNK1, JNK2, JNK3, KIT, KIT(D816V), LKB1, MLK1, PAK4, PDGFRB, PLK4, RSK2, SNARK, SRPK3, TAK1, or TYK2 kinase.

In another aspect, the present invention provides methods for inhibiting a protein kinase, comprising contacting to a cell with the compound of Formula (I). In certain embodiment, the compound of Formula (I) effectively inhibits activity of one or more kinases selected from SYK, PYK2, FAK, ZAP70, PIM1, FLT3, RET, JAK2, JAK3, LRRK2, LRRK2 (G2019S), ALK, AURKA, AXL, BMPR2, CSF1R, JNK1, JNK2, JNK3, KIT, KIT(D816V), LKB1, MLK1, PAK4, PDGFRB, PLK4, RSK2, SNARK, SRPK3, TAK1, and TYK2.

In another aspect, the present invention provides methods for treating a protein kinase-mediated disease or condition comprising administering to a subject in need of such treatment a therapeutically effective amount of the compound of Formula (I) or a pharmaceutically acceptable salt, a pharmaceutical composition or a medicament thereof. The protein kinase includes, but is not limited to, SYK, PYK2, FAK, ZAP70, PIM1, FLT3, RET, JAK2, JAK3, LRRK2, LRRK2 (G2019S), ALK, AURKA, AXL, BMPR2, CSF1R, JNK1, JNK2, JNK3, KIT, KIT(D816V), LKB1, MLK1, PAK4, PDGFRB, PLK4, RSK2, SNARK, SRPK3, TAK1, and TYK2.

In certain embodiments, protein kinase-mediated diseases or conditions are inflammatory diseases or conditions, respiratory diseases or autoimmune diseases or conditions, such as asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, breast cancer, HIV associated diseases or lupus.

In another aspect, the present invention provides methods for treating a neurological/neurodegenerative disease or condition by administering to a subject a therapeutically effective amount of the compound of Formula (I) or a pharmaceutically acceptable salt. In certain embodiment, such neurological/neurodegenerative disease or condition includes, for example, Alzheimer's disease, cerebral edema, cerebral ischemia, multiple sclerosis, neuropathies, Parkinson's disease, blunt or surgical trauma (including post-surgical cognitive dysfunction and spinal cord or brain stem injury), as well as the neurological aspects of disorders such as degenerative disc disease and sciatica.

In another aspect, the present invention provides methods for treating a cardiovascular disease by administering to a subject a therapeutically effective amount of the compound of Formula (I) or a pharmaceutically acceptable salt. Such a cardiovascular disease affects the heart or blood vessels and includes, for example, atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

In another aspect, the present invention provides methods of treating a kinase-mediated disease or condition by administering to a subject a therapeutically effective amount of the compound of Formula (I) or a pharmaceutically acceptable salt in combination with a second therapeutic agent.

In the above methods for using the compound of the invention, the compound of Formula (I) or a pharmaceutically acceptable salt is administered to a system comprising cells or tissues. In certain embodiments, the compound of Formula (I), a pharmaceutically acceptable salt, a pharmaceutical composition or a medicament thereof is administered to a human or animal subject.

DETAILED DESCRIPTION OF THE INVENTION

The present invention provides a group of pyrido[4,3,-d] pyrimidin-5-one derivatives and pharmaceutically acceptable salts thereof that are useful for inhibiting one or more protein kinases and for treating diseases and disorders that are mediated by the protein kinases, for example, cell proliferative disease, autoimmune diseases, infection, cardiovascular disease, and neurodegenerative diseases. The present invention also provides methods of synthesizing and administering the pyrido[4,3,-d]pyrimidin-5-one derivatives. The present invention provides pharmaceutical formulations comprising at least one of the compounds together with a pharmaceutically acceptable carrier, diluent or excipient therefor. The invention also provides useful intermediates generated during syntheses of the pyrido[4,3,-d]pyrimidin-5-one derivative compounds.

Disclosed herein is a novel class of compounds having Formula (I), and pharmaceutical acceptable salts, N-oxide derivatives, prodrug derivatives, protected derivatives, individual isomers and mixture of isomers thereof for inhibiting protein kinases.

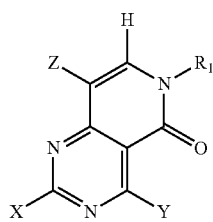

Formula (I)

When $R^1$ is H and X is $NR^2R^3$ or $NR^4R^5$, then
Y is $NHR^6$ and
Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano; wherein:
  $R^2$ and $R^3$, taken together with the nitrogen atom to which they are bonded form:
  i) a 3-8 membered saturated or partially saturated monocyclic group having no heteroatom other than the nitrogen atom to which $R^2$ and $R^3$ are bonded, wherein said 3-8 membered saturated or partially saturated monocyclic group is independently substituted at one or more carbon atoms with 1-2 $R^7$ and optionally substituted at one or more carbon atoms with 0-4 $R^8$, wherein $R^7$ is hydroxy, heterocycloalkyl, or $NR^9R^9$ and $R^8$ is hydroxy $(C_1-C_6)$alkyl, aryl, $COOR^S$, $(CH_2)_nNR^9R^9$, or $(CH_2)_n NR^9R^{10}$, wherein each n is independently 1, 2, or 3 and the aryl is optionally substituted with halo; or ii) an 8-10 membered bicyclic aryl group having 0-5 heteroatoms independently selected from nitrogen, oxygen, sulfur, sulfoxide, or sulfone;

each $R^9$ is independently selected from H, $C_1-C_6$ alkyl, $C_3-C_6$ alkynyl, $C_2-C_6$ alkyl cyano, $C_2-C_6$ alkyl sulfone, $C_3-C_6$ cycloalkyl sulfone, $C_2-C_6$ sulfonamide, $C_3-C_6$ cycloalkyl, $C_3-C_8$ heterocycloalkyl, aryl, aryl$(C_1-C_6)$ alkyl, or heteroaryl, wherein the alkyl, alkynyl, alkylcyano, alkylsulfone, sulfonamide, cycloalkyl, heterocycloalkyl, aryl, arylalkyl, or heteroaryl is optionally substituted with $R^{25}$;

$R^{10}$ is $C(O)R^9$, $COOR^9$, $C(O)NR^9R^9$, or $S(O)_nR^9$, in which n is 1 or 2;

$R^4$ is selected from H, $C_1-C_6$ alkyl, or hydroxy$(C_1-C_6)$ alkyl;

$R^5$ is aryl$(C_1-C_3)$alkyl, wherein the aryl group is independently substituted at one or more carbon atoms with 1-3 $R^{11}$, wherein $R^{11}$ is independently selected from $OR^9$, $NR^9R^9$, $NR^9COR^9$, or $NR^9S(O)_nR^9$, wherein n is 1 or 2;

$R^6$ is selected from $C_1-C_6$ alkyl, $C_2-C_6$ alkenyl, $C_3-C_6$ alkynyl, $C_3-C_6$ cycloalkyl, $C_3-C_8$ heterocycloalkyl, $C_4-C_6$ cycloalkenyl, aryl, aryl$(C_1-C_6)$alkyl, or heteroaryl, in which the heterocycloalkyl, aryl, or heteroaryl of $R^6$ is optionally substituted with an aryl selected from the group consisting of:
i) a 5-6 membered monocyclic aryl group;
ii) an 8-10 membered bicyclic aryl group having 0-5 heteroatoms independently selected from nitrogen, oxygen, sulfur, sulfoxide, or sulfone;
iii) an 8-10 membered unsaturated or partially unsaturated bicyclic aryl group having 0-5 heteroatoms independently selected from nitrogen, oxygen, sulfur, sulfoxide, or sulfone; and
iv) an 8-10 membered unsaturated or partially unsaturated bicyclic aryl group having a carbonyl, carboxamide, or sulfoxamide; or the heterocycloalkyl, aryl, or heteroaryl of $R^6$ can be also optionally substituted at one or more carbon atoms with $R^{12}$, wherein each $R^{12}$ is independently selected from $C_1-C_6$ alkyl, $CF_3$, $OCF_3$, $S(O)_n(C_1-C_4)$alkyl, halo$(C_1-C_4)$alkyl, $C_2-C_6$ alkenyl, $C_3-C_6$ alkynyl, $C_3-C_6$ cycloalkyl, $C_3-C_8$ heterocycloalkyl, $C_4-C_6$ cycloalkenyl, aryl, aryl $(C_1-C_6)$alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O) R^{13}$, $C(O)NR^{13}R^{13}$, $CONR^{15}R^{16}$, $S(O)_nR^{13}$, $S(O)_n NR^{13}R^{13}$, or $NR^{15}R^{16}$, wherein each n is independently 1 or 2 and the alkyl, alkenyl, alkynyl, cycloalkyl, heterocycloalkyl, cycloalkenyl, aryl, arylalkyl, haloalkyl, or heteroaryl is optionally substituted with $R^{25}$, wherein the aryl and heteroaryl of $R^{12}$ is independently selected from:
i) a 5-6 membered monocyclic aryl group;
ii) an 8-10 membered bicyclic aryl group having 0-5 heteroatoms independently selected from nitrogen, oxygen, sulfur, sulfoxide or sulfone;
iii) an 8-10 membered unsaturated or partially unsaturated bicyclic aryl group having 0-5 heteroatoms independently nitrogen, oxygen, sulfur, sulfoxide or sulfone; or
iv) an 8-10 membered unsaturated or partially unsaturated bicyclic aryl group having a carbonyl, carboxamide, or sulfoxamide;

each $R^{13}$ is independently selected from H, $C_1-C_6$ alkyl, $C_2-C_6$ alkenyl, $C_3-C_6$ alkynyl, $C_2-C_6$ alkyl cyano, $C_2-C_6$ alkyl sulfone, $C_2-C_6$ sulfonamide, $C_3-C_6$ cycloalkyl, $C_3-C_8$ heterocycloalkyl, $C_4-C_6$ cycloalkenyl, aryl, aryl$(C_1-C_6)$alkyl, haloalkyl or heteroaryl, wherein the alkyl, alkenyl, alkynyl, alkyl cyano, alkyl sulfone, alkyl sulfonamide, cycloalkyl, heterocycloalkyl, cycloalkenyl, aryl, arylalkyl, haloalkyl, or heteroaryl is optionally substituted with $R^{25}$;

$R^{14}$ is $C(O)R^{13}$, $COOR^{13}$, $C(O)NR^{13}R^{13}$, $SO_2NR^{13}R^{13}$, or $S(O)_nR^{13}$, wherein n is 1 or 2;

$R^{15}$ and $R^{16}$, taken together with the nitrogen atom to which they are bonded, form:
i) a 3-8 membered saturated or partially saturated monocyclic group, wherein the 3-8 membered saturated or partially saturated monocyclic group is optionally substituted with $R^{25}$;
ii) an 8-12 membered saturated or partially saturated bicyclic group, wherein the 8-12 membered saturated or partially saturated bicyclic group is optionally substituted with $R^{25}$;
iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or
iv) a 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$; and each $R^{25}$ is independently selected from hydroxy, hydroxy $(C_1-C_6)$alkyl, $C_1-C_6$ alkyl, $C_2-C_6$ alkenyl, $C_3-C_6$ alkynyl, $C_3-C_6$ cycloalkyl, $C_3-C_8$ heterocycloalkyl, $C_4-C_6$ cycloalkenyl, aryl$(C_1-C_6)$alkyl, aryl, halo, haloalkyl, oxo, oxime, $CF_3$, $SR^{13}$, $OCF_3$, $OR^{13}$, $OC(O)CH_2R^{13}$, $NR^{13}R^{13}$, $NR^{13}R^{14}$, $NHC(O)R^{13}$, $(CH_2)_nNR^{13}R^{13}$, $COOR^{13}$, CN, $C(O)R^{13}$, $C(O)CF_3$, $CONR^{15}R^{16}$, $CONH_2$, $S(O)_6R^{13}$, $S(O)_nNR^{13}R^{13}$, or $NR^{15}R^{16}$, wherein each n is independently 1 or 2 and the heterocycloalkyl is optionally substituted with $C_1-C_3$ alkyl.

When $R^1$ is H and Y is $NHR^{17}$ or $R^{17}$, then
X is $OR^{18}$, $NR^{15}R^{16}$, $NHR^{18}$, $NR^{18}R^{19}$, or $NR^{19}R^{20}$ and
Z is H, halogen, $C_1-C_3$ alkyl, $C_2-C_4$ alkynyl, aryl, heteroaryl, or $C_3-C_8$ cycloalkyl, wherein the alkyl, alkynyl, cycloalkyl, aryl, or heteroaryl is optionally substituted with halo, alkyl, or cyano, wherein:

$R^{17}$ is selected from aryl$(C_1-C_6)$alkyl, aryl, or heteroaryl, wherein the aryl, or the heteroaryl is substituted at one or more carbon atoms with at least one $R^{21}$ and 0-2 $R^{22}$ and the aryl group of said aryl$(C_1-C_6)$alkyl is optionally substituted with halo;

$R^{21}$ is independently selected from amino, hydroxy, $CF_3$, $OCF_3$, O-aryl, $S(O)_nR^{13}$, or $NR^{15}R^{16}$ ($R^{15}R^{16}$ are as described above);

$R^{22}$ is independently H, $C_1-C_6$ alkyl, $CF_3$, $OCF_3$, $S(O)_n (C_1-C_4)$alkyl, halo$(C_1-C_4)$alkyl, $C_2-C_6$ alkenyl, $C_2-C_6$ alkynyl, $C_3-C_6$ cycloalkyl, $C_3-C_8$ heterocycloalkyl, $C_4-C_6$ cycloalkenyl, aryl, aryl$(C_1-C_6)$alkyl, heteroaryl, halo, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O) NR^{13}R^{13}$, $CONR^{15}R^{16}$, $S(O)_nR^{13}$, $S(O)_nNR^{13}R^{13}$, $NR^{13}C(O)NR^{13}R^{13}$, $NR^{13}C(O)R^{13}$, $NR^{13}(COOR^{13})$, $NR^{13}S(O)_nR^{13}$, or $NR^{15}R^{16}$, wherein each n is independently 1 or 2 and wherein the alkyl, alkenyl, alkynyl, cycloalkyl, heterocycloalkyl, cycloalkenyl, aryl, arylalkyl, haloalkyl, or heteroaryl is optionally substituted with $R^{25}$;

$R^{18}$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, hydroxy ($C_2$-$C_6$)alkyl, amino($C_2$-$C_6$)alkyl, haloalkyl, or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$;

each $R^{19}$ is independently selected from $C_1$-$C_6$ alkyl, $C_2$-$C_6$ alkenyl, $C_3$-$C_6$ alkynyl, hydroxy($C_2$-$C_6$)alkyl, amino($C_2$-$C_6$)alkyl, $C_2$-$C_6$ alkyl cyano, $C_2$-$C_6$ alkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$) alkyl, haloalkyl, or heteroaryl, wherein the alkyl, alkenyl, alkynyl, alkyl cyano, alkylsulfone, sulfonamide, cycloalkyl, heterocycloalkyl, cycloalkenyl, aryl, arylalkyl, haloalkyl, or heteroaryl is optionally substituted with $R^{25}$;

$R^{20}$ is $C(O)R^{19}COOR^{19}$, $C(O)NR^{19}R^{19}$ or $S(O)_nR^{19}$, in which n is 1 or 2;

each $R^{25}$ is independently selected from hydroxy, hydroxy ($C_1$-$C_6$)alkyl, $C_1$-$C_6$ alkyl, $C_2$-$C_6$ alkenyl, $C_3$-$C_6$ alkynyl, $C_3$-$C_6$cycloalkyl, $C_3$-$C_8$ heterocycloalkyl, $C_4$-$C_6$ cycloalkenyl, aryl($C_1$-$C_6$)alkyl, aryl, halo, haloalkyl, oxo, oxime, $CF_3$, $SR^{13}$, $OCF_3$, $OR^{13}$, $OC(O)CH_2R^{13}$, $NR^{13}R^{13}$, $NR^{13}R^{14}$, $NHC(O)R^{13}$, $(CH_2)_nNR^{13}R^{13}$, $COOR^{13}$, $CN$, $C(O)R^{13}$, $C(O)CF_3$, $CONR^{15}R^{16}$, $CONH_2$, $S(O)_nR^{13}$, $S(O)_nNR^{13}R^{13}$, or $NR^{15}R^{16}$, wherein each n is independently 1 or 2 and the heterocycloalkyl is optionally substituted with $C_1$-$C_3$ alkyl.

When $R^1$ is $CH_3$, then

X is $NH_2$ or $NHR^6$ as described above,

Y is $NHR^6$ or $R^6$ as described above, and

Z is H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl, or heteroaryl is optionally substituted with halo, alkyl, or cyano.

In certain aspect, $R^1$ is H, X is $NR^2R^3$, and Y is $NHR^6$. Z can be H, halogen, $C_1$-$C_3$ alkyl, $C_2$-$C_4$ alkynyl, aryl, heteroaryl, or $C_3$-$C_8$ cycloalkyl, in which the alkyl, cycloalkyl, aryl, alkynyl, or heteroaryl is optionally substituted with halo, alkyl, or cyano. $NHR^6$ is described below.

$NR^2R^3$ is a 3-8 membered saturated or partially saturated monocyclic group having no heteroatom other than the nitrogen atom to which $R^2$ and $R^3$ are bonded, wherein said 3-8 membered saturated or partially saturated monocyclic group is independently substituted at one or more carbon atoms with 1-2 $R^7$ and optionally substituted at one or more carbon atoms with 0-4 $R^8$. $R^7$ is hydroxy, heterocycloalkyl, or $NR^9R^9$ and $R^8$ is hydroxy($C_1$-$C_6$)alkyl, aryl, $COOR^S$, $(CH_2)_nNR^9R^9$, or $(CH_2)_nNR^9R^{10}$, in which each n is independently 1, 2, or 3. The aryl is optionally substituted with halo. The 3-8 membered saturated or partially saturated monocyclic group can be optionally substituted with hydroxy or amine. In one embodiment, the 3-8 membered saturated or partially saturated monocyclic group is azetidine, piperidine or pyrrolidine, in which the azetidine, piperidine or pyrrolidine is independently substituted with 1-3 hydroxy or amino group and optionally and independently substituted with hydroxymethyl at the one or more carbon atoms. In another embodiment, $NR^2R^3$ is selected from an 8-10 membered bicyclic aryl group having 0-5 heteroatoms independently selected from nitrogen, oxygen, sulfur, sulfoxide, or sulfone.

In certain aspects, $R^1$ is H, X is $NR^4R^5$, and Y is $NHR^6$. Z can be H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl, or heteroaryl is optionally substituted with halo, alkyl, or cyano. $NHR^6$ is described below.

$R^4$ is selected from H, $C_1$-$C_6$ alkyl, or hydroxy($C_1$-$C_6$)alkyl and $R^5$ is aryl($C_1$-$C_3$)alkyl. The aryl group of aryl($C_1$-$C_3$) alkyl of $R^5$ is independently substituted at the one or more carbon atoms with 1-3 $R^{11}$. $R^{11}$ is independently selected from $OR^9$, $NR^9R^9$, $NR^9COR^9$, or $NR^9S(O)_nR^9$, in which n is 1 or 2. $R^9$ is independently selected from H, $C_1$-$C_6$ alkyl, $C_2$-$C_6$ alkenyl, $C_3$-$C_6$ alkynyl, $C_2$-$C_6$ alkyl cyano, $C_2$-$C_6$ alkyl sulfone, $C_3$-$C_6$ alkyl sulfone, $C_3$-$C_6$ cycloalkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl, or heteroaryl, in which the alkyl, alkenyl, alkynyl, alkyl cyano, alkyl sulfone, sulfonamide, cycloalkyl, heterocycloalkyl, cycloalkenyl, aryl, arylalkyl, haloalkyl, or heteroaryl is optionally substituted with $R^{25}$.

In certain aspects, Y is $NHR^6$. $R^6$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$.

In one embodiment, the aryl of $R^6$ is an optionally substituted aryl selected from the group consisting of: i) a 5-6 membered monocyclic aryl group; ii) an 8-10 membered bicyclic aryl group having 0-5 heteroatoms independently selected from nitrogen, oxygen, sulfur, sulfoxide, or sulfone; iii) an 8-10 membered unsaturated or partially unsaturated bicyclic aryl group having 0-5 heteroatoms independently selected from nitrogen, oxygen, sulfur, sulfoxide or sulfone; and iv) an 8-10 membered unsaturated or partially unsaturated bicyclic aryl group having a carbonyl, carboxamide, or sulfoxamide. The aryl of $R^6$ is optionally substituted at one or more carbon atoms with $R^{12}$. The aryl of $R^6$ is phenyl optionally substituted at one or more carbon atoms with $R^{12}$ In one embodiment, $R^{12}$ is independently selected from $C_1$-$C_6$ alkyl, $OCF_3$, $CF_3$, $S(O)_n(C_1$-$C_4$)alkyl, halo($C_1$-$C_4$) alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, $CN$, $C(O)R^{13}$, $C(O)C(O)R^{13}$, $C(O)NR^{13}R^{13}$, $CONR^{15}R^{16}$, $S(O)_nR^{13}$, $S(O)_nNR^{13}R^{13}$, or $NR^{15}R^{16}$, wherein each n is independently 1 or 2; and wherein the alkyl, alkenyl, alkynyl, cycloalkyl, heterocycloalkyl, cycloalkenyl, aryl, arylalkyl, haloalkyl, or heteroaryl is optionally substituted with $R^{25}$. In one embodiment, $R^{12}$ is independently selected from $C_1$-$C_6$ alkyl, $CF_3$, $OCF_3$, $S(O)_n(C_1$-$C_4$)alkyl, halo($C_1$-$C_4$)alkyl, $C_2$-$C_6$ alkenyl, $C_2$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, heteroaryl, halo, $SR^{13}$, $OR^{13}$, $OC(O)R^{13}$, $NR^{13}R^{13}$, $NR^{13}R^{14}$, $COOR^{13}$, $NO_2$, $CN$, $C(O)R^{13}$, $C(O)NR^{13}R^{13}$, $CONR^{15}R^{16}$, $S(O)_nR^{13}$, $S(O)_nNR^{13}R^{13}$, or $NR^{15}R^{16}$, wherein each n is independently 1 or 2. In one embodiment, $R^{12}$ is independently selected from $CF_3$, $OCF_3$, $COOCH_3$, methoxy, methyl, fluoro, chloro, bromo, iodo, $S(O)_2CH_3$, morpholino, piperazinyl, or acetylpiperazinyl. In one embodiment, the aryl of $R^{12}$ is independently selected from: i) a 5-6 membered monocyclic aryl group; ii) an 8-10 membered bicyclic aryl group having 0-5 heteroatoms independently selected from nitrogen, oxygen, sulfur, sulfoxide, or sulfone; iii) an 8-10 membered unsaturated or partially unsaturated bicyclic aryl group having 0-5 heteroatoms independently nitrogen, oxygen, sulfur, sulfoxide, or sulfone; or iv) an 8-10 membered unsaturated or partially unsaturated bicyclic aryl group having a carboxamide, or sulfoxamide.

In one embodiment, $R^{12}$ can be $SR^{13}$, $OR^{13}$, $OC(O)R^{13}$, $NR^{13}R^{13}$, $NR^{13}R^{14}$, $COOR^{13}$, CN, $C(O)R^{13}$, $C(O)NR^{13}R^{13}$, $S(O)_nR^{13}$, $S(O)_nNR^{13}R^{13}$, or $NR^{15}R^{16}$, in which each $R^{13}$ is independently selected from H, $C_1$-$C_6$ alkyl, $C_2$-$C_6$ alkenyl, $C_2$-$C_6$ alkynyl, $C_2$-$C_6$ alkylcyano, $C_2$-$C_6$ alkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, alkoxy, aryl($C_1$-$C_6$)alkyl, haloalkyl, or heteroaryl and $R^{14}$ is $C(O)R^{13}$, $COOR^{13}$, $C(O)NR^{13}R^{13}$, $SO_2NR^{13}R^{13}$, or $S(O)_nR^{13}$, wherein n is 1 or 2 and the alkyl, alkenyl, alkynyl, alkyl cyano, alkyl sulfone, alkyl sulfonamide, cycloalkyl, heterocycloalkyl, cycloalkenyl, aryl, alkoxy, arylalkyl, haloalkyl, or heteroaryl is optionally substituted with $R^{25}$.

In one embodiment, $R^{12}$ is $NR^{15}R^{16}$, in which $R^{15}$ and $R^{16}$, taken together with the nitrogen atom to which they are bonded, form: i) a 3-8 membered saturated or partially saturated monocyclic group, wherein the 3-8 membered saturated or partially saturated monocyclic group is optionally substituted with $R^{25}$; ii) an 8-12 membered saturated or partially saturated bicyclic group, wherein the 8-12 membered saturated or partially saturated bicyclic group is optionally substituted with $R^{25}$; iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or iv) an 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$.

In one embodiment, $R^6$ is the optionally substituted 5-6 membered monocyclic aryl group or 9-10 membered bicyclic aryl group. In one embodiment, the optionally substituted 5-6 membered monocyclic aryl group is phenyl. In another embodiment, 9-10 membered bicyclic aryl group is naphthyl, quinolinyl, indazoyl, indolyl, or dihydrobenzodioxynyl. In one embodiment, the phenyl of $R^6$ is optionally substituted with 1-4 groups of methyl (—$CH_3$), methoxy (—$OCH_3$), methylsulfone (—$S(O)_2CH_3$), amino ($NH_2$), hydroxyl (—OH), $CF_3$, $OCF_3$, halo (F, Br, I, or Cl), phenyl, phenoxy, piperazinyl, acetylpiperrazinyl, or morpholino.

In one embodiment, $R^1$ is H; Y is $NHR^{17}$ or $R^{17}$; and X is $NHR^{18}$. Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano.

In one embodiment, $R^{17}$ is aryl($C_1$-$C_6$)alkyl, aryl or heteroaryl, wherein the aryl or the heteroaryl of $R^{17}$ is substituted at two or more carbon atoms with at least one $R^{21}$ and 0-2 $R^{22}$.

In one embodiment, $R^{21}$ is amino, hydroxy, $CF_3$, $OCF_3$, O-aryl, $S(O)_nR^{13}$, or $NR^{15}R^{16}$.

In embodiment, $R^{22}$ can be independently selected from H, $C_1$-$C_6$ alkyl, $CF_3$, $OCF_3$, $S(O)_n(C_1$-$C_4)$alkyl, halo($C_1$-$C_4$)alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl $C_1$-$C_6$ alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O)NR^{13}R^{13}$, $S(O)_nR^{13}$, $S(O)_nNR^{13}R^{13}$, or $NR^{15}R^{16}$, in which each n is independently 1 or 2; and the alkyl, alkenyl, alkynyl, cycloalkyl, heterocycloalkyl, cycloalkenyl, aryl, arylalkyl, haloalkyl, heteroarylalkyl, or heteroaryl is optionally substituted with $R^{25}$; and the aryl group of said aryl($C_1$-$C_6$)alkyl is optionally substituted with halo.

In one embodiment, the aryl of O-aryl of $R^{21}$ is independently selected from: i) a 5-6 membered monocyclic aryl group; ii) an 8-10 membered bicyclic aryl group having 0-5 heteroatoms independently selected from nitrogen, oxygen, sulfur, sulfoxide or sulfone; iii) an 8-10 membered unsaturated or partially unsaturated bicyclic aryl group having 0-5 heteroatoms independently nitrogen, oxygen, sulfur, sulfoxide or sulfone; or iv) an 8-10 membered unsaturated or partially unsaturated bicyclic aryl group having a carboxamide or sulfoxamide.

In one embodiment, the aryl or heteroaryl of $R^{17}$ is a 5-6 membered monocyclic aryl group substituted with at least one group selected from $CF_3$, $OCF_3$, O-aryl, or $NR^{15}R^{16}$ at the one or more carbon atoms. In one embodiment, the monocyclic aryl group is phenyl substituted with at least one group selected from $CF_3$, $OCF_3$, O-aryl, or $NR^{15}R^{16}$ at the one or more carbon atoms, in which $NR^{15}R^{16}$ is optionally substituted morpholino, piperazinyl, homopiperazinyl, thiomorpholino, piperidinyl, or pyrrolidinyl. The piperazinyl, homopiperazinyl, piperidinyl, or pyrrolidinyl is optionally substituted at one or more carbon atoms with 1, 2 or 3 $R^{25}$ or at one nitrogen atom with $R^{13}$ or $R^{14}$.

$R^{18}$ is selected from $C_1$-$C_6$ alkyl, $C_3$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$.

In one embodiment, $R^{18}$ is $C_1$-$C_6$ alkyl optionally substituted with one or more aryl, alkyl, halo, $R^{23}$ or $R^{24}$. Each $R^{23}$ is independently $CF_3$, $OCF_3$, $SR^{13}$, $OR^{13}$, $NR^{13}R^{13}$, $S(O)_nNR^{13}R^{13}$, $S(O)_nR^{13}$, or $NR^{15}R^{16}$, each of n being independently 1 or 2. Each $R^{24}$ is selected from a 5-8 membered monocyclic group having 1-3 heteroatoms, an 8-12 membered bicyclic group having 1-5 heteroatoms, or an 11-14 membered tricyclic group having 1-8 heteroatoms. The heteroatoms of $R^{24}$ are independently oxygen, nitrogen, or sulfur and $R^{24}$ is optionally substituted with $R^{13}$ or $R^{14}$. Zero, one, two, three or four atoms of $R^{24}$ are optionally and independently substituted with $R^{13}$. In one embodiment, the aryl group attached to $C_1$-$C_6$ alkyl of $R^{18}$ is optionally and independently substituted at one or more carbon atoms with 1-3 $R^{11}$ which is independently selected from $OR^9$, $NR^9R^9$, $NR^9COR^9$, or $NR^9S(O)_nR^9$, wherein n is 1 or 2. In one embodiment, the $C_1$-$C_6$ alkyl of $R^{18}$ is $C_2$-$C_4$ alkyl optionally substituted with 1-3 groups selected from amino, hydroxy, phenyl, benzyl, or morpholino.

In another embodiment, $R^{18}$ is $C_3$-$C_6$ alkenyl optionally substituted with one or more, aryl, alkyl, halo, $R^{23}$, or $R^{24}$. Each $R^{23}$ is independently selected from $CF_3$, $OCF_3$, $SR^{13}$, $OR^{13}$, $NR^{13}R^{13}$, $S(O)_nNR^{13}R^{13}$, $S(O)_nR^{13}$, or $NR^{15}R^{16}$, in which each n is independently 1 or 2. Each $R^{24}$ is independently selected from: a 5-8 membered monocyclic group having 1-3 heteroatoms; an 8-12 membered bicyclic having 1-5 heteroatoms; or an 11-14 membered tricyclic group having 1-8 heteroatoms and the heteroatoms of $R^{24}$ is independently selected from oxygen, nitrogen or sulfur. $R^{24}$ is optionally substituted with $R^{13}$ or $R^{14}$. In some embodiment, zero, one, two, three or four atoms of $R^{24}$ are optionally and independently substituted with $R^{13}$.

In yet another embodiment, $R^{18}$ is $C_3$-$C_6$ cycloalkyl optionally substituted with one or more, aryl, alkyl, halo, $R^{23}$ or $R^{24}$. Each $R^{23}$ is independently selected from $CF_3$, $OCF_3$, $SR^{13}$, $OR^{13}$, $NR^{13}R^{13}$, $(CH_2)_nNR^{13}R^{13}$, $S(O)_nNR^{13}R^{13}$, $S(O)_nR^{13}$, or $NR^{15}R^{16}$, in which each n is independently 1 or 2. Each $R^{24}$ is independently selected from a 5-8 membered monocyclic group having 1-3 heteroatoms, an 8-12 membered bicyclic group having 1-5 heteroatoms, or an 11-14 membered tricyclic group having 1-8 heteroatoms, and the heteroatoms of $R^{24}$ is independently selected from oxygen, nitrogen or sulfur. $R^{24}$ is optionally substituted with $R^{13}$ or $R^{14}$. In one embodiment, zero, one, two, three or four atoms of $R^{24}$ are optionally and independently substituted with $R^{13}$.

In yet another embodiment, $R^{18}$ is $C_3$-$C_8$ heterocycloalkyl. In one embodiment, the $C_3$-$C_8$ heterocycloalkyl is a 5-7 membered monocycle having a heteroatom. The heteroatom is independently selected from oxygen, nitrogen, sulfur, or sulfone and the nitrogen atom is optionally substituted with $R^{19}$. $R^{19}$ is independently selected from hydroxy($C_2$-$C_6$)alkyl, amino($C_2$-$C_6$)alkyl, $C_2$-$C_6$ alkyl cyano, $C_2$-$C_6$ alkyl sulfone, $C_2$-$C_6$ sulfonamide, $C_3$-$C_6$ cycloalkyl, or $C_4$-$C_8$ heterocycloalkyl. In one embodiment, the 5-7 monocycle is optionally substituted morpholine, tetrahydrofuran, thiomorpholine, piperazine, or homopiperazine.

In certain aspects, $R^1$ is H, Y is $NHR^{17}$ or $R^{17}$, and X is $OR^{18}$. Z is H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl, or heteroaryl is optionally substituted with halo, alkyl, or cyano. $R^{17}$ and $R^{18}$ are described above.

In certain aspects, $R^1$ is H; Y is $NHR^{17}$ or $R^{17}$; and X is $NR^{18}R^{19}$. Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano. $R^{17}$ and $R^{18}$ are as described above. $R^{19}$ is independently selected from hydroxy($C_2$-$C_6$)alkyl, amino($C_2$-$C_6$)alkyl, $C_2$-$C_6$ alkyl cyano, $C_2$-$C_6$ alkyl sulfone, $C_2$-$C_6$ sulfonamide, $C_3$-$C_6$ cycloalkyl, or $C_4$-$C_8$ heterocycloalkyl.

In certain aspects, $R^1$ is H; Y is $NHR^{17}$ or $R^{17}$; and X is $NR^{19}R^{20}$. Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano. $R^{17}$ is described above. $R^{19}$ is independently selected from hydroxy($C_2$-$C_6$)alkyl, amino($C_2$-$C_6$)alkyl, $C_2$-$C_6$ alkyl cyano, $C_2$-$C_6$ alkyl sulfone, $C_2$-$C_6$ sulfonamide, $C_3$-$C_6$ cycloalkyl, or $C_4$-$C_8$ heterocycloalkyl. $R^{20}$ is selected from $C(O)R^{19}$, $COOR^{19}$, $C(O)NR^{19}R^{19}$, or $S(O)_nR^{19}$, in which n is 1 or 2.

In one embodiment, $R^1$ is H; Y is $NHR^{17}$ or $R^{17}$; and X is $NR^{15}R^{16}$. Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano. $R^{17}$ is described above. $R^{15}$ and $R^{16}$ of $NR^{15}R^{16}$, taken together with the nitrogen atom to which they are bonded, form: i) a 3-8 membered saturated or partially saturated monocyclic group, wherein the 3-8 membered saturated or partially saturated monocyclic group is optionally substituted with $R^{25}$; ii) an 8-12 membered saturated or partially saturated bicyclic group, wherein the 8-12 membered saturated or partially saturated bicyclic group is optionally substituted with $R^{25}$; iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or iv) an 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$.

In one embodiment, $NR^{15}R^{16}$ is the 4-6 membered saturated monocyclic group optionally and independently substituted at one or more carbon atoms with 1-4 $R^{25}$. In one embodiment, the 4-6 membered saturated monocyclic group is selected from piperidine or pyrrolidine optionally substituted with 1-4 groups selected from hydroxy, amino, $C_1$-$C_6$ alkyl, hydroxy($C_1$-$C_6$)alkyl, amino($C_1$-$C_6$)alkyl, or phenyl. In another embodiment, $NR^{15}R^{16}$ is a 5-8 membered saturated heterocyclic group having 1-2 heteroatoms selected from nitrogen, oxygen, sulfur, sulfone, or sulfoxide, wherein said 5-8 membered saturated heterocyclic group is optionally substituted with hydroxy, amino, $C_1$-$C_6$ alkyl, or phenyl at one or more carbon atoms or nitrogen atoms. The 5-8 membered saturated heterocyclic group is selected from morpholine, thiomorpholine, piperazine or homopiperazine optionally substituted with 1-4 groups selected from hydroxy, amino, $C_1$-$C_6$ alkyl and phenyl, wherein each $C_1$-$C_6$ alkyl is optionally substituted with one or more amino, or hydroxy. The 1-2 heteroatoms are nitrogen and nitrogen atoms are independently substituted with $C_1$-$C_6$ alkyl, $C(O)C_1$-$C_3$ alkyl, or $S(O)_2C_1$-$C_3$ alkyl, wherein the alkyl is optionally and independently substituted with amino or hydroxy.

In one embodiment, the aryl group of $R^{25}$ is selected from: i) a 5-6 membered monocyclic aryl group; ii) an 8-10 membered bicyclic aryl group having 0-5 heteroatoms independently selected from nitrogen, oxygen, sulfur, sulfoxide or sulfone; iii) an 8-10 membered unsaturated or partially unsaturated bicyclic aryl group having 0-5 heteroatoms independently selected from nitrogen, oxygen, sulfur, sulfoxide, or sulfone; or iv) an 8-10 membered unsaturated or partially unsaturated bicyclic aryl group having a carbonyl, carboxamide, or sulfoxamide.

In one embodiment, $R^1$ is methyl, X is selected from $NH_2$ or $NHR^6$, and Y is selected from $R^6$ or $NHR^6$.

In one embodiment, Z is H, halo, $C_1$-$C_3$ alkyl, alkynyl or phenyl.

Examples of the present invention includes:
4-(3,5-dimethoxyphenylamino)-2-(4-hydroxypiperidin-1-yl)pyrido[4,3,-d]pyrimidin-6(6H)-one;
4-(3,5-dimethoxyphenylamino)-2-(4-hydroxy-4-(hydroxymethyl)piperidin-1-yl)pyrido[4,3d]pyrimidin-5 (6H)-one;
2-(4-aminopiperidin-1-yl)-4-(3,5-dimethoxyphenylamino) pyrido[4,3-d]pyrimidin-5(6H)-one hydrochloride;
4-(3,5-dimethoxyphenylamino)-2-(4-morpholinopiperidin-1-yl)pyrido[4,3-d]pyrimidin-5(6H)-one;
methyl 1-(4-(3,5-dimethoxyphenylamino)-5-oxo-5,6-dihydropyrido[4,3-d]pyrimidin-2-yl)-4-hydroxy piperidine-4-carboxylate;
2-(4-hydroxypiperidin-1-yl)-4-(3-(trifluoromethyl)phenylamino)pyrido[4,3-d]pyrimidine-5(6H)-one;
(R)-2-(3-aminopyrrolidin-1-yl)-4-(3-(trifluoromethyl)phenylamino)pyrido[4,3-d]pyrimidin-5(6H)-one hydrochloride;
(S)-2-(pyrrolidin-3-ylamino)-4-(4-trifluoromethylamino) pyrido[4,3-d]pyrimidin-5(6H)-one;
2-((1R,4R)-4-aminocyclohexylamino)-4-(3-(trifluoromethyl)phenylamino)pyrido[4,3-d]pyrimidin-5(6H)-one;
2-(2-morpholinoethoxy)-4-(3-(trifluoro methyl)phenylamino)pyrido[4,3-d]pyrimidin-5(6H)-one;
2-(4-aminopiperidin-1-yl)-4-(3-(trifluoro methyl)phenylamino)pyrido[4,3-d]pyrimidin-5(6H)-one hydrochloride;
2-(4-methylpiperazin-1-yl)-4-(3-(trifluoro methyl)phenylamino)pyrido[4,3-d]pyrimidin-5(6H)-one;

2-(3,4-dihydroisoquinolin-2(1H)-yl)-4-(3-(trifluoromethyl)phenylamino)pyrido[4,3-d]pyrimidin-5(6H)-one;
(R)-2-(3-hydroxypyrrolidin-1-yl)-4-(3-(trifluoromethyl)phenylamino)pyrido[4,3-d]pyrimidin-5(6H)-one;
2-(piperidin-1-yl)-4-(3-(trifluoromethyl)phenylamino)pyrido[4,3-d]pyrimidin-5(6H)-one;
2-(4-aminopiperidin-1-yl)-4-(3-(trifluoro methyl)phenylamino)pyrido[4,3-d]pyrimidin-5(6H)-one hydrochloride;
2-(4-hydroxypiperidin-1-yl)-4-(4-(trifluoromethyl)phenylamino)pyrido[4,3-d]pyrimidin-5(6H)-one;
2-(4-(2-hydroxyethyl)piperazin-1-yl)-4-(3-(trifluoromethyl)phenylamino)pyrido[4,3-d]pyrimidin-5(6H)-one;
N-(2-((5-oxo-4-(3-(trifluoromethyl)phenylamino)-5,6-dihydropyrido[4,3-d]pyrimidin-2-ylamino)methyl)phenyl)methanesulfonamide;
(S)-2-(3-hydroxypyrrolidin-1-yl)-4-(3-(trifluoromethyl)phenylamino)pyrido[4,3-d]pyrimidin-5(6H)-one;
2-(4-aminopiperidin-1-yl)-4-(4-(trifluoro methyl)phenylamino)pyrido[4,3-d]pyrimidin-5(6H)-one hydrochloride;
N-(1-(5-oxo-4-(4-(trifluoromethyl)phenylamino)-5,6-dihydropyrido[4,3-d]pyrimidin-2-yl)piperidin-4-yl)cyclopropanesulfonamide;
2-(piperidin-4-ylamino)-4-(4-(trifluoromethyl)phenylamino)pyrido[4,3-d]pyrimidin-5(6H)-one hydrochloride;
(S)-2-(3-aminopyrrolidin-1-yl)-4-(3-(trifluoromethyl)phenylamino)pyrido[4,3-d]pyrimidin-5(6H)-one hydrochloride;
2-morpholino-4-(4-(trifluoromethyl)phenylamino)pyrido[4,3-d]pyrimidin-5(6H)-one;
2-((1R,4R)-4-hydroxycyclohexylamino)-4-(3-(trifluoromethyl)phenylamino)pyrido[4,3-d]pyrimidin-5(6H)-one;
2-(4-oxopiperidin-1-yl)-4-(3-(trifluoromethyl)phenylamino)pyrido[4,3-d]pyrimidin-5(6H)-one;
2-(3,4-dihydroisoquinolin-2(1H)-yl)-4-(4-(trifluoromethyl)phenylamino)pyrido[4,3-d]pyrimidin-5(6H)-one;
2-(3-(3-(trifluoromethyl)phenyl)-6,7-dihydro-[1,2,3]triazolo[1,5-a]pyrazin-5(4H)-yl)-4-(4-(trifluoromethyl)phenylamino)pyrido[4,3-d]pyrimidin-5(6H)-one;
2-(cyclopropylamino)-4-(4-(trifluoromethyl)phenylamino)pyrido[4,3-d]pyrimidin-5(6H)-one;
2-(cyclopentylamino)-4-(4-(trifluoromethyl)phenylamino)pyrido[4,3-d]pyrimidin-5(6H)-one;
(R)-2-(pyrrolidin-3-ylamino)-4-(4-(trifluoromethyl)phenylamino)pyrido[4,3-d]pyrimidin-5(6H)-one hydrochloride;
2-(3-(trifluoromethyl)-5,6-dihydro-[1,2,4]triazolo[4,3-d]pyrazin-7(8H)-yl)-4-(4-(trifluoromethyl)phenylamino)pyrido[4,3-d]pyrimidin-5(6H)-one;
2-(benzylamino)-4-(4-(trifluoromethyl)phenylamino)pyrido[4,3-d]pyrimidin-5(6H)-one;
2-(benzyl(methyl)amino)-4-(4-(trifluoromethyl)phenylamino)pyrido[4,3-d]pyrimidin-5(6H)-one;
(S)-2-(1-(4-fluorophenyl)ethylamino)-4-(4-(trifluoromethyl)phenylamino)pyrido[4,3-d]pyrimidin-5(6H)-one;
2-((tetrahydro-2H-pyran-4-yl)methylamino)-4-(4-(trifluoromethyl)phenyl amino)pyrido[4,3-d]pyrimidin-5(6H)-one;
2-(4-fluorobenzylamino)-4-(4-(trifluoromethyl)phenylamino)pyrido[4,3-d]pyrimidin-5(6H)-one;
2-(piperidin-4-ylmethylamino)-4-(4-(trifluoromethyl)phenylamino)pyrido[4,3-d]pyrimidin-5(6H)-one hydrochloride;
2-(tetrahydro-2H-pyran-4-ylamino)-4-(4-(trifluoromethyl)phenylamino)pyrido[4,3-d]pyrimidin-5(6H)-one;
2-(1,4-diazepan-1-yl)-4-(4-(trifluoromethyl)phenylamino)pyrido[4,3-d]pyrimidin-5(6H)-one hydrochloride;
2-(thiazolidin-3-yl)-4-(4-(trifluoromethyl)phenylamino)pyrido[4,3-d]pyrimidin-5(6H)-one;
N-(2-((5-oxo-4-(4-(trifluoromethyl)phenylamino)-5,6-dihydropyrido[4,3-d]pyrimidin-2-ylamino)methyl)phenyl)methanesulfonamide;
(S)-2-(1-cyclohexylethylamino)-4-(4-(trifluoromethyl)phenylamino)pyrido[4,3-d]pyrimidin-5(6H)-one;
2-(cyclohexylamino)-4-(4-(trifluoromethyl)phenylamino)pyrido[4,3-d]pyrimidin-5(6H)-one;
(R)-2-(1-methylpyrrolidin-3-ylamino)-4-(4-(trifluoromethyl)phenylamino)pyrido[4,3-d]pyrimidin-5(6H)-one;
(R)-2-(1-isopropylpyrrolidin-3-ylamino)-4-(4-(trifluoromethyl)phenylamino)pyrido[4,3-d]pyrimidin-5(6H)-one;
2-((1-methylpiperidin-4-yl)methylamino)-4-(4-(trifluoromethyl)phenylamino) pyrido[4,3-d]pyrimidin-5(6H)-one;
2-((1-isopropylpiperidin-4-yl)methylamino)-4-(4-(trifluoromethyl)phenyl amino)pyrido[4,3-d]pyrimidin-5(6H)-one;
2-(4-((dimethylamino)methyl)piperidin-1-yl)-4-(4-(trifluoromethyl)phenylamino) pyrido[4,3-d]pyrimidin-5(6H)-one;
2-(4-methylthiazol-2-ylamino)-4-(4-(trifluoromethyl)phenylamino)pyrido[4,3-d]pyrimidin-5(6H)-one;
(S)-2-(1-(methylsulfonyl)pyrrolidin-3-ylamino)-4-(4-(trifluoromethyl)phenyl amino)pyrido[4,3-d]pyrimidin-5(6H)-one;
2-(4-(2-hydroxyethyl)piperazin-1-yl)-4-(4-(trifluoromethyl)phenylamino)pyrido[4,3-d]pyrimidin-5(6H)-one;
2-(4-(hydroxymethyl)piperidin-1-yl)-4-(4-(trifluoromethyl)phenylamino)pyrido[4,3-d]pyrimidin-5(6H)-one;
ethyl 1-(5-oxo-4-(4-(trifluoromethyl)phenylamino)-5,6-dihydropyrido[4,3-d]pyrimidin-2-yl)piperidine-4-carboxylate;
2-(4-(4-(2-hydroxyethyl)piperazine-1-carbonyl)piperidin-1-yl)-4-(4-(trifluoro methyl)phenylamino)pyrido[4,3-d]pyrimidin-5(6H)-one;
2-(4-(4-(hydroxymethyl)piperidine-1-carbonyl)piperidin-1-yl)-4-(4-(trifluoro methyl)phenylamino)pyrido[4,3-d]pyrimidin-5(6H)-one;
2-((1S,2R)-2-aminocyclohexylamino)-4-(3-(trifluoromethyl)phenylamino)pyrido[4,3-d]pyrimidin-5(6H)-one;
2-((1S,2S)-2-aminocyclohexylamino)-4-(3-(trifluoromethyl)phenylamino)pyrido[4,3-d]pyrimidin-5(6H)-one;
2-((1R,2S)-2-aminocyclohexylamino)-4-(2-(trifluoromethyl)phenylamino)pyrido[4,3-d]pyrimidin-5(6H)-one;
2-((1R,2R)-2-aminocyclohexylamino)-4-(2-(trifluoromethyl)phenylamino)pyrido[4,3-d]pyrimidin-5(6H)-one;
2-((1R,4R)-4-aminocyclohexylamino)-4-(2-(trifluoromethyl)phenylamino)pyrido[4,3-d]pyrimidin-5(6H)-one;
2-(4-ethylpiperazin-1-yl)-4-(3-(trifluoromethyl)phenylamino)pyrido[4,3-d]pyrimidin-5(6H)-one;
2-(2-morpholinoethylamino)-4-(3(trifluoromethyl)phenylamino)pyrido[4,3-d]pyrimidin-5(6H)-one;
2-(3-aminocyclohexylamino)-4-(3-(trifluoromethyl)phenylamino)pyrido[4,3-d]pyrimidin-5(6H)-one;
2-(4-(methylsulfonyl)piperazin-1-yl)-4-(3-(trifluoromethyl)phenylamino)pyrido[4,3-d]pyrimidin-5(6H)-one;
2-(morpholinoamino)-4-(3-(trifluoromethyl)phenylamino)pyrido[4,3-d]pyrimidin-5(6H)-one;
2-(4-acetylpiperazin-1-yl)-4-(3-(trifluoro methyl)phenylamino)pyrido[4,3-d]pyrimidin-5(6H)-one;
(R)-2-(2-hydroxy-1-phenylethylamino)-4-(3-(trifluoromethyl)phenylaminopyrido[4,3-d]pyrimidin-5(6H)-one;
(S)-2-(2-hydroxy-1-phenylethylamino)-4-(3-(trifluoromethyl)phenylaminopyrido[4,3-d]pyrimidin-5(6H)-one;
(R)-2-(1-hydroxy-3-phenylpropan-2-ylamino)-4-(3-(trifluoromethyl)phenyl amino)pyrido[4,3-d]pyrimidin-5(6H)-one;

(S)-2-(1-hydroxy-3-phenylpropan-2-ylamino)-4-(3-(trifluoromethyl)phenyl amino)pyrido[4,3-d]pyrimidin-5(6H)-one;

1-(5-oxo-4-(3-(trifluoromethyl)phenylamino)-5,6-dihydropyrido[4,3-d]pyrimidin-2-yl)piperidine-4-carboxamide;

(R)-2,2,2-trifluoro-N-(1-(5-oxo-4-(3-(trifluoromethyl)phenylamino)-5,6-dihydropyrido[4,3-d]pyrimidin-2-yl)pyrrolidin-3-yl)acetamide;

2-(4-(4-chlorophenyl)-4-hydroxy piperidin-1-yl)-4-(3-(trifluoromethyl)phenylamino)pyrido[4,3-d]pyrimidin-5(6H)-one;

2-((1S,2S)-2-(phenylsulfonyl)cyclohexylamino)-4-(3-(trifluoromethyl)phenyl amino)pyrido[4,3-d]pyrimidin-5(6H)-one;

2-((1S,2R)-2-aminocyclohexylamino)-4-(4-(trifluoromethyl)phenylamino)pyrido[4,3-d]pyrimidin-5(6H)-one;

2-thiomorpholino-4-(3-(trifluoromethyl)phenylamino)pyrido[4,3-d]pyrimidin-5(6H)-one;

2-(4-sulfonylpyrido)-4-(3-(trifluoro methyl)phenylamino)pyrido[4,3-d]pyrimidin-5(6H)-one;

2-(4-morpholinopiperidin-1-yl)-4-(3-(trifluoromethyl)phenylamino)pyrido[4,3-d]pyrimidin-5(6H)-one;

N-((1R,2S)-2-(5-oxo-4-(3-(trifluoro methyl)phenylamino)-5,6-dihydropyrido[4,3-d]pyrimidin-2-ylamino)cyclohexyl)acetamide;

N-((1R,4R)-4-(5-oxo-4-(3-(trifluoro methyl)phenylamino)-5,6-dihydropyrido[4,3-d]pyrimidin-2-ylamino)cyclohexyl)acetamide;

2-((1R,2R)-2-(dimethylamino)cyclohexylamino)-4-(3-(trifluoromethyl)phenyl amino)pyrido[4,3-d]pyrimidin-5(6H)-one;

2-(4-aminopiperidin-1-yl)-4-(3-bromophenylamino)pyrido[4,3-d]pyrimidin-5(6H)-one hydrochloride;

4-(3-bromophenylamino)-2-(4-hydroxypiperidin-1-yl)pyrido[4,3-d]pyrimidin-5(6H)-one;

2-(4-aminopiperidin-1-yl)-4-(3-bromophenylamino)pyrido[4,3-d]pyrimidin-5(6H)-one hydrochloride;

4-(3-bromophenylamino)-2-(4-(dimethylamino)piperidin-1-yl)pyrido[4,3-d]pyrimidin-5(6H)-one;

(S)-4-(3-bromophenylamino)-2-(4-(1-hydroxypropan-2-ylamino)piperidin-1-yl)pyrido[4,3-d]pyrimidin-5(6H)-one;

(R)-2-(4-(3-aminopyrrolidin-1-yl)piperidin-1-yl)-4-(3-bromophenylamino)pyrido[4,3-d]pyrimidin-5(6H)-one hydrochloride;

(R)-2-(3-aminopyrrolidin-1-yl)-4-(3-bromophenylamino)pyrido[4,3-d]pyrimidin-5(6H)-one hydrochloride;

4-(3-bromophenylamino)-2-(3-hydroxypiperidin-1-yl)pyrido[4,3-d]pyrimidin-5(6H)-one;

(R)-2-(3-aminopyrrolidin-1-yl)-4-(4-bromophenylamino)pyrido[4,3-d]pyrimidin-5(6H)-one hydrochloride;

(S)-2-(3-aminopyrrolidin-1-yl)-4-(4-bromophenylamino)pyrido[4,3-d]pyrimidin-5(6H)-one hydrochloride;

4-(4-bromophenylamino)-2-(4-hydroxypiperidin-1-yl)pyrido[4,3-d]pyrimidin-5(6H)-one;

2-(4-aminopiperidin-1-yl)-4-(4-bromophenylamino)pyrido[4,3-d]pyrimidin-5(6H)-one hydrochloride;

(S)-4-(3-bromophenylamino)-2-(4-(1-hydroxypropan-2-ylamino)piperidin-1-yl)pyrido[4,3-d]pyrimidin-5(6H)-one;

4-(3-bromophenylamino)-2-(4-(dimethylamino)piperidin-1-yl)pyrido[4,3-d]pyrimidin-5(6H)-one;

2-(4-aminopiperidin-1-yl)-4-(m-tolylamino)pyrido[4,3-d]pyrimidin-5(6H)-one hydrochloride;

2-(4-hydroxypiperidin-1-yl)-4-(m-tolylamino)pyrido[4,3-d]pyrimidin-5(6H)-one;

2-((1R,2R)-2-aminocyclohexylamino)-4-(3,5-bis(trifluoromethyl)phenylamino) pyrido[4,3-d]pyrimidin-5(6H)-one;

(2-((1R,2S)-2-aminocyclohexylamino)-4-(3-(trifluoromethyl)phenylamino)pyrido[4,3-d]pyrimidin-5(6H)-one with (2-((1S,2R)-2-aminocyclohexylamino)-4-(3-(trifluoromethyl)phenylamino)pyrido[4,3-d]pyrimidin-5(6H)-one;

4-(3,5-bis(trifluoromethyl)phenylamino)-2-(4-hydroxypiperidin-1-yl)pyrido[4,3-d]pyrimidin-5(6H)-one;

4-(3,5-bis(trifluoromethyl)phenylamino)-2-morpholinopyrido[4,3-d]pyrimidin-5(6H)-one;

4-(3,5 bis(trifluoromethyl)phenylamino)-2-((1r,4r)-4-hydroxycyclohexyl amino)pyrido[4,3-d]pyrimidin-5(6H)-one;

2-(2-aminobenzylamino)-4-(3,5-bis(trifluoromethyl)phenylamino)pyrido[4,3-d]pyrimidin-5(6H)-one;

4-(3,5-bis(trifluoromethyl)phenylamino)-2-(4-methylpiperazin-1-yl)pyrido[4,3-d]pyrimidin-5(6H)-one;

2-(4-aminopiperidin-1-yl)-4-(3,5-bis(trifluoromethyl)phenylamino)pyrido[4,3-d]pyrimidin-5(6H)-one hydrochloride;

(S)-4-(3,5-bis(trifluoromethyl)phenylamino)-2-(pyrrolidin-3-ylamino)pyrido[4,3-d]pyrimidin-5(6H)-one hydrochloride;

4-(3,5-bis(trifluoromethyl)phenylamino)-2-(piperidin-4-ylamino)pyrido[4,3-d]pyrimidin-5(6H)-one hydrochloride;

4-(3,5-bis(trifluoromethyl)phenylamino)-2-(1-methylpiperidin-4-ylamino)pyrido[4,3-d]pyrimidin-5(6H)-one;

(S)-4-(3,5-bis(trifluoromethyl)phenylamino)-2-(1-methylpyrrolidin-3-ylamino) pyrido[4,3-d]pyrimidin-5(6H)-one;

4-(3,5-bis(trifluoromethyl)phenylamino)-2-(4-(dimethylamino)piperidin-1-yl)pyrido[4,3-d]pyrimidin-5(6H)-one;

4-(3,5-bis(trifluoromethyl)phenylamino)-2-(4-(hydroxymethyl)piperidin-1-yl)pyrido[4,3-d]pyrimidin-5(6H)-one;

4-(3,5-bis(trifluoromethyl)phenylamino)-2-(4-(2-hydroxyethyl)piperazin-1-yl)pyrido[4,3-d]pyrimidin-5(6H)-one;

(R)-4-(3,5-bis(trifluoromethyl)phenylamino)-2-(3-hydroxypyrrolidin-1-yl)pyrido[4,3-d]pyrimidin-5(6H)-one;

4-(3,5-bis(trifluoromethyl)phenylamino)-2-(3-hydroxyazetidin-1-yl)pyrido[4,3-d]pyrimidin-5(6H)-one;

4-(3,5-bis(trifluoromethyl)phenylamino)-2-(4-(2-hydroxyethyl)piperidin-1-yl)pyrido[4,3-d]pyrimidin-5(6H)-one;

N-((1r,4r)-4-(4-(3,5-bis(trifluoromethyl)phenylamino)-5-oxo-5,6-dihydropyrido[4,3-d]pyrimidin-2-ylamino)cyclohexyl)acetamide;

4-(3,5-bis(trifluoromethyl)phenylamino)-2-(3-oxopiperazin-1-yl)pyrido[4,3-d]pyrimidin-5(6H)-one;

4-(3,5-bis(trifluoromethyl)phenylamino)-2-(piperazin-1-yl)pyrido[4,3-d]pyrimidin-5(6H)-one hydrochloride;

methyl 1-(4-(3,5-bis(trifluoromethyl)phenylamino)-5-oxo-5,6-dihydropyrido[4,3-d]pyrimidin-2-yl)-4-hydroxy piperidine-4-carboxylate;

4-(3,5-bis(trifluoromethyl)phenylamino)-2-(4-hydroxy-4-(hydroxymethyl)piperidin-1-yl)pyrido[4,3-d]pyrimidin-5(6H)-one;

2-((1R,4R)-4-aminocyclohexylamino)-4-(3,5-bis(trifluoromethyl)phenylamino) pyrido[4,3-d]pyrimidin-5(6H)-one;

4-(3,5-bis(trifluoromethyl)phenylamino)-2-(4-(hydroxyimino)piperidin-1-yl)pyrido[4,3-d]pyrimidin-5(6H)-one;

(S)-4-(phenoxyphenylamino)-2-(pyrrolidin-3-ylamino)pyrido[4,3-d]pyrimidin-5(6H)-one hydrochloride;

2-(4-hydroxypiperidin-1-yl)-4(4-(methylsulfonyl)phenylamino)pyrido[4,3d]pyrimidin-5(6H)-one;

N-(2-((4-(4-(methylsulfonyl)phenylamino)-5-oxo-5,6-dihydropyrido[4,3-d]pyrimidin-2-ylamino)methyl)phenyl)methanesulfonamide;

2-(4-hydroxypiperidin-1-yl)-4-(4-(methyl sulfonyl)phenylamino)pyrido[4,3-d]pyrimidin-5(6H)-one;

4-(4-(methylsulfonyl)phenylamino)-2-(4-morpholinopiperidin-1-yl)pyrido[4,3-d]pyrimidin-5(6H)-one;

2-(4-hydroxypiperidin-1-yl)-4-(3-(methyl sulfonyl)phenylamino)pyrido[4,3-d]pyrimidin-5(6H)-one;

N-(2-((4-(4-(methylsulfonyl)phenylamino)-5-oxo-5,6-dihydropyrido[4,3-d]pyrimidin-2-ylamino)methyl)phenyl)cyclopropane sulfonamide;

N-methyl-N-(2-((4-(4-(methylsulfonyl)phenylamino)-5-oxo-5,6-dihydropyrido[4,3-d]pyrimidin-2-ylamino)methyl)phenyl)cyclopropanesulfonamide;

(S)-2-(3-aminopyrrolidin-1-yl)-4-(4-(methylsulfonyl)phenylamino)pyrido[4,3-d]pyrimidin-5(6H)-one;

2-(4-hydroxypiperidin-1-yl)-4-(4-morpholinophenylamino)pyrido[4,3-d]pyrimidin-5(6H)-one;

4-(4-(4-acetylpiperazin-1-yl)phenylamino)-2-(4-(hydroxymethyl)piperidin-1-yl)pyrido[4,3-d]pyrimidin-5(6H)-one;

(S)-4-(4-morpholinophenylamino)-2-(pyrrolidin-3-ylamino)pyrido[4,3-d]pyrimidin-5(6H)-one hydrochloride;

2-(4-(hydroxymethyl)piperidin-1-yl)-4-(4-sulfonylphenylamino)pyrido[4,3-d]pyrimidin-5(6H)-one;

4-(4-(4-acetylpiperazin-1-yl)phenylamino)-2-(4-(hydroxymethyl)piperidin-1-yl)pyrido[4,3-d]pyrimidin-5(6H)-one;

2-(4-(hydroxymethyl)piperidin-1-yl)-4-(4-morpholinophenylamino)pyrido[4,3-d]pyrimidin-5(6H)-one;

4-(4-(5-oxo-2-(piperidin-4-ylmethylamino)-5,6-dihydropyrido[4,3-d]pyrimidin-4-ylamino)phenyl)morpholine 4-oxide hydrochloride;

4-(4-morpholinophenylamino)-2-(piperidin-4-ylmethylamino)pyrido[4,3-d]pyrimidin-5(6H)-one hydrochloride;

N-methyl-N-(2-((4-(4-morpholinophenylamino)-5-oxo-5,6-dihydropyrido[4,3-d]pyrimidin-2-ylamino)methyl)phenyl)cyclopropanesulfonamide;

N-(2-((4-(4-morpholinophenylamino)-5-oxo-5,6-dihydropyrido[4,3-d]pyrimidin-2-ylamino)methyl)phenyl)cyclopropanesulfonamide;

N-(2-((4-(4-morpholinophenylamino)-5-oxo-5,6-dihydropyrido[4,3-d]pyrimidin-2-ylamino)methyl)phenyl)methanesulfonamide;

2-(2-aminobenzylamino)-4-(4-morpholinophenylamino)pyrido[4,3-d]pyrimidin-5(6H)-one;

2-((1R,2R)-2-aminocyclohexylamino)-4-(4-morpholinophenylamino)pyrido[4,3-d]pyrimidin-5(6H)-one;

2-((1R,2S)-2-aminocyclohexylamino)-4-(4-morpholinophenylamino)pyrido[4,3-d]pyrimidin-5(6H)-one;

2-((1R,2R)-2-aminocyclohexylamino)-4-(benzo[d][1,3]dioxol-5-ylamino)pyrido[4,3-d]pyrimidin-5(6H)-one;

2-(4-hydroxypiperidin-1-yl)-4-(3,4,5-triemethoxyphenylamino)pyrido[4,3d]pyrimidin-5(6H)-one;

2-(4-hydroxypiperidin-1-yl)-4-(4-methoxy-3-(trifluoromethyl)phenylamino)pyrido[4,3d]pyrimidin-5(6H)-one;

2-(4-(hydroxymethyl)piperidin-1-yl)-4-(4-methoxy-3-(trifluoromethyl)phenylamino) pyrido[4,3d]pyrimidin-5(6H)-one;

2-(4-hydroxy-4-(hydroxymethyl)piperidin-1-yl)-4-(4-methoxy-3-(trifluoromethyl)phenylamino)pyrido[4,3d]pyrimidin-5(6H)-one;

2-(4-hydroxypiperidin-1-yl)-4-(3-methoxy-5-(trifluoromethyl)phenylamino)pyrido[4,3d]pyrimidin-5(6H)-one;

2-(4-(hydroxymethyl)piperidin-1-yl)-4-(3-methoxy-5-(trifluoromethyl)phenylamino) pyrido[4,3d]pyrimidin-5(6H)-one;

2-(4-hydroxy-4-(hydroxymethyl)piperidin-1-yl)-4-(3-methoxy-5-(trifluoromethyl)phenyl amino)pyrido[4,3d]pyrimidin-5(6H)-one;

2-(4-hydroxy-4-(hydroxymethyl)piperidin-1-yl)-4-(3,4,5-trimethoxyphenylamino)pyrido[4,3-d]pyrimidin-5(6H)-one;

4-(3,5-dimethylphenylamino)-2-(4-hydroxy-4-(hydroxymethyl)piperidin-1-yl)pyrido[4,3-d]pyrimidin-5(6H)-one;

4-(4-chloro-3-methoxyphenylamino)-2-(4-hydroxypiperidin-1-yl)pyrido[4,3-d]pyrimidin-5(6H)-one;

2-(4-hydroxypiperidin-1-yl)-4-(3-methoxy-5-(trifluoromethyl)phenylamino)pyrido[4,3-d]pyrimidin-5(6H)-one;

2-(4-(hydroxymethyl)piperidin-1-yl)-4-(3-methoxy-5-(trifluoromethyl)phenylamino) pyrido[4,3-d]pyrimidin-5(6H)-one;

2-(4-hydroxy-4-(hydroxymethyl)piperidin-1-yl)-4-(3-methoxy-5-(trifluoromethyl)phenylamino)pyrido[4,3-d]pyrimidin-5(6H)-one;

4-(4-chloro-3-(trifluoromethyl)phenylamino)-2-(4-hydroxypiperidin-1-yl)pyrido[4,3-d]pyrimidin-5(6H)-one;

4-(4-chloro-3-(trifluoromethyl)phenylamino)-2-(4-(hydroxymethyl)piperidin-1-yl)pyrido[4,3-d]pyrimidin-5(6H)-one;

4-(4-chloro-3-(trifluoromethyl)phenylamino)-2-(4-hydroxy-4-(hydroxymethyl)piperidin-1-yl)pyrido[4,3-d]pyrimidin-5(6H)-one 4-(3-chloro-5-(trifluoromethyl)phenylamino)-2-(4-hydroxy-4-(hydroxymethyl)piperidin-1-yl)pyrido[4,3-d]pyrimidin-5(6H)-one;

4-(3-bromo-5-(trifluoromethyl)phenylamino)-2-(4-hydroxy-4-(hydroxymethyl)piperidin-1-yl)pyrido[4,3-d]pyrimidin-5(6H)-one;

4-(4-chloro-3-(trifluoromethoxy)phenylamino)-2-(4-hydroxy-4-(hydroxymethyl)piperidin-1-yl)pyrido[4,3-d]pyrimidin-5(6H)-one;

2-(4-hydroxypiperidine-1-yl)-6-methyl-4-(3-(trifluoromethyl)phenylamino)pyrido[4,3-d]pyrimidin-5(6H)-one;

6-methyl-4-(phenylamino)-2-(3-(trifluoromethyl)phenylamino)pyrido[4,3-d]pyrimidin-5(6H)-one;

methyl 4-(6-methyl-2-morpholino-5-oxo-5,6-dihydropyrido[4,3-d]pyrimidin-4-ylamino)benzoate;

6-methyl-2-(methylamino)-4-(4-(piperazine-1-carbonyl)phenylamino)pyrido[4,3-d]pyrimidin-5(6H)-one hydrochloride;

methyl 4-(6-methyl-2-(methylamino)-5-oxo-5,6-dihydropyrido[4,3-d]pyrimidin-4-ylamino)benzoate;

2-amino-6-methyl-4-(phenylamino)pyrido[4,3-d]pyrimidin-5(6H)-one;

4-(4-fluorobenzylamino)-6-methyl-2-(methylamino)pyrido[4,3-d]pyrimidin-5(6H)-one;

6-methyl-2-(methylamino)-4-(phenylamino)pyrido[4,3-d]pyrimidin-5(6H)-one;

2-(4-methoxybenzylamino)-6-methyl-4-(phenylamino)pyrido[4,3-d]pyrimidin-5(6H)-one;

2-(4-hydroxycyclohexylamino)-6-methyl-4-(phenylamino)pyrido[4,3-d]pyrimidin-5(6H)-one;

4-(4-methoxyphenyl)-6-methyl-2-(methylamino)pyrido[4,3-d]pyrimidin-5(6H)-one;

2-(4-(hydroxymethyl)piperidin-1-yl)-4-(4-methoxyphenyl)pyrido[4,3-d]pyrimidin-5(6H)-one;

4-(4-methoxyphenyl)-6-methyl-2-(methylamino)pyrido[4,3-d]pyrimidin-5(6H)-one;

4-(4-aminophenyl)-6-methyl-2-(methylamino)pyrido[4,3-d]pyrimidin-5(6H)-one hydrochloride;

1-(4-fluorophenyl)-3-(4-(6-methyl-2-(methylamino)-5-oxo-5,6-dihydropyrido[4,3-d]pyrimidin-4-yl)phenyl)urea;

8-bromo-2-(4-hydroxypiperidin-1-yl)-4-(3-(trifluoromethyl)phenylamino)pyrido[4,3-d]pyrimidin-5(6H)-one;

8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one;

8-chloro-2-(4-hydroxypiperidin-1-yl)-4-(3-(trifluoromethyl)phenylamino)pyrido[4,3-d]pyrimidin-5(6H)-one;

8-bromo-2-(4-hydroxy-4-(hydroxymethyl)piperidin-1-yl)-4-(3-(trifluoromethyl)phenyl amino)pyrido[4,3-d]pyrimidin-5(6H)-one;

(R)-2-(3-aminopyrrolidin-1-yl)-8-bromo-4-(3-(trifluoromethyl)phenylamino)pyrido[4,3-d]pyrimidin-5(6H)-one hydrochloride;

(R)-2-(3-aminopyrrolidin-1-yl)-8-bromo-4-(4-bromo-3-methylphenylamino)pyrido[4,3-d]pyrimidin-5(6H)-one hydrochloride;

8-bromo-2-(4-hydroxypiperidin-1-yl)-4-(3-(trifluoromethyl)phenylamino)pyrido[4,3-d]pyrimidin-5(6H)-one;

8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one;

8-chloro-2-(4-hydroxypiperidin-1-yl)-4-(3-(trifluoromethyl)phenylamino)pyrido[4,3-d]pyrimidin-5(6H)-one;

8-bromo-2-(4-hydroxy-4-(hydroxymethyl)piperidin-1-yl)-4-(3-(trifluoromethyl)phenyl amino)pyrido[4,3-d]pyrimidin-5(6H)-one;

(R)-2-(3-aminopyrrolidin-1-yl)-8-bromo-4-(3-(trifluoromethyl)phenylamino)pyrido[4,3-d]pyrimidin-5(6H)-one hydrochloride;

(R)-2-(3-aminopyrrolidin-1-yl)-8-bromo-4-(4-bromo-3-methylphenylamino)pyrido[4,3-d]pyrimidin-5(6H)-one hydrochloride;

8-bromo-2-(4-hydroxypiperidin-1-yl)-4-(3-(trifluoromethyl)phenylamino)pyrido[4,3-d]pyrimidin-5(6H)-one;

8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one;

8-chloro-2-(4-hydroxypiperidin-1-yl)-4-(3-(trifluoromethyl)phenylamino)pyrido[4,3-d]pyrimidin-5(6H)-one;

2-(4-hydroxypiperidin-1-yl)-4-(3-methoxy-5-(trifluoromethyl)phenylamino)pyrido[4,3-d]pyrimidin-5(6H)-one;

2-(4-(hydroxymethyl)piperidin-1-yl)-4-(3-methoxy-5-(trifluoromethyl)phenylamino) pyrido[4,3-d]pyrimidin-5(6H)-one;

4-(4-chloro-3-(trifluoromethyl)phenylamino)-2-(4-hydroxypiperidin-1-yl)pyrido[4,3-d]pyrimidin-5(6H)-one;

4-(4-chloro-3-(trifluoromethyl)phenylamino)-2-(4-(hydroxymethyl)piperidin-1-yl)pyrido[4,3-d]pyrimidin-5(6H)one;

4-(4-chloro-3-methoxyphenylamino)-2-(4-hydroxy-4-(hydroxymethyl)piperidin-1-yl)pyrido[4,3-d]pyrimidin-5(6H)-one;

2-(4-hydroxy-4-(hydroxymethyl)piperidin-1-yl)-4-(3-methoxy-5-(trifluoromethyl)phenylamino)pyrido[4,3-d]pyrimidin-5(6H)-one;

4-(4-chloro-3-(trifluoromethyl)phenylamino)-2-(4-hydroxy-4-(hydroxymethyl)piperidin-1-yl)pyrido[4,3-d]pyrimidin-5(6H)-one;

8-bromo-2-(4-hydroxy-4-(hydroxymethyl)piperidin-1-yl)-4-(3-(trifluoromethyl)phenyl amino)pyrido[4,3-d]pyrimidin-5(6H)-one;

4-(3,4-dimethoxyphenylamino)-2-(4-hydroxypiperidin-1-yl)pyrido[4,3-d]pyrimidin-5(6H)-one;

4-(3-bromo-4-methoxyphenylamino)-2-(4-hydroxypiperidin-1-yl)pyrido[4,3-d]pyrimidin-5(6H)-one;

(R)-2-(3-aminopyrrolidin-1-yl)-8-bromo-4-(4-phenoxyphenylamino)pyrido[4,3-d]pyrimidin-5(6H)-one hydrochloride;

8-bromo-2-(4-hydroxy-4-(hydroxymethyl)piperidin-1-yl)-4-(4-phenoxyphenyl amino)pyrido[4,3-d]pyrimidin-5(6H)-one;

4-(3,4-dimethoxyphenylamino)-2-(4-hydroxy-4-(hydroxymethyl)piperidin-1-yl)pyrido[4,3-d]pyrimidin-5(6H)-one;

4-(3-bromo-4-methoxyphenylamino)-2-(4-hydroxy-4-(hydroxymethyl)piperidin-1-yl)pyrido[4,3-d]pyrimidin-5(6H)-one;

2-(4-aminopiperidin-1-yl)-8-bromo-4-(4-phenoxyphenylamino)pyrido[4,3-d]pyrimidin-5(6H)-one hydrochloride;

(R)-2-(3-aminopyrrolidin-1-yl)-8-iodo-4-(4-phenoxyphenylamino)pyrido[4,3-d]pyrimidin-5(6H)-one hydrochloride;

4-(4-chloro-3-(trifluoromethyl)phenylamino)-2-(4-hydroxy-4-(hydroxymethyl)piperidin-1-yl)-8-iodopyrido[4,3-d]pyrimidin-5(6H)-one;

4-(4-chloro-3-(trifluoromethyl)phenylamino)-2-(4-hydroxypiperidin-1-yl)-8-iodopyrido[4,3-d]pyrimidin-5(6H)-one;

(R)-2-(3-aminopyrrolidin-1-yl)-8-bromo-4-(4-chloro-3-(trifluoromethyl)phenylamino)pyrido[4,3-d]pyrimidin-5(6H)-one hydrochloride;

2-(4-hydroxypiperidin-1-yl)-8-iodo-4-(4-(trifluoromethyl)phenylamino)pyrido[4,3-d]pyrimidin-5(6H)-one;

2-(4-hydroxypiperidin-1-yl)-4-(4-morpholino-3-(trifluoromethyl)phenylamino)pyrido[4,3-d]pyrimidin-5(6H)-one;

(R)-2-(3-aminopyrrolidin-1-yl)-8-bromo-4-(4-methoxy-3-(trifluoromethyl)phenylamino)pyrido[4,3-d]pyrimidin-5(6H)-one hydrochloride;

(R)-2-(3-aminopyrrolidin-1-yl)-8-bromo-4-(4-chloro-3-(trifluoromethoxy)phenylamino) pyrido[4,3-d]pyrimidin-5(6H)-one hydrochloride;

4-(4-chloro-3-(trifluoromethoxy)phenylamino)-2-(4-hydroxypiperidin-1-yl)pyrido[4,3-d]pyrimidin-5(6H)-one;

4-(3-bromo-5-(trifluoromethyl)phenylamino)-2-(4-hydroxypiperidin-1-yl)pyrido[4,3-d]pyrimidin-5(6H)-one;

(R)-6-(3-aminopyrrolidin-1-yl)-4-iodo-8-(4-(trifluoromethyl)phenylamino)isoquinolin-1(2H)-one hydrochloride;

(R)-6-(3-aminopyrrolidin-1-yl)-4-bromo-8-(4-(trifluoromethyl)phenylamino)isoquinolin-1(2H)-one hydrochloride;

(S)-6-(3-aminopyrrolidin-1-yl)-4-bromo-8-(4-(trifluoromethyl)phenylamino)isoquinolin-1(2H)-one hydrochloride;

4-(2,3-dihydrobenzo[b][1,4]dioxin-6-ylamino)-2-(4-hydroxypiperidin-1-yl)pyrido[4,3-d]pyrimidin-5(6H)-one;

2-(4-hydroxypiperidin-1-yl)-4-(naphthalen-2-ylamino)pyrido[4,3-d]pyrimidin-5(6H)-one;

2-(4-hydroxypiperidin-1-yl)-4-(quinolin-5-ylamino)pyrido[4,3-d]pyrimidin-5(6H)-one;

4-(3H-indol-2-ylamino)-2-(4-hydroxypiperidin-1-yl)pyrido[4,3-d]pyrimidin-5(6H)-one; and 2-(4-hydroxypiperidin-1-yl)-4-(4-phenoxyphenylamino)-8-phenylpyrido[4,3-d]pyrimidin-5(6H)-one.

The term "alkyl," used alone or as part of a larger moiety such as "arylalkyl" or "cycloalkyl" refers to a straight or branched hydrocarbon radical having from 1 to 15 carbon atoms (unless stated otherwise) and includes, for example, methyl, ethyl, n-propyl, isopropyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as N, S, and O.

The term "heterocycloalkyl" means a non-aromatic monocyclic or polycyclic ring comprising carbon and hydrogen atoms and at least one heteroatom, preferably, 1 to 4 heteroatoms selected from N, O, S, sulfone, or sulfoxide. A heterocycloalkyl group can have one or more carbon-carbon double bonds or carbon-heteroatom double bonds in the ring group as long as the ring group is not rendered aromatic by their presence. Examples of heterocycloalkyl groups include azetidine, aziridinyl, pyrrolidinyl, pyrrolidino, piperidinyl, piperidino, piperazinyl, homopiperazinyl, piperazino, morpholinyl, morpholino, thiomorpholinyl, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkenyl" refers to straight and branched hydrocarbon radicals having from 2 to 6 carbon atoms and one double bond and includes ethenyl, 3-buten-1-yl, 2-ethenylbutyl, 3-hexen-1-yl, and the like. An alkenyl can be unsubstituted or substituted with one or more suitable substituents.

As used herein, the term "alkynyl" refers to straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like. An alkynyl can be unsubstituted or substituted with one or more suitable substituents.

As used herein, the term "alkoxy" refers to the alkyl groups above bound through oxygen, examples of which include methoxy, ethoxy, isopropoxy, tert-butoxy, and the like. In addition, alkoxy also refers to polyethers such as —O—$(CH_2)_2$—O—$CH_3$, and the like. An alkoxy can be unsubstituted or substituted with one or more suitable substituents.

As used herein, the term "aryl" refers to unsubstituted or substituted aromatic monocyclic or polycyclic groups and includes, for example, phenyl and naphthyl. The term "aryl" also includes phenyl rings fused to non-aromatic carbocyclic ring or to a heterocyclyl group. The term "aryl" may be interchangeably used with "aryl ring," aromatic group," and "aromatic aromatic ring." Heteroaryl groups have 4 to 14 atoms, 1 to 9 of which are independently selected from the group consisting of O, S and N. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "monocyclic aryl group" refers to an unsubstituted or substituted aryl and includes, for example, phenyl.

As used herein, the term "haloalkyl" refers to any alkyl radical having one or more hydrogen atoms replaced by a halogen atom. Examples of haloalkyl include —$CF_3$, —$CFH_2$, —$CF_2H$, and the like.

As used herein, the term "arylalkyl" refers to any alkyl radical having one or more hydrogen atoms replaced by an aryl group. Examples of arylalkyl include benzyl ($C_6H_5CH_2$—) and the like.

As used herein, the term "hydroxyalkyl" refers to any hydroxy derivative of alkyl radical. The term "hydroxyalkyl" includes any alkyl radical having one or more hydrogen atoms replaced by a —OH group.

As used herein, the term "kinase panel" refers to a list of kinases, including but not limited to, ABL1(E255K)-phosphorylated, ABL1(T315I)-phosphorylated, ABL1-phosphorylated, ACVR1B, ADCK3, AKT1, AKT2, ALK, AURKA, AURKB, AXL, BMPR2, BRAF, BRAF(V600E), BTK, CDK11, CDK2, CDK3, CDK7, CDK9, CHEK1, CSF1R, CSNK1D, CSNK1G2, DCAMKL1, DYRK1B, EGFR, EGFR(L858R), EPHA2, ERBB2, ERBB4, ERK1, FAK, FGFR2, FGFR3, FLT1, FLT3, FLT4, GSK3B, IGF1R, IKK-α, IKK-β, INSR, JAK2(JH1domain-catalytic), JAK3 (JH1domain-catalytic), JNK1, JNK2, JNK3, KIT, KIT (D816V), KIT(V559D,T670I), LKB1, LRRK2, LRRK2 (G2019S), MAP3K4, MAPKAPK2, MARK3, MEK1, MEK2, MET, MKNK1, MKNK2, MLK1, MTOR, p38-alpha, p38-beta, PAK1, PAK2, PAK4, PCTK1, PDGFRA, PDGFRB, PDPK1, PIK3C2B, PIK3CA, PIK3CG, PIM1, PIM2, PIM3, PKAC-alpha, PLK1, PLK3, PLK4, PRKCE, PYK2, RAF1, RET, RIOK2, ROCK2, RSK2, SNARK, SRC, SRPK3, SYK, TAK1, TGFBR1, TIE2, TRKA, TSSK1B, TYK2(JH1domain-catalytic), ULK2, VEGFR2, YANK3 and ZAP70. Kinase assay panels containing the kinases described herein are commercially available for biochemically profiling kinase inhibitors for their selectivity.

As used herein, the term "dermatological disorder" refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, and urticaria.

As used herein, the term "neurogenerative disease" or "nervous system disorder" refers to conditions that alter the structure or function of the brain, spinal cord or peripheral nervous system, including but not limited to Alzheimer's disease, cerebral edema, cerebral ischemia, multiple sclerosis, neuropathies, Parkinson's disease, those found after blunt or surgical trauma (including post-surgical cognitive dysfunction and spinal cord or brain stem injury), as well as the neurological aspects of disorders such as degenerative disk disease and sciatica. The acronym "CNS" refers to the central nervous system (brain and spinal cord).

As used herein, the term "respiratory disease" refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

As used herein, the term "cancer" refers to an abnormal growth of cells which tend to proliferate in an uncontrolled way and, in some cases, to metastasize. The types of cancer include, but is not limited to, solid tumors, such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

As used herein, the term "fibrosis" or "fibrosing disorder" refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

As used herein, the term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function, which may be partial or complete, temporary or permanent. Inflammation takes many forms and includes, but is not limited to, inflammation that is one or more of the following, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporarl arteritis); joints (arthritis: crystalline, osteo-, psoriatic, reactive, rheumatoid, Reiter's); gastrointestinal tract; skin (dermatitis); or multiple organs and tissues (systemic lupus erythematosus).

As used herein, the term "cardiovascular disease" refers to diseases affecting the heart or blood vessels or both, including but not limited to atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

As used herein, the term "bone disease" means a disease or condition of the bone, including, but not limited to, inappropriate bone remodeling, loss or gain, osteopenia, osteomalacia, osteofibrosis, osteoporosis and Paget's disease.

As used herein, the term "inhibitor" refers to a compound which inhibits one or more kinases described herein. For example, the term "SYK inhibitor" refers to a compound which inhibits the SYK receptor or reduces the signaling effect.

As used herein, the term "pharmaceutically acceptable" refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

As used herein, the term "pharmaceutical combination" means a product that results from the mixing or combining of more than one active ingredient.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "prodrug" refers to an agent that is converted into the parent drug in vivo.

As used herein, the term "protein kinase-mediated disease" or a "disorder or disease or condition mediated by inappropriate protein kinase activity" refers to any disease state mediated or modulated by protein kinases described herein. Such disease states include, but are not limited to, asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, bullous disorders, collagenoses, contact dermatitis eczema, Kawasaki Disease, rosacea, Sjogren-Larsso Syndrome, rheumatoid arthritis, multiple sclerosis, inflammatory bowel syndrome, HIV, lupus, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, gastrointestinal cancer, Alzheimer's disease, Parkinson's disease, osteoporosis, osteopenia, osteomalacia, osteofibrosis, Paget's disease, diabetes, blood vessel proliferative disorders, ocular diseases, cardiovascular disease, restenosis, fibrosis, atherosclerosis, arrhythmia, angina, myocardial ischemia, myocardial infarction, cardiac or vascular aneurysm, vasculitis, stroke, peripheral obstructive arteriopathy, reperfusion injury following ischemia of an organ or a tissue, endotoxic, surgical or traumatic shock, hypertension, valvular heart disease, heart failure, abnormal blood pressure, vasoconstriction, vascular abnormality, transplant rejection and infectious diseases including viral and fungal infections.

As used herein, the term "kinase-mediated disease" or "kinase-mediated disease" or a "disorder or disease or condition mediated by inappropriate kinase activity" refers to any disease state mediated or modulated by a kinase mechanism. For example "SYK-mediated disease" refers to any disease state mediated or modulated by SYK mechanisms. Such SYK-mediated disease states include, but are not limited to, inflammatory, respiratory diseases and autoimmune diseases, such as, by way of example only, asthma, chronic obstructive pulmonary disease (COPD), adult respiratory distress syndrome (ARDs), ulcerative colitis, Crohn's disease, bronchitis, dermatitis, allergic rhinitis, psoriasis, scleroderma, urticaria, rheumatoid arthritis, multiple sclerosis, cancer, HIV associated disease and lupus.

As used herein, the term "PYK2-mediated disease" or a "disorder or disease or condition mediated by inappropriate PYK2 activity" refers to any disease state mediated or modulated by PYK2 kinase mechanisms. Such disease states include, but are not limited to, osteoporosis, arthritis, myeloid leukemia, hypo-osmolality, sarcoma, blast crisis, glioma, erythroleukemia and cancer.

As used herein, the term "ZAP70-mediated disease" or a "disorder or disease or condition mediated by inappropriate ZAP70 activity" refers to any disease state mediated or modulated by ZAP70 kinase mechanisms. Such disease states include, but are not limited to, immunodeficiency diseases characterized by a selective absence of CD8-positive T-cells.

As used herein, the term "FAK-mediated disease" or a "disorder or disease or condition mediated by inappropriate FAK activity" refers to any disease state mediated or modulated by FAK kinase mechanisms. Such disease states include, but are not limited to, cancer, macular degeneration or a condition associated with aberrantly increased levels of angiogenesis.

As used herein, the term "PIM1-mediated disease" or a "disorder or disease or condition mediated by inappropriate PIM1 activity" refers to any disease state mediated or modulated by PIM1 kinase mechanisms. Such disease states include, but are not limited to, cancer, myeloproliferative diseases, autoimmune diseases, allergic reactions and in organ transplantation rejection syndromes.

As used herein, the term "FLT3-mediated disease" or a "disorder or disease or condition mediated by inappropriate FLT3 activity" refers to any disease state mediated or modulated by FLT3 kinase mechanisms. Such disease states include, but are not limited to, leukemia including acute myelogenous leukemia or a condition associated with aberrantly increased levels of FLT3 kinase.

As used herein, the term "RET-mediated disease" or a "disorder or disease or condition mediated by inappropriate RET activity" refers to any disease state mediated or modulated by RET kinase mechanisms. Such disease states include, but are not limited to, thyroid cancer, a condition associated with aberrantly increased levels of RET kinase.

As used herein, the term "JAK2-mediated disease" or a "disorder or disease or condition mediated by inappropriate JAK2 activity" refers to any disease state mediated or modulated by JAK2 kinase mechanisms. Such disease states include, but are not limited to, polycythemia vera, essential thrombocythemia, other myeloproliferative disorders cancer, or a condition associated with aberrantly increased levels of JAK2 kinase.

As used herein, the term "LRRK2-mediated disease" or a "disorder or disease or condition mediated by inappropriate LRRK2 activity" refers to any disease state mediated or modulated by LRRK2 kinase mechanisms. Such disease states include, but are not limited to, Parkinson's disease, other neurodegenerative disease or a condition associated with aberrantly increased levels of angiogenesis.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "solvate" refers to a complex of variable stoichiometry formed by a solute (in this invention, a compound of Formula (I) or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "administration" or "administering" of the subject compound refers to providing a compound of the invention and/or prodrugs thereof to a subject in need of treatment.

As used herein, the term "carrier" refers to chemical compounds or agents that facilitate the incorporation of a compound described herein into cells or tissues.

As used herein, the term "acceptable" with respect to a formulation, composition or ingredient, as used herein, means having no persistent detrimental effect on the general health of the subject being treated.

As used herein, the term "diluent" refers to chemical compounds that are used to dilute a compound described herein prior to delivery. Diluents can also be used to stabilize compounds described herein.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

I. Human Protein Kinases

Protein kinases play a central role in the regulation of a wide variety of cellular processes and maintaining control over cellular function. Protein kinases catalyze and regulate the process of phosphorylation, whereby the kinases covalently attach phosphate groups to proteins or lipid targets in response to a variety of extracellular signals. Examples of such stimuli include hormones, neurotransmitters, growth and differentiation factors, cell cycle events, environmental stresses and nutritional stresses. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

The compounds of the present invention were screened against the kinase panel and inhibited the activity of at least one kinase on the panel. Examples of kinases include, but are not limited to, SYK, ZAP70, PYK2, FAK, ALK, AXL, CSF1R, FLT3, JAK2(JH1domain-catalytic), JAK3 (JH1domain-catalytic), PDGFRB, RET, PIM1, AURKA, AURKB, BMPR2, JNK1, JNK2, JNK3, KIT, KIT(D816V), KIT(V559D, T6701), LKB1, LRRK2, LRRK2(G2019S), MLK1, PAK4, PLK4, RSK2, SNARK, SRPK3, TAK1 and TYK2 kinases and mutant forms thereof. As such, the compounds and compositions of the invention are useful for treating diseases or disorders in which such kinases contribute to the pathology and/or symptomology of a disease or disorder associated with such kinases. Such diseases or disorders include, but are not limited to, pancreatic cancer, papillary thyroid carcinoma, ovarian carcinoma, human adenoid cystic carcinoma, non small cell lung cancer, secretory breast carcinoma, congenital fibrosarcoma, congenital mesoblastic nephroma, acute myelogenous leukemia, psoriasis, metastasis, cancer-related pain and neuroblastoma, autoimmune diseases, inflammatory diseases, bone diseases, metabolic diseases, neurological and neurodegenerative diseases, cancer, cardiovascular diseases, respiratory diseases, allergies and asthma, Alzheimer's disease, and hormone related diseases, benign and malignant proliferative disorders, diseases resulting from inappropriate activation of the immune system and diseases resulting from inappropriate activation of the nervous systems, allograft rejection, graft vs. host disease, diabetic retinopathy, choroidal neovascularization due to age-related macular degeneration, psoriasis, arthritis, osteoarthritis, rheumatoid arthritis, synovial pannus invasion in arthritis, multiple sclerosis, myasthenia gravis, diabetes mellitus, diabetic angiopathy, retinopathy of prematurity, infantile hemangiomas, non-small cell lung, bladder and head and neck cancers, prostate cancer, breast cancer, ovarian cancer, gastric and pancreatic cancer, psoriasis, fibrosis, atherosclerosis, restenosis, autoimmune disease, allergy, respiratory diseases, asthma, transplantation rejection, inflammation, thrombosis, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, Alzheimer's disease, Parkinson's disease, disorders or conditions related to nerve damage and axon degeneration subsequent to a brain or spinal cord injury, acute or chronic cancer, ocular diseases, viral infections, heart disease, lung or pulmonary diseases or kidney or renal diseases and bronchitis.

The compounds described herein are inhibitors of kinase activity and have therapeutic benefit in the treatment of disorders associated with inappropriate kinase activity, in particular in the treatment and prevention of disease states mediated by kinase. Therefore, the present invention provides methods of regulating, and in particular inhibiting, signal transduction cascades in which a kinase plays a role. The method generally involves administering to a subject or contacting a cell expressing the kinase with an effective amount of a compound described herein, prodrug, or an acceptable salt, hydrate, solvate, N-oxide and/or composition thereof, to regulate or inhibit the signal transduction cascade. The methods are also used to regulate, and in particular inhibit, downstream processes or cellular responses elicited by activation of the particular kinase signal transduction cascade. The methods are also practiced in in vitro contexts or in in vivo contexts as a therapeutic approach towards the treatment or prevention of diseases characterized by, caused by or associated with activation of the kinase-dependent signal transduction cascade.

2. Pharmaceutical Composition

For the therapeutic uses of compounds provided herein, including compounds of Formula (I), or pharmaceutically acceptable salts, solvates, N-oxides, prodrugs and isomers thereof, such compounds are administered in therapeutically effective amounts either alone or as part of a pharmaceutical composition. Accordingly, provided herein are pharmaceutical compositions, which comprise at least one compound provided herein, including at least one compound of Formula (I), pharmaceutically acceptable salts and/or solvates thereof, and one or more pharmaceutically acceptable carriers, diluents, adjuvant or excipients. In addition, such compounds and compositions are administered singly or in combination with one or more additional therapeutic agents. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or otic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

Pharmaceutically acceptable salt forms include pharmaceutically acceptable acidic/anionic or basic/cationic salts. Pharmaceutically acceptable acidic/anionic salts include, acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid addition salt is formed by reaction of the free base form a compound of Formula (I) with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of formula (I) can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

The free acid or free base forms of the compounds of the invention may be prepared from the corresponding base addition salt or acid addition salt from, respectively. For example a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details see Saulnier et al., (1994), Bioorganic and Medicinal Chemistry Letters, Vol. 4, p. 1985; the entire teachings of which are incorporated herein by reference).

Protected derivatives of the compounds of the invention may be made by means known to those of ordinary skill in the art. A detailed description of techniques applicable to the creation of protecting groups and their removal can be found in T. W. Greene, "Protecting Groups in Organic Chemistry," 3rd edition, John Wiley and Sons, Inc., 1999, the entire teachings of which are incorporated herein by reference.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, the entire teachings of which are incorporated herein by reference Compounds of Formula (I) are made by processes described herein and in the Examples. In certain embodiments, compounds of Formula (I) are made by (a) optionally converting a compound of the invention into a pharmaceutically acceptable salt; (c) optionally converting a salt form of a compound of the invention to a non-salt form; (d) optionally converting an unoxidized form of a compound of the invention into a pharmaceutically acceptable N-oxide; (e) optionally converting an N-oxide form of a compound of the invention to its unoxidized form; (f) optionally resolving an individual isomer of a compound of the invention from a mixture of isomers; (g) optionally converting a non-derivatized compound of the invention into a pharmaceutically acceptable prodrug derivative; and (h) optionally converting a prodrug derivative of a compound of the invention to its non-derivatized form.

The teachings of all patents, published applications and references cited herein are incorporated by reference in their entirety.

EXAMPLES

The present invention is further exemplified by the following examples that illustrate the preparation of compounds of Formula (I) according to the invention. The examples are for illustrative purpose only and are not intended, nor should they be construed as limiting the invention in any manner

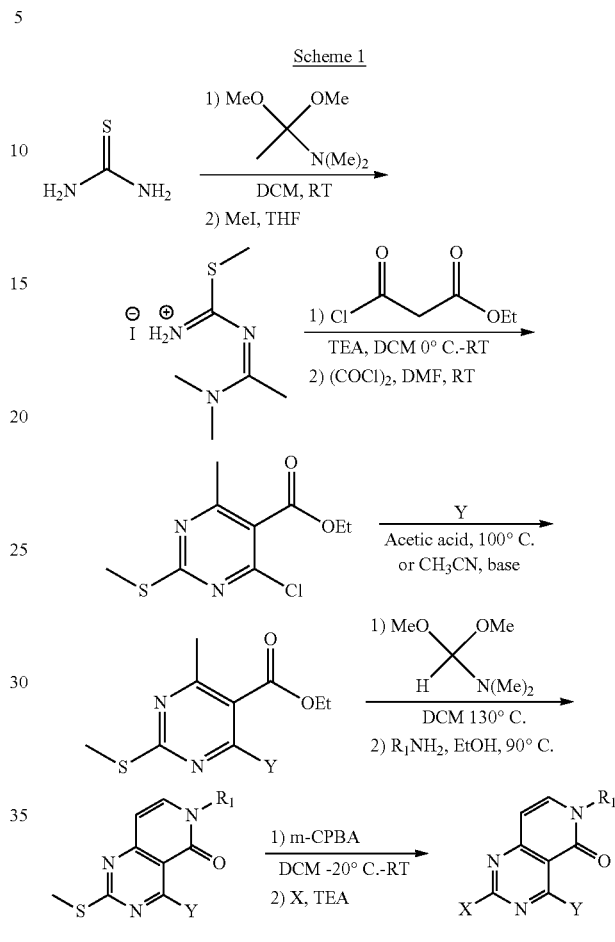

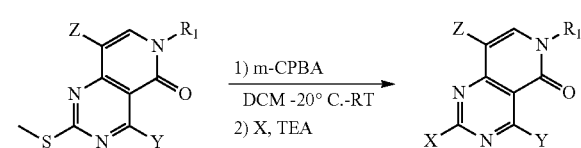

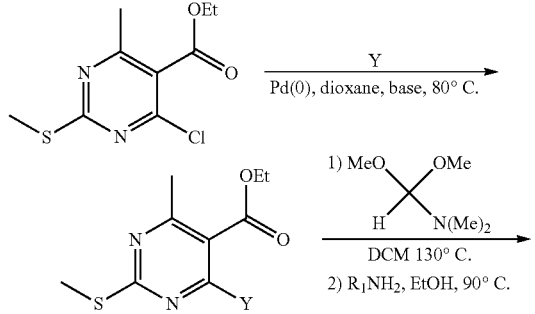

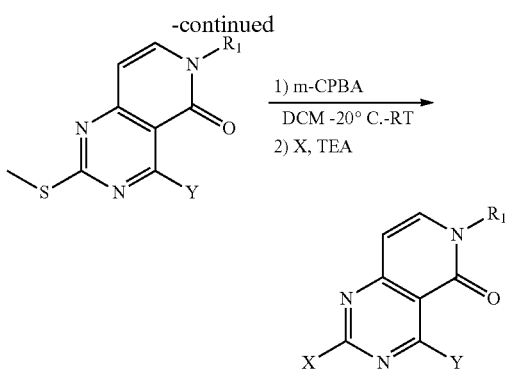

Example 1

Synthesis of 4-(3,5-dimethoxyphenylamino)-2-(4-hydroxypiperidin-1-yl)pyrido[4,3,-d]pyrimidin-6(6H)-one Compound No. 1

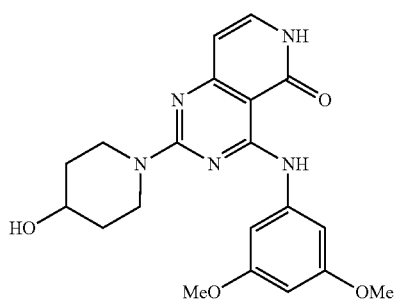

Example 1a (1-Dimethylamino-ethylidene)-2-methyl-isothiourea

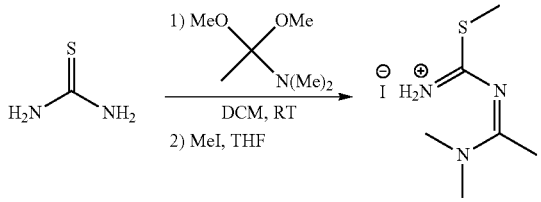

To the slurry of thiourea (13.6 g, 178.6 mmol) in 130 mL DCM was added N,N-dimethylacetamide dimethylacetal (25 g, 187.6 mmol). The reaction mixture was stirred at room temperature for 5 hours. The mixture was condensed under reduced pressure providing an orange residue. To the residue was added 100 mL THF resulting orange suspension. To the suspension was added iodomethane (14.5 mL) under ice bath, and it was warmed to room temperature. The mixture was further stirred at room temperature for 2 hours resulting precipitates. The reaction was monitored by TLC. The precipitates obtained from the solution were filtered and washed with cold THF yielding pale brown solids (44.89 g, 87.5%).

Example 1b

Ethyl-4-hydroxy-6-methyl-2-(methylthio)pyrimidine-5-carboxylate

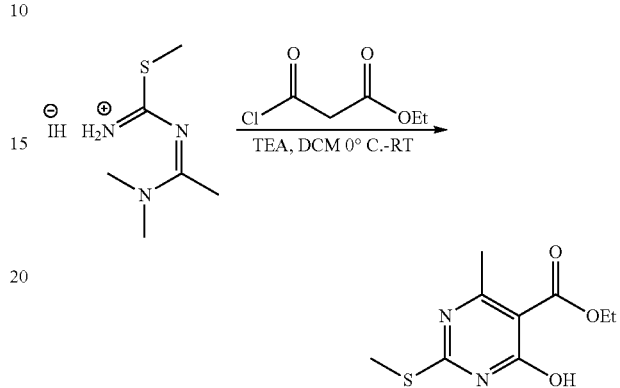

To the slurry of (1-dimethylamino-ethylidene)-2-methyl-isothiourea (25 g, 7.1 mmol) in 200 mL DCM was added ethyl-3-chloro-oxo-propionate (15.7 g, 104.5 mmol). The reaction mixture was cooled under ice bath. To the solution was slowly added triethylamine (30.3 mL, 220 mmol) dropwise, and the mixture was further stirred at room temperature for 2-3 hours. The reaction mixture was washed with water, 2N HCl solution. The separated organic layer was dried over MgSO$_4$, condensed under reduced pressure yielding yellow residue. The residue was recrystallized from EtOAC yielding light yellow solids (6.49 g, 33%). MS m/z: 229.1 (M+H)$^+$.

Example 1c

Ethyl 4-chloro-6-methyl-2-(methylthio)pyrimidine-5-carboxylate

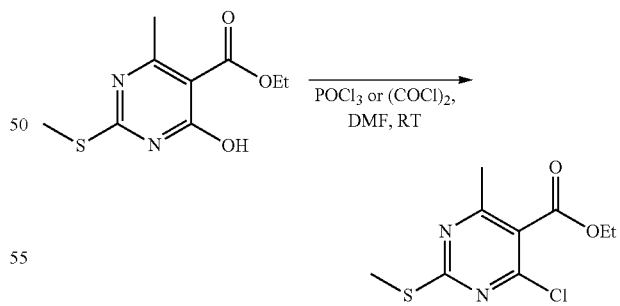

A 100 mL round-bottomed flask was charged with ethyl-4-hydroxy-6-methyl-2-(methylthio)pyrimidine-5-carboxylate (6.49 g, 28.4 mmol) in 14 mL POCl$_3$. To the solution was added N,N-diisopropylethylamine (1.2 mL), the reaction mixture was stirred at 80~90° C. for 2 hours. The mixture was condensed under reduced pressure yielding the dark brown residue. To the residue was added iced water, then diluted with DCM, and saturated aqueous NaHCO$_3$ solution. The separated organic layer was dried over MgSO$_4$. The solvent was removed by a rotavapor providing dark brown oily product (6.76 g, 96%). MS m/z: 246.9 (M+H)+, 248.9 (isotope).

Example 1d

Ethyl 4-(3,5-dimethoxyphenylamino)-6-methyl-2-(methylthio)pyrimidine-5-carboxylate

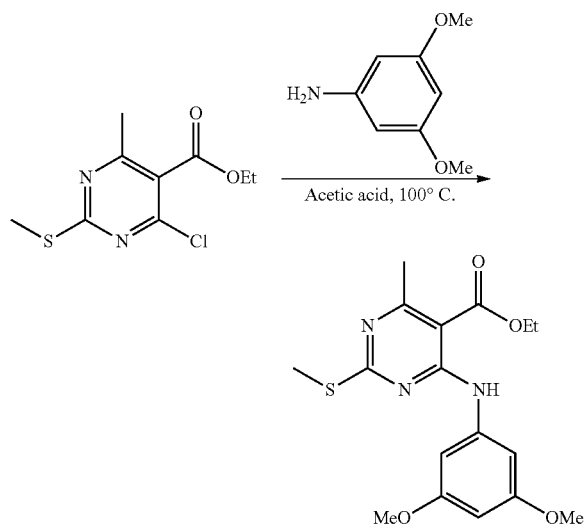

A 200 mL RB flask was charged with ethyl 4-chloro-6-methyl-2-(methylthio)pyrimidine-5-carboxylate (2.76 g, 11.1 mmol) in 40 mL acetonitrile. To the solution was added 3,5-dimethoxy aniline (1.784 g, 11.4 mmol), and conc. HCl solution (494 uL, 5.6 mmol), the reaction mixture was stirred at 60~70° C. for 2 hours. The mixture was diluted with ethyl acetate and saturated aqueous NaHCO3 solution. It was stirred for an additional 5 minutes. The separated organic layer was dried over MgSO4, and condensed under reduced pressure yielding the residue. The residue was recrystallized from acetonitrile, dried under reduced pressure providing pale yellow solids (2.92 g, 72%). MS m/z: 364.1 (M+H)+.

Example 1e (E)-Ethyl 4-(3,5-dimethoxyphenylamino)-6-(2-(dimethylamino)vinyl)-2-(methylthio)pyrimidine-5-carboxylate

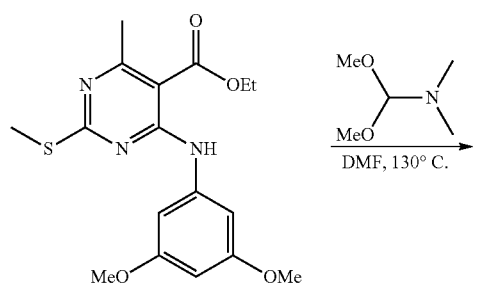

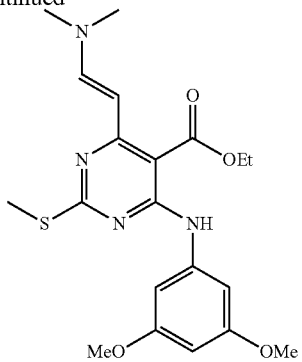

To the solution of ethyl 4-(3,5-dimethoxyphenylamino)-6-methyl-2(methylthio)pyrimidine-5-carboxylate (2.7 g, 7.4 mmol) in 30 mL DMF was added N,N-dimethylformamide dimethylacetal (1.58 mL, 11.1 mmol). The reaction mixture was stirred at 130° C. for 2 hour. After monitoring the reaction by TLC was cooled to room temperature, then the mixture was diluted with DCM and water. After extracted three times by DCM from the aqueous layer, the combined organic layer was dried over MgSO4. The solution was condensed under reduced pressure yielding crude mixture (3.16 g). The mixture was used for the next step without further purification.

Example 1f 4-(3,5-Dimethoxyphenylamino)-2-(methylthio)pyrido[4,3-d]pyrimidin-5(6H)-one

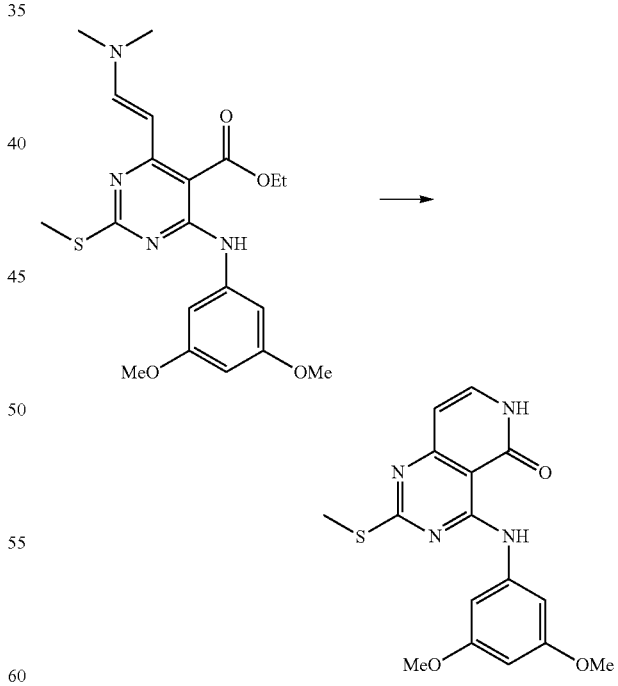

The crude of (E)-ethyl 4-(3,5-dimethoxyphenylamino)-6-(2-(dimethylamino)vinyl)-2-(methylthio)pyrimidine-5-carboxylate (3.16 g) was dissolved in 45 mL EtOH. To the solution was added 30% NH4OH solution (5.2 mL), the reaction mixture was stirred at 75-85° C. for 10 hours. The mixture was cooled to room temperature. The solids formed from the solution were filtered. The filtrate was condensed under reduced pressure resulting in the solid residue. The residue was recrystallized from ethyl acetate. The combined solids were dried under reduced pressure yielding light yellow solids (1.47 g). MS m/z: 344.9 (M+H)⁺.

Example 1g 4-(3,5-dimethoxyphenylamino)-2-(4-hydroxypiperidin-1-yl)pyrido[4,3,-d]pyrimidin-6(6H)-one

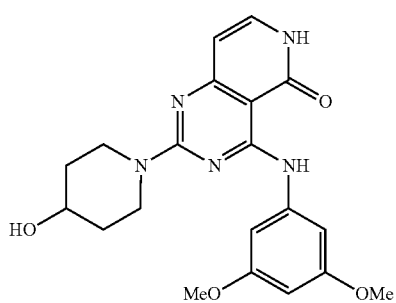

→

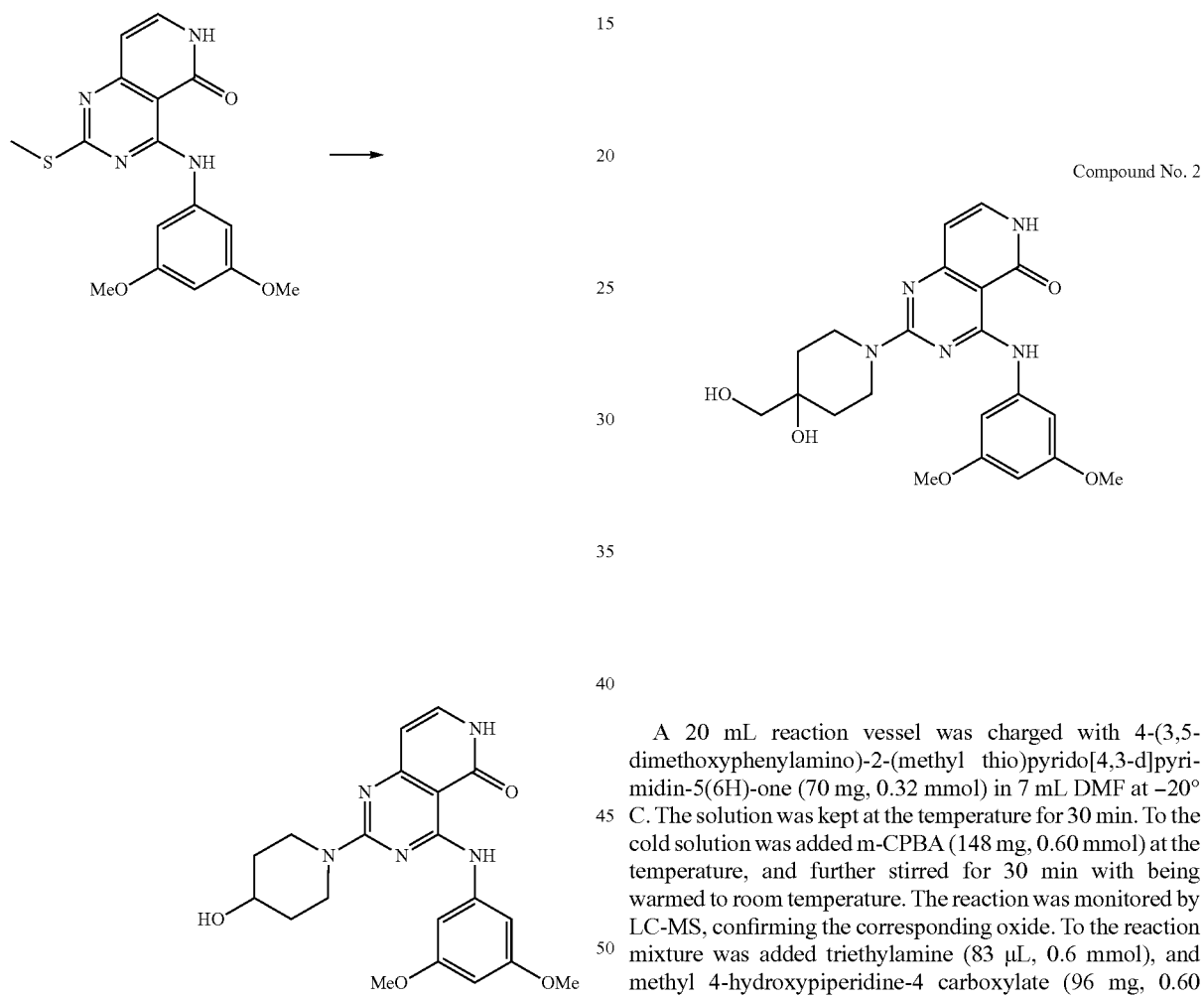

A 20 mL reaction vessel was charged with 4-(3,5-dimethoxyphenylamino)-2-(methyl thio)pyrido[4,3-d]pyrimidin-5(6H)-one (151 mg, 0.44 mmol) in 7 mL DMF at −20° C. The solution was kept at the temperature for 30 min. To the solution was added m-CPBA (146.4 mg, 1.32 mmol) at the temperature, and further stirred for 30 min with being warmed to room temperature. The reaction was monitored by LC-MS, confirming the corresponding oxide. To the reaction mixture was added triethylamine (354 µL, 1.32 mmol), and 4-hydroxypiperidine (134 mg, 1.32 mmol), and stirred at the temperature for 2 h. The reaction was monitored by LC-MS. The solvent was removed by a rotavapor yielding light brown residue. To the residue was added acetonitrile (10 mL) providing the title compound 4-(3,5-dimethoxyphenylamino)-2-(4-hydroxypiperidin-1-yl)pyrido[4,3,-d]pyrimidin-6(6H)-one (131 mg, 75%). MS ink: 398 (M+H)⁺.

Example 2

Synthesis of 4-(3,5-dimethoxyphenylamino)-2-(4-hydroxy-4-(hydroxymethyl)piperidin-1-yl)pyrido[4,3d]pyrimidin-5(6H)-one

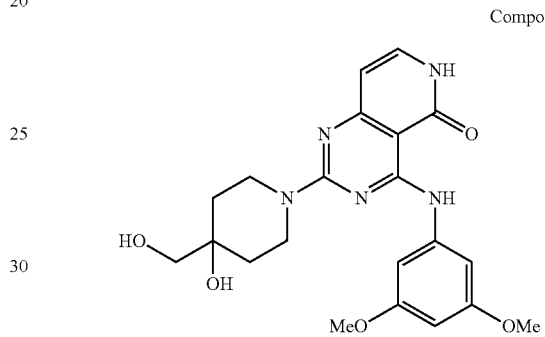

Compound No. 2

A 20 mL reaction vessel was charged with 4-(3,5-dimethoxyphenylamino)-2-(methyl thio)pyrido[4,3-d]pyrimidin-5(6H)-one (70 mg, 0.32 mmol) in 7 mL DMF at −20° C. The solution was kept at the temperature for 30 min. To the cold solution was added m-CPBA (148 mg, 0.60 mmol) at the temperature, and further stirred for 30 min with being warmed to room temperature. The reaction was monitored by LC-MS, confirming the corresponding oxide. To the reaction mixture was added triethylamine (83 µL, 0.6 mmol), and methyl 4-hydroxypiperidine-4 carboxylate (96 mg, 0.60 mmol), and stirred at the temperature for 2 h. The reaction was monitored by LC-MS. The solvent was removed by a rotavapor yielding light yellow solid, methyl 1-(4-hydroxy-(3,5-dimethoxyphenylamino)-5-oxo-5,6-dihydropyrido[4,3-d]pyrimidin-2-yl)-4-hydroxypiperidine-4-carboxylate (57 mg, 63%). It was dissolved in 8 mL dry THF in a 20 mL reaction vessel. To the mixture was added 1.0 M DIBAL in toluene (1.95 mL, 1.95 mmol) at 0° C. It was stirred at the temperature for 2 hours. The reaction mixture was quenched with 20 mL MeOH. The solvents were removed by a rotavapor yielding a light yellow residue. The residue was redissolved in the mixture of MeOH and DCM yielding the white precipitates. They were filtered and the filtrate was condensed under reduced pressure providing the white powder, the title compound, (26 mg, 24%). MS m/z: 458 (M+1)⁺.

Example 3

Synthesis of 2-(4-aminopiperidin-1-yl)-4-(3,5-dimethoxyphenylamino)pyrido[4,3-d]pyrimidin-5(6H)-one hydrochloride

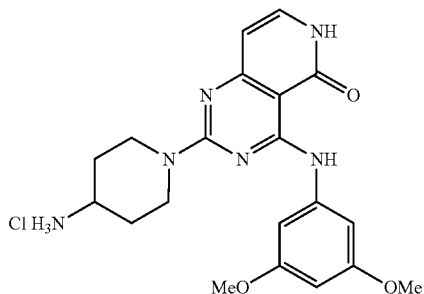

Compound No. 3

The title compound (Compound 3; MS m/z: 398 (M+H)$^+$) was prepared as described in Example 1g starting from 4-(3,5-dimethoxyphenylamino)-2-(methylthio)pyrido[4,3-d]pyrimidin-5(6H)-one (40 mg, 0.29 mmol) and 4-(boc-amino)piperidine and treating with 4 N HCl in dioxane (17 mg).

The following 4-(3,5-dimethoxyphenylamino)-2-(amino substituted)pyrido[4,3-d]pyrimidin-5(6H)-one compounds were prepared from 4-(3,5 Dimethoxyphenylamino)-2-(methylthio)pyrido[4,3-d]pyrimidin-5(6H)-one and the corresponding amine following the procedure similar to that described in Example 1g.

| NO. | Structure | Name | Mass (M + 1) |
|---|---|---|---|
| 4 | 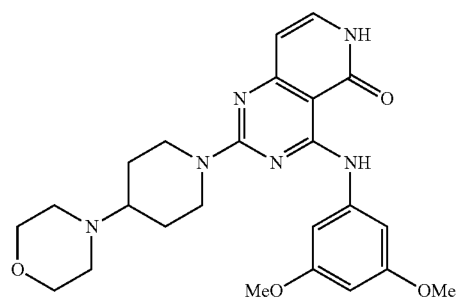 [SMILES: COc1cc(Nc2nc(N3CCC(N4CCOCC4)CC3)nc3cc[nH]c(=O)c23)cc(OC)c1] | 4-(3,5-dimethoxyphenylamino)-2-(4-morpholinopiperidin-1-yl)pyrido[4,3-d]pyrimidin-5(6H)-one | 467 |
| 5 | 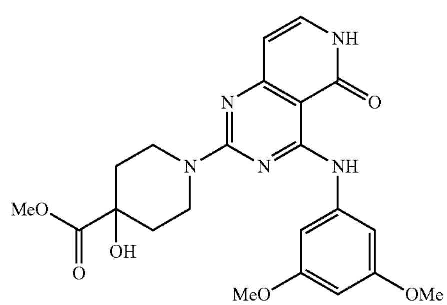 [SMILES: COC(=O)C1(O)CCN(c2nc(Nc3cc(OC)cc(OC)c3)c3c(=O)[nH]ccc3n2)CC1] | methyl 1-(4-(3,5-dimethoxyphenylamino)-5-oxo-5,6-dihydropyrido[4,3-d]pyrimidin-2-yl)-4-hydroxypiperidine-4-carboxylate | 456 |

Example 6

Synthesis of 2-(4-hydroxypiperidin-1-yl)-4-(3-(trifluoromethyl)phenylamino) pyrido[4,3-d]pyrimidine-5(6H)-one Compound No. 6

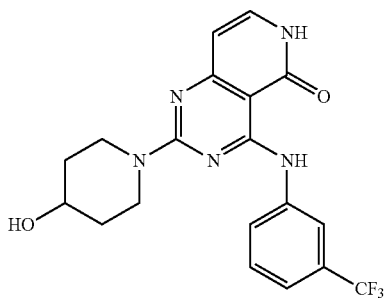

Example 6a

Ethyl 4-methyl-2-(methylthio)-6-(3-(trifluoromethyl)phenylamino) pyrimidine-5-carboxylate

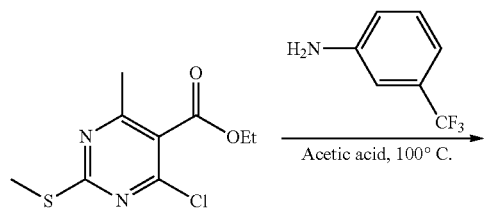

The title compound; (MS m/z: 372.2 (M+H)⁺) was prepared as described in example 1d by starting from ethyl 4-chloro-6-methyl-2-(methyl thio)pyrimidine-5-carboxylate (1.2 g, 4.86 mmol) and 3-(trifluoromethyl)aniline (611 uL, 4.86 mmol) and continuing until the reaction yielded dark brown solids (ethyl 4-methyl-2-(methylthio)-6-(3-(trifluoromethyl)phenylamino)pyrimidine-5-carboxylate (1.76 g, 97.4%)).

Example 6b (E)-Ethyl 4-(2-(dimethylamino)vinyl)-2-(methylthio)-6-(3-(trifluoromethyl)phenylamino)pyrimidine-5-carboxylate

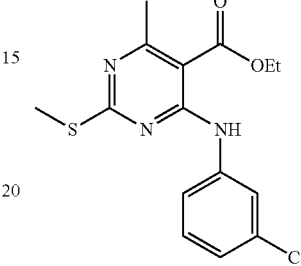

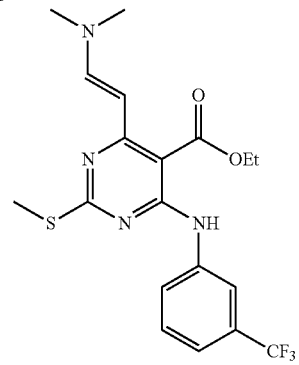

The title compound was prepared as described in Example 1e by starting from ethyl 4-methyl-2-(methylthio)-6-(3-(trifluoromethyl)phenylamino)pyrimidine-5-carboxylate 1.76 g (4.74 mmol) and N,N-dimethyl formamide dimethylacetal (947 uL, 7.1 mmol) and continuing until the reaction yielded the crude title compound. This was used for the next step without further purification.

Example 6c 2-(Methylthio)-4-(3-(trifluoromethyl)phenylamino) pyrido[4,3-d]pyrimidin-5(6H)-one

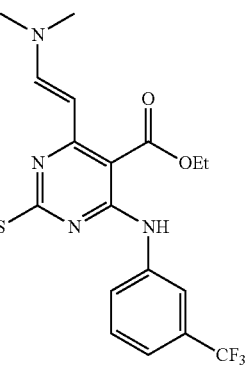

-continued

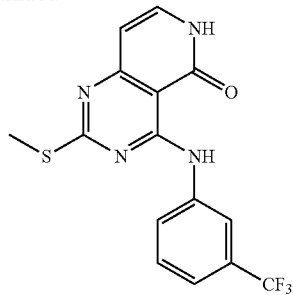

The title compound was prepared as described in Example 1f by starting from (E)-ethyl 4-(2-(dimethylamino)vinyl)-2-(methylthio)-6-(3-(trifluoromethyl)phenylamino)pyrimidine-5-carboxylate and 30% NH$_4$OH solution and continuing until the reaction yield brown solids, 2-(methylthio)-4-(3-(trifluoro methyl)phenylamino)pyrido[4,3-d]pyrimidin-5(6H)-one (912 mg). MS m/z: 353.1 (M+H)$^+$.

Example 6d 2-(4-hydroxypiperidin-1-yl)-4-(3-(trifluoromethyl) phenylamino) pyrido[4,3-d]pyrimidine-5(6H)-one

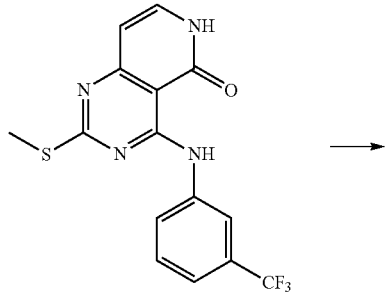

The title compound was prepared as described in Example 1g by starting from 2-(methylthio)-4-(3-(trifluoromethyl) phenylamino)pyrido[4,3-d]pyrimidin-5(6H)-one (100 mg, 0.26 mmol) and 4-hydroxypiperidine to yield the title compound (73 mg) as white solids. MS m/z: 406 (M+H)$^+$, $^1$H NMR (300 MHz), δ ppm 1.21-1.35 (m, 4H), 3.76-3.78 (m, 1H), 4.26-4.28 (m, 4H), 6.17 (d, J=7.2 Hz, 1H), 7.38-7.68 (m, 4H), 7.90 (s, 1H), 8.61 (s, 1H), 11.42 (s, 1H), 12.10 (s, 1H).

Example 7

Synthesis of (R)-2-(3-aminopyrrolidin-1-yl)-4-(3-(trifluoromethyl)phenylamino) pyrido[4,3-d]pyrimidin-5(6H)-one hydrochloride Compound No. 7

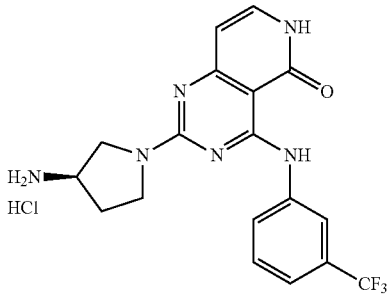

The title compound (Compound No. 7) was prepared as described in Example 1g by starting from 2-(methylthio)-4-(3-(trifluoro methyl)phenylamino)pyrido[4,3-d]pyrimidin-5(6H)-one (100 mg, 0.28 mmol) and (R)-(+)-(Boc-amino)pyrollidine (107 mg, 0.57 mmol) (93 mg, 93%) and treating with 4 N HCl in dioxane. MS m/z: 405.2 (M+1)$^+$. $^1$H NMR (300 MHz, DMSO-d6) δ ppm 12.46 (d, 9 Hz, 1H), 8.37 (s, 3H), 7.94-7.52 (m, 3H), 6.75 (d, 36.6 Hz, 1H), 4.00-3.86 (m, 5H), 2.40-2.09 (m, 2H).

Example 8

Synthesis of (S)-2-(pyrrolidin-3-ylamino)-4-(4-trifluoromethylamino)pyrido[4,3-d]pyrimidin-5(6H)-one Compound No. 8

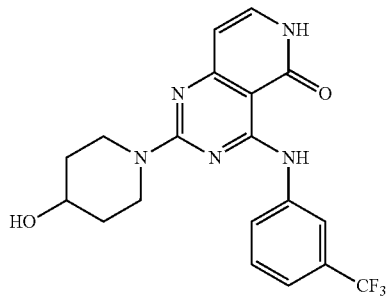

Compound No. 8 was prepared as described in Example 1g starting from 2-(methylthio)-4-(4-(trifluoro methyl)phenylamino)pyrido[4,3-d]pyrimidin-5(6H)-one (160 mg, 0.45 mmol) and (S)-(−)-1-boc-3-aminopyrrolidine (167 mg, 0.90 mmol) and treated with 4 N HCl in dioxane to yield the title compound (110 mg, 57%). MS m/z: 391 (M+1)$^+$.

The following 4-(3-(trifluoromethyl)phenylamino)-2-(amino substituted)pyrido[4,3-d]pyrimidin-5(6H)-one compounds were prepared from 4-(3-(trifluoromethyl)phenylamino)-2-(methylthio) pyrido[4,3-d]pyrimidin-5(6H)-one and the corresponding amine following the procedure similar to that described in Example 6d.

| NO. | Structure | Name, NMR (300 MHz, DMSO-d6) | Mass (M + 1) |
|---|---|---|---|
| 9 | 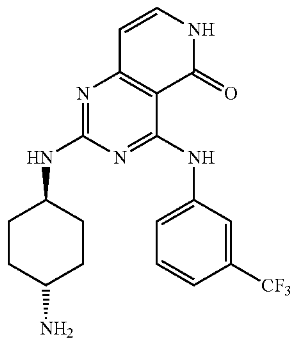 | 2-((1R,4R)-4-aminocyclohexylamino)-4-(3-(trifluoromethyl)phenylamino)pyrido[4,3-d]pyrimidin-5(6H)-one | 419 |
| 10 | 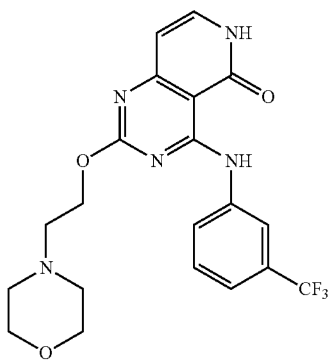 [SMILES: O=c1[nH]ccc2nc(OCCN3CCOCC3)nc(Nc3cccc(C(F)(F)F)c3)c12] | 2-(2-morpholinoethoxy)-4-(3-(trifluoromethyl)phenylamino)pyrido[4,3-d]pyrimidin-5(6H)-one<br>12.11 (s, 1H), 11.45 (br s, 1H), 8.54 (s, 1H), 7.68 (d, J = 6.30 Hz, 1H), 7.61~7.57 (m, 1H), 7.43~7.40 (m, 2H), 6.17 (d, J = 5.40 Hz, 1H), 4.44 (s 1H), 3.81 (s, 4H), 3.55~3.47 (m, 4H), 2.45~2.39 (m, 4H) | 436 |
| 11 | 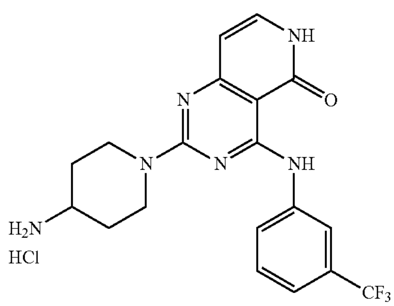 [SMILES: Cl ; NC1CCN(c2nc(Nc3cccc(C(F)(F)F)c3)c3c(=O)[nH]ccc3n2)CC1] | 2-(4-aminopiperidin-1-yl)-4-(3-(trifluoromethyl)phenylamino)pyrido[4,3-d]pyrimidin-5(6H)-one hydrochloride | 405 |
| 12 | 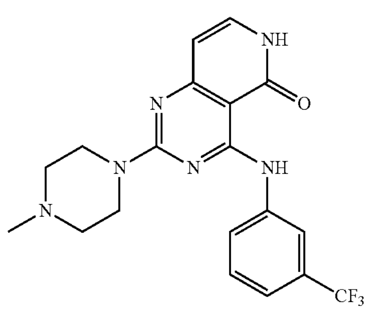 [SMILES: CN1CCN(c2nc(Nc3cccc(C(F)(F)F)c3)c3c(=O)[nH]ccc3n2)CC1] | 2-(4-methylpiperazin-1-yl)-4-(3-(trifluoromethyl)phenylamino)pyrido[4,3-d]pyrimidin-5(6H)-one | 405 |

-continued

| NO. | Structure | Name, NMR (300 MHz, DMSO-d6) | Mass (M + 1) |
|---|---|---|---|
| 13 | 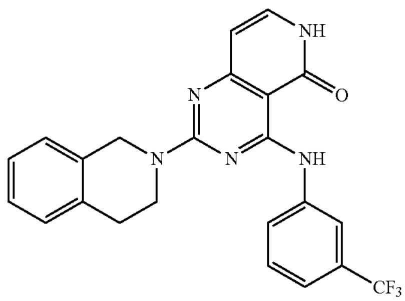 [SMILES: O=c1[nH]ccc2nc(N3CCc4ccccc4C3)nc(Nc3cccc(C(F)(F)F)c3)c12] | 2-(3,4-dihydroisoquinolin-2(1H)-yl)-4-(3-(trifluoromethyl)phenylamino)pyrido[4,3-d]pyrimidin-5(6H)-one | 438 |
| 14 | 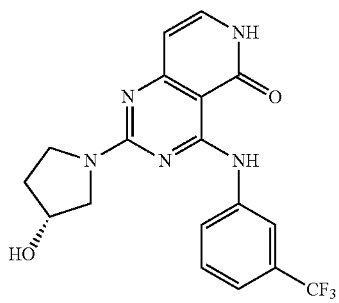 [SMILES: O=c1[nH]ccc2nc(N3CC[C@@H](O)C3)nc(Nc3cccc(C(F)(F)F)c3)c12] | (R)-2-(3-hydroxypyrrolidin-1-yl)-4-(3-(trifluoromethyl)phenylamino)pyrido[4,3-d]pyrimidin-5(6H)-one | 392 |
| 15 | 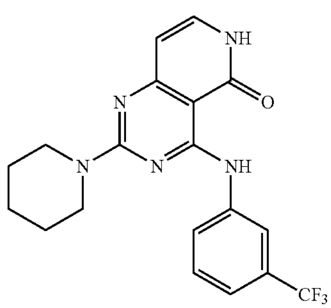 [SMILES: O=c1[nH]ccc2nc(N3CCCCC3)nc(Nc3cccc(C(F)(F)F)c3)c12] | 2-(piperidin-1-yl)-4-(3-(trifluoromethyl)phenylamino)pyrido[4,3-d]pyrimidin-5(6H)-one | 390 |
| 16 | 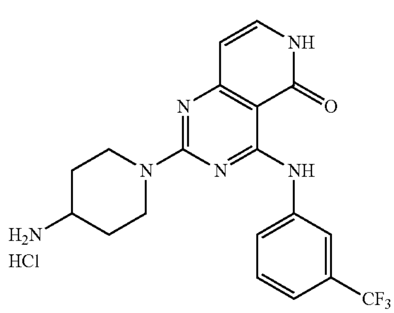 [SMILES: Cl ; NC1CCN(c2nc(Nc3cccc(C(F)(F)F)c3)c3c(=O)[nH]ccc3n2)CC1] | 2-(4-aminopiperidin-1-yl)-4-(3-(trifluoromethyl)phenylamino)pyrido[4,3-d]pyrimidin-5(6H)-one hydrochloride | 405 |
| 17 | 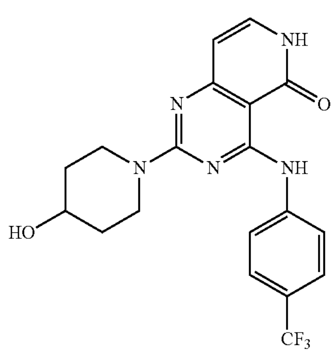 [SMILES: O=c1[nH]ccc2nc(N3CCC(O)CC3)nc(Nc3ccc(C(F)(F)F)cc3)c12] | 2-(4-hydroxypiperidin-1-yl)-4-(4-(trifluoromethyl)phenylamino)pyrido[4,3-d]pyrimidin-5(6H)-one | 405 |

-continued

| NO. | Structure | Name, NMR (300 MHz, DMSO-d6) | Mass (M + 1) |
|---|---|---|---|
| 18 | 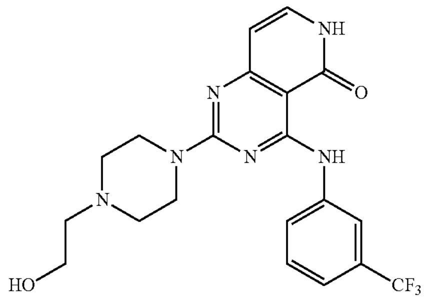 [SMILES: O=c1[nH]ccc2nc(N3CCN(CCO)CC3)nc(Nc3cccc(C(F)(F)F)c3)c12] | 2-(4-(2-hydroxyethyl)piperazin-1-yl)-4-(3-(trifluoromethyl)phenylamino)pyrido[4,3-d]pyrimidin-5(6H)-one<br>12.11 (s, 1H), 11.45 (br s, 1H), 8.54 (s, 1H), 7.68 (d, J = 6.30 Hz, 1H), 7.61~7.57 (m, 1H), 7.43~7.40 (m, 2H), 6.17 (d, J = 5.40 Hz, 1H), 4.44 (s 1H), 3.81 (s, 4H), 3.55~3.47 (m, 4H), 2.45~2.39 (m, 4H) | 435 |
| 19 | 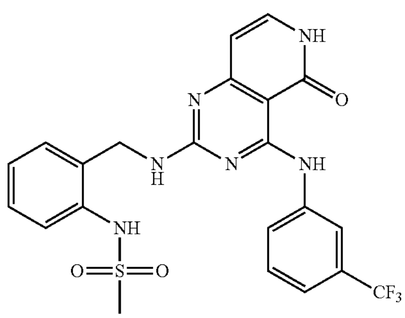 [SMILES: CS(=O)(=O)Nc1ccccc1CNc1nc(Nc2cccc(C(F)(F)F)c2)c2c(=O)[nH]ccc2n1] | N-(2-((5-oxo-4-(3-(trifluoromethyl)phenylamino)-5,6-dihydropyrido[4,3-d]pyrimidin-2-ylamino)methyl)phenyl)methanesulfonamide<br>12.21 (s, 1H), 8.14 (s, 1H), 7.95 (s, 1H), 7.65~7.20 (m, 8H), 6.54 (d, J = 7.20 Hz, 1H), 3.06 (s, 2H), 2.89 (s, 3H) | 505 |
| 20 | 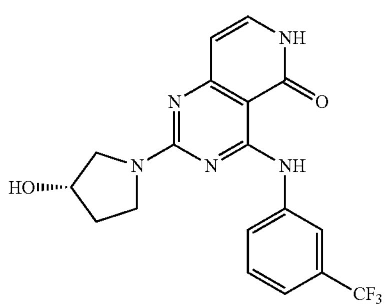 [SMILES: O=c1[nH]ccc2nc(N3CC[C@H](O)C3)nc(Nc3cccc(C(F)(F)F)c3)c12] | (S)-2-(3-hydroxypyrrolidin-1-yl)-4-(3-(trifluoromethyl)phenylamino)pyrido[4,3-d]pyrimidin-5(6H)-one | 392 |
| 21 | 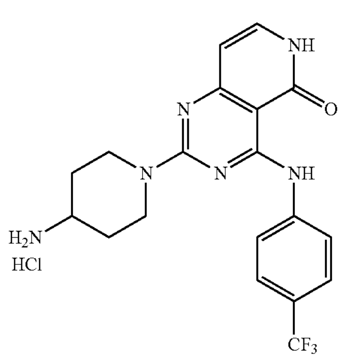 [SMILES: Cl ; NC1CCN(c2nc(Nc3ccc(C(F)(F)F)cc3)c3c(=O)[nH]ccc3n2)CC1] | 2-(4-aminopiperidin-1-yl)-4-(4-(trifluoromethyl)phenylamino)pyrido[4,3-d]pyrimidin-5(6H)-one hydrochloride | 405 |

| NO. | Structure | Name, NMR (300 MHz, DMSO-d6) | Mass (M + 1) |
|---|---|---|---|
| 22 | 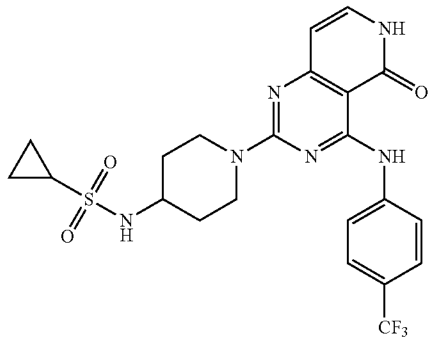 [SMILES: O=c1[nH]ccc2nc(N3CCC(NS(=O)(=O)C4CC4)CC3)nc(Nc3ccc(C(F)(F)F)cc3)c12] | N-(1-(5-oxo-4-(4-(trifluoromethyl) phenylamino)-5,6-dihydropyrido[4,3-d] pyrimidin-2-yl)piperidin-4-yl) cyclopropanesulfonamide | 509 |
| 23 | 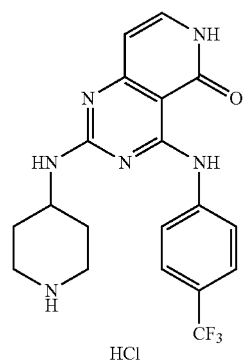 [SMILES: O=c1[nH]ccc2nc(NC3CCNCC3)nc(Nc3ccc(C(F)(F)F)cc3)c12 ; Cl] | 2-(piperidin-4-ylamino)-4-(4-(trifluoromethyl)phenylamino)pyrido[4,3-d] pyrimidin-5(6H)-one hydrochloride | 405 |
| 24 | 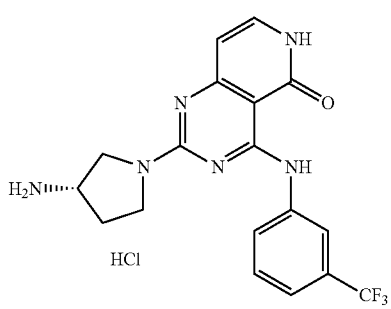 [SMILES: N[C@H]1CCN(c2nc(Nc3cccc(C(F)(F)F)c3)c3c(=O)[nH]ccc3n2)C1 ; Cl] | (S)-2-(3-aminopyrrolidin-1-yl)-4-(3-(trifluoromethyl)phenylamino)pyrido[4,3-d]pyrimidin-5(6H)-one hydrochloride | 391 |
| 25 | 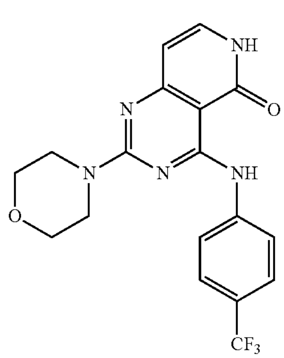 [SMILES: O=c1[nH]ccc2nc(N3CCOCC3)nc(Nc3ccc(C(F)(F)F)cc3)c12] | 2-morpholino-4-(4-(trifluoromethyl) phenylamino)pyrido[4,3-d]pyrimidin-5(6H)-one | 392 |

| NO. | Structure | Name, NMR (300 MHz, DMSO-d6) | Mass (M + 1) |
|---|---|---|---|
| 26 | 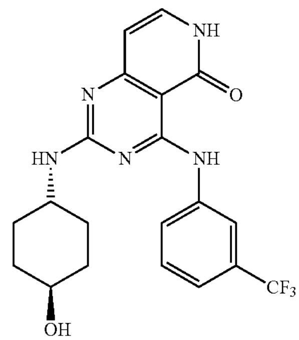 | 2-((1R,4R)-4-hydroxycyclohexylamino)-4-(3-(trifluoromethyl)phenylamino)pyrido[4,3-d]pyrimidin-5(6H)-one | 420 |
| 27 | 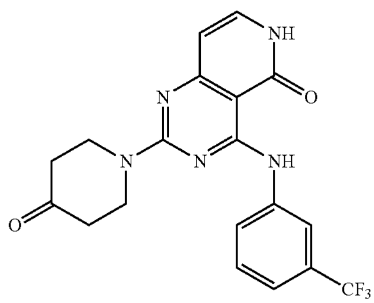 [SMILES: O=C1CCN(c2nc(Nc3cccc(C(F)(F)F)c3)c3c(=O)[nH]ccc3n2)CC1] | 2-(4-oxopiperidin-1-yl)-4-(3-(trifluoromethyl)phenylamino)pyrido[4,3-d]pyrimidin-5(6H)-one | 404 |
| 28 | 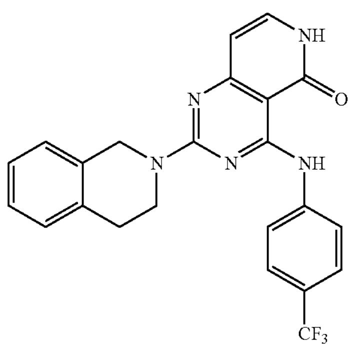 [SMILES: O=c1[nH]ccc2nc(N3CCc4ccccc4C3)nc(Nc3ccc(C(F)(F)F)cc3)c12] | 2-(3,4-dihydroisoquinolin-2(1H)-yl)-4-(4-(trifluoromethyl)phenylamino)pyrido[4,3-d]pyrimidin-5(6H)-one | 438 |
| 29 | 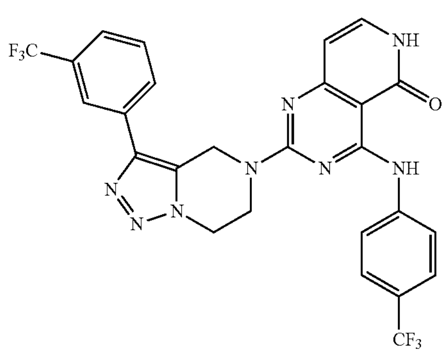 [SMILES: O=c1[nH]ccc2nc(N3CCn4nnc(-c5cccc(C(F)(F)F)c5)c4C3)nc(Nc3ccc(C(F)(F)F)cc3)c12] | 2-(3-(3-(trifluoromethyl)phenyl)-6,7-dihydro-[1,2,3]triazolo[1,5-a]pyrazin-5(4H)-yl)-4-(4-(trifluoromethyl)phenylamino)pyrido[4,3-d]pyrimidin-5(6H)-one | 573 |

-continued

| NO. | Structure | Name, NMR (300 MHz, DMSO-d6) | Mass (M + 1) |
|---|---|---|---|
| 30 | 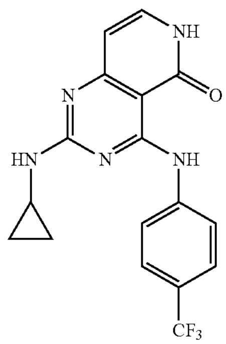 [SMILES: O=c1[nH]ccc2nc(NC3CC3)nc(Nc3ccc(C(F)(F)F)cc3)c12] | 2-(cyclopropylamino)-4-(4-(trifluoromethyl)phenylamino)pyrido[4,3-d]pyrimidin-5(6H)-one | 362 |
| 31 | 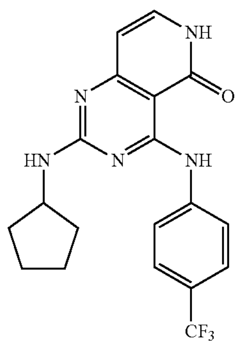 [SMILES: O=c1[nH]ccc2nc(NC3CCCC3)nc(Nc3ccc(C(F)(F)F)cc3)c12] | 2-(cyclopentylamino)-4-(4-(trifluoromethyl)phenylamino)pyrido[4,3-d]pyrimidin-5(6H)-one | 390 |
| 32 | 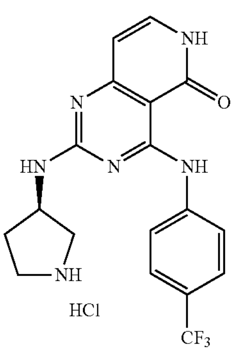 [SMILES: O=c1[nH]ccc2nc(N[C@@H]3CCNC3)nc(Nc3ccc(C(F)(F)F)cc3)c12 ; Cl] | (R)-2-(pyrrolidin-3-ylamino)-4-(4-(trifluoromethyl)phenylamino)pyrido[4,3-d]pyrimidin-5(6H)-one hydrochloride | 391 |
| 33 | 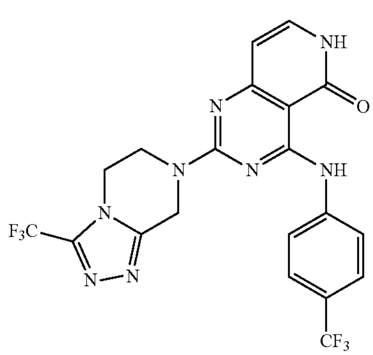 [SMILES: O=c1[nH]ccc2nc(N3CCn4c(nnc4C(F)(F)F)C3)nc(Nc3ccc(C(F)(F)F)cc3)c12] | 2-(3-(trifluoromethyl)-5,6-dihydro-[1,2,4]triazolo[4,3-a]pyrazin-7(8H)-yl)-4-(4-(trifluoromethyl)phenylamino)pyrido[4,3-d]pyrimidin-5(6H)-one | 497 |

| NO. | Structure | Name, NMR (300 MHz, DMSO-d6) | Mass (M + 1) |
|---|---|---|---|
| 34 | 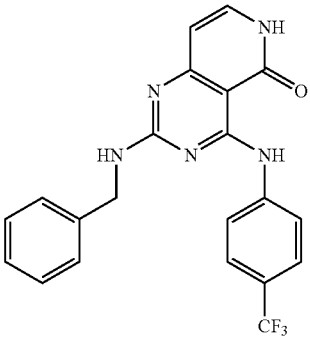 [SMILES: O=c1[nH]ccc2nc(NCc3ccccc3)nc(Nc3ccc(C(F)(F)F)cc3)c12] | 2-(benzylamino)-4-(4-(trifluoromethyl)phenylamino)pyrido[4,3-d]pyrimidin-5(6H)-one | 412 |
| 35 | 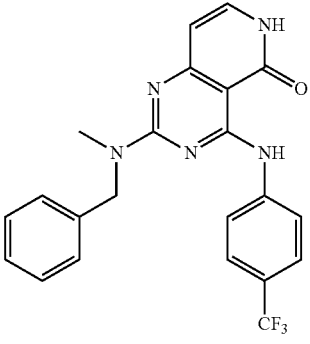 [SMILES: CN(Cc1ccccc1)c1nc(Nc2ccc(C(F)(F)F)cc2)c2c(=O)[nH]ccc2n1] | 2-(benzyl(methyl)amino)-4-(4-(trifluoromethyl)phenylamino)pyrido[4,3-d]pyrimidin-5(6H)-one | 426 |
| 36 | 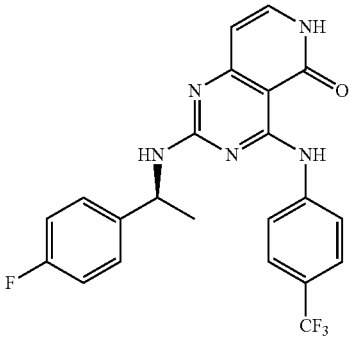 [SMILES: C[C@H](Nc1nc(Nc2ccc(C(F)(F)F)cc2)c2c(=O)[nH]ccc2n1)c1ccc(F)cc1] | (S)-2-(1-(4-fluorophenyl)ethylamino)-4-(4-(trifluoromethyl)phenylamino)pyrido[4,3-d]pyrimidin-5(6H)-one | 444 |
| 37 | 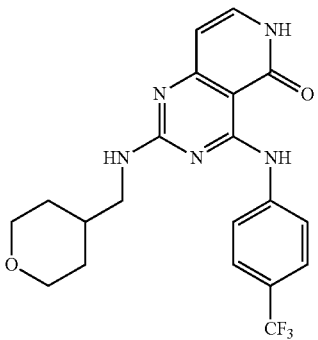 [SMILES: O=c1[nH]ccc2nc(NCC3CCOCC3)nc(Nc3ccc(C(F)(F)F)cc3)c12] | 2-((tetrahydro-2H-pyran-4-yl)methylamino)-4-(4-(trifluoromethyl)phenylamino)pyrido[4,3-d]pyrimidin-5(6H)-one | 420 |

| NO. | Structure | Name, NMR (300 MHz, DMSO-d6) | Mass (M + 1) |
|---|---|---|---|
| 38 | 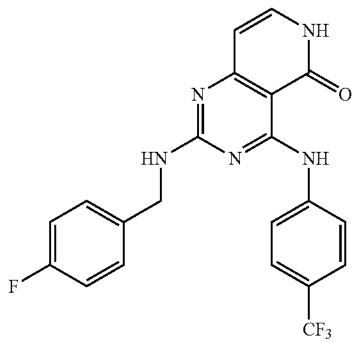 [SMILES: O=c1[nH]ccc2nc(NCc3ccc(F)cc3)nc(Nc3ccc(C(F)(F)F)cc3)c12] | 2-(4-fluorobenzylamino)-4-(4-(trifluoromethyl)phenylamino)pyrido[4,3-d]pyrimidin-5(6H)-one | 430 |
| 39 | 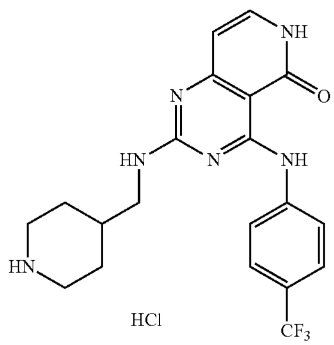 [SMILES: O=c1[nH]ccc2nc(NCC3CCNCC3)nc(Nc3ccc(C(F)(F)F)cc3)c12 ; Cl] | 2-(piperidin-4-ylmethylamino)-4-(4-(trifluoromethyl)phenylamino)pyrido[4,3-d]pyrimidin-5(6H)-one hydrochloride | 419 |
| 40 | 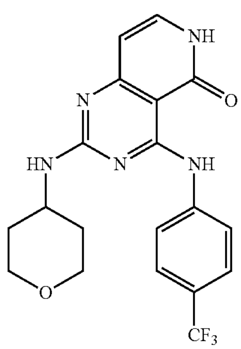 [SMILES: O=c1[nH]ccc2nc(NC3CCOCC3)nc(Nc3ccc(C(F)(F)F)cc3)c12] | 2-(tetrahydro-2H-pyran-4-ylamino)-4-(4-(trifluoromethyl)phenylamino)pyrido[4,3-d]pyrimidin-5(6H)-one | 406 |
| 41 | 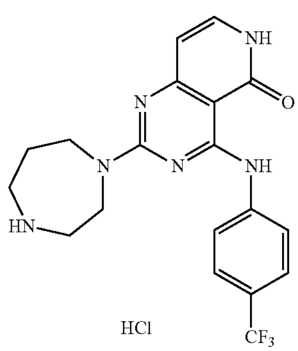 [SMILES: O=c1[nH]ccc2nc(N3CCCNCC3)nc(Nc3ccc(C(F)(F)F)cc3)c12 ; Cl] | 2-(1,4-diazepan-1-yl)-4-(4-(trifluoromethyl)phenylamino)pyrido[4,3-d]pyrimidin-5(6H)-one hydrochloride | 405 |

| NO. | Structure | Name, NMR (300 MHz, DMSO-d6) | Mass (M + 1) |
|---|---|---|---|
| 42 | 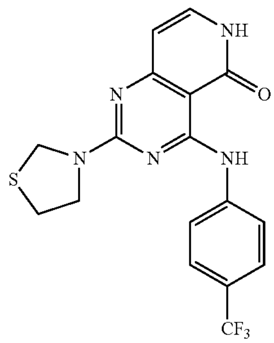 [SMILES: O=c1[nH]ccc2nc(N3CCSC3)nc(Nc3ccc(C(F)(F)F)cc3)c12] | 2-(thiazolidin-3-yl)-4-(4-(trifluoromethyl)phenylamino)pyrido[4,3-d]pyrimidin-5(6H)-one | 394 |
| 43 | 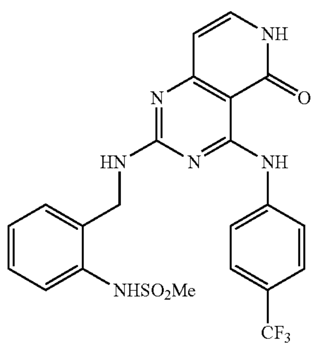 | N-(2-((5-oxo-4-(4-(trifluoromethyl)phenylamino)-5,6-dihydropyrido[4,3-d]pyrimidin-2-ylamino)methyl)phenyl)methanesulfonamide | 505 |
| 44 | 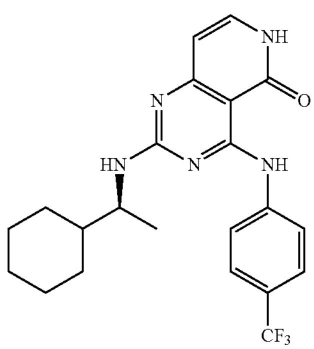 [SMILES: C[C@H](Nc1nc(Nc2ccc(C(F)(F)F)cc2)c2c(=O)[nH]ccc2n1)C1CCCCC1] | (S)-2-(1-cyclohexylethylamino)-4-(4-(trifluoromethyl)phenylamino)pyrido[4,3-d]pyrimidin-5(6H)-one | 432 |
| 45 | 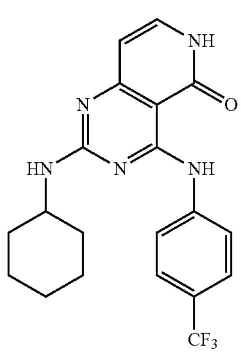 [SMILES: O=c1[nH]ccc2nc(NC3CCCCC3)nc(Nc3ccc(C(F)(F)F)cc3)c12] | 2-(cyclohexylamino)-4-(4-(trifluoromethyl)phenylamino)pyrido[4,3-d]pyrimidin-5(6H)-one | 404 |

| NO. | Structure | Name, NMR (300 MHz, DMSO-d6) | Mass (M + 1) |
|---|---|---|---|
| 46 | 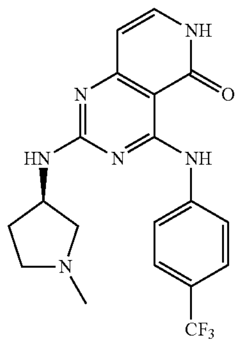 [SMILES: CN1CC[C@@H](Nc2nc(Nc3ccc(C(F)(F)F)cc3)c3c(=O)[nH]ccc3n2)C1] | (R)-2-(1-methylpyrrolidin-3-ylamino)-4-(4-(trifluoromethyl)phenylamino)pyrido[4,3-d]pyrimidin-5(6H)-one | 405 |
| 47 | 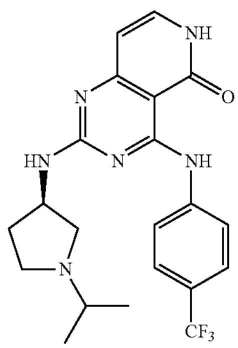 [SMILES: CC(C)N1CC[C@@H](Nc2nc(Nc3ccc(C(F)(F)F)cc3)c3c(=O)[nH]ccc3n2)C1] | (R)-2-(1-isopropylpyrrolidin-3-ylamino)-4-(4-(trifluoromethyl)phenylamino)pyrido[4,3-d]pyrimidin-5(6H)-one | 433 |
| 48 | 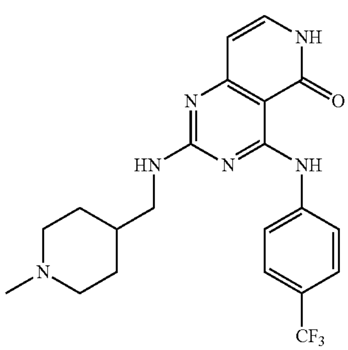 [SMILES: CN1CCC(CNc2nc(Nc3ccc(C(F)(F)F)cc3)c3c(=O)[nH]ccc3n2)CC1] | 2-((1-methylpiperidin-4-yl)methylamino)-4-(4-(trifluoromethyl)phenylamino)pyrido[4,3-d]pyrimidin-5(6H)-one | 433 |
| 49 | 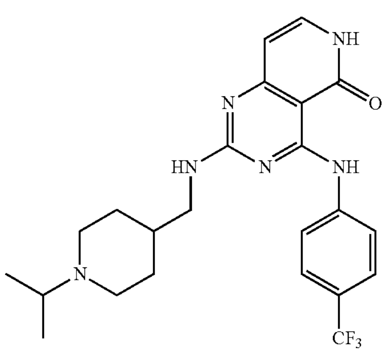 [SMILES: CC(C)N1CCC(CNc2nc(Nc3ccc(C(F)(F)F)cc3)c3c(=O)[nH]ccc3n2)CC1] | 2-((1-isopropylpiperidin-4-yl)methylamino)-4-(4-(trifluoromethyl)phenylamino)pyrido[4,3-d]pyrimidin-5(6H)-one | 461 |

-continued

| NO. | Structure | Name, NMR (300 MHz, DMSO-d6) | Mass (M + 1) |
|---|---|---|---|
| 50 | 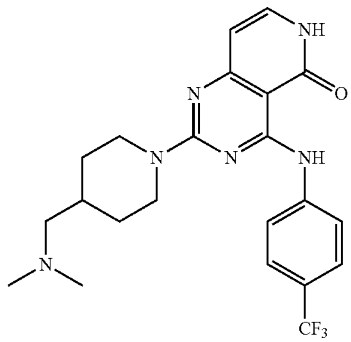 [SMILES: CN(C)CC1CCN(c2nc(Nc3ccc(C(F)(F)F)cc3)c3c(=O)[nH]ccc3n2)CC1] | 2-(4-((dimethylamino)methyl)piperidin-1-yl)-4-(4-(trifluoromethyl)phenylamino)pyrido[4,3-d]pyrimidin-5(6H)-one | 447 |
| 51 | 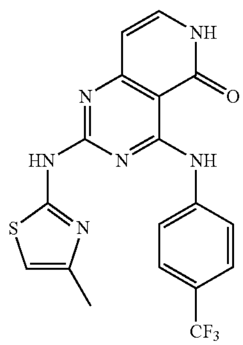 [SMILES: Cc1csc(Nc2nc(Nc3ccc(C(F)(F)F)cc3)c3c(=O)[nH]ccc3n2)n1] | 2-(4-methylthiazol-2-ylamino)-4-(4-(trifluoromethyl)phenylamino)pyrido[4,3-d]pyrimidin-5(6H)-one | 419 |
| 52 | 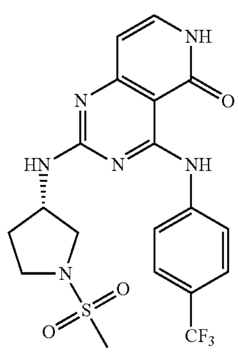 [SMILES: CS(=O)(=O)N1CC[C@H](Nc2nc(Nc3ccc(C(F)(F)F)cc3)c3c(=O)[nH]ccc3n2)C1] | (S)-2-(1-(methylsulfonyl)pyrrolidin-3-ylamino)-4-(4-(trifluoromethyl)phenylamino)pyrido[4,3-d]pyrimidin-5(6H)-one | 469 |
| 53 | 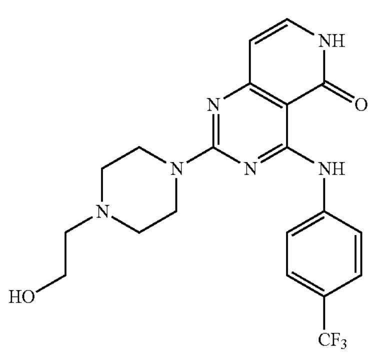 [SMILES: O=c1[nH]ccc2nc(N3CCN(CCO)CC3)nc(Nc3ccc(C(F)(F)F)cc3)c12] | 2-(4-(2-hydroxyethyl)piperazin-1-yl)-4-(4-(trifluoromethyl)phenylamino)pyrido[4,3-d]pyrimidin-5(6H)-one | 435 |

| NO. | Structure | Name, NMR (300 MHz, DMSO-d6) | Mass (M + 1) |
|---|---|---|---|
| 54 | 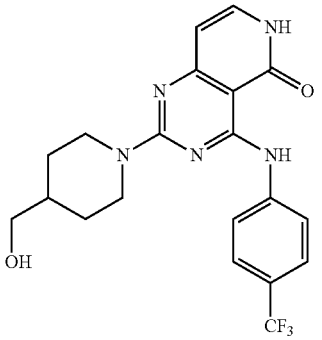 [SMILES: O=c1[nH]ccc2nc(N3CCC(CO)CC3)nc(Nc3ccc(C(F)(F)F)cc3)c12] | 2-(4-(hydroxymethyl)piperidin-1-yl)-4-(4-(trifluoromethyl)phenylamino)pyrido[4,3-d]pyrimidin-5(6H)-one | 420 |
| 55 | 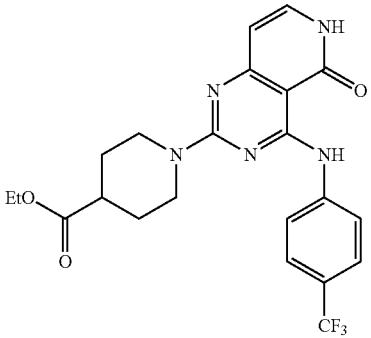 [SMILES: CCOC(=O)C1CCN(c2nc(Nc3ccc(C(F)(F)F)cc3)c3c(=O)[nH]ccc3n2)CC1] | ethyl 1-(5-oxo-4-(4-(trifluoromethyl)phenylamino)-5,6-dihydropyrido[4,3-d]pyrimidin-2-yl)piperidine-4-carboxylate | 462 |
| 56 | 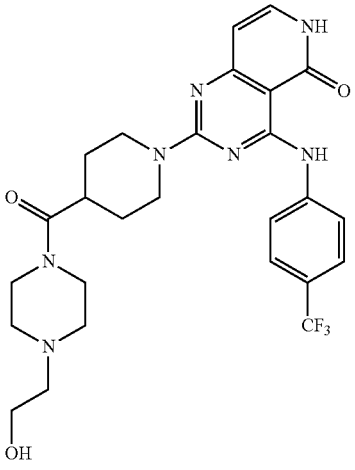 [SMILES: O=C(C1CCN(c2nc(Nc3ccc(C(F)(F)F)cc3)c3c(=O)[nH]ccc3n2)CC1)N1CCN(CCO)CC1] | 2-(4-(4-(2-hydroxyethyl)piperazine-1-carbonyl)piperidin-1-yl)-4-(4-(trifluoromethyl)phenylamino)pyrido[4,3-d]pyrimidin-5(6H)-one | 546 |
| 57 | 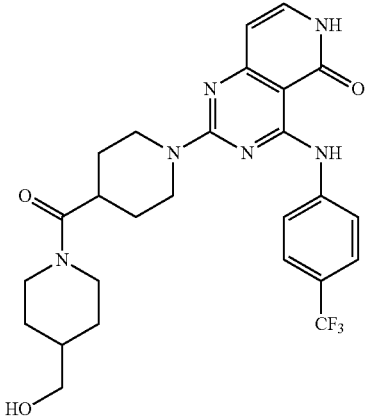 [SMILES: O=C(C1CCN(c2nc(Nc3ccc(C(F)(F)F)cc3)c3c(=O)[nH]ccc3n2)CC1)N1CCC(CO)CC1] | 2-(4-(4-(hydroxymethyl)piperidine-1-carbonyl)piperidin-1-yl)-4-(4-(trifluoromethyl)phenylamino)pyrido[4,3-d]pyrimidin-5(6H)-one | 531 |

-continued

| NO. | Structure | Name, NMR (300 MHz, DMSO-d6) | Mass (M + 1) |
|---|---|---|---|
| 58 | 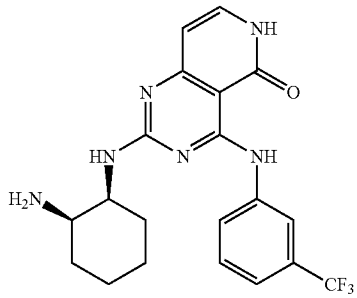 [SMILES: N[C@@H]1CCCC[C@@H]1Nc1nc(Nc2cccc(C(F)(F)F)c2)c2c(=O)[nH]ccc2n1] | 2-((1S,2R)-2-aminocyclohexylamino)-4-(3-(trifluoromethyl)phenylamino)pyrido[4,3-d]pyrimidin-5(6H)-one | 419 |
| 59 | 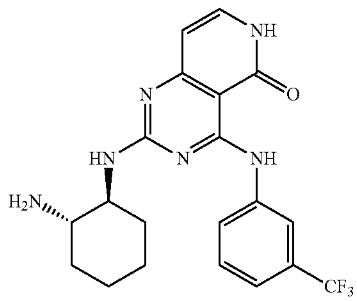 [SMILES: N[C@H]1CCCC[C@@H]1Nc1nc(Nc2cccc(C(F)(F)F)c2)c2c(=O)[nH]ccc2n1] | 2-((1S,2S)-2-aminocyclohexylamino)-4-(3-(trifluoromethyl)phenylamino)pyrido[4,3-d]pyrimidin-5(6H)-one | 419 |
| 60 | 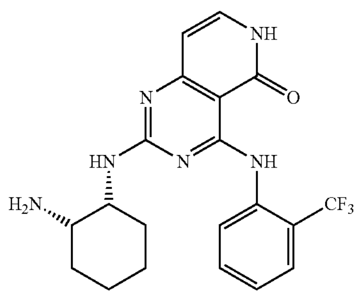 | 2-((1R,2S)-2-aminocyclohexylamino)-4-(2-(trifluoromethyl)phenylamino)pyrido[4,3-d]pyrimidin-5(6H)-one 12.0 (s, 1H), 8.50 (s, 1H), 7.85-7.80 (m, 2H), 7.73 (m, 1H), 7.52 (m, 1H), 6.06 (d, 1H), 3.1 (m, 1H), 1.77 (br s, 2H), 1.55 (br s, 5H), 1.32 (br s, 2H) | 419 |
| 61 | 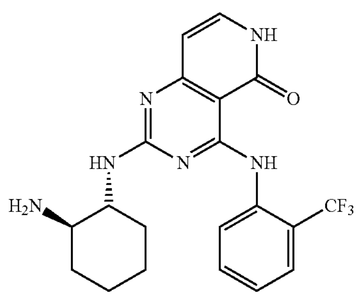 | 2-((1R,2R)-2-aminocyclohexylamino)-4-(2-(trifluoromethyl)phenylamino)pyrido[4,3-d]pyrimidin-5(6H)-one 12.02 (s, 1H), 8.43 (s, 1H), 7.83-7.78 (m, 2H), 7.62 (m, 1H), 7.50 (m, 1H), 6.04 (d, 1H), 3.0 (m, 1H), 2.0 (br d, 2H), 1.69 (br d, 2H), 1.27-1.17 (br, 5H) | 419 |
| 62 | 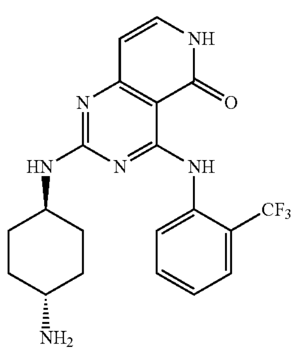 [SMILES: N[C@H]1CC[C@H](Nc2nc(Nc3ccccc3C(F)(F)F)c3c(=O)[nH]ccc3n2)CC1] | 2-((1R,4R)-4-aminocyclohexylamino)-4-(2-(trifluoromethyl)phenylamino)pyrido[4,3-d]pyrimidin-5(6H)-one 12.0 (s, 1H), 8.44 (d, 1H), 7.88-7.82 (m, 2H), 7.72 (t, 1H), 7.49 (d, 1H), 6.04 (d, 1H), 1.95-1.85 (m, 5H), 1.32-1.19 (m, 5H) | 419 |

| NO. | Structure | Name, NMR (300 MHz, DMSO-d6) | Mass (M + 1) |
|---|---|---|---|
| 63 | 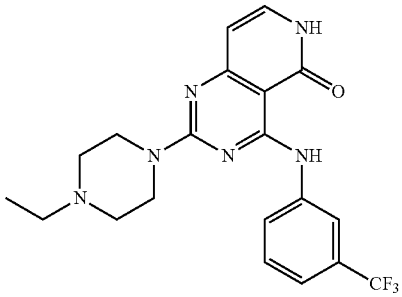 [SMILES: CCN1CCN(c2nc(Nc3cccc(C(F)(F)F)c3)c3c(=O)[nH]ccc3n2)CC1] | 2-(4-ethylpiperazin-1-yl)-4-(3-(trifluoromethyl)phenylamino)pyrido[4,3-d]pyrimidin-5(6H)-one | 419 |
| 64 | 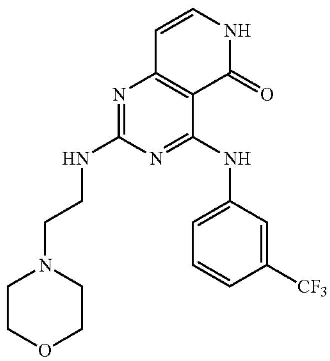 [SMILES: O=c1[nH]ccc2nc(NCCN3CCOCC3)nc(Nc3cccc(C(F)(F)F)c3)c12] | 2-(2-morpholinoethylamino)-4-(3-(trifluoromethyl)phenylamino)pyrido[4,3-d]pyrimidin-5(6H)-one | 435 |
| 65 | 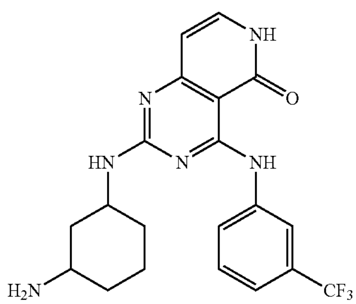 [SMILES: NC1CCCC(Nc2nc(Nc3cccc(C(F)(F)F)c3)c3c(=O)[nH]ccc3n2)C1] | 2-(3-aminocyclohexylamino)-4-(3-(trifluoromethyl)phenylamino)pyrido[4,3-d]pyrimidin-5(6H)-one | 419 |
| 66 | 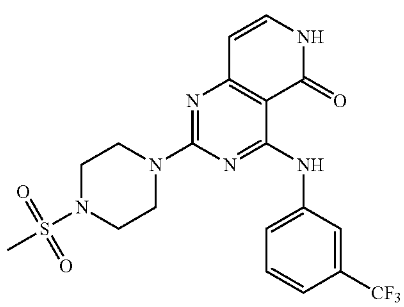 [SMILES: CS(=O)(=O)N1CCN(c2nc(Nc3cccc(C(F)(F)F)c3)c3c(=O)[nH]ccc3n2)CC1] | 2-(4-(methylsulfonyl)piperazin-1-yl)-4-(3-(trifluoromethyl)phenylamino)pyrido[4,3-d]pyrimidin-5(6H)-one | 469 |
| 67 | 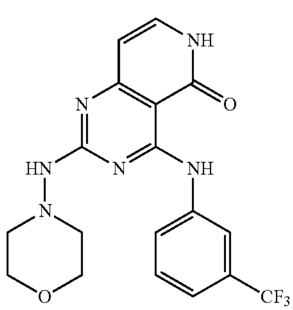 [SMILES: O=c1[nH]ccc2nc(NN3CCOCC3)nc(Nc3cccc(C(F)(F)F)c3)c12] | 2-(morpholinoamino)-4-(3-(trifluoromethyl)phenylamino)pyrido[4,3-d]pyrimidin-5(6H)-one<br>12.12 (s, 1H), 11.50 (s, 1H), 8.50 (s, 1H), 7.68-7.56 (m, 2H), 7.44-7.7.41 (m, 2H), 6.20-6.17 (d, 1H), 4.12 (s, 4H), 2.73 (m, 4H) | 407 |

| NO. | Structure | Name, NMR (300 MHz, DMSO-d6) | Mass (M + 1) |
|---|---|---|---|
| 68 | 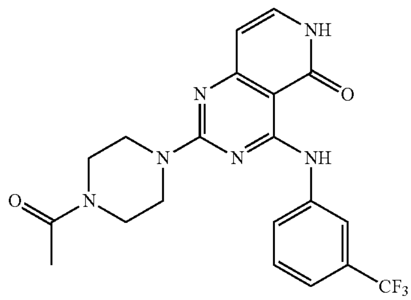 [SMILES: CC(=O)N1CCN(c2nc(Nc3cccc(C(F)(F)F)c3)c3c(=O)[nH]ccc3n2)CC1] | 2-(4-acetylpiperazin-1-yl)-4-(3-(trifluoromethyl)phenylamino)pyrido[4,3-d]pyrimidin-5(6H)-one<br>12.14 (s, 1H), 11.55 (s, 1H), 8.48 (s, 1H), 7.73 (d, J = 7.50 Hz, 1H), 7.63~7.56 (m, 2H), 7.45 (t, J = 7.50, 1H), 6.20 (d, J = 7.20 Hz, 1H), 3.84 (d, J = 2.13 Hz, 4H), 3.54 (s, 4H), 2.06 (s, 3H) | 433 |
| 69 | 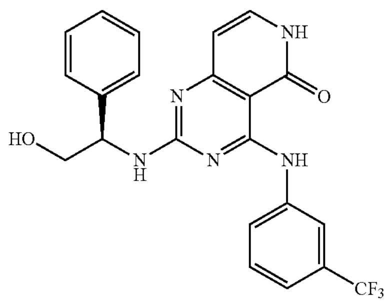 [SMILES: O=c1[nH]ccc2nc(N[C@@H](CO)c3ccccc3)nc(Nc3cccc(C(F)(F)F)c3)c12] | (R)-2-(2-hydroxy-1-phenylethylamino)-4-(3-(trifluoromethyl)phenylaminopyrido[4,3-d]pyrimidin-5(6H)-one<br>12.18 (s, 1H), 8.14 (s, 1H), 7.84~7.76 (m, 2H), 7.66~7.48 (m, 2H), 7.43~7.17 (m, 6H), 6.11 (d, J = 7.20 Hz, 1H), 5.05 (s, 1H), 4.93 (s, 1H), 4.09~4.04 (m, 1H), 3.73~3.46 (m, 1H) | 442 |
| 70 | 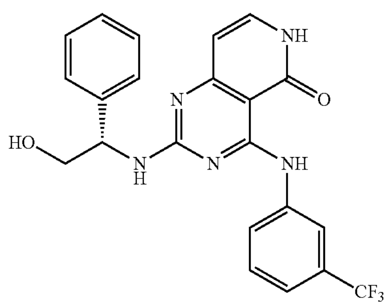 [SMILES: O=c1[nH]ccc2nc(N[C@H](CO)c3ccccc3)nc(Nc3cccc(C(F)(F)F)c3)c12] | (S)-2-(2-hydroxy-1-phenylethylamino)-4-(3-(trifluoromethyl)phenylaminopyrido[4,3-d]pyrimidin-5(6H)-one<br>12.19 (s, 1H), 8.14 (s, 1H), 8.01 (d, J = 7.80, 1H), 7.91~7.82 (m, 4H), 7.66~7.19 (m, 4H), 6.11 (d, J = 7.50 Hz, 1H), 5.25~5.23 (m, 1H), 5.07~4.90 (m, 1H), 4.16~4.12 (m, 2H), 3.65~3.51 (m, 1H) | 442 |
| 71 | 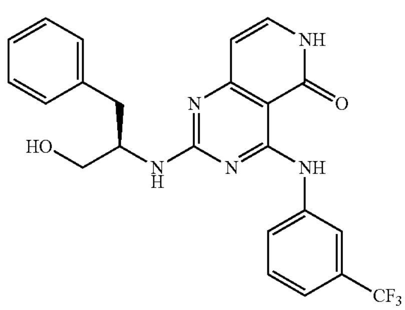 [SMILES: O=c1[nH]ccc2nc(N[C@@H](CO)Cc3ccccc3)nc(Nc3cccc(C(F)(F)F)c3)c12] | (R)-2-(1-hydroxy-3-phenylpropan-2-ylamino)-4-(3-(trifluoromethyl)phenylamino)pyrido[4,3-d]pyrimidin-5(6H)-one<br>12.14 (s, 1H), 8.41 (s, 1H), 7.87 (s, 2H), 7.83 (d, J = 10.00 Hz, 2H), 7.57 (t, J = 10.40 Hz, 1H), 7.46~7.12 (m, 6H), 6.05 (d, J = 7.50 Hz, 1H), 4.80 (s, 1H), 4.20 (s, 1H), 3.49~3.29 (m, 2H), 2.97~2.85 (m, 1H), 2.78 (d, J = 6.90 Hz, 1H) | 456 |
| 72 | 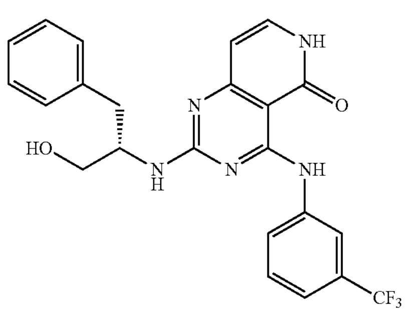 [SMILES: O=c1[nH]ccc2nc(N[C@H](CO)Cc3ccccc3)nc(Nc3cccc(C(F)(F)F)c3)c12] | (S)-2-(1-hydroxy-3-phenylpropan-2-ylamino)-4-(3-(trifluoromethyl)phenylamino)pyrido[4,3-d]pyrimidin-5(6H)-one<br>12.14 (s, 1H), 11.42 (s, 1H), 8.41 (s, 1H), 7.95 (s, 2H), 7.83~7.73 (m, 2H), 7.57 (t, J = 15.90 Hz, 1H), 7.47~7.09 (m, 4H), 6.05 (d, J = 7.20 Hz, 1H), 4.22~4.20 (m, 1H), 2.97~2.85 (m, 3H), 2.76~2.73 (m, 2H) | 456 |

| NO. | Structure | Name, NMR (300 MHz, DMSO-d6) | Mass (M + 1) |
|---|---|---|---|
| 73 | 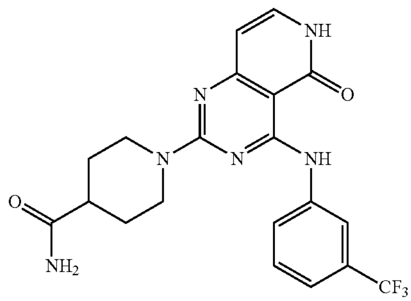 [SMILES: NC(=O)C1CCN(c2nc(Nc3cccc(C(F)(F)F)c3)c3c(=O)[nH]ccc3n2)CC1] | 1-(5-oxo-4-(3-(trifluoromethyl)phenyl-amino)-5,6-dihydropyrido[4,3-d]pyrimidin-2-yl)piperidine-4-carboxamide 12.12 (s, 1H), 8.61 (s, 1H), 7.65~7.56 (m, 1H), 7.51~7.38 (m, 3H), 7.32 (s, 1H), 6.17 (d, J = 7.50 Hz, 1H), 4.68 (s, 2H), 3.02 (t, J = 12.90 Hz, 1H), 2.45~2.40 (m, 4H), 1.80~1.56 (m, 4H) | 432 |
| 74 | 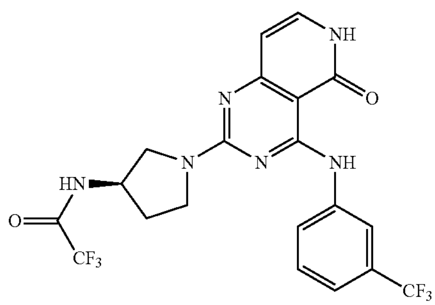 [SMILES: O=C(N[C@@H]1CCN(c2nc(Nc3cccc(C(F)(F)F)c3)c3c(=O)[nH]ccc3n2)C1)C(F)(F)F] | (R)-2,2,2-trifluoro-N-(1-(5-oxo-4-(3-(trifluoromethyl)phenylamino)-5,6-dihydropyrido[4,3-d]pyrimidin-2-yl)pyrrolidin-3-yl)acetamide 12.24 (s, 1H), 11.48 (s, 1H), 9.75 (d, J = 6.6 Hz, 1H), 7.74-7.67 (m, 2H), 7.42-7.30 (m, 2H), 6.21-6.17 (m, 1H), 3.87-3.79 (m, 1H), 3.74-3.55 (m, 4H), 2.07-2.04 (m, 2H) | 487 |
| 75 | 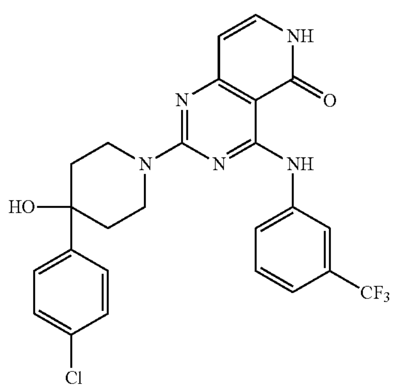 [SMILES: O=c1[nH]ccc2nc(N3CCC(O)(c4ccc(Cl)cc4)CC3)nc(Nc3cccc(C(F)(F)F)c3)c12] | 2-(4-(4-chlorophenyl)-4-hydroxy-piperidin-1-yl)-4-(3-(trifluoromethyl)phenylamino)pyrido[4,3-d]pyrimidin-5(6H)-one 12.13 (s, 1H), 8.66 (s, 1H), 7.88-7.83 (m, 4H), 7.62-7.38 (m, 5H), 6.19-6.17 (d, J = 7.2 Hz, 1H), 5.40-5.34 (m, 1H), 3.14-3.11 (m, 6H), 2.15-2.05 (m, 2H) | 516 |
| 76 | 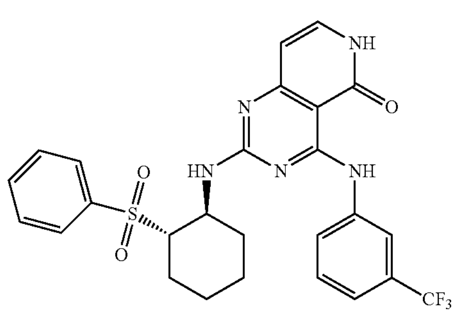 [SMILES: O=c1[nH]ccc2nc(N[C@H]3CCCC[C@@H]3S(=O)(=O)c3ccccc3)nc(Nc3cccc(C(F)(F)F)c3)c12] | 2-((1S,2S)-2-(phenylsulfonyl)cyclohexyl-amino)-4-(3-(trifluoromethyl)phenyl-amino)pyrido[4,3-d]pyrimidin-5(6H)-one | 544 |

-continued

| NO. | Structure | Name, NMR (300 MHz, DMSO-d6) | Mass (M + 1) |
|---|---|---|---|
| 77 | 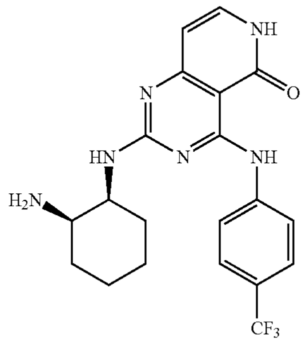 [SMILES: N[C@@H]1CCCC[C@@H]1Nc1nc(Nc2ccc(C(F)(F)F)cc2)c2c(=O)[nH]ccc2n1] | 2-((1S,2R)-2-aminocyclohexylamino)-4-(4-(trifluoromethyl)phenylamino)pyrido[4,3-d]pyrimidin-5(6H)-one | 419 |
| 78 | 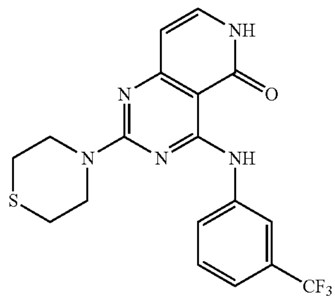 [SMILES: O=c1[nH]ccc2nc(N3CCSCC3)nc(Nc3cccc(C(F)(F)F)c3)c12] | 2-thiomorpholino-4-(3-(trifluoromethyl)phenylamino)pyrido[4,3-d]pyrimidin-5(6H)-one<br>12.12 (s, 1H), 11.50 (s, 1H), 8.50 (s, 1H) 7.68-7.56 (m, 2H), 7.44-7.41 (m, 2H), 6.20-6.17 (m, 1H), 4.12 (s, 4H), 2.73 (m, 4H) | 408 |
| 79 | 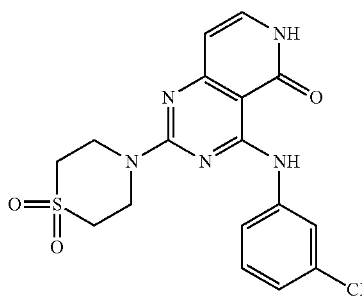 | 2-(4-sulfonylpyrido)-4-(3-(trifluoromethyl)phenylamino)pyrido[4,3-d]pyrimidin-5(6H)-one | 440 |
| 80 | 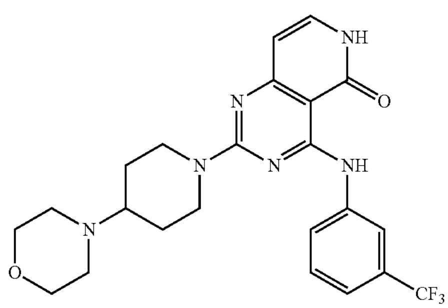 [SMILES: O=c1[nH]ccc2nc(N3CCC(N4CCOCC4)CC3)nc(Nc3cccc(C(F)(F)F)c3)c12] | 2-(4-morpholinopiperidin-1-yl)-4-(3-(trifluoromethyl)phenylamino)pyrido[4,3-d]pyrimidin-5(6H)-one | 475 |
| 81 | 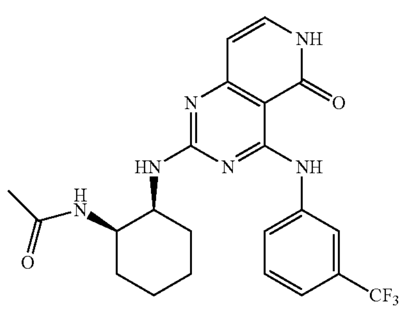 [SMILES: CC(=O)N[C@@H]1CCCC[C@@H]1Nc1nc(Nc2cccc(C(F)(F)F)c2)c2c(=O)[nH]ccc2n1] | N-((1R,2S)-2-(5-oxo-4-(3-(trifluoromethyl)phenylamino)-5,6-dihydropyrido[4,3-d]pyrimidin-2-ylamino)cyclohexyl)acetamide<br>12.51 (s, 1H), 8.30 (s, 1H), 7.89-7.80 (m, 3H), 7.70-7.60 (m, 2H), 6.38-6.35 (d, J = 6.9, 1H), 4.13 (s, 1H), 1.64 (s, 3H), 1.54-1.37 (m, 8H), 1.96 (s, 2H) | 461 |

| NO. | Structure | Name, NMR (300 MHz, DMSO-d6) | Mass (M + 1) |
|---|---|---|---|
| 82 | 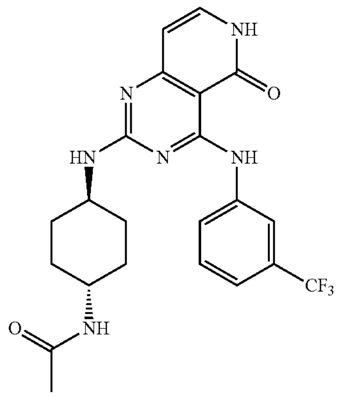 [SMILES: CC(=O)N[C@H]1CC[C@H](Nc2nc(Nc3cccc(C(F)(F)F)c3)c3c(=O)[nH]ccc3n2)CC1] | N-((1R,4R)-4-(5-oxo-4-(3-(trifluoro-methyl)phenylamino)-5,6-dihydropyrido[4,3-d]pyrimidin-2-ylamino)cyclohexyl)acetamide<br>12.43 (s, 1H), 8.43 (s, 1H), 7.90-7.55 (m, 6H), 6.35 (s, 1H), 3.49 (s, 1H), 3.46 (s, 1H), 2.48 (s, 1H), 1.85-1.79 (m, 4H), 1.78-1.74 (m, 4H) | 461 |
| 83 | 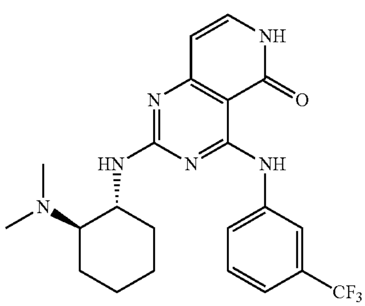 [SMILES: CN(C)[C@@H]1CCCC[C@H]1Nc1nc(Nc2cccc(C(F)(F)F)c2)c2c(=O)[nH]ccc2n1] | 2-((1R,2R)-2-(dimethylamino)cyclohexylamino)-4-(3-(trifluoromethyl)phenylamino)pyrido[4,3-d]pyrimidin-5(6H)-one<br>12.33 (s, 1H), 8.81 (s, 1H), 7.58 (m, 2H), 7.41 (s, 1H), 7.37-7.35 (m, 1H), 7.29-7.27 (d, J = 8.4 Hz, 1H), 6.06-6.03 (d, J = 6.9 Hz, 1H), 3.91 (m, 1H), 2.15 (m, 7H), 1.98 (m, 1H), 1.80-1.77 (m, 2H), 1.64 (m, 1H), 1.78 (m, 5H) | 447 |

Example 84

Synthesis of 2-(4-aminopiperidin-1-yl)-4-(3-bromophenylamino)pyrido[4,3-d]pyrimidin-5(6H)-one hydrochloride

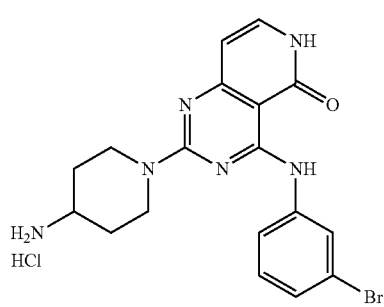

Compound No. 84

Compound 84 was prepared as described in Example 1g starting from 2-(methylthio)-4-(3-bromophenylamino)pyrido[4,3-d]pyrimidin-5(6H)-one (80 mg, 0.23 mmol) and 4-(boc-amino)piperidine (70 mg, 0.35 mmol) and treating with 4 N HCl in dioxane to yield the title compound (15 mg, 15%). MS m/z: 405.2 (M+1)⁺. ¹H NMR (300 MHz, DMSO-d6) δ ppm 12.12 (s, 1H), 11.92 (s, 1H), 8.24 (s, 1H), 8.09 (s, 3H), 7.59-7.50 (m, 2H), 7.40-7.36 (m, 2H), 6.48 (s, 1H), 4.70 (s, 2H), 2.08-0.87 (m, 7H).

The following 4-(3-bromophenylamino)-2-(amino substituted)pyrido[4,3-d]pyrimidin-5(6H)-one compounds were prepared from 4-(3-bromophenylamino)-2-(methylthio)pyrido[4,3-d]pyrimidin-5(6H)-one and the corresponding amine following the procedure similar to that described in Example 84.

| NO. | Structure | Name | Mass (M + 1) |
|---|---|---|---|
| 85 | 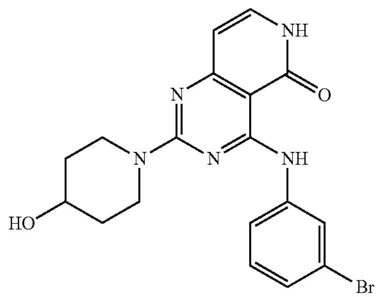 [SMILES: O=c1[nH]ccc2nc(N3CCC(O)CC3)nc(Nc3cccc(Br)c3)c12] | 4-(3-bromophenylamino)-2-(4-hydroxy-piperidin-1-yl)pyrido[4,3-d]pyrimidin-5(6H)-one | 417 |
| 86 | 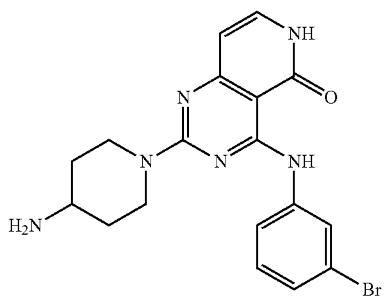 [SMILES: NC1CCN(c2nc(Nc3cccc(Br)c3)c3c(=O)[nH]ccc3n2)CC1] | 2-(4-aminopiperidin-1-yl)-4-(3-bromophenylamino)pyrido[4,3-d]pyrimidin-5(6H)-one hydrochloride | 416 |
| 87 | 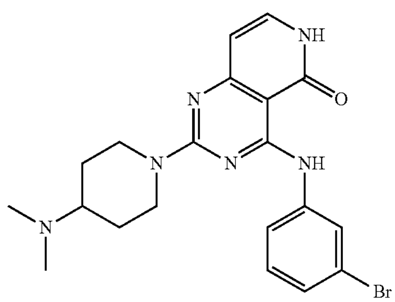 [SMILES: CN(C)C1CCN(c2nc(Nc3cccc(Br)c3)c3c(=O)[nH]ccc3n2)CC1] | 4-(3-bromophenylamino)-2-(4-(dimethylamino)piperidin-1-yl)pyrido[4,3-d]pyrimidin-5(6H)-one | 444 |
| 88 | 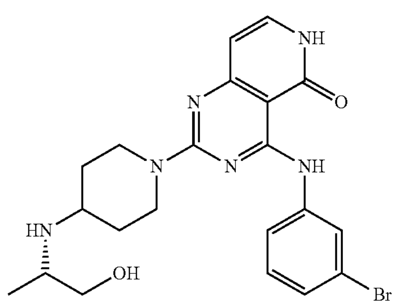 | (S)-4-(3-bromophenylamino)-2-(4-(1-hydroxypropan-2-ylamino)piperidin-1-yl)pyrido[4,3-d]pyrimidin-5(6H)-one | 474 |
| 89 | 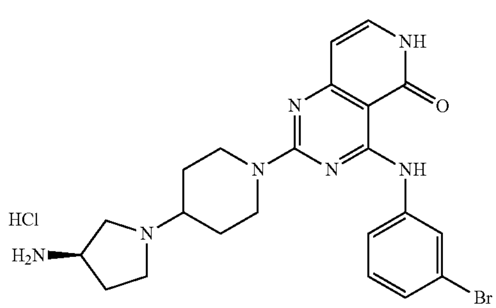 [SMILES: Cl ; N[C@@H]1CCN(C2CCN(c3nc(Nc4cccc(Br)c4)c4c(=O)[nH]ccc4n3)CC2)C1] | (R)-2-(4-(3-aminopyrrolidin-1-yl)piperidin-1-yl)-4-(3-bromophenylamino)pyrido[4,3-d]pyrimidin-5(6H)-one hydrochloride | 485 |

-continued
| NO. | Structure | Name | Mass (M + 1) |
|---|---|---|---|
| 90 | 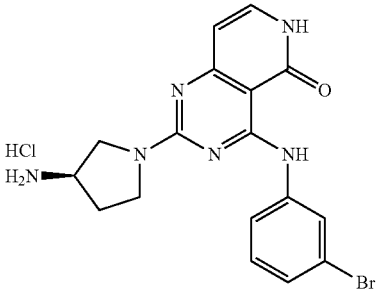 [SMILES: Cl ; N[C@@H]1CCN(c2nc(Nc3cccc(Br)c3)c3c(=O)[nH]ccc3n2)C1] | (R)-2-(3-aminopyrrolidin-1-yl)-4-(3-bromophenylamino)pyrido[4,3-d]pyrimidin-5(6H)-one hydrochloride | 422 |
| 91 | 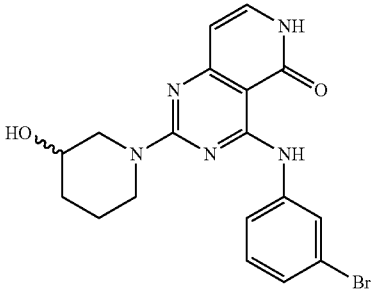 [SMILES: O=c1[nH]ccc2nc(N3CCCC(O)C3)nc(Nc3cccc(Br)c3)c12] | 4-(3-bromophenylamino)-2-(3-hydroxy-piperidin-1-yl)pyrido[4,3-d]pyrimidin-5(6H)-one | 417 |
| 92 | 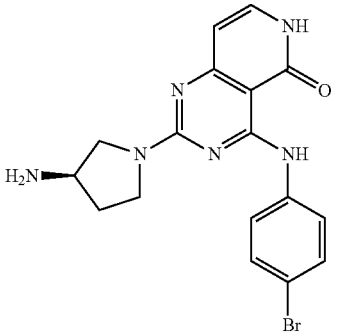 [SMILES: N[C@@H]1CCN(c2nc(Nc3ccc(Br)cc3)c3c(=O)[nH]ccc3n2)C1] | (R)-2-(3-aminopyrrolidin-1-yl)-4-(4-bromophenylamino)pyrido[4,3-d]pyrimidin-5(6H)-one hydrochloride | 402 |
| 93 | 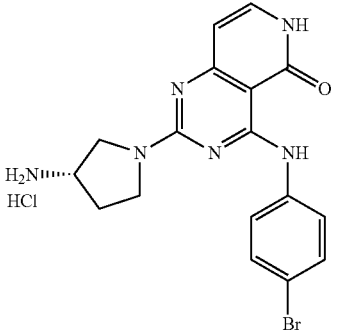 [SMILES: Cl ; N[C@H]1CCN(c2nc(Nc3ccc(Br)cc3)c3c(=O)[nH]ccc3n2)C1] | (S)-2-(3-aminopyrrolidin-1-yl)-4-(4-bromophenylamino)pyrido[4,3-d]pyrimidin-5(6H)-one hydrochloride | 402 |

| NO. | Structure | Name | Mass (M + 1) |
|---|---|---|---|
| 94 | 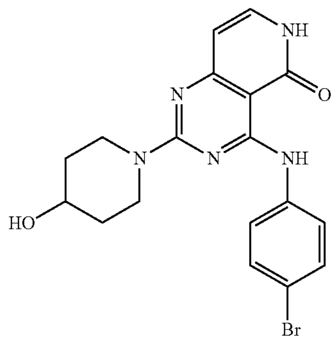 [SMILES: O=c1[nH]ccc2nc(N3CCC(O)CC3)nc(Nc3ccc(Br)cc3)c12] | 4-(4-bromophenylamino)-2-(4-hydroxy-piperidin-1-yl)pyrido[4,3-d]pyrimidin-5(6H)-one | 417 |
| 95 | 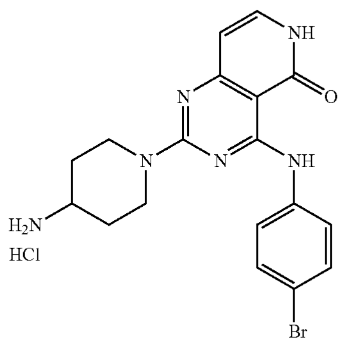 [SMILES: Cl ; NC1CCN(c2nc(Nc3ccc(Br)cc3)c3c(=O)[nH]ccc3n2)CC1] | 2-(4-aminopiperidin-1-yl)-4-(4-bromo-phenylamino)pyrido[4,3-d]pyrimidin-5(6H)-one hydrochloride | 416 |
| 96 | 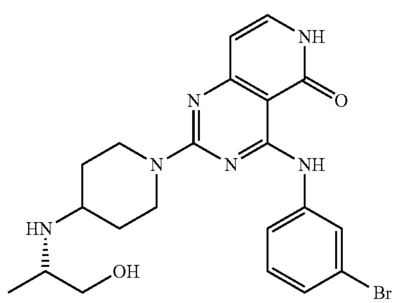 | (S)-4-(3-bromophenylamino)-2-(4-(1-hydroxypropan-2-ylamino)piperidin-1-yl)pyrido[4,3-d]pyrimidin-5(6H)-one | 473 |
| 97 | 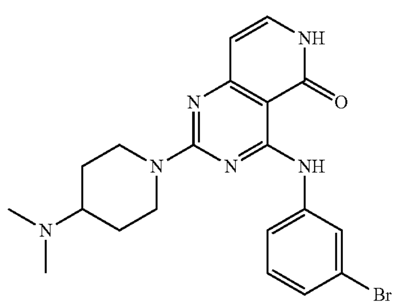 [SMILES: CN(C)C1CCN(c2nc(Nc3cccc(Br)c3)c3c(=O)[nH]ccc3n2)CC1] | 4-(3-bromophenylamino)-2-(4-(dimethylamino)piperidin-1-yl)pyrido[4,3-d]pyrimidin-5(6H)-one | 443 |
| 98 | 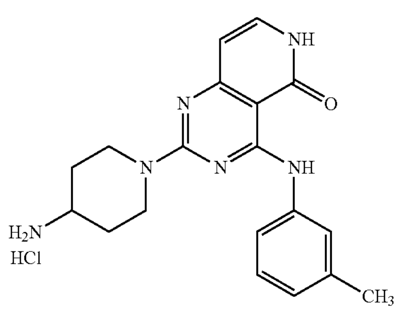 [SMILES: Cl ; Cc1cccc(Nc2nc(N3CCC(N)CC3)nc3cc[nH]c(=O)c23)c1] | 2-(4-aminopiperidin-1-yl)-4-(m-tolyl-amino)pyrido[4,3-d]pyrimidin-5(6H)-one hydrochloride | 351 |

| NO. | Structure | Name | Mass (M + 1) |
|---|---|---|---|
| 99 | 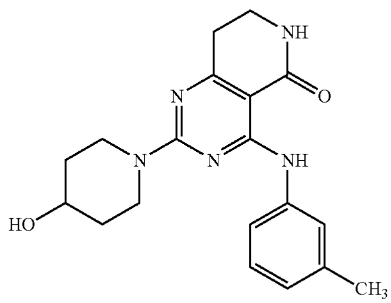 [SMILES: Cc1cccc(Nc2nc(N3CCC(O)CC3)nc3c2C(=O)NCC3)c1] | 2-(4-hydroxypiperidin-1-yl)-4-(m-tolyl-amino)pyrido[4,3-d]pyrimidin-5(6H)-one | 352 |

Example 100

Synthesis of 2-((1R,2R)-2-aminocyclohexylamino)-4-(3,5-bis(trifluoromethyl)phenylamino) pyrido[4,3-d]pyrimidin-5(6H)-one Compound No. 100

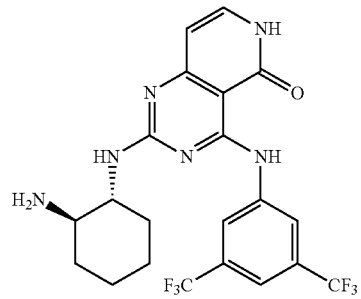

Example 100a

Ethyl 4-(3,5-bis(trifluoromethyl)phenylamino)-6-methyl-2-(methylthio) pyrimidine-5-carboxylate

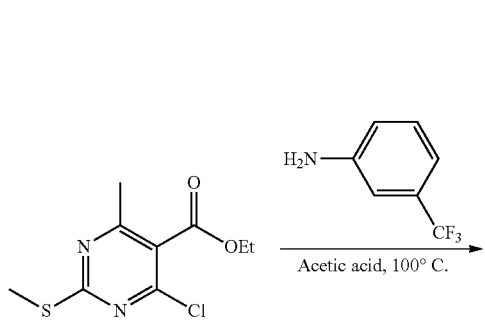

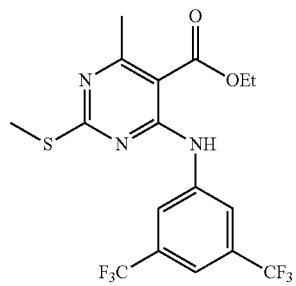

The title compound was prepared as described in Example 1d by starting from ethyl 4-chloro-6-methyl-2-(methyl thio) pyrimidine-5-carboxylate (1.2 g, 4.86 mmol) and 3,5-bis(trifluoromethyl)aniline (777 uL, 4.86 mmol) and continuing until the reaction yielded the brown solids, title compound ethyl 4-(3,5-bis(trifluoromethyl)phenylamino)-6-methyl-2-(methylthio)pyrimidine-5-carboxylate (1.53 g, 70.2%). MS m/z: 440.1 (M+1)⁺.

Example 100b (E)-Ethyl 4-(3,5-bis(trifluoromethyl)phenylamino)-6-(2-(dimethylamino)vinyl)-2-(methylthio)pyrimidine-5-carboxylate

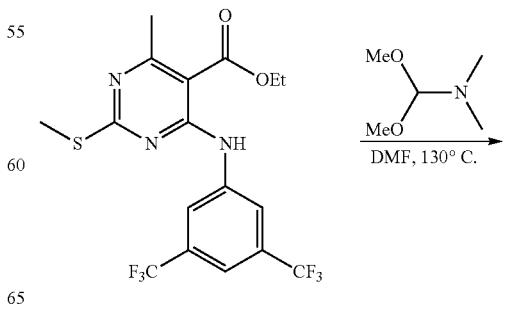

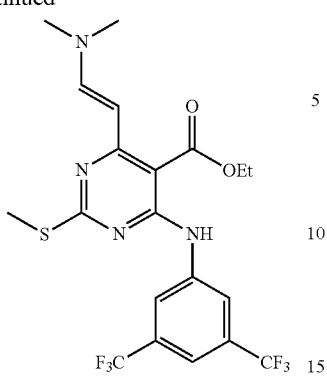

The title compound was prepared as described in Example 1e by starting from ethyl 4-(3,5-bis(trifluoro methyl)phenylamino)-6-methyl-2-(methylthio)pyrimidine-5-carboxylate (1.52 g, 3.6 mmol) and N,N-dimethylformamide dimethylacetal (743 uL, 5.2 mmol) and continuing until the reaction yielded the crude title compound (E)-ethyl 4-(3,5-bis(trifluoromethyl)phenylamino)-6-(2-(dimethylamino)vinyl)-2-(methylthio)pyrimidine-5-carboxylate. The resultant compound was used for the next step without further purification.

Example 100c 4-(3,5-bis(trifluoromethyl)phenylamino)-2-(methylthio)pyrido[4,3-d]pyrimidin-5(6H)-one

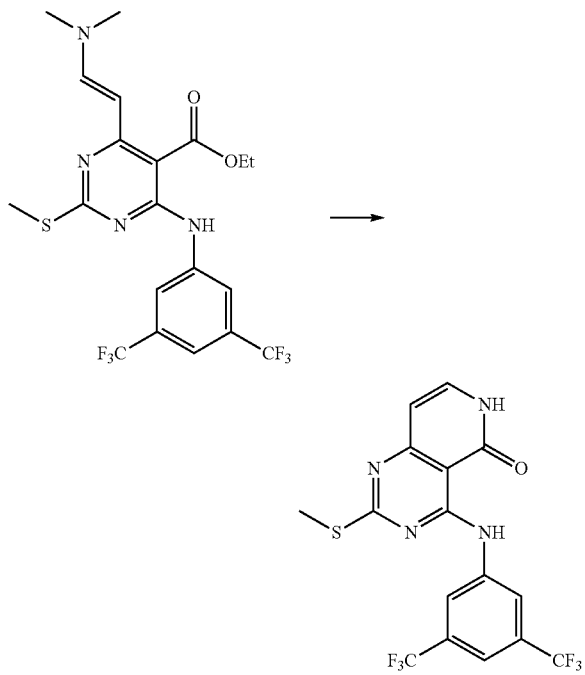

The title compound was prepared as described in Example 1f by starting from (E)-ethyl 4-(3,5-bis(trifluoromethyl)phenylamino)-6-(2-(dimethylamino)vinyl)-2-(methylthio)pyrimidine-5-carboxylate and aq. NH4OH solution and continuing until the reaction yielded pale yellow solids, title compound (537 mg). MS m/z: 421.1 (M+1)+.

Example 100d 2-((1R,2R)-2-amino cyclohexylamino)-4-(3,5-bis(trifluoromethyl)phenylamino)pyrido[4,3-d]pyrimidin-5(6H)-one

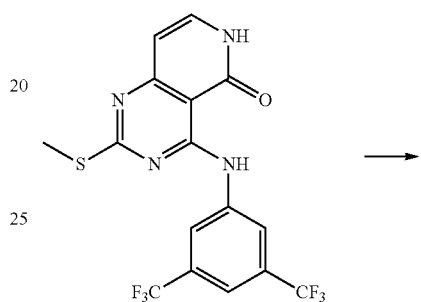

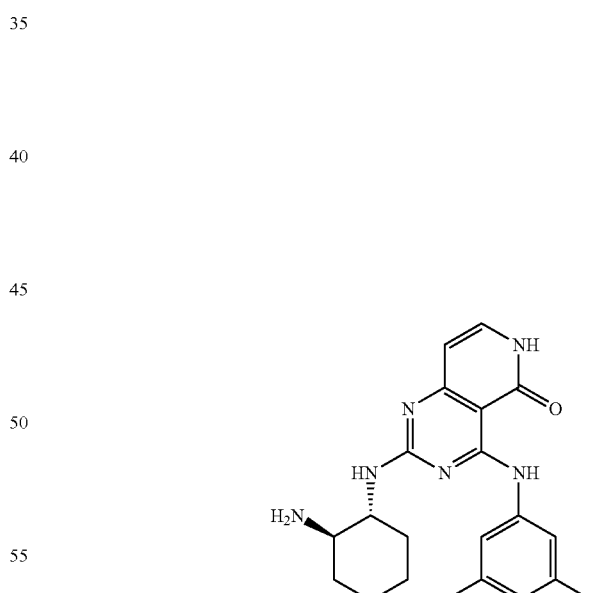

The title compound was prepared as described in Example 1g by starting from 4-(3,5-bis(trifluoromethyl)phenylamino)-2-(methylthio)pyrido[4,3-d]pyrimidin-5(6H)-one (100 mg, 0.24 mmol) and (±)-trans-1,2-diamino cyclohexane and continuing until the reaction yielded the title compound, 2-((1R,2R)-2-aminocyclohexylamino)-4-(3,5-bis(trifluoromethyl)phenylamino)pyrido[4,3-d]pyrimidin-5(6H)-one. MS m/z: 487 (M+1)+ 1H NMR (300 MHz, DMSO-d6) δ ppm 1.25-1.97 (m, 10H), 6.10 (d, J=7.2 Hz, 1H), 7.41-7.44 (m, 3H), 7.41-7.76 (m, 4H), 8.47 (s, 2H), 12.49 (s, 1H).

Example 101

Synthesis of (2-((1R,2S)-2-aminocyclohexylamino)-4-(3-(trifluoromethyl)phenylamino)pyrido[4,3-d]pyrimidin-5(6H)-one with (2-((1S,2R)-2-aminocyclohexylamino)-4-(3-(trifluoromethyl)phenylamino)pyrido[4,3-d]pyrimidin-5(6H)-one

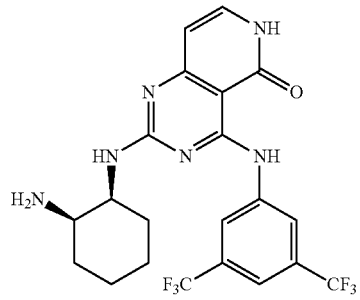

Compound No. 101

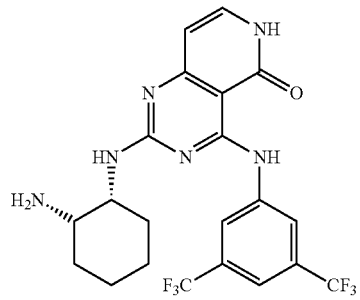

The title compound was prepared as described in Example 2d by starting from 2-(methylthio)-4-(3-(trifluoromethyl)phenylamino)pyrido[4,3-d]pyrimidin-5(6H)-one 100 mg (0.26 mmol), (1R,2S)-2-aminocyclo hexylamine and continuing until the reaction yielded white solids, the title compound, (2-((1R,2S)-2-aminocyclohexylamino)-4-(3-(trifluoromethyl)phenylamino)pyrido[4,3-d]pyrimidin-5(6H)-one (92 mg, 77.4%). MS m/z: 419.3 (M+H)⁺.

Example 102

Synthesis of 4-(3,5-bis(trifluoromethyl)phenylamino)-2-(4-hydroxypiperidin-1-yl)pyrido[4,3-d]pyrimidin-5(6H)-one

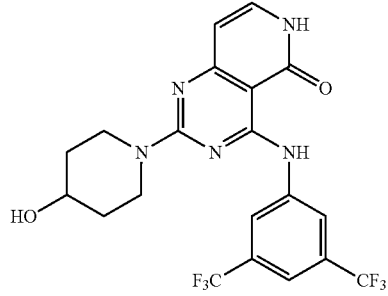

Compound No. 102

Compound No. 102 was prepared as described in Example 1g by starting from 4-(3,5-bis(trifluoromethyl)phenylamino)-2-(methylthio)pyrido[4,3-d]pyrimidin-5(6H)-one (70 mg, 0.17 mmol) and 4-hydroxy piperidine (20.6 mg, 0.2 mmol) and continuing until the reaction yielded light brown solids of Compound No. 102 (60 mg, 76%). MS m/z:, ¹H NMR (300 MHz, DMSO-d6) δ ppm 474.1 (M+1)⁺, 12.27 (s, 1H), 8.47 (s, 2H), 7.74 (s, 1H), 7.41 (d, J=7.2 Hz, 1H), 6.17 (d, J=7.2 Hz, 1H), 4.24 (b, 2H), 3.78 (m, 1H), 3.45-3.39 (m, 2H), 1.81-1.77 (m, 2H), 1.38 (m, 2H).

The following 4-(3,5-bis-(trifluoromethyl)phenylamino)-2-(amino substituted)pyrido[4,3-d]pyrimidin-5(6H)-one compounds were prepared from 4-(3,5-bis(trifluoromethyl)phenylamino)-2-(methylthio)pyrido[4,3-d]pyrimidin-5(6H)-one and the corresponding amine following the procedure similar to that described in Example 100d.

| NO. | Structure | Name | Mass (M + 1) |
|---|---|---|---|
| 103 | (structure shown) | 4-(3,5-bis(trifluoromethyl)phenylamino)-2-morpholinopyrido[4,3-d]pyrimidin-5(6H)-one | 460 |

-continued

| NO. | Structure | Name | Mass (M + 1) |
|---|---|---|---|
| 104 | 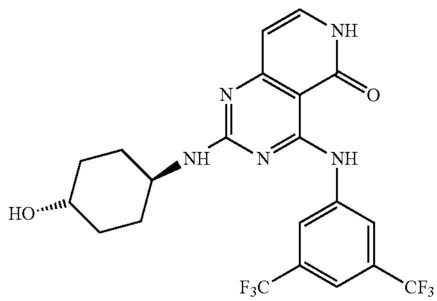 | 4-(3,5 bis(trifluoromethyl)phenylamino)-2-((1r,4r)-4-hydroxycyclohexyl-amino)pyrido[4,3-d]pyrimidin-5(6H)-one | 488 |
| 105 | 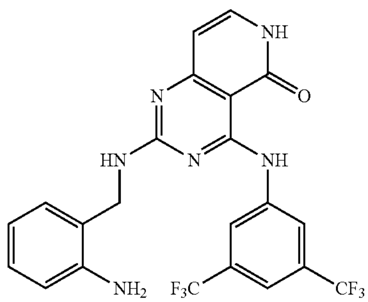 [SMILES: Nc1ccccc1CNc1nc(Nc2cc(C(F)(F)F)cc(C(F)(F)F)c2)c2c(=O)[nH]ccc2n1] | 2-(2-aminobenzylamino)-4-(3,5-bis(trifluoromethyl)phenylamino)pyrido[4,3-d]pyrimidin-5(6H)-one | 495 |
| 106 | 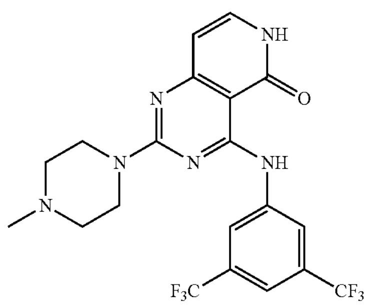 [SMILES: CN1CCN(c2nc(Nc3cc(C(F)(F)F)cc(C(F)(F)F)c3)c3c(=O)[nH]ccc3n2)CC1] | 4-(3,5-bis(trifluoromethyl)phenylamino)-2-(4-methylpiperazin-1-yl)pyrido[4,3-d]pyrimidin-5(6H)-one | 473 |
| 107 | 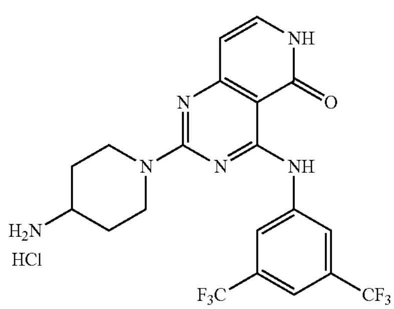 [SMILES: Cl ; NC1CCN(c2nc(Nc3cc(C(F)(F)F)cc(C(F)(F)F)c3)c3c(=O)[nH]ccc3n2)CC1] | 2-(4-aminopiperidin-1-yl)-4-(3,5-bis(trifluoromethyl)phenylamino)pyrido[4,3-d]pyrimidin-5(6H)-one hydrochloride | 473 |
| 108 | 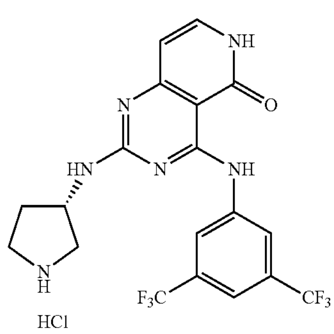 [SMILES: O=c1[nH]ccc2nc(N[C@H]3CCNC3)nc(Nc3cc(C(F)(F)F)cc(C(F)(F)F)c3)c12 ; Cl] | (S)-4-(3,5-bis(trifluoromethyl)phenyl-amino)-2-(pyrrolidin-3-ylamino)pyrido[4,3-d]pyrimidin-5(6H)-one hydrochloride | 459 |

| NO. | Structure | Name | Mass (M + 1) |
|---|---|---|---|
| 109 | 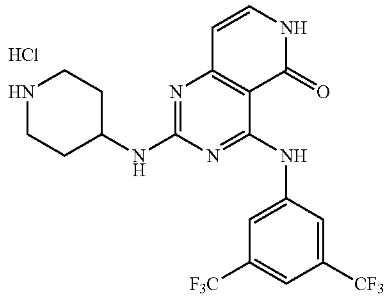 [SMILES: Cl ; O=c1[nH]ccc2nc(NC3CCNCC3)nc(Nc3cc(C(F)(F)F)cc(C(F)(F)F)c3)c12] | 4-(3,5-bis(trifluoromethyl)phenylamino)-2-(piperidin-4-ylamino)pyrido[4,3-d]pyrimidin-5(6H)-one hydrochloride | 473 |
| 110 | 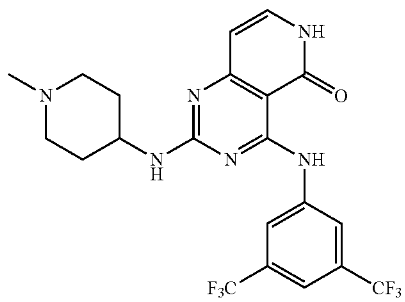 [SMILES: CN1CCC(Nc2nc(Nc3cc(C(F)(F)F)cc(C(F)(F)F)c3)c3c(=O)[nH]ccc3n2)CC1] | 4-(3,5-bis(trifluoromethyl)phenylamino)-2-(1-methylpiperidin-4-ylamino)pyrido[4,3-d]pyrimidin-5(6H)-one | 487 |
| 111 | 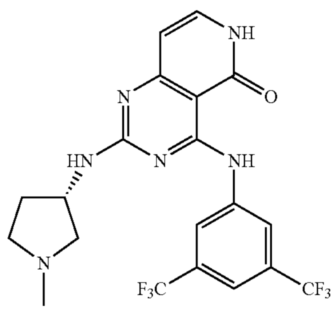 [SMILES: CN1CC[C@H](Nc2nc(Nc3cc(C(F)(F)F)cc(C(F)(F)F)c3)c3c(=O)[nH]ccc3n2)C1] | (S)-4-(3,5-bis(trifluoromethyl)phenylamino)-2-(1-methylpyrrolidin-3-ylamino)pyrido[4,3-d]pyrimidin-5(6H)-one | 473 |
| 112 | 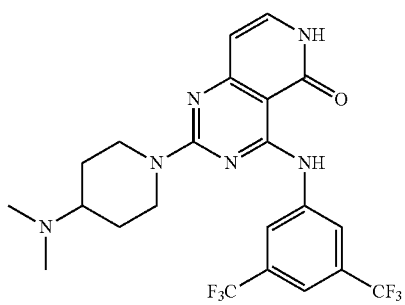 [SMILES: CN(C)C1CCN(c2nc(Nc3cc(C(F)(F)F)cc(C(F)(F)F)c3)c3c(=O)[nH]ccc3n2)CC1] | 4-(3,5-bis(trifluoromethyl)phenylamino)-2-(4-(dimethylamino)piperidin-1-yl)pyrido[4,3-d]pyrimidin-5(6H)-one | 501 |
| 113 | 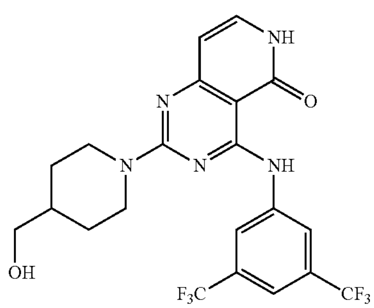 [SMILES: O=c1[nH]ccc2nc(N3CCC(CO)CC3)nc(Nc3cc(C(F)(F)F)cc(C(F)(F)F)c3)c12] | 4-(3,5-bis(trifluoromethyl)phenylamino)-2-(4-(hydroxymethyl)piperidin-1-yl)pyrido[4,3-d]pyrimidin-5(6H)-one | 488 |

| NO. | Structure | Name | Mass (M + 1) |
|---|---|---|---|
| 114 | 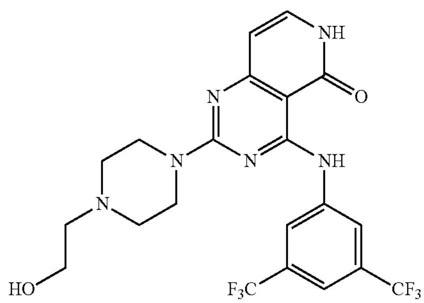 [SMILES: O=c1[nH]ccc2nc(N3CCN(CCO)CC3)nc(Nc3cc(C(F)(F)F)cc(C(F)(F)F)c3)c12] | 4-(3,5-bis(trifluoromethyl)phenylamino)-2-(4-(2-hydroxyethyl)piperazin-1-yl)pyrido[4,3-d]pyrimidin-5(6H)-one | 503 |
| 115 | 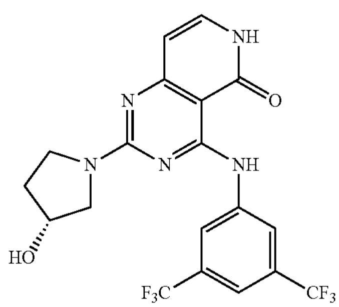 [SMILES: O=c1[nH]ccc2nc(N3CC[C@@H](O)C3)nc(Nc3cc(C(F)(F)F)cc(C(F)(F)F)c3)c12] | (R)-4-(3,5-bis(trifluoromethyl)phenylamino)-2-(3-hydroxypyrrolidin-1-yl)pyrido[4,3-d]pyrimidin-5(6H)-one | 460 |
| 116 | 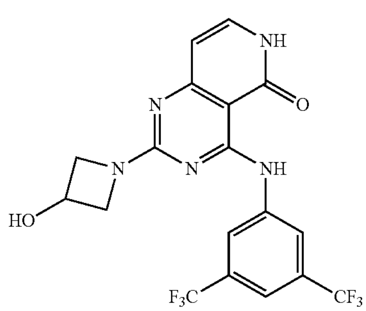 [SMILES: O=c1[nH]ccc2nc(N3CC(O)C3)nc(Nc3cc(C(F)(F)F)cc(C(F)(F)F)c3)c12] | 4-(3,5-bis(trifluoromethyl)phenylamino)-2-(3-hydroxyazetidin-1-yl)pyrido[4,3-d]pyrimidin-5(6H)-one | 446 |
| 117 | 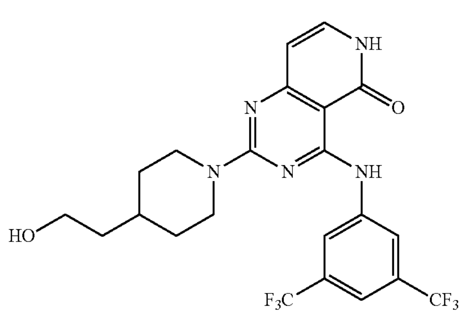 [SMILES: O=c1[nH]ccc2nc(N3CCC(CCO)CC3)nc(Nc3cc(C(F)(F)F)cc(C(F)(F)F)c3)c12] | 4-(3,5-bis(trifluoromethyl)phenylamino)-2-(4-(2-hydroxyethyl)piperidin-1-yl)pyrido[4,3-d]pyrimidin-5(6H)-one | 502 |

| NO. | Structure | Name | Mass (M + 1) |
|---|---|---|---|
| 118 | 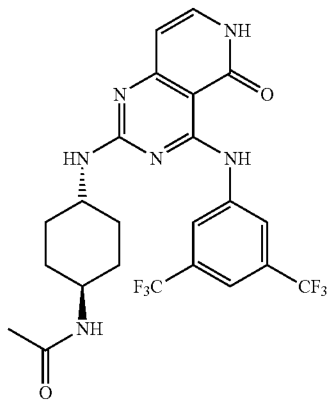 | N-((1r,4r)-4-(4-(3,5-bis(trifluoromethyl)phenylamino)-5-oxo-5,6-dihydropyrido[4,3-d]pyrimidin-2-ylamino)cyclohexyl)acetamide | 529 |
| 119 | 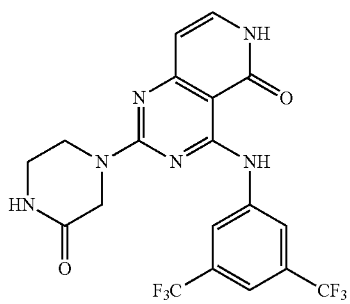 [SMILES: O=C1CN(c2nc(Nc3cc(C(F)(F)F)cc(C(F)(F)F)c3)c3c(=O)[nH]ccc3n2)CCN1] | 4-(3,5-bis(trifluoromethyl)phenylamino)-2-(3-oxopiperazin-1-yl)pyrido[4,3-d]pyrimidin-5(6H)-one | 473 |
| 120 | 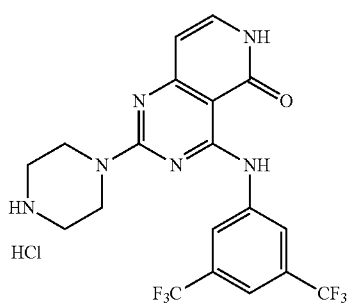 [SMILES: Cl ; O=c1[nH]ccc2nc(N3CCNCC3)nc(Nc3cc(C(F)(F)F)cc(C(F)(F)F)c3)c12] | 4-(3,5-bis(trifluoromethyl)phenylamino)-2-(piperazin-1-yl)pyrido[4,3-d]pyrimidin-5(6H)-one hydrochloride | 495 |
| 121 | 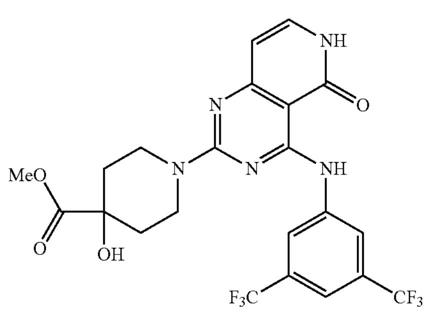 [SMILES: COC(=O)C1(O)CCN(c2nc(Nc3cc(C(F)(F)F)cc(C(F)(F)F)c3)c3c(=O)[nH]ccc3n2)CC1] | methyl 1-(4-(3,5-bis(trifluoromethyl)phenylamino)-5-oxo-5,6-dihydropyrido[4,3-d]pyrimidin-2-yl)-4-hydroxypiperidine-4-carboxylate | 532 |

| NO. | Structure | Name | Mass (M + 1) |
|---|---|---|---|
| 122 | 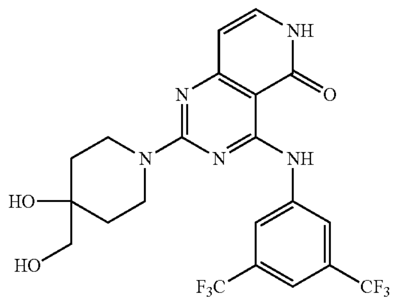 [SMILES: O=c1[nH]ccc2nc(N3CCC(O)(CO)CC3)nc(Nc3cc(C(F)(F)F)cc(C(F)(F)F)c3)c12] | 4-(3,5-bis(trifluoromethyl)phenylamino)-2-(4-hydroxy-4-(hydroxymethyl)piperidin-1-yl)pyrido[4,3-d]pyrimidin-5(6H)-one | 504 |
| 123 | 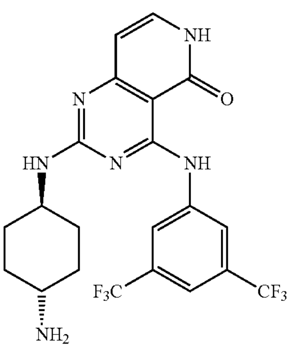 | 2-((1R,4R)-4-aminocyclohexylamino)-4-(3,5-bis(trifluoromethyl)phenylamino)pyrido[4,3-d]pyrimidin-5(6H)-one | 487 |
| 124 | 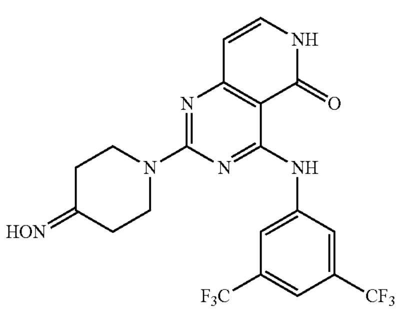 | 4-(3,5-bis(trifluoromethyl)phenylamino)-2-(4-(hydroxyimino)piperidin-1-yl)pyrido[4,3-d]pyrimidin-5(6H)-one | 487 |

Example 125

Synthesis of (S)-4-(phenoxyphenylamino)-2-(pyrrolidin-3-ylamino)pyrido[4,3-d]pyrimidin-5(6H)-one hydrochloride

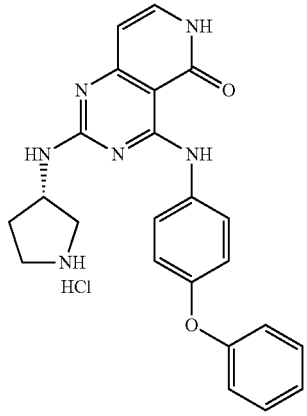

Compound No. 125

Compound No. 125 was prepared as described in Example 1g by starting from 2-(methylthio)-4-(4-phenoxy phenylamino)pyrido[4,3-d]pyrimidin-5(6H)-one (87 mg, 0.23 mmol) and (S)-(−)-1-boc-3-amino pyrrolidine (129 mg, 0.69 mmol) and treating with 4 N HCl in dioxane continuing until the reaction yielded the title compound (54 mg, 52%). MS m/z: 415 (M+1)⁺.

Example 126

Synthesis of 2-(4-hydroxypiperidin-1-yl)-4(4-(methylsulfonyl)phenylamino)pyrido[4,3d]pyrimidin-5(6H)-one

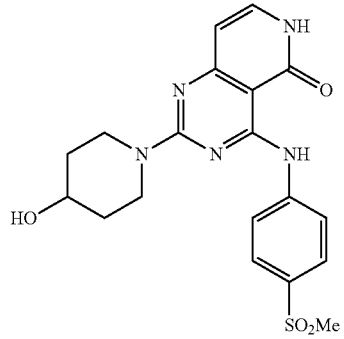

Compound No. 126

Compound No. 126 was prepared as described in Example 1g by starting from 4-(4-(methylsulfonyl)phenylamino)-2-(methylthio)pyrido[4,3-d]pyrimidin-5(6H)-one (60 mg, 0.17 mmol) and 4-hydroxypiperidine (34.1 mg, 0.33 mmol) and continuing until the reaction yielded yellow solids (39 mg, 57%). MS m/z: 416.4 (M+1)⁺.

The following 4-(4-(methylsulfonyl)phenylamino)-2-(amino substituted)pyrido[4,3-d]pyrimidin-5(6H)-one compounds were prepared from 4-(4-(methylsulfonyl)phenylamino)-2-(methylthio)pyrido[4,3-d]pyrimidin-5(6H)-one and the corresponding amine following the procedure similar to that described in Example 126.

| NO. | Structure | Name | Mass (M + 1) |
|---|---|---|---|
| 127 | 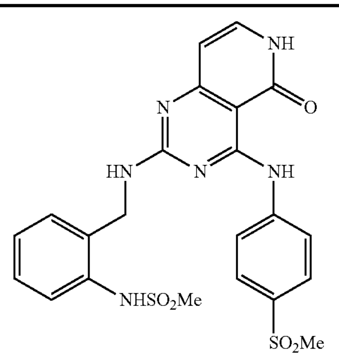 | N-(2-((4-(4-(methylsulfonyl)phenylamino)-5-oxo-5,6-dihydropyrido[4,3-d]pyrimidin-2-ylamino)methyl)phenyl)methanesulfonamide | 515 |
| 128 | 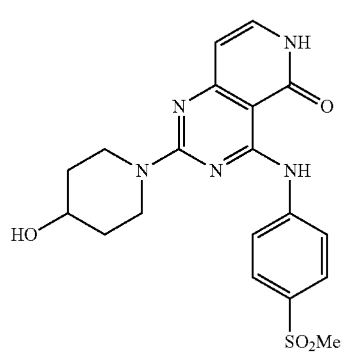 [SMILES: CS(=O)(=O)c1ccc(Nc2nc(N3CCC(O)CC3)nc3cc[nH]c(=O)c23)cc1] | 2-(4-hydroxypiperidin-1-yl)-4-(4-(methylsulfonyl)phenylamino)pyrido[4,3-d]pyrimidin-5(6H)-one | 416 |

| NO. | Structure | Name | Mass (M + 1) |
|---|---|---|---|
| 129 | 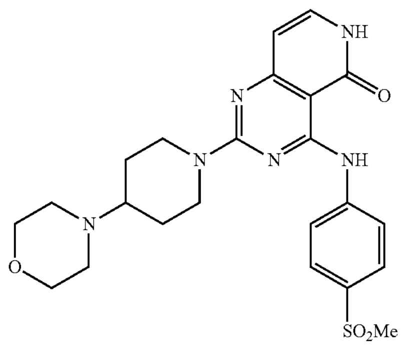 [SMILES: CS(=O)(=O)c1ccc(Nc2nc(N3CCC(N4CCOCC4)CC3)nc3cc[nH]c(=O)c23)cc1] | 4-(4-(methylsulfonyl)phenylamino)-2-(4-morpholinopiperidin-1-yl)pyrido[4,3-d]pyrimidin-5(6H)-one | 485 |
| 130 | 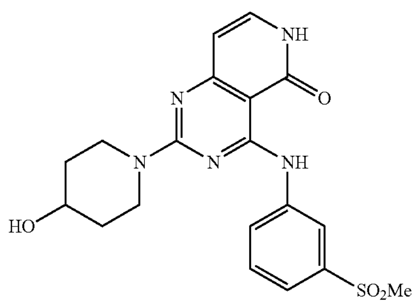 [SMILES: CS(=O)(=O)c1cccc(Nc2nc(N3CCC(O)CC3)nc3cc[nH]c(=O)c23)c1] | 2-(4-hydroxypiperidin-1-yl)-4-(3-(methylsulfonyl)phenylamino)pyrido[4,3-d]pyrimidin-5(6H)-one | 415 |
| 131 | 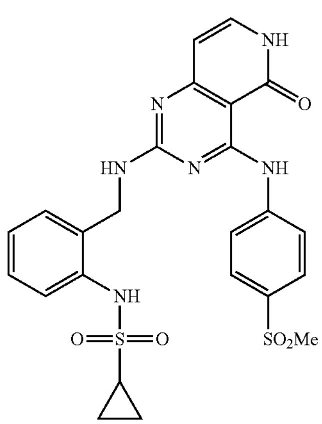 [SMILES: CS(=O)(=O)c1ccc(Nc2nc(NCc3ccccc3NS(=O)(=O)C3CC3)nc3cc[nH]c(=O)c23)cc1] | N-(2-((4-(4-(methylsulfonyl)phenylamino)-5-oxo-5,6-dihydropyrido[4,3-d]pyrimidin-2-ylamino)methyl)phenyl)cyclopropanesulfonamide | 541 |

-continued

| NO. | Structure | Name | Mass (M + 1) |
|---|---|---|---|
| 132 | 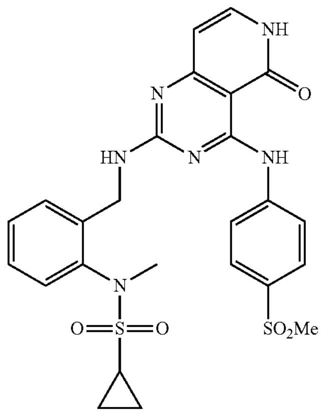 [SMILES: CN(c1ccccc1CNc1nc(Nc2ccc(S(C)(=O)=O)cc2)c2c(=O)[nH]ccc2n1)S(=O)(=O)C1CC1] | N-methyl-N-(2-((4-(4-(methylsulfonyl)phenylamino)-5-oxo-5,6-dihydropyrido[4,3-d]pyrimidin-2-ylamino)methyl)phenyl)cyclopropanesulfonamide | 555 |
| 133 | 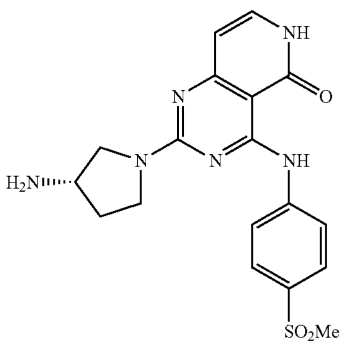 [SMILES: CS(=O)(=O)c1ccc(Nc2nc(N3CC[C@H](N)C3)nc3cc[nH]c(=O)c23)cc1] | (S)-2-(3-aminopyrrolidin-1-yl)-4-(4-(methylsulfonyl)phenylamino)pyrido[4,3-d]pyrimidin-5(6H)-one | 401 |

Example 134

Synthesis of 2-(4-hydroxypiperidin-1-yl)-4-(4-morpholinophenylamino)pyrido[4,3-d]pyrimidin-5(6H)-one

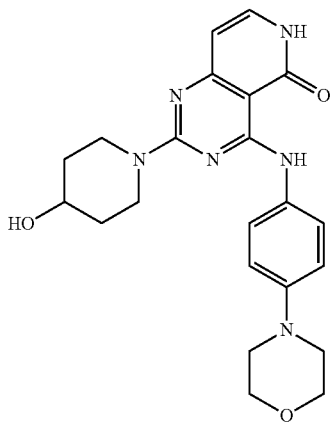

Compound No. 134

A 20 mL reaction vessel was charged with 2-(methylthio)-4-(4-morpholinophenylamino)pyrido[4,3-d]pyrimidin-5(6H)-one (74 mg, 0.20 mmol) and 4-hydroxypiperidine (60.6 mg, 0.60 mmol) in 7 mL DMF at −20° C. The solution was kept at the temperature for 30 minutes. To the solution was added m-CPBA (148 mg, 0.6 mmol) at the temperature, and further stirred for 30 minutes with being warmed to room temperature. The reaction was monitored by LC-MS, confirming the corresponding oxide. To the reaction mixture was added triethylamine (354 µL, 1.32 mmol), and 4-hydroxypiperidine (134 mg, 1.32 mmol), and stirred at the temperature for 2 hours. The reaction was monitored by LC-MS. The solvent was removed by a rotavapor yielding light brown residue. The residue was dissolved in 10 mL THF. To the solution was added CuI (0.4 mmol, 76.2 mg), and disopropylethylamine (69 µL, 0.4 mmol). The mixture was stirred at room temperature for 30 minutes. The mixture was diluted with EtOAc, and washed with 30% ammonium hydroxide solution. The separated organic layer was dried over sodium sulfate. The solvent was removed by a rotavapor yielding the brown residue. To the residue was added acetonitrile (10 mL) resulting in precipitates. Filtered and dried under reduced pressure to give the yellow solids (9 mg, 11%). MS m/z: 423.2 (M+1)$^+$.

The following 4-(4-morphlinophenylamino)-2-(amino substituted)pyrido[4,3-d]pyrimidin-5(6H)-one compounds were prepared from 4-(4-morpholinophenylamino)-2-(methylthio)pyrido[4,3-d]pyrimidin-5(6H)-one and the corresponding amine following the procedure similar to that described in Example 134.

| NO. | Structure | Name, NMR (300 MHz, DMSO-d6) | Mass (M + 1) |
|---|---|---|---|
| 135 | 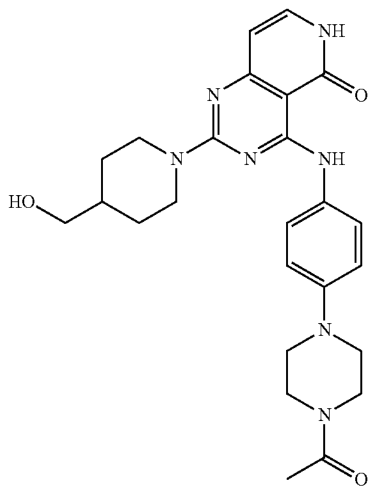 [SMILES: CC(=O)N1CCN(c2ccc(Nc3nc(N4CCC(CO)CC4)nc4cc[nH]c(=O)c34)cc2)CC1] | 4-(4-(4-acetylpiperazin-1-yl)phenylamino)-2-(4-(hydroxymethyl)piperidin-1-yl)pyrido[4,3-d]pyrimidin-5(6H)-one | 478 |
| 136 | 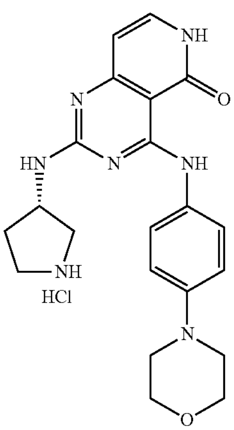 [SMILES: O=c1[nH]ccc2nc(N[C@H]3CCNC3)nc(Nc3ccc(N4CCOCC4)cc3)c12 ; Cl] | (S)-4-(4-morpholinophenylamino)-2-(pyrrolidin-3-ylamino)pyrido[4,3-d]pyrimidin-5(6H)-one hydrochloride | 408 |
| 137 | 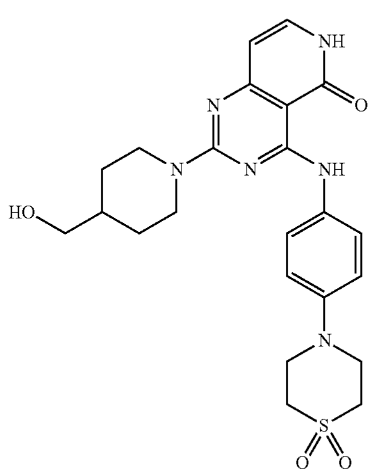 [SMILES: O=c1[nH]ccc2nc(N3CCC(CO)CC3)nc(Nc3ccc(N4CCS(=O)(=O)CC4)cc3)c12] | 2-(4-(hydroxymethyl)piperidin-1-yl)-4-(4-sulfonylphenylamino)pyrido[4,3-d]pyrimidin-5(6H)-one | 485 |

-continued

| NO. | Structure | Name, NMR (300 MHz, DMSO-d6) | Mass (M + 1) |
|---|---|---|---|
| 138 | 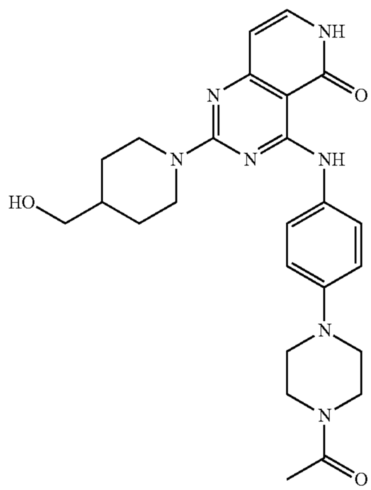 [SMILES: CC(=O)N1CCN(c2ccc(Nc3nc(N4CCC(CO)CC4)nc4cc[nH]c(=O)c34)cc2)CC1] | 4-(4-(4-acetylpiperazin-1-yl)phenylamino)-2-(4-(hydroxymethyl)piperidin-1-yl)pyrido[4,3-d]pyrimidin-5(6H)-one | 478 |
| 139 | 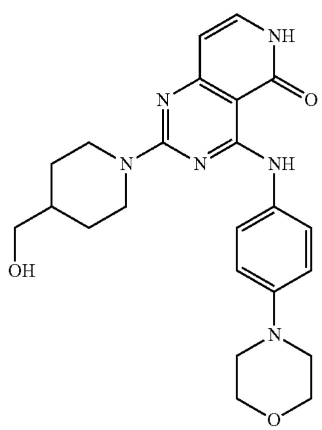 [SMILES: O=c1[nH]ccc2nc(N3CCC(CO)CC3)nc(Nc3ccc(N4CCOCC4)cc3)c12] | 2-(4-(hydroxymethyl)piperidin-1-yl)-4-(4-morpholinophenylamino)pyrido[4,3-d]pyrimidin-5(6H)-one | 437 |
| 140 | 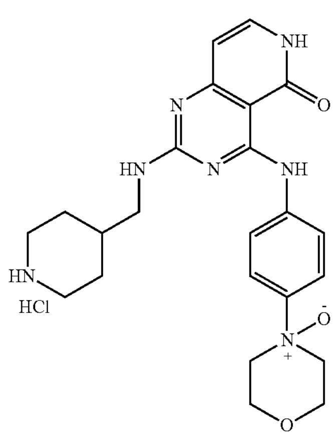 | 4-(4-(5-oxo-2-(piperidin-4-ylmethylamino)-5,6-dihydropyrido[4,3-d]pyrimidin-4-ylamino)phenyl)morpholine 4-oxide hydrochloride | 452 |

-continued

| NO. | Structure | Name, NMR (300 MHz, DMSO-d6) | Mass (M + 1) |
|---|---|---|---|
| 141 | 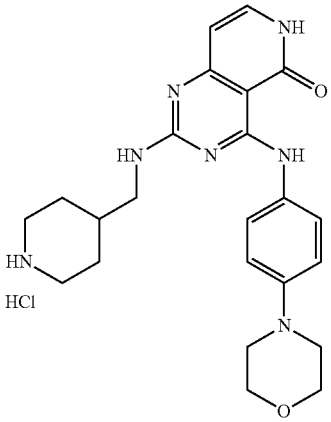 [SMILES: Cl ; O=c1[nH]ccc2nc(NCC3CCNCC3)nc(Nc3ccc(N4CCOCC4)cc3)c12] | 4-(4-morpholinophenylamino)-2-(piperidin-4-ylmethylamino)pyrido[4,3-d]pyrimidin-5(6H)-one hydrochloride | 436 |
| 142 | 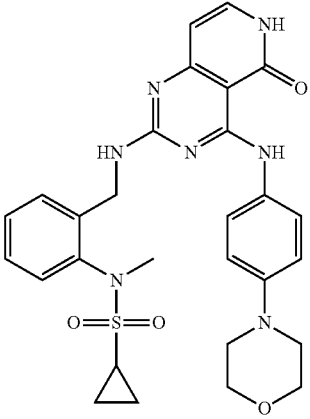 [SMILES: CN(c1ccccc1CNc1nc(Nc2ccc(N3CCOCC3)cc2)c2c(=O)[nH]ccc2n1)S(=O)(=O)C1CC1] | N-methyl-N-(2-((4-(4-morpholinophenylamino)-5-oxo-5,6-dihydropyrido[4,3-d]pyrimidin-2-ylamino)methyl)phenyl)cyclopropanesulfonamide | 562 |
| 143 | 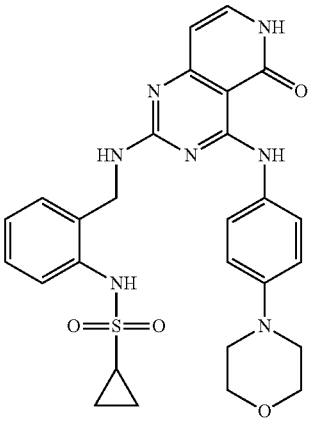 [SMILES: O=c1[nH]ccc2nc(NCc3ccccc3NS(=O)(=O)C3CC3)nc(Nc3ccc(N4CCOCC4)cc3)c12] | N-(2-((4-(4-morpholinophenylamino)-5-oxo-5,6-dihydropyrido[4,3-d]pyrimidin-2-ylamino)methyl)phenyl)cyclopropanesulfonamide | 548 |

| NO. | Structure | Name, NMR (300 MHz, DMSO-d6) | Mass (M + 1) |
|---|---|---|---|
| 144 | 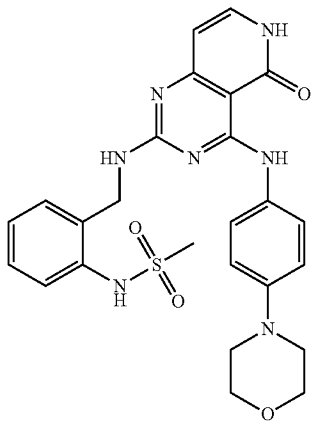 [SMILES: CS(=O)(=O)Nc1ccccc1CNc1nc(Nc2ccc(N3CCOCC3)cc2)c2c(=O)[nH]ccc2n1] | N-(2-((4-(4-morpholinophenylamino)-5-oxo-5,6-dihydropyrido[4,3-d]pyrimidin-2-ylamino)methyl)phenyl)methanesulfonamide | 522 |
| 145 | 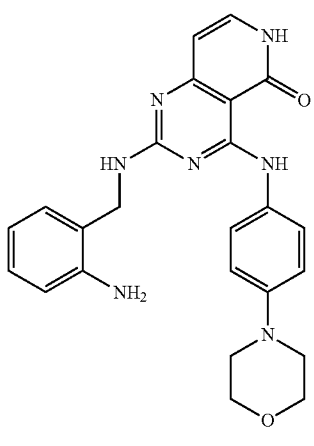 [SMILES: Nc1ccccc1CNc1nc(Nc2ccc(N3CCOCC3)cc2)c2c(=O)[nH]ccc2n1] | 2-(2-aminobenzylamino)-4-(4-morpholinophenylamino)pyrido[4,3-d]pyrimidin-5(6H)-one | 444 |
| 146 | 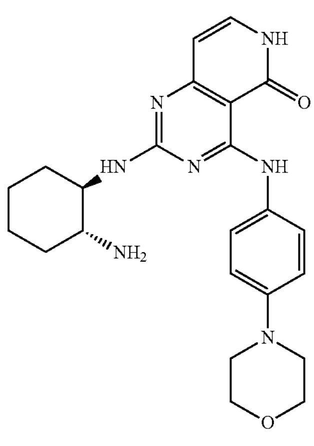 [SMILES: N[C@@H]1CCCC[C@H]1Nc1nc(Nc2ccc(N3CCOCC3)cc2)c2c(=O)[nH]ccc2n1] | 2-((1R,2R)-2-aminocyclohexylamino)-4-(4-morpholinophenylamino)pyrido[4,3-d]pyrimidin-5(6H)-one | 436 |

| NO. | Structure | Name, NMR (300 MHz, DMSO-d6) | Mass (M + 1) |
|---|---|---|---|
| 147 | 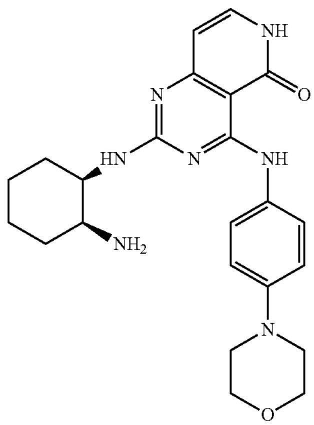 [SMILES: N[C@H]1CCCC[C@H]1Nc1nc(Nc2ccc(N3CCOCC3)cc2)c2c(=O)[nH]ccc2n1] | 2-((1R,2S)-2-aminocyclohexylamino)-4-(4-morpholinophenylamino)pyrido[4,3-d]pyrimidin-5(6H)-one | 436 |
| 148 | 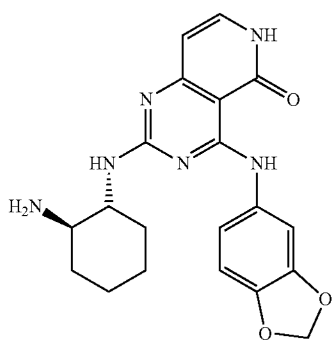 | 2-((1R,2R)-2-aminocyclohexylamino)-4-(benzo[d][1,3]dioxol-5-ylamino)pyrido[4,3-d]pyrimidin-5(6H)-one<br>11.83 (d, J = 10.50 Hz, 1H), 7.83 (d, J = 1.50 Hz, 1H), 7.56 (d, J = 7.50 Hz, 1H), 7.50 (d, J = 8.10 Hz, 1H), 7.33 (s, 1H), 6.16 (d, J = 7.20 Hz, 1H), 6.01 (s, 1H), 3.89 (s, 1H), 3.71 (d, J = 10.80 Hz, 1H), 2.00 (s, 2H), 1.70 (s, 2H), 1.22 (s, 4H) | 395 |

Example 149

Synthesis of 2-(4-hydroxypiperidin-1-yl)-4-(3,4,5-triemethoxyphenylamino)pyrido[4,3d]pyrimidin-5(6H)-one Compound No. 149

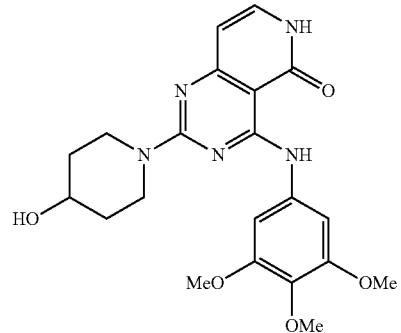

Prepared as described in Example 1g starting from 4-(3,4,5-trimethoxyphenylamino)-2-(methylthio)pyrido[4,3-d]pyrimidin-5(6H)-one (112 mg, 0.30 mmol), and 4-hydroxypiperidine (91 mg, 0.90 mmol) to give the pale brown solids (112 mg, 87%). MS m/z: 428 (M+1)+ 1H NMR (300 MHz, DMSO-d6) δ ppm 1.16-1.81 (m, 6H), 3.64 (s, 3H), 3.80 (s, 6H), 4.35 (d, J=13.2 Hz, 2H), 4.80 (d, J=4.2 Hz, 1H), 6.14 (d, J=7.2 Hz, 1H), 7.08 (s, 2H), 7.36 (d, J=6.9 Hz, 1H), 11.35 (s, 1H), 11.87 (s, 1H).

Example 150

Synthesis of 2-(4-hydroxypiperidin-1-yl)-4-(4-methoxy-3-(trifluoromethyl)phenylamino)pyrido[4,3d]pyrimidin-5(6H)-one Compound No. 150

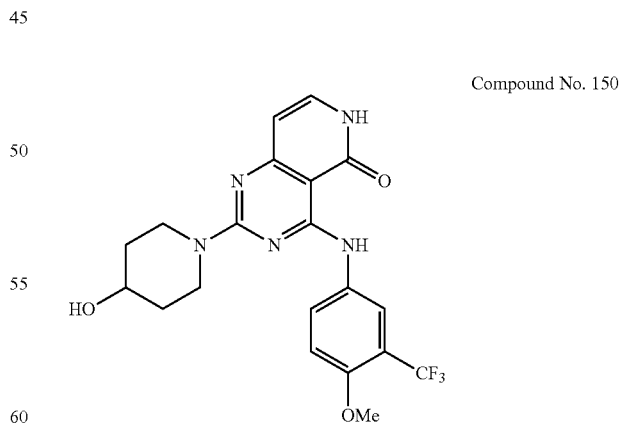

Compound No. 150 was prepared as described in Example 1g by starting from 4-(4-methoxy-3-(trifluoromethyl)phenylamino)-2-(methylthio)pyrido[4,3-d]pyrimidin-5(6H)-one (70 mg, 0.18 mmol) and 4-hydroxy piperidine (55 mg, 0.54 mmol) and continuing until the reaction yielded light yellow solids (57 mg, 73%). MS m/z: 436 (M+1)+.

Example 151

Synthesis of 2-(4-(hydroxymethyl)piperidin-1-yl)-4-(4-methoxy-3-(trifluoromethyl)phenylamino)pyrido[4,3d]pyrimidin-5(6H)-one

Example 152

Synthesis of 2-(4-hydroxy-4-(hydroxymethyl)piperidin-1-yl)-4-(4-methoxy-3-(trifluoromethyl)phenylamino)pyrido[4,3d]pyrimidin-5(6H)-one

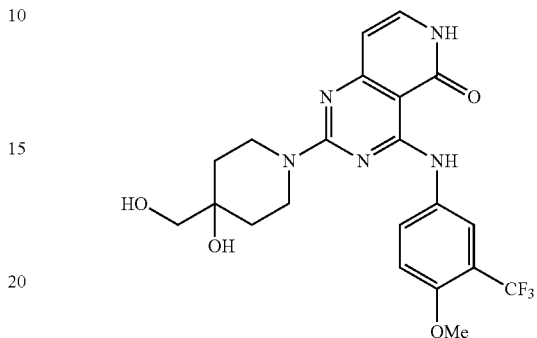

Compound No. 152

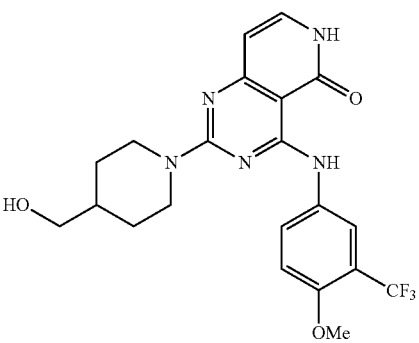

Compound No. 151

Compound No. 151 was prepared as described in Example 1g by starting from 4-(4-methoxy-3-(trifluoromethyl)phenylamino)-2-(methylthio)pyrido[4,3-d]pyrimidin-5(6H)-one (70 mg, 0.18 mmol) and 4-piperidine methanol (67 mg, 0.54 mmol) and continuing until the reaction yielded light yellow solids (67 mg, 83%). MS m/z: 450.4 (M+1)$^+$.

A 20 mL reaction vessel was charged with 4-(4-methoxy-3-(trifluoromethyl)phenylamino)-2-(methylthio)pyrido[4,3-d]pyrimidin-5(6H)-one (70 mg, 0.18 mmol) in 7 mL DMF at −20° C. The solution was kept at the temperature for 30 min. To the cold solution was added m-CPBA (133 mg, 0.54 mmol) at the temperature, and further stirred for 30 min with being warmed to room temperature. The reaction was monitored by LC-MS, confirming the corresponding oxide. To the reaction mixture was added triethylamine (75 μL, 1.32 mmol) and methyl 4-hydroxy piperidine-4 carboxylate (57 mg, 0.36 mmol), and stirred at the temperature for 2 hours. The reaction was monitored by LC-MS. The solvent was removed by a rotavapor yielding light yellow solid, methyl 4-hydroxy-1-(4-(4-methoxy-3-(trifluoromethyl)phenylamino)-5-oxo-5,6-dihydro pyrido[4,3-d]pyrimidin-2-yl)piperidine-4-carboxylate (65 mg, 73%). It was dissolved in 8 mL dry THF in a 20 mL reaction vessel. To the mixture was added 1.0 M DIBAL in toluene (1.95 mL, 1.95 mmol) at 0° C. It was stirred at the temperature for 2 hours. The reaction mixture was quenched with 20 mL MeOH. The solvents were removed by a rotavapor yielding a light yellow residue. The residue was dissolved in the mixture of MeOH and DCM yielding the white precipitates. They were filtered and the filtrate was condensed under reduced pressure providing a white powder, the title compound, (25 mg, 41%). MS m/z: 466 (M+1)$^+$.

The following compounds were prepared from the procedure similar to that described for Example 151 and 152.

| NO. | Structure | Name | Mass (M + 1) |
|---|---|---|---|
| 153 | 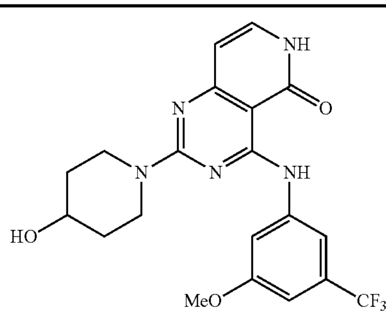 | 2-(4-hydroxypiperidin-1-yl)-4-(3-methoxy-5-(trifluoromethyl)phenylamino)pyrido[4,3d]pyrimidin-5(6H)-one | 435 |

| NO. | Structure | Name | Mass (M + 1) |
|---|---|---|---|
| 154 | 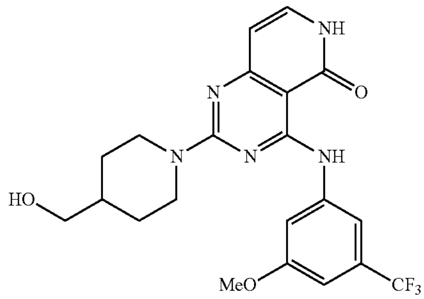 [SMILES: COc1cc(Nc2nc(N3CCC(CO)CC3)nc3cc[nH]c(=O)c23)cc(C(F)(F)F)c1] | 2-(4-(hydroxymethyl)piperidin-1-yl)-4-(3-methoxy-5-(trifluoromethyl)phenylamino)pyrido[4,3d]pyrimidin-5(6H)-one | 450 |
| 155 | 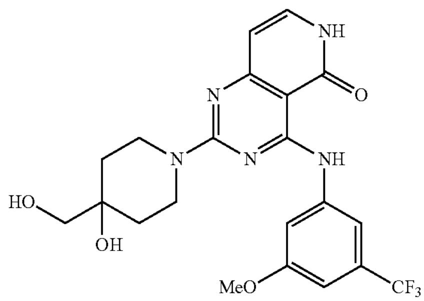 [SMILES: COc1cc(Nc2nc(N3CCC(O)(CO)CC3)nc3cc[nH]c(=O)c23)cc(C(F)(F)F)c1] | 2-(4-hydroxy-4-(hydroxymethyl)piperidin-1-yl)-4-(3-methoxy-5-(trifluoromethyl)phenylamino)pyrido[4,3d]pyrimidin-5(6H)-one | 466 |
| 156 | 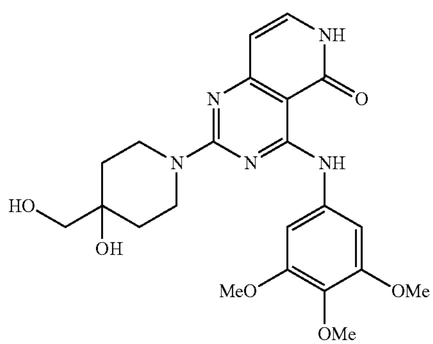 [SMILES: COc1cc(Nc2nc(N3CCC(O)(CO)CC3)nc3cc[nH]c(=O)c23)cc(OC)c1OC] | 2-(4-hydroxy-4-(hydroxymethyl)piperidin-1-yl)-4-(3,4,5-trimethoxyphenylamino)pyrido[4,3d]pyrimidin-5(6H)-one | 458 |
| 157 | 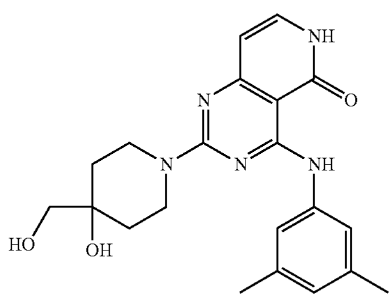 [SMILES: Cc1cc(C)cc(Nc2nc(N3CCC(O)(CO)CC3)nc3cc[nH]c(=O)c23)c1] | 4-(3,5-dimethylphenylamino)-2-(4-hydroxy-4-(hydroxymethyl)piperidin-1-yl)pyrido[4,3-d]pyrimidin-5(6H)-one | 396 |
| 158 | 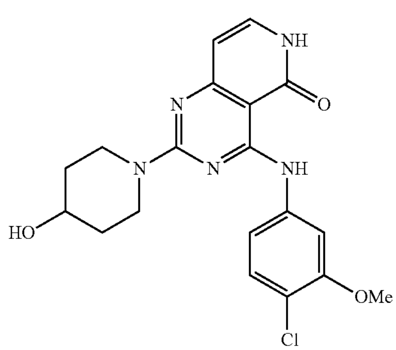 [SMILES: COc1cc(Nc2nc(N3CCC(O)CC3)nc3cc[nH]c(=O)c23)ccc1Cl] | 4-(4-chloro-3-methoxyphenylamino)-2-(4-hydroxypiperidin-1-yl)pyrido[4,3-d]pyrimidin-5(6H)-one | 402 |

| NO. | Structure | Name | Mass (M + 1) |
|---|---|---|---|
| 159 | 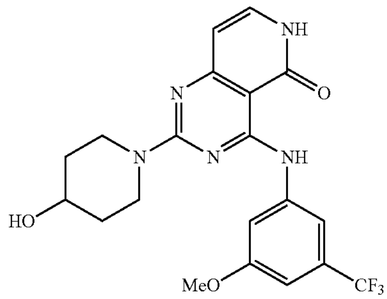 [SMILES: COc1cc(Nc2nc(N3CCC(O)CC3)nc3cc[nH]c(=O)c23)cc(C(F)(F)F)c1] | 2-(4-hydroxypiperidin-1-yl)-4-(3-methoxy-5-(trifluoromethyl)phenylamino)pyrido[4,3-d]pyrimidin-5(6H)-one | 436 |
| 160 | 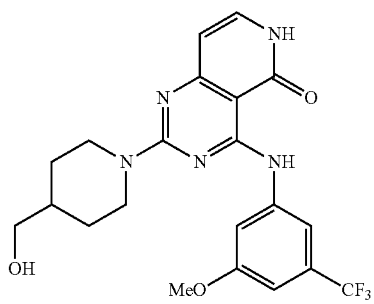 [SMILES: COc1cc(Nc2nc(N3CCC(CO)CC3)nc3cc[nH]c(=O)c23)cc(C(F)(F)F)c1] | 2-(4-(hydroxymethyl)piperidin-1-yl)-4-(3-methoxy-5-(trifluoromethyl)phenylamino)pyrido[4,3-d]pyrimidin-5(6H)-one | 450 |
| 161 | 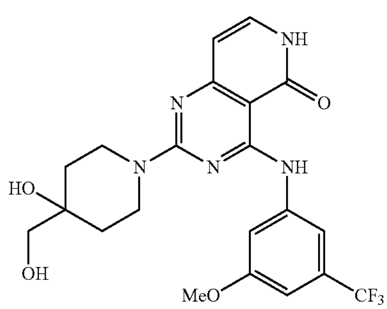 [SMILES: COc1cc(Nc2nc(N3CCC(O)(CO)CC3)nc3cc[nH]c(=O)c23)cc(C(F)(F)F)c1] | 2-(4-hydroxy-4-(hydroxymethyl)piperidin-1-yl)-4-(3-methoxy-5-(trifluoromethyl)phenylamino)pyrido[4,3-d]pyrimidin-5(6H)-one | 466 |
| 162 | 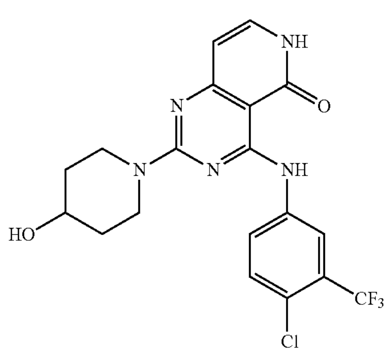 [SMILES: O=c1[nH]ccc2nc(N3CCC(O)CC3)nc(Nc3ccc(Cl)c(C(F)(F)F)c3)c12] | 4-(4-chloro-3-(trifluoromethyl)phenylamino)-2-(4-hydroxypiperidin-1-yl)pyrido[4,3-d]pyrimidin-5(6H)-one | 440 |

| NO. | Structure | Name | Mass (M + 1) |
|---|---|---|---|
| 163 | 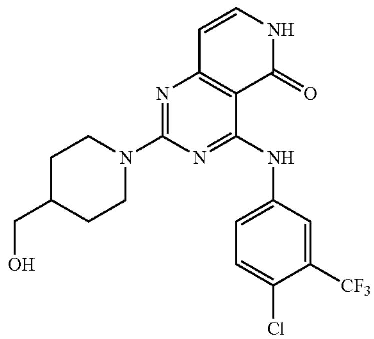 [SMILES: O=c1[nH]ccc2nc(N3CCC(CO)CC3)nc(Nc3ccc(Cl)c(C(F)(F)F)c3)c12] | 4-(4-chloro-3-(trifluoromethyl)phenylamino)-2-(4-(hydroxymethyl)piperidin-1-yl)pyrido[4,3-d]pyrimidin-5(6H)-one | 454 |
| 164 | 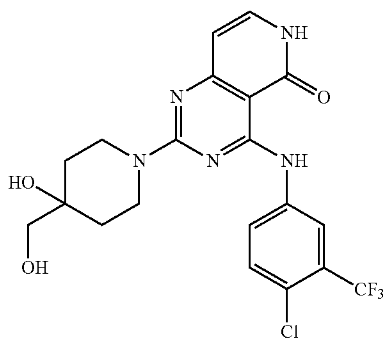 [SMILES: O=c1[nH]ccc2nc(N3CCC(O)(CO)CC3)nc(Nc3ccc(Cl)c(C(F)(F)F)c3)c12] | 4-(4-chloro-3-(trifluoromethyl)phenylamino)-2-(4-hydroxy-4-(hydroxymethyl)piperidin-1-yl)pyrido[4,3-d]pyrimidin-5(6H)-one | 470 |
| 165 | 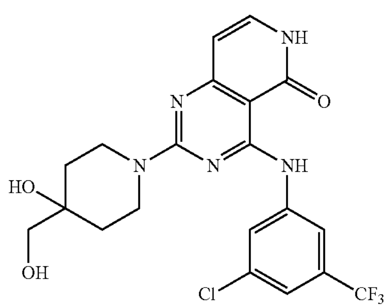 [SMILES: O=c1[nH]ccc2nc(N3CCC(O)(CO)CC3)nc(Nc3cc(Cl)cc(C(F)(F)F)c3)c12] | 4-(3-chloro-5-(trifluoromethyl)phenylamino)-2-(4-hydroxy-4-(hydroxymethyl)piperidin-1-yl)pyrido[4,3-d]pyrimidin-5(6H)-one | 470 |
| 166 | 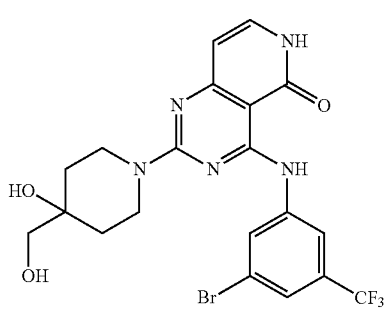 [SMILES: O=c1[nH]ccc2nc(N3CCC(O)(CO)CC3)nc(Nc3cc(Br)cc(C(F)(F)F)c3)c12] | 4-(3-bromo-5-(trifluoromethyl)phenylamino)-2-(4-hydroxy-4-(hydroxymethyl)piperidin-1-yl)pyrido[4,3-d]pyrimidin-5(6H)-one | 514 |

| NO. | Structure | Name | Mass (M + 1) |
|---|---|---|---|
| 167 | 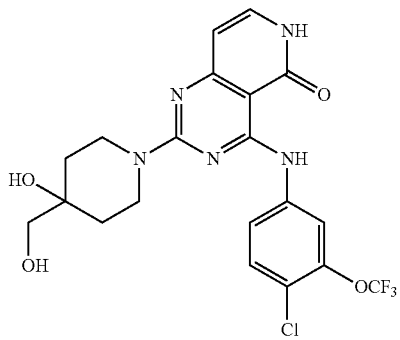 [SMILES: O=c1[nH]ccc2nc(N3CCC(O)(CO)CC3)nc(Nc3ccc(Cl)c(OC(F)(F)F)c3)c12] | 4-(4-chloro-3-(trifluoromethoxy)phenylamino)-2-(4-hydroxy-4-(hydroxymethyl)piperidin-1-yl)pyrido[4,3-d]pyrimidin-5(6H)-one | 486 |

Example 168

Synthesis of 2-(4-hydroxypiperidine-1-yl)-6-methyl-4-(3-(trifluoromethyl)phenylamino)pyrido[4,3-d]pyrimidin-5(6H)-one

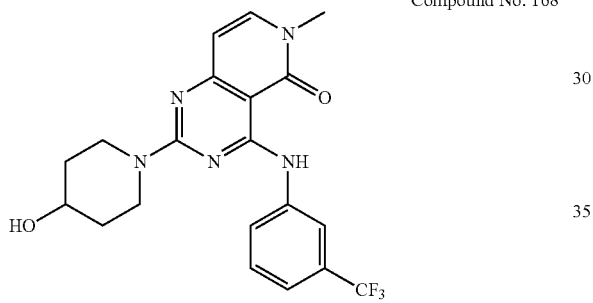

Compound No. 168

Compound No. 168 was prepared as described in Example 2d by starting from 6-methyl-2-(methylthio)-4-(3-trifluoromethyl)phenylamino)pyrido[4,3-d]pyrimidin-5(6H)-one (90 mg, 0.24 mmol) and 4-hydroxy piperidine (35 mg, 0.35 mmol) and continuing until the reaction yielded the title compound (35 mg, 33%). MS m/z: 420 (M+1)⁺.

The following compounds were prepared from the procedure similar to that described in Example 159.

| NO. | Structure | Name | Mass (M + 1) |
|---|---|---|---|
| 169 | 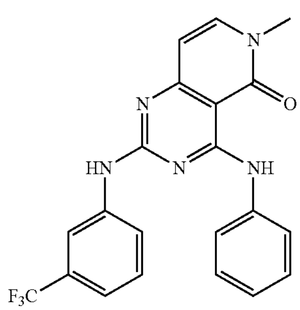 [SMILES: Cn1ccc2nc(Nc3cccc(C(F)(F)F)c3)nc(Nc3ccccc3)c2c1=O] | 6-methyl-4-(phenylamino)-2-(3-(trifluoromethyl)phenylamino)pyrido[4,3-d]pyrimidin-5(6H)-one | 412 |

| NO. | Structure | Name | Mass (M + 1) |
|---|---|---|---|
| 170 | 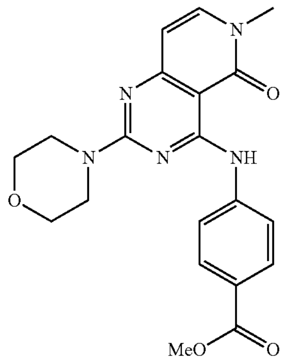 [SMILES: COC(=O)c1ccc(Nc2nc(N3CCOCC3)nc3ccn(C)c(=O)c23)cc1] | methyl 4-(6-methyl-2-morpholino-5-oxo-5,6-dihydropyrido[4,3-d]pyrimidin-4-ylamino)benzoate | 396 |
| 171 | 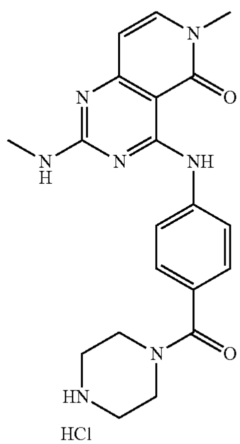 [SMILES: CNc1nc(Nc2ccc(C(=O)N3CCNCC3)cc2)c2c(=O)n(C)ccc2n1 ; Cl] | 6-methyl-2-(methylamino)-4-(4-(piperazine-1-carbonyl)phenylamino)pyrido[4,3-d]pyrimidin-5(6H)-one hydrochloride | 394 |
| 172 | 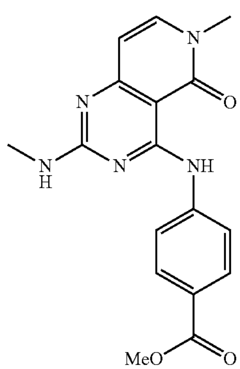 [SMILES: CNc1nc(Nc2ccc(C(=O)OC)cc2)c2c(=O)n(C)ccc2n1] | methyl 4-(6-methyl-2-(methylamino)-5-oxo-5,6-dihydropyrido[4,3-d]pyrimidin-4-ylamino)benzoate | 340 |
| 173 | 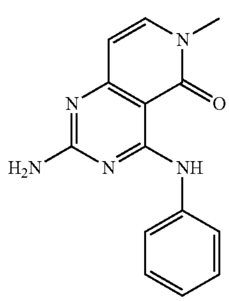 [SMILES: Cn1ccc2nc(N)nc(Nc3ccccc3)c2c1=O] | 2-amino-6-methyl-4-(phenylamino)pyrido[4,3-d]pyrimidin-5(6H)-one | 268 |

-continued

| NO. | Structure | Name | Mass (M + 1) |
|---|---|---|---|
| 174 | 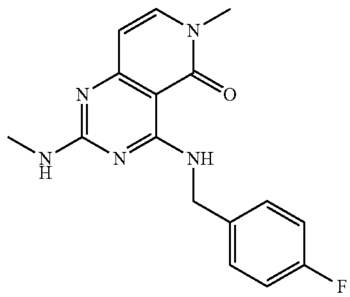 [SMILES: CNc1nc(NCc2ccc(F)cc2)c2c(=O)n(C)ccc2n1] | 4-(4-fluorobenzylamino)-6-methyl-2-(methylamino)pyrido[4,3-d]pyrimidin-5(6H)-one | 314 |
| 175 | 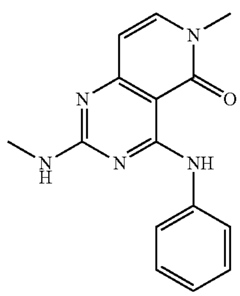 | 6-methyl-2-(methylamino)-4-(phenylamino)pyrido[4,3-d]pyrimidin-5(6H)-one | 282 |
| 176 | 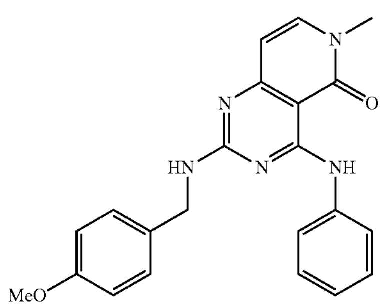 [SMILES: COc1ccc(CNc2nc(Nc3ccccc3)c3c(=O)n(C)ccc3n2)cc1] | 2-(4-methoxybenzylamino)-6-methyl-4-(phenylamino)pyrido[4,3-d]pyrimidin-5(6H)-one | 388 |
| 177 | 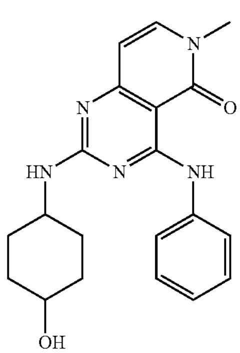 [SMILES: Cn1ccc2nc(NC3CCC(O)CC3)nc(Nc3ccccc3)c2c1=O] | 2-(4-hydroxycyclohexylamino)-6-methyl-4-(phenylamino)pyrido[4,3-d]pyrimidin-5(6H)-one | 366 |

Example 178

Synthesis of 4-(4-methoxyphenyl)-6-methyl-2-(methylamino)pyrido[4,3-d]pyrimidin-5(6H)-one Compound No. 178

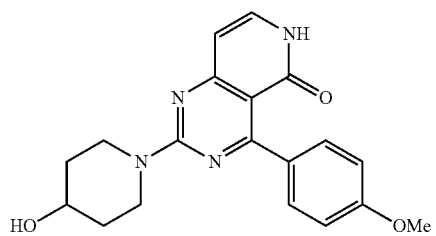

Example 178a

Ethyl 4-(4-methoxyphenyl)-6-methyl-2-(methylthio)pyrimidine-5-carboxylate

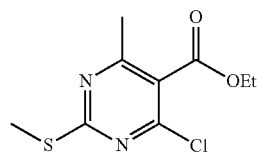 

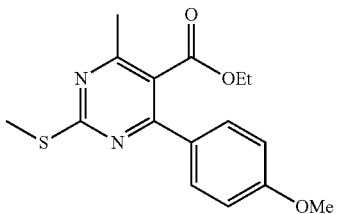

A 20 mL reaction vessel was charged with ethyl 4-chloro-6-methyl-2-(methylthio)pyrimidine-5-carboxylate (1.00 g, 4.06 mmol), 4-(tert-butoxycarbonylamino)phenylboronic acid (1.00 g, 4.22 mmol), and tetrakis(triphenyl)phosphine) palladium(0) (0.17 g, 0.15 mmol) in 10 mL dioxane. The reaction mixture was purged with N₂ for 25 minutes with stirring. To the mixture was added potassium carbonate (1.17 g, 8.44 mmol) in 4 mL H₂O. The biphasic mixture was purged with N₂ for 10 minutes. The mixture was stirred at 90° C. for 14 hours. The mixture was diluted with EtOAc, and washed with H₂O. The separated organic layer was dried over Na₂SO₄. The solvents were removed by a rotavapor yielding brown oily residue. The residue was purified by silica gel chromatography using a gradient 0-5% MeOH in dichloromethane providing white solid (1.12 g, 68%). MS m/z: 319 (M+1)⁺.

Example 178b (E)-Ethyl 4-(2-(dimethylamino)vinyl)-6-methyl-2-(methylthio)pyrimidine-5-carboxylate

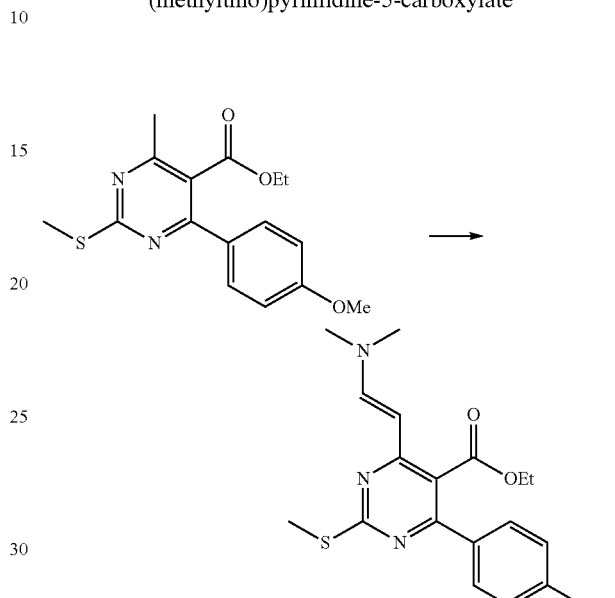

To the solution of ethyl 4-(4-methoxyphenyl)-6-methyl-2-(methylthio)pyrimidine-5-carboxylate (0.67 g, 1.75 mmol) in 5 mL DMF was added N,N-dimethylformamide dimethyl acetal (0.32 mL, 2.50 mmol). The reaction mixture was stirred at 130° C. for 2 hours. After monitoring the reaction by TLC was cooled to room temperature, then the mixture was diluted with DCM and water. After extracted three times by DCM from the aqueous layer, the combined organic layer was dried over MgSO₄. The solution was condensed under reduced pressure yielding crude mixture (467 mg). The mixture was used for the next step without further purification.

Example 178c 4-(4-Methoxyphenylamino)-6-methyl-(methylthio)pyrido[4,3-d]pyrimidin-5(6H)-one

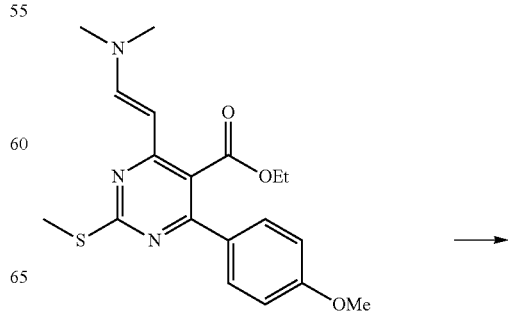

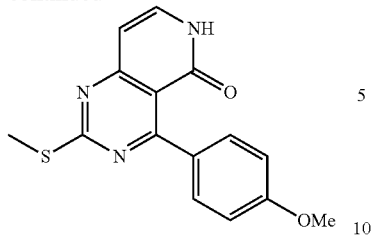

The crude of (E)-ethyl 4-(2-(dimethylamino)vinyl)-6-(4-methoxyphenyl)-2-(methylthio)pyrimidine-5-carboxylate (467 mg) was dissolved in 45 mL EtOH. To the solution was added 30% NH$_4$OH solution (3.0 mL), the reaction mixture was stirred at 90° C. for 10 hour. The mixture was cooled to room temperature. The solid formed from the solution were filtered. It was purified by silica gel chromatography using a gradient of 0-5% MeOH in dichloromethane providing light yellow solid (246 mg, 46% for the two steps). MS m/z: 344.9 (M+H)$^+$.

Example 178d 4-(4-Methoxyphenyl)-6-methyl-2-(methylamino)pyrido[4,3,-d]pyrimidin-5(6H)-one

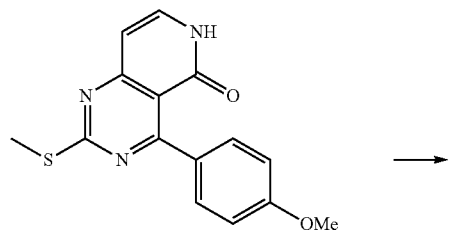

A 20 mL reaction vessel was charged with (4-methoxyphenylamino)-6-methyl(methylthio)pyrido[4,3-d]pyrimidin-5(6H)-one (69 mg, 0.23 mmol) in 4 mL DMF at −20° C. The solution was kept at the temperature for 30 minutes. To the solution was added m-CPBA (170 mg, 0.69 mmol) at the temperature, and further stirred for 30 minutes with being warmed to room temperature. The reaction was monitored by LC-MS, confirming the corresponding oxide. To the reaction mixture was added triethylamine (96 μL, 0.69 mmol) and 4-hydroxypiperidine (70 mg, 0.69 mmol), and stirred at the temperature for 2 hours. The reaction was monitored by LC-MS. The solvent was removed by a rotavapor yielding a light brown residue. To the residue was added acetonitrile (10 mL) resulting precipitates. They were filtered and dried under reduced pressure providing the title compound as light yellow solid (56 mg, 69%). MS m/z: 353 (M+H)$^+$.

The following compounds were prepared from the procedure similar to that described in Example 178.

| NO. | Structure | Name | Mass (M + 1) |
|---|---|---|---|
| 179 | 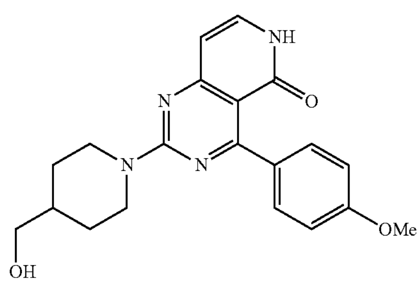 [SMILES: COc1ccc(-c2nc(N3CCC(CO)CC3)nc3cc[nH]c(=O)c23)cc1] | 2-(4-(hydroxymethyl)piperidin-1-yl)-4-(4-methoxyphenyl)pyrido[4,3-d]pyrimidin-5(6H)-one | 367 |
| 180 | 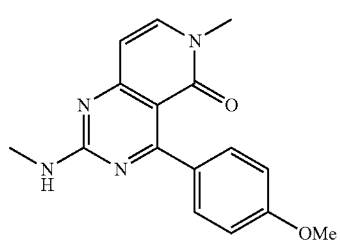 [SMILES: CNc1nc(-c2ccc(OC)cc2)c2c(=O)n(C)ccc2n1] | 4-(4-methoxyphenyl)-6-methyl-2-(methylamino)pyrido[4,3-d]pyrimidin-5(6H)-one | 297 |

| NO. | Structure | Name | Mass (M + 1) |
|---|---|---|---|
| 181 | 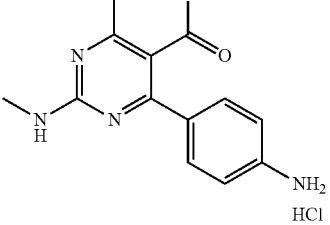 | 4-(4-aminophenyl)-6-methyl-2-(methylamino)pyrido[4,3-d]pyrimidin-5(6H)-one hydrochloride | 282 |
| 182 | 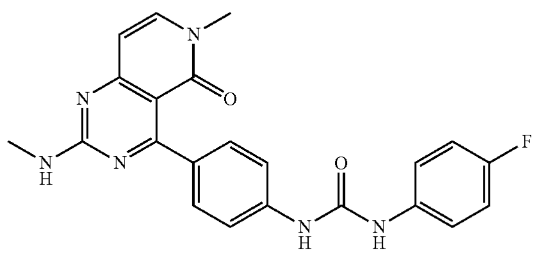 [SMILES: CNc1nc(-c2ccc(NC(=O)Nc3ccc(F)cc3)cc2)c2c(=O)n(C)ccc2n1] | 1-(4-fluorophenyl)-3-(4-(6-methyl-2-(methylamino)-5-oxo-5,6-dihydropyrido[4,3-d]pyrimidin-4-yl)phenyl)urea | 419 |

Example 183

Synthesis of 8-bromo-2-(4-hydroxypiperidin-1-yl)-4-(3-(trifluoromethyl)phenylamino)pyrido[4,3-d]pyrimidin-5(6H)-one Example 183a 8-bromo-2-(methylthio)-4-(3-(trifluoromethyl)phenylamino)pyrido[4,3-d]pyrimidin-5(6H)-one

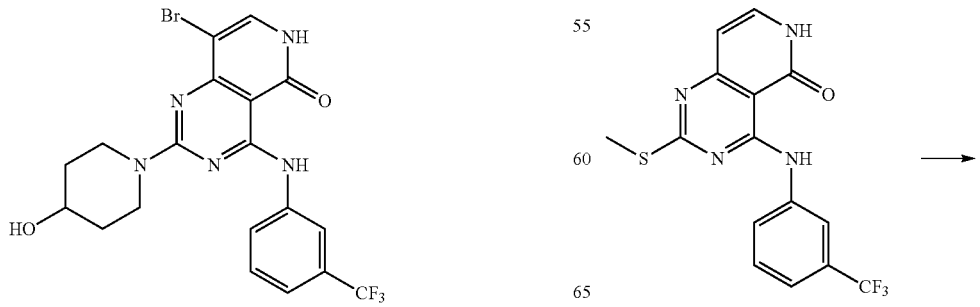

Compound No. 183

-continued

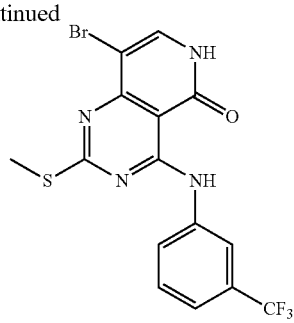

A 20 mL reaction vessel was charged with 2-(methylthio)-4-(3-(trifluoromethyl)phenylamino)pyrido[4,3-d]pyrimidin-5(6H)-one (135 mg, 0.38 mmol), and N-bromosuccinimide (68 mg, 0.38 mmol) in 7 mL dry DMF. The reaction mixture was stirred at room temperature for 2 hours. The solvent was removed under reduced pressuring yielding yellow residue. The residue was recrystallized from acetonitrile providing yellow solid (100 mg, 74%). MS m/z: 431, 433 (M+H)$^+$.

Example 183b 2-(4-hydroxypiperidin-1-yl)-4-(3-(trifluoromethyl)phenylamino)pyrido[4,3-d]pyrimidine-5(6H)-one

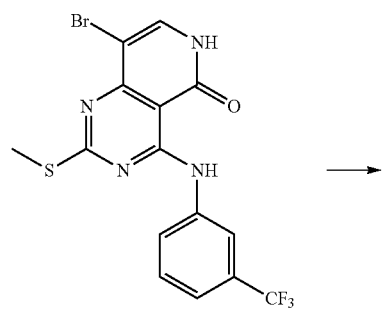

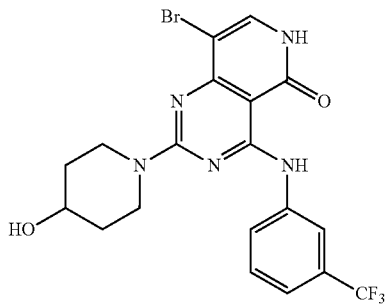

The title compound was prepared as described in Example 1g by starting from 8-bromo-2-(methylthio)-4-(3-(trifluoromethyl)phenylamino)pyrido[4,3-d]pyrimidin-5(6H)-one (60 mg, 0.26 mmol) and 4-hydroxypiperidine and continuing until the reaction yielded the title compound (40 mg, 60%)) as grey solid. MS m/z: 484 and 486 (M+H)$^+$.

Example 184

Synthesis of 8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one Compound No. 184

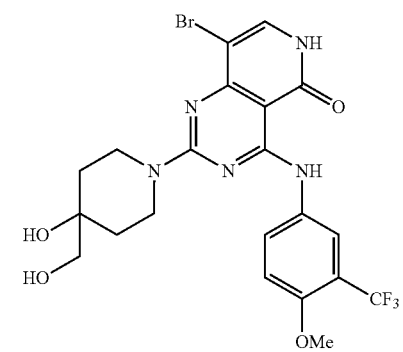

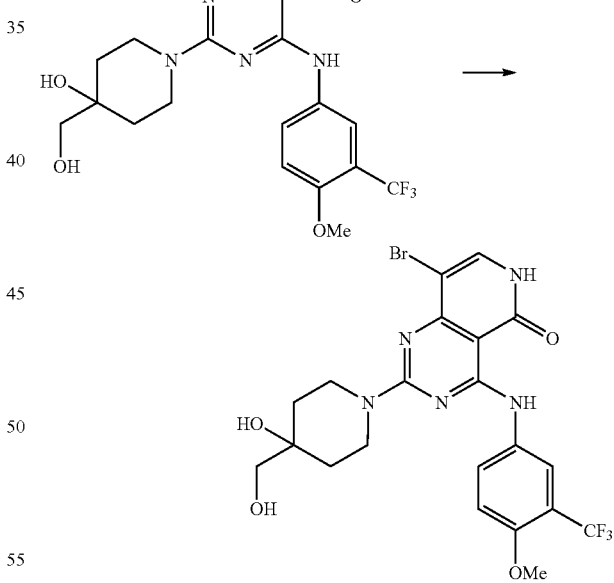

The title compound was prepared as described in Example 183a by starting from 2-(4-hydroxy-4-(hydroxylmethyl)piperidin-1-yl)-4-(4-methoxy-3-(trifluoromethyl)phenylamino)pyrido[4,3-d]pyrimidin-5(6H)-one and N-bromosuccinimide and continuing until the reaction yielded the title compound as pale brown solid. MS m/z: 544 and 546 (M+H)$^+$.

The following compounds were prepared from the procedure similar to that described in Examples 183 and 184.

| NO. | Structure | Name | Mass (M + 1) |
|---|---|---|---|
| 185 | 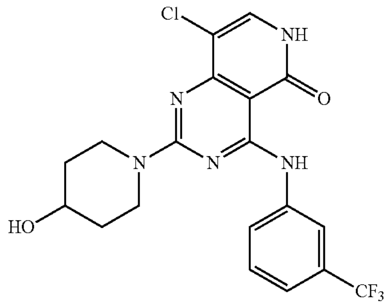 [SMILES: O=c1[nH]cc(Cl)c2nc(N3CCC(O)CC3)nc(Nc3cccc(C(F)(F)F)c3)c12] | 8-chloro-2-(4-hydroxypiperidin-1-yl)-4-(3-(trifluoromethyl)phenylamino)pyrido[4,3-d]pyrimidin-5(6H)-one | 440 |
| 186 | 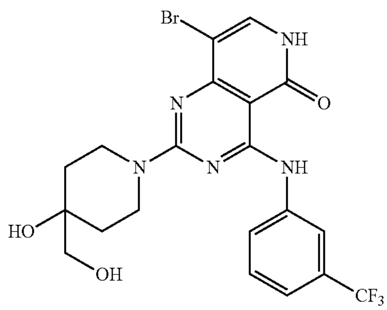 [SMILES: O=c1[nH]cc(Br)c2nc(N3CCC(O)(CO)CC3)nc(Nc3cccc(C(F)(F)F)c3)c12] | 8-bromo-2-(4-hydroxy-4-(hydroxymethyl)piperidin-1-yl)-4-(3-(trifluoromethyl)phenylamino)pyrido[4,3-d]pyrimidin-5(6H)-one | 514 |
| 187 | 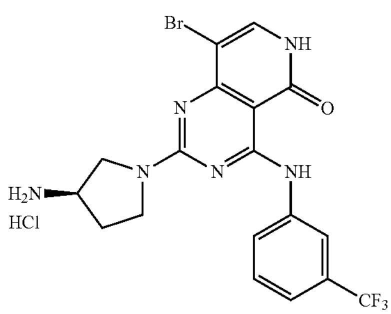 [SMILES: Cl ; N[C@@H]1CCN(c2nc(Nc3cccc(C(F)(F)F)c3)c3c(=O)[nH]cc(Br)c3n2)C1] | (R)-2-(3-aminopyrrolidin-1-yl)-8-bromo-4-(3-(trifluoromethyl)phenylamino)pyrido[4,3-d]pyrimidin-5(6H)-one hydrochloride | 469 |
| 188 | 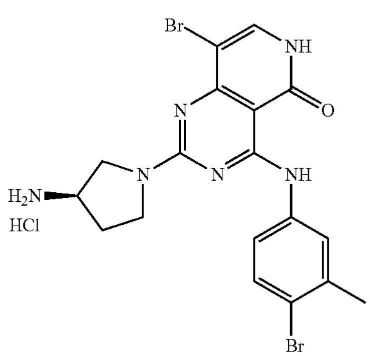 [SMILES: Cl ; Cc1cc(Nc2nc(N3CC[C@@H](N)C3)nc3c(Br)c[nH]c(=O)c23)ccc1Br] | (R)-2-(3-aminopyrrolidin-1-yl)-8-bromo-4-(4-bromo-3-methylphenylamino)pyrido[4,3-d]pyrimidin-5(6H)-one hydrochloride | 529 |

The following compounds were prepared from the procedure similar to that described for Example 183 and 184.

| NO. | Structure | Name | Mass (M + 1) |
|---|---|---|---|
| 189 | 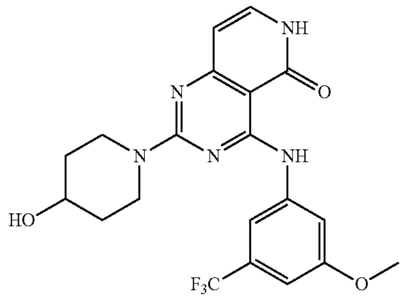 [SMILES: COc1cc(Nc2nc(N3CCC(O)CC3)nc3cc[nH]c(=O)c23)cc(C(F)(F)F)c1] | 2-(4-hydroxypiperidin-1-yl)-4-(3-methoxy-5-(trifluoromethyl)phenylamino)pyrido[4,3-d]pyrimidin-5(6H)-one | 436 |
| 190 | 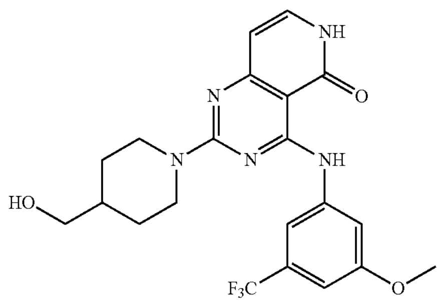 [SMILES: COc1cc(Nc2nc(N3CCC(CO)CC3)nc3cc[nH]c(=O)c23)cc(C(F)(F)F)c1] | 2-(4-(hydroxymethyl)piperidin-1-yl)-4-(3-methoxy-5-(trifluoromethyl)phenylamino)pyrido[4,3-d]pyrimidin-5(6H)-one | 450 |
| 191 | 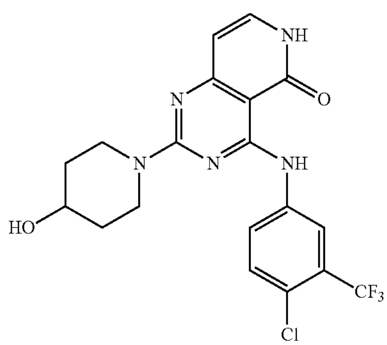 [SMILES: O=c1[nH]ccc2nc(N3CCC(O)CC3)nc(Nc3ccc(Cl)c(C(F)(F)F)c3)c12] | 4-(4-chloro-3-(trifluoromethyl)phenylamino)-2-(4-hydroxypiperidin-1-yl)pyrido[4,3-d]pyrimidin-5(6H)-one | 440 |
| 192 | 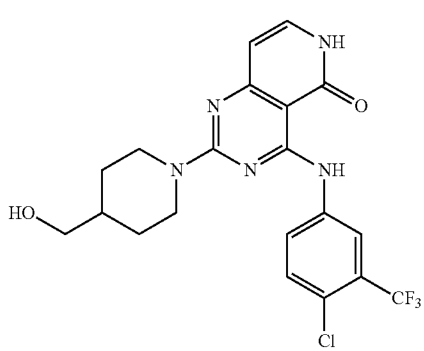 [SMILES: O=c1[nH]ccc2nc(N3CCC(CO)CC3)nc(Nc3ccc(Cl)c(C(F)(F)F)c3)c12] | 4-(4-chloro-3-(trifluoromethyl)phenylamino)-2-(4-(hydroxymethyl)piperidin-1-yl)pyrido[4,3-d]pyrimidin-5(6H)-one | 454 |

-continued

| NO. | Structure | Name | Mass (M + 1) |
|---|---|---|---|
| 193 | 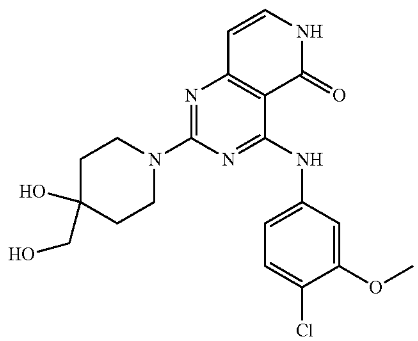 [SMILES: COc1cc(Nc2nc(N3CCC(O)(CO)CC3)nc3cc[nH]c(=O)c23)ccc1Cl] | 4-(4-chloro-3-methoxyphenylamino)-2-(4-hydroxy-4-(hydroxymethyl)piperidin-1-yl)pyrido[4,3-d]pyrimidin-5(6H)-one | 432 |
| 194 | 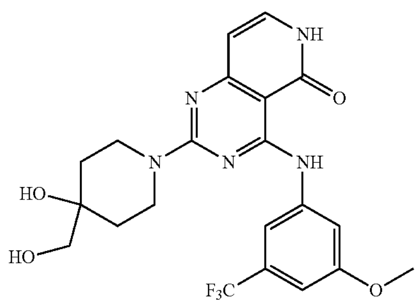 [SMILES: COc1cc(Nc2nc(N3CCC(O)(CO)CC3)nc3cc[nH]c(=O)c23)cc(C(F)(F)F)c1] | 2-(4-hydroxy-4-(hydroxymethyl)piperidin-1-yl)-4-(3-methoxy-5-(trifluoromethyl)phenylamino)pyrido[4,3-d]pyrimidin-5(6H)-one | 466 |
| 195 | 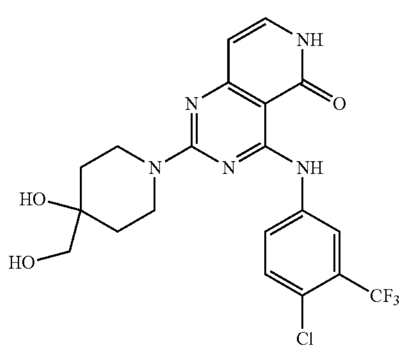 [SMILES: O=c1[nH]ccc2nc(N3CCC(O)(CO)CC3)nc(Nc3ccc(Cl)c(C(F)(F)F)c3)c12] | 4-(4-chloro-3-(trifluoromethyl)phenylamino)-2-(4-hydroxy-4-(hydroxymethyl)piperidin-1-yl)pyrido[4,3-d]pyrimidin-5(6H)-one | 470 |
| 196 | 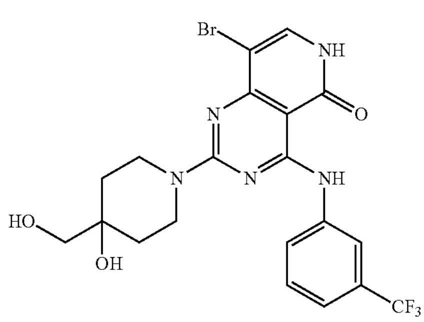 [SMILES: O=c1[nH]cc(Br)c2nc(N3CCC(O)(CO)CC3)nc(Nc3cccc(C(F)(F)F)c3)c12] | 8-bromo-2-(4-hydroxy-4-(hydroxymethyl)piperidin-1-yl)-4-(3-(trifluoromethyl)phenylamino)pyrido[4,3-d]pyrimidin-5(6H)-one | 514 |

-continued

| NO. | Structure | Name | Mass (M + 1) |
|---|---|---|---|
| 197 | 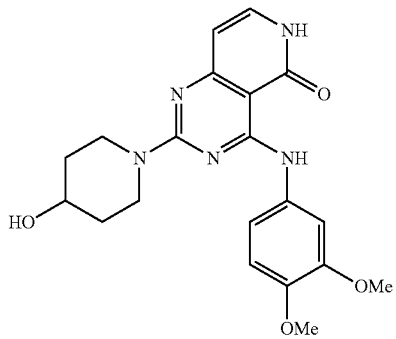 [SMILES: COc1ccc(Nc2nc(N3CCC(O)CC3)nc3cc[nH]c(=O)c23)cc1OC] | 4-(3,4-dimethoxyphenylamino)-2-(4-hydroxy-piperidin-1-yl)pyrido[4,3-d]pyrimidin-5(6H)-one | 398 |
| 198 | 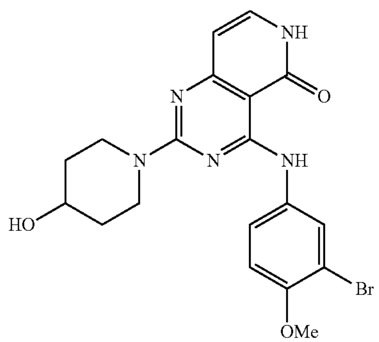 [SMILES: COc1ccc(Nc2nc(N3CCC(O)CC3)nc3cc[nH]c(=O)c23)cc1Br] | 4-(3-bromo-4-methoxyphenylamino)-2-(4-hydroxypiperidin-1-yl)pyrido[4,3-d]pyrimidin-5(6H)-one | 447 |
| 199 | 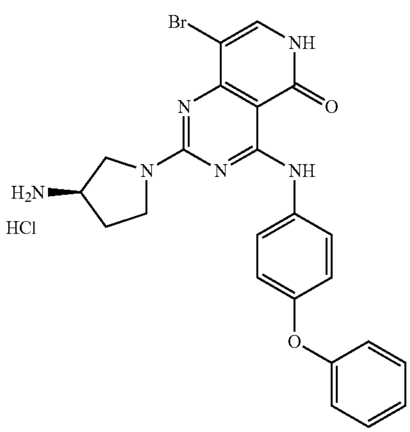 [SMILES: Cl ; N[C@@H]1CCN(c2nc(Nc3ccc(Oc4ccccc4)cc3)c3c(=O)[nH]cc(Br)c3n2)C1] | (R)-2-(3-aminopyrrolidin-1-yl)-8-bromo-4-(4-phenoxyphenylamino)pyrido[4,3-d]pyrimidin-5(6H)-one hydrochloride | 493 |
| 200 | 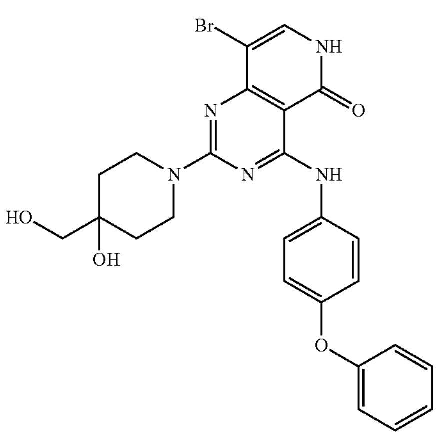 [SMILES: O=c1[nH]cc(Br)c2nc(N3CCC(O)(CO)CC3)nc(Nc3ccc(Oc4ccccc4)cc3)c12] | 8-bromo-2-(4-hydroxy-4-(hydroxymethyl)piperidin-1-yl)-4-(4-phenoxyphenylamino)pyrido[4,3-d]pyrimidin-5(6H)-one | 538 |

-continued

| NO. | Structure | Name | Mass (M + 1) |
|---|---|---|---|
| 201 | 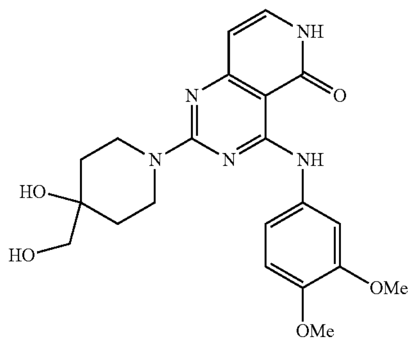 [SMILES: COc1ccc(Nc2nc(N3CCC(O)(CO)CC3)nc3cc[nH]c(=O)c23)cc1OC] | 4-(3,4-dimethoxyphenylamino)-2-(4-hydroxy-4-(hydroxymethyl)piperidin-1-yl)pyrido[4,3-d]pyrimidin-5(6H)-one | 428 |
| 202 | 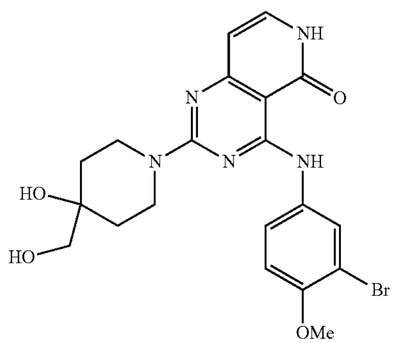 [SMILES: COc1ccc(Nc2nc(N3CCC(O)(CO)CC3)nc3cc[nH]c(=O)c23)cc1Br] | 4-(3-bromo-4-methoxyphenylamino)-2-(4-hydroxy-4-(hydroxymethyl)piperidin-1-yl)pyrido[4,3-d]pyrimidin-5(6H)-one | 477 |
| 203 | 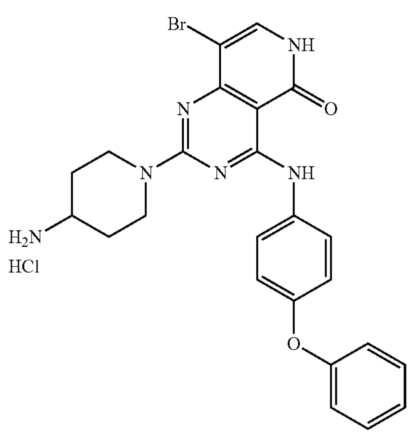 [SMILES: Cl ; NC1CCN(c2nc(Nc3ccc(Oc4ccccc4)cc3)c3c(=O)[nH]cc(Br)c3n2)CC1] | 2-(4-aminopiperidin-1-yl)-8-bromo-4-(4-phenoxyphenylamino)pyrido[4,3-d]pyrimidin-5(6H)-one hydrochloride | 507 |
| 204 | 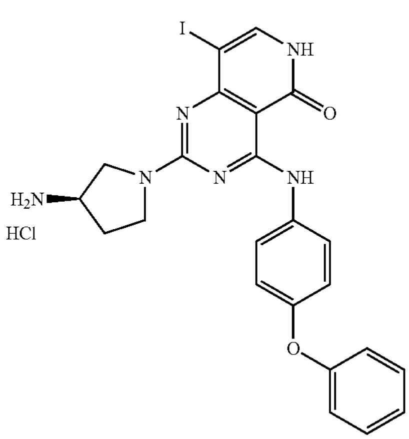 [SMILES: Cl ; N[C@@H]1CCN(c2nc(Nc3ccc(Oc4ccccc4)cc3)c3c(=O)[nH]cc(I)c3n2)C1] | (R)-2-(3-aminopyrrolidin-1-yl)-8-iodo-4-(4-phenoxyphenylamino)pyrido[4,3-d]pyrimidin-5(6H)-one hydrochloride | 541 |

-continued

| NO. | Structure | Name | Mass (M + 1) |
|---|---|---|---|
| 205 | 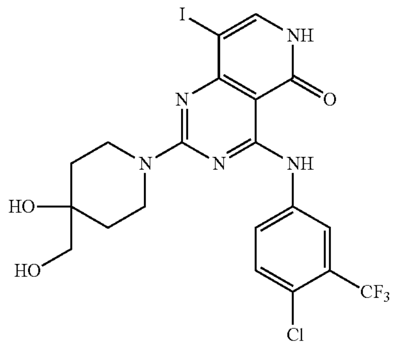 [SMILES: O=c1[nH]cc(I)c2nc(N3CCC(O)(CO)CC3)nc(Nc3ccc(Cl)c(C(F)(F)F)c3)c12] | 4-(4-chloro-3-(trifluoromethyl)phenylamino)-2-(4-hydroxy-4-(hydroxymethyl)piperidin-1-yl)-8-iodopyrido[4,3-d]pyrimidin-5(6H)-one | 596 |
| 206 | 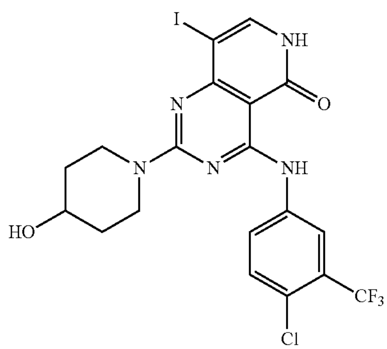 [SMILES: O=c1[nH]cc(I)c2nc(N3CCC(O)CC3)nc(Nc3ccc(Cl)c(C(F)(F)F)c3)c12] | 4-(4-chloro-3-(trifluoromethyl)phenylamino)-2-(4-hydroxypiperidin-1-yl)-8-iodopyrido[4,3-d]pyrimidin-5(6H)-one | 566 |
| 207 | 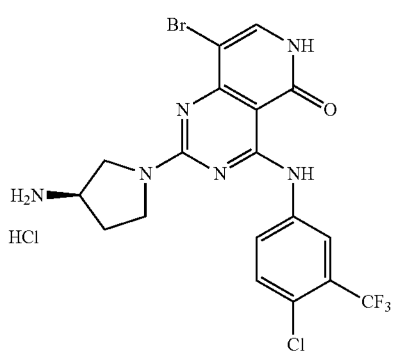 [SMILES: Cl ; N[C@@H]1CCN(c2nc(Nc3ccc(Cl)c(C(F)(F)F)c3)c3c(=O)[nH]cc(Br)c3n2)C1] | (R)-2-(3-aminopyrrolidin-1-yl)-8-bromo-4-(4-chloro-3-(trifluoromethyl)phenylamino)pyrido[4,3-d]pyrimidin-5(6H)-one hydrochloride | 509 |
| 208 | 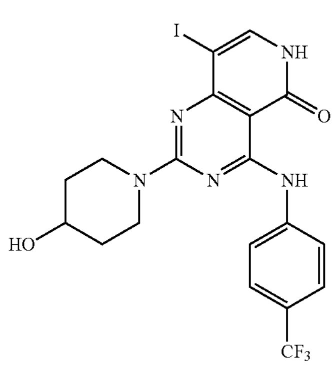 [SMILES: O=c1[nH]cc(I)c2nc(N3CCC(O)CC3)nc(Nc3ccc(C(F)(F)F)cc3)c12] | 2-(4-hydroxypiperidin-1-yl)-8-iodo-4-(4-(trifluoromethyl)phenylamino)pyrido[4,3-d]pyrimidin-5(6H)-one | 503 |

| NO. | Structure | Name | Mass (M + 1) |
|---|---|---|---|
| 209 | 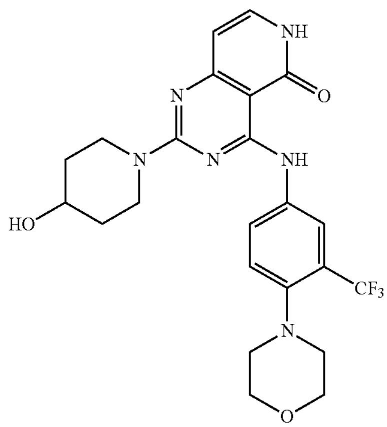 [SMILES: O=c1[nH]ccc2nc(N3CCC(O)CC3)nc(Nc3ccc(N4CCOCC4)c(C(F)(F)F)c3)c12] | 2-(4-hydroxypiperidin-1-yl)-4-(4-morpholino-3-(trifluoromethyl)phenylamino)pyrido[4,3-d]pyrimidin-5(6H)-one | 491 |
| 210 | 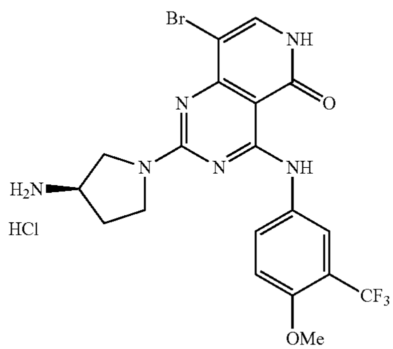 [SMILES: Cl ; COc1ccc(Nc2nc(N3CC[C@@H](N)C3)nc3c(Br)c[nH]c(=O)c23)cc1C(F)(F)F] | (R)-2-(3-aminopyrrolidin-1-yl)-8-bromo-4-(4-methoxy-3-(trifluoromethyl)phenylamino)pyrido[4,3-d]pyrimidin-5(6H)-one hydrochloride | 499 |
| 211 | 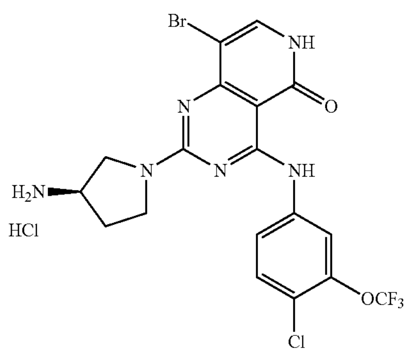 [SMILES: Cl ; N[C@@H]1CCN(c2nc(Nc3ccc(Cl)c(OC(F)(F)F)c3)c3c(=O)[nH]cc(Br)c3n2)C1] | (R)-2-(3-aminopyrrolidin-1-yl)-8-bromo-4-(4-chloro-3-(trifluoromethoxy)phenylamino)pyrido[4,3-d]pyrimidin-5(6H)-one hydrochloride | 519 |
| 212 | 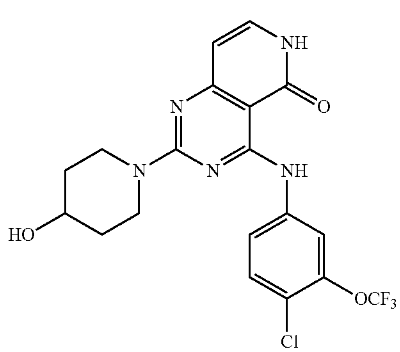 [SMILES: O=c1[nH]ccc2nc(N3CCC(O)CC3)nc(Nc3ccc(Cl)c(OC(F)(F)F)c3)c12] | 4-(4-chloro-3-(trifluoromethoxy)phenylamino)-2-(4-hydroxypiperidin-1-yl)pyrido[4,3-d]pyrimidin-5(6H)-one | 456 |

| NO. | Structure | Name | Mass (M + 1) |
|---|---|---|---|
| 213 | 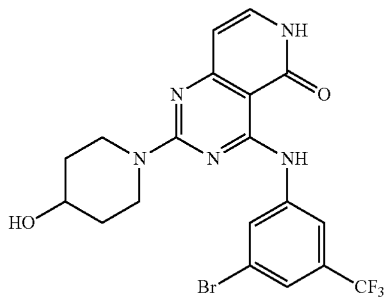 [SMILES: O=c1[nH]ccc2nc(N3CCC(O)CC3)nc(Nc3cc(Br)cc(C(F)(F)F)c3)c12] | 4-(3-bromo-5-(trifluoromethyl)phenylamino)-2-(4-hydroxypiperidin-1-yl)pyrido[4,3-d]pyrimidin-5(6H)-one | 485 |
| 214 | 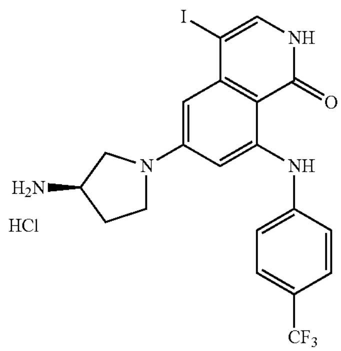 [SMILES: Cl ; N[C@@H]1CCN(c2cc(Nc3ccc(C(F)(F)F)cc3)c3c(=O)[nH]cc(I)c3c2)C1] | (R)-6-(3-aminopyrrolidin-1-yl)-4-iodo-8-(4-(trifluoromethyl)phenylamino)isoquinolin-1(2H)-one hydrochloride | 517 |
| 215 | 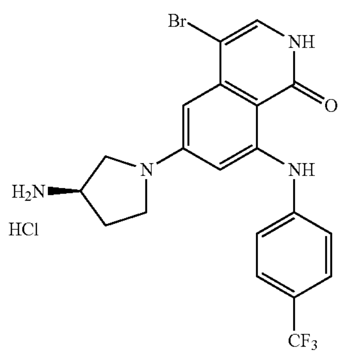 [SMILES: Cl ; N[C@@H]1CCN(c2cc(Nc3ccc(C(F)(F)F)cc3)c3c(=O)[nH]cc(Br)c3c2)C1] | (R)-6-(3-aminopyrrolidin-1-yl)-4-bromo-8-(4-(trifluoromethyl)phenylamino)isoquinolin-1(2H)-one hydrochloride | 471 |
| 216 | 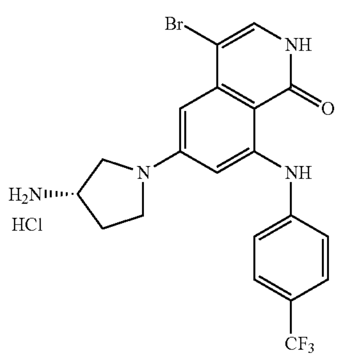 [SMILES: Cl ; N[C@H]1CCN(c2cc(Nc3ccc(C(F)(F)F)cc3)c3c(=O)[nH]cc(Br)c3c2)C1] | (S)-6-(3-aminopyrrolidin-1-yl)-4-bromo-8-(4-(trifluoromethyl)phenylamino)isoquinolin-1(2H)-one hydrochloride | 471 |

-continued

| NO. | Structure | Name | Mass (M + 1) |
|---|---|---|---|
| 217 | 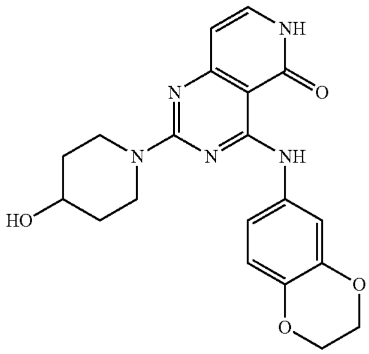 [SMILES: O=c1[nH]ccc2nc(N3CCC(O)CC3)nc(Nc3ccc4c(c3)OCCO4)c12] | 4-(2,3-dihydrobenzo[b][1,4]dioxin-6-ylamino)-2-(4-hydroxypiperidin-1-yl)pyrido[4,3-d]pyrimidin-5(6H)-one | 396 |
| 218 | 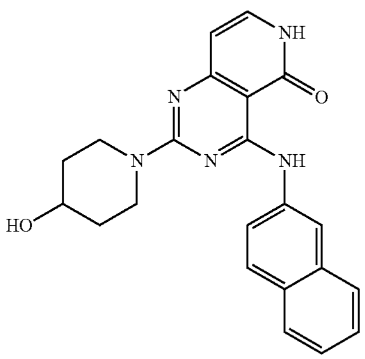 [SMILES: O=c1[nH]ccc2nc(N3CCC(O)CC3)nc(Nc3ccc4ccccc4c3)c12] | 2-(4-hydroxypiperidin-1-yl)-4-(naphthalen-2-ylamino)pyrido[4,3-d]pyrimidin-5(6H)-one | 388 |
| 219 | 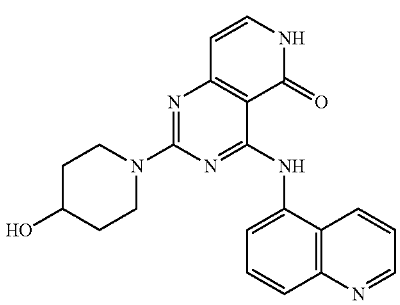 [SMILES: O=c1[nH]ccc2nc(N3CCC(O)CC3)nc(Nc3cccc4ncccc34)c12] | 2-(4-hydroxypiperidin-1-yl)-4-(quinolin-5-ylamino)pyrido[4,3-d]pyrimidin-5(6H)-one | 389 |
| 220 | 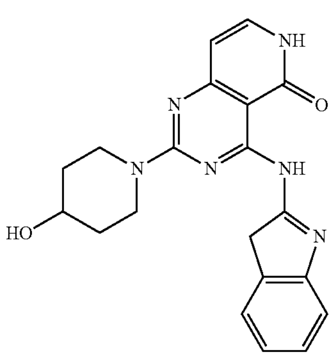 [SMILES: O=c1[nH]ccc2nc(N3CCC(O)CC3)nc(NC3=Nc4ccccc4C3)c12] | 4-(3H-indol-2-ylamino)-2-(4-hydroxypiperidin-1-yl)pyrido[4,3-d]pyrimidin-5(6H)-one | 377 |

Example 221

Synthesis of 2-(4-hydroxypiperidin-1-yl)-4-(4-phenoxyphenylamino)-8-phenylpyrido[4,3-d]pyrimidin-5(6H)-one Compound No. 221

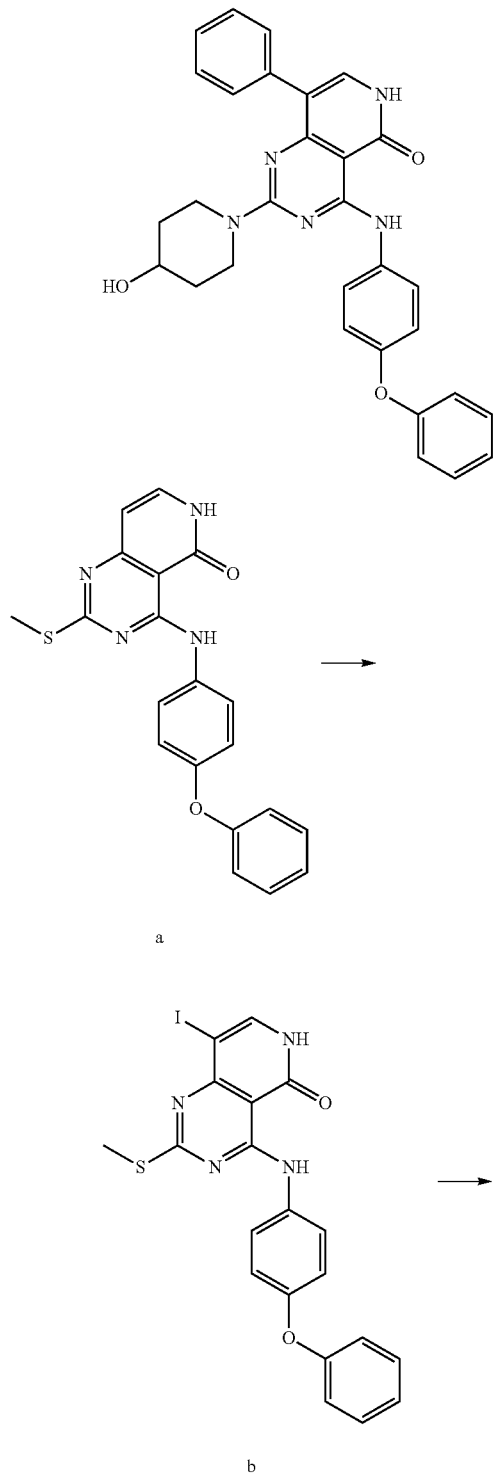

a b

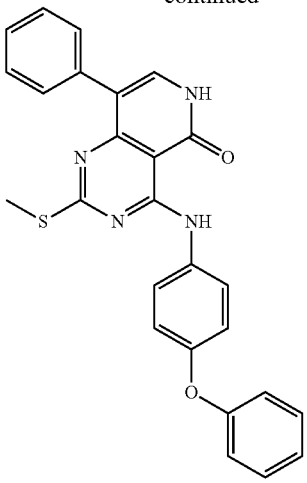

c

A 20 mL reaction vessel was charged with 2-(methylthio)-4-(4-phenoxyphenyl amino)pyrido[4,3-d]pyrimidin-5(6H)-one (221a, 182 mg, 0.48 mmol) and N-iodosuccinmide (158 mg, 0.70 mmol) in 8 mL dry DMF. The reaction mixture was stirred at 60° C. for 2 hours. The solvent was removed under reduced pressure yielding the pale brown solid (221b) after being recrystallized from acetonitrile (210 mg, 87%). A 20 mL reaction vessel was charged with 8-iodo-2-(methylthio)-4-(4-phenoxyphenylamino)pyrido[4,3-d]pyrimidin-5(6H)-one (221b, 52 mg, 0.10 mmol), benzenboronic acid (18 mg, 0.15 mmol), tetrakis(triphenyphosphine)palladium (0) (6 mg, 0.005 mmol), and 2.0 M aq. sodium carbonate solution in 6 ml dioxane. The mixture was purged with nitrogen for 30 min. Then the reaction mixture was heated at 80° C. for 3 h. The solvent was removed under reduced pressure yielding the brown residue. The residue was purified by silica gel chromatography using a gradient of 0-5% MeOH in dichloromethane yielding 221c. Then 221 was prepared as described in Example 1g starting from 2-(methylthio)-4-(4-phenoxyphenylamino)-8-phenylpyrido[4,3-d]pyrimidin-5 (6H)-one, and 4-hydroxypiperidine to give title compound. MS m/z: 506 (M+H)$^+$.

Biological Assays

1. Kinase Inhibition Assay

Compounds of the present invention were assayed to measure their capacity to inhibit a kinase panel which includes, but are not limited to, spleen tyrosine kinase (SYK), zeta-chain-associated protein kinase 70 (ZAP70), PTK2B protein tyrosine kinase 2 (PYK2), focal adhesion kinase (FAK), provirus integration of maloney kinase 1 (PIM1), rearranged during transfection kinase (RET), Fms-like tyrosine kinase 3 (FLT3), Janus kinase 2 (JAK2), and leucine-rich repeat kinase 2 (LRRK2).

FLT3 is a member of the type III receptor tyrosine kinase (RTK) family. The ligand for FLT3 is expressed by the marrow stromal cells and other cells and synergizes with other growth factors to stimulate proliferation of stem cells, progenitor cells, dendritic cells, and natural killer cells. FLT3 has been implicated in hematopoietic disorders which are pre-malignant disorders including myeloproliferative disorders, such as thrombocythemia, essential thrombocytosis (ET), angiogenic myeloid metaplasia, myelofibrosis (MF), myelofibrosis with myeloid metaplasia (MMM), chronic idiopathic myelofibrosis (IMF), and polycythemia vera (PV), the cytopenias, and pre-malignant myelodysplastic syndromes. Hematological malignancies include leukemias, lymphomas (non-Hodgkin's lymphoma), Hodgkin's disease (also called Hodgkin's lymphoma), and myeloma-for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. Aberrant expression FLT3 has been documented in both adult and childhood leukemias including acute myeloid leukemia (AML), AML with trilineage myelodysplasia (AML/TMDS), acute lymphoblastic leukemia (ALL), and myelodysplastic syndrome (MDS).

RET is the receptor for members of the glial cell line derived neurotrophic factor (GDNF) family of extracellular signalling molecules (GFL's). RET signal transducition is central to the development of normal kidneys and the enteric nervous system. RET loss of function mutations are associated with the development of Hirschsprung's disease, while gain of function mutations are associated with development of various types of cancer, including medullar thyroid carcinoma and multiple endocrine neoplasias type II and III.

Spleen tyrosine kinase (SYK) is a member of the SYK family of tyrosine kinases which are non-receptor cytoplasmic tyrosine kinases sharing a characteristic dual SH2 domain separated by a linker domain. SYK plays a role in transmitting signals from a variety of cell surface receptors including CD74, Fc Receptor, and integrins. Abnormal function of SYK has been implicated in instances of hematopoeitic malignancies. Several transforming viruses, such as Epstein Barr virus, bovine leukemia virus, and mouse mammary tumor virus, are known to contain "Immunoreceptor Tyrosine Activation Motifs" (ITAMs) that lead to activation of SYK.

ZAP70 is an enzyme belonging to the protein tyrosine kinase family, and it plays a role in thymocyte development, T-cell development, and lymphocyte activation. ZAP70 is phosphorylated on tyrosine residues upon T-cell antigen receptor (TCR) stimulation and functions in the initial step of TCR-mediated signal transduction in combination with the Src family kinases, Lek and Fyn. Mutations in this gene cause selective T-cell defect, a severe combined immunodeficiency disease characterized by a selective absence of CD8-positive T-cells.

PYK2 is a cytoplasmic protein tyrosine kinase involved in calcium-induced regulation of ion channels and activation of the map kinase signaling pathway. The encoded protein may represent an important signaling intermediate between neuropeptide-activated receptors or neurotransmitters that increase calcium flux and the downstream signals that regulate neuronal activity. The encoded protein undergoes rapid tyrosine phosphorylation and activation in response to increases in the intracellular calcium concentration, nicotinic acetylcholine receptor activation, membrane depolarization, or protein kinase C activation. Its activation is highly correlated with the stimulation of c-Jun N-terminal kinase activity. PYK2 is implicated in diseases such as osteoporosis, arthritis, myeloid leukemia, hypo-osmolality, sarcoma, blast crisis, glioma, erythroleukemia, and cancer.

FAK (encoded by the gene PTK2) is a non-receptor tyrosine kinase that integrates signals from integrins and growth factor receptor. FAK plays a role in the regulation of cell survival, growth, spreading, migration and invasion and is regulated and activated by phosphorylation on multiple tyrosine residues. Overexpression of FAK mRNA and/or protein has been implicated in cancers of the breast, colon, thyroid, and prostate. Phosphorylation of FAK is increased in malignant tissues as compared to normal tissues.

JAK1 is a member of the protein-tyrosine kinase (PTK) family and characterized by the presence of a second phosphotransferase-related domain immediately N-terminal to the PTK domain. JAK1 is involved in the interferon-alpha/beta and -gamma signal transduction pathways. The reciprocal interdependence between JAK1 and TYK2 activities in the interferon-alpha pathway, and between JAK1 and JAK2 in the interferon-gamma pathway may reflect a requirement for these kinases in the correct assembly of interferon receptor complexes.

JAK2 has been implicated in signaling by members of the type II cytokine receptor family (e.g. interferon receptors), the GM-CSF receptor family (IL-3R, IL-5R and GM-CSF-R), the gp130 receptor family (e.g. IL-6R), and the single chain receptors (e.g. Epo-R, Tpo-R, GH-R, PRL-R). JAK2 gene fusions with the TEL(ETV6) (TEL-JAK2) and PCM1 genes have been found in leukemia patients. Further, mutations in JAK2 have been implicated in polycythemia vera, essential thrombocythemia, and other myeloproliferative disorders. This mutation, a change of valine to phenylalanine at the 617 position, rendered hematopoietic cells more sensitive to growth factors such as erythropoietin and thrombopoietin.

JAK3 is a tyrosine kinase of the Janus family. JAK3 is predominantly expressed in immune cells and transduces a signal in response to its activation via tyrosine phosphorylation by interleukin receptors. Mutations that abrogate Janus kinase 3 function cause an autosomal severe combined immunodeficiency disease (SCID). Mice that do not express JAK3 have T-cells and B-cells that fail to respond to many cytokines. Since JAK3 expression is restricted mostly to hematopoietic cells, its role in cytokine signaling is thought to be more restricted than other JAKs. JAK3 is involved in signal transduction by receptors that employ the common gamma chain (γC) of the type I cytokine receptor family (e.g. IL-2R, IL-4R, IL-7R, IL-9R, IL-15R, and IL-21R).

Provirus Integration of Maloney Kinase (PIM-Kinase) was identified as one of the frequent proto-oncogenes capable of being transcriptionally activated by Maloney retrovirus integration event in mice, causing lymphomas in affected mice. PIM 1, 2 and 3 are serine/threonine kinases normally function in survival and proliferation of hematopoietic cells in response to growth factors and cytokines. Transgenic mice overexpressing PIM1 or PIM2 show increased incidence of T-cell lymphomas, while overexpression in conjunction with c-myc is associated with incidence of B-cell. Aberrent PIM expression has been reported in many human malignancies including prostate cancer, hepatocellular carcinoma, and pancreatic cancer. PIM kinases are involved in the early differentiation process of Helper T-cells, which coordinate the immunological response in autoimmune diseases, allergic reaction and tissue transplant rejection. In addition to a potential role in cancer treatment and myeloproliferative diseases, an inhibitor of PIM can be useful to control expansion of immune cells in other pathologic condition such as autoimmune diseases, allergic reactions and in organ transplantation rejection syndroms.

Methods

Inhibition of Enzymatic SYK, ZAP70, PYK2, FAK, PIM1, RET, FLT3, JAK2 and LRRK2 Kinase Activity Compounds of the invention were initially diluted to 10 mM in 100% DMSO (CALBIOCHEM™) for storage and made into kinase buffer solution to create a compound concentration ranging from 1 uM and 10 uM. Serial dilutions of compounds of the invention were dispensed into a 96-well plate (GREINER BIOSCIENCES™) at 6 µL each. Purified full-length human SYK, ZAP70, PIM1, PYK2 and truncated human FAK, RET, FLT3, JAK2, and LRRK2 (CARNA BIOSCIENCES™) were diluted in kinase buffer and added to the compound solutions and pre-incubated for 30 minutes at room temperature (1 hour for PYK2). Next, ATP (TEKNOVA™) and substrate solution (suggested manufacture substrates of PerkinElmer™, for example, Ulight™-TK peptide for SYK, Ulight™-PolyGT for ZAP70, FAK, and PYK2, and Ulight™-CREBtide for PIM1 (PERKINELMER™)) was added (12 uL each) to the wells containing the compound solution and enzyme. The reaction mixture was incubated for 1 hour (2 hours for PYK2). Following the incubation, the stop solution made with EDTA, water, and Lance detection buffer (PERKINELMER™) was added (12 µL each) to stop phosphorylation. Following the addition of the stop solution and 5 minutes of shaking, the detection solution containing the Europium-labeled antibody (suggested manufacture substrates of PerkinElmer™, for example, PT66 for SYK, ZAP70, PYK2, and FAK, and Anti-Creb for PIM1), water, and Lance detection buffer was added (12 µL each) to the reaction mixture and incubated again for 50 minutes. Substrate phosphorylation was a function of the 665 nm emission measured following the addition of the detection solution and 50 minutes of incubation.

Results

Compounds of Formula (I) exhibited useful pharmacological properties. As used herein, zero % inhibition indicates no inhibition on the kinase activity (e.g., as seen in control treated with no inhibitor), whereas 100% inhibition indicates complete inhibition of the kinase activity.

Compounds of Formula (I) exhibited various levels of inhibition of the protein kinases on the panel. Certain compounds exhibited percentage inhibition of greater than 80% against one or more of the kinase at 1 µM concentration as shown in Table 2.

For example, Compound 6 of Formula (I), namely, 2-(4-hydroxypiperidin-1-yl)-4-(3-(trifluoromethyl)phenylamino)pyrido[4,3-d]pyrimidine-5(6H)-one, was shown to inhibit the kinase activity of SYK (88%), Zap70 (49%), PYK2 (83%), FAK (78%) and PIM1 (32%) at a concentration of 1 µM and that of RET (IC50, 94.2 nM) and LRRK2 (IC50, 54 nM; see Table 2). Table 2 illustrates the percentage/molar inhibition of SYK, ZAP70, PYK2, FAK, PIM1, RET, FLT3, JAK2 and LRRK2 by the representative compounds of Formula (I).

TABLE 2

Inhibition Activity of Various Kinases

| Compound no. | SYK | ZAP70 | PYK2 | FAK | PIM1 |
|---|---|---|---|---|---|
| 6 | 88% | 49% | 83% | 78% | 32% |
| 7 | 92.6% | 42.0% | 84.9% | 83.5% | 51.4% |
| 9 | 84% | 32% | 89% | 83% | 64% |
| 84 | 95.7% | 54.6% | 92.8% | 92.9% | 71.2% |
| 100 | 37.7% | 9% | 88.4% | 21.9% | n.d. |
| 101 | 90% | 45% | 85% | 77% | 61% |
| 126 | 95.1% | 49.3% | 39.5% | 80.8% | 12.7% |
| 151 | 8.2 nM | n.d. | 90.2 nM | 216.9 nM | n.d. |
| 152 | 2.7 nM | n.d. | 84.3 nM | 337.1 nM | n.d. |
| 168 | 3% | 6.2% | 1% | 4.9% | 7.3% |
| R406 | 96.8% | 58.5% | 74.3% | 46.5% | n.d. |

| | RET | FLT3 | JAK2 | LRRK2 |
|---|---|---|---|---|
| 1 | 200.2 nM | 242.1 nM | 59.4 nM | n.d. |
| 2 | 363.2 nM | 367.6 nM | 73.8 nM | n.d. |
| 6 | 94.2 nM | n.d. | n.d. | 54 nM |
| 8 | 2.6 nM | 0.2 nM | 12.7 nM | n.d. |
| 102 | n.d. | n.d. | n.d. | 325 nM |
| 125 | 3.4 nM | 0.6 nM | 24.9 nM | n.d. |
| 134 | 7.3 nM | n.d. | 3.7 nM | n.d. |
| 136 | 1.3 nM | 0.1 nM | 3.9 nM | n.d. |
| 137 | 5.8 nM | 12.4 nM | 1.6 nM | n.d. |
| 139 | 4.1 nM | 9.1 nM | 1.6 nM | n.d. |
| 149 | 32.7 nM | 151.1 nM | 151 nM | n.d. |
| 150 | 115.3 nM | 106 nM | 65.3 nM | n.d. |
| 178 | 7.5 uM | 4.8 uM | n.d. | n.d. |
| Staurosporine | 2.2 nM | 0.2 nM | 0.3 nM | 7.8 nM |

* n.d., not determined

2. Tumor Necrosis Factor (TNF)-α Release Assay

Compounds of the invention are tested for their effects on TNF-α release in human acute monocytic leukemia cell line (THP-1) to illustrate efficacy of the invention at the cellular level. TNF-α is a cytokine involved in systemic inflammation and is a member of a group of cytokines that stimulate the acute phase reaction. The primary role of TNF-α is in the regulation of immune cells. TNF-α is known to induce apoptotic cell death and inflammation and to inhibit early tumorigenesis and viral replication. Dysregulation and, in particular, overproduction of TNF-α have been implicated in a variety of human diseases, autoimmune disease, inflammation, arthritis, cancer and many other diseases associated TNF-α dysregulation.

Production or release of TNF-α is controlled by type of stimulus to which the cell responds. SYK activity is involved in mediating TNF-α production. When stimulated by IgG, cells increase TNF-α production in a SYK dependent manner (i.e., the SYK dependent pathway). However, when stimulated by lipopolysaccharide (LPS), they produce TNF-α in a SYK independent manner.

Methods

Compounds of the invention were tested for their TNF-α release effect on THP-1 cells. For SYK dependent TNF-α release assay (i.e., via IgG stimulation), THP-1 cells derived from human monocytic cells were obtained from the American Type Culture Collection (ATCC, Manassas, Va.). This cell line was maintained with an Roswell Park Memorial Institute (RPMI) medium (GIBCO™) containing 10 fetal bovine serum (FBS; GIBCO™) and 0.05 mM 2-mercaptoethanol. The THP-1 cells were seeded at $1 \times 10^5$ cells/100 µL/well into human IgG (10 m/well, INVITROGEN™)-coated 96 well culture plate, and serially diluted compound was then added. After an 18-hour incubation period at 37° C., supernatants were collected for the determination of the TNF-α level by enzyme-linked immunosorbent assay (ELISA), and the remaining cells were subjected to an MTT (yellow tetrazolium salt) assay to determine the cytotoxic effects of compound.

For SYK independent TNF-α release assay (i.e., via lipopolysaccharide (LPS)-stimulation), THP-1 cells derived from human monocytic cells were obtained from the American Type Culture Collection (ATCC, Manassas, Va.). This cell line was maintained with an RPMI medium (GIBCO™) containing 10 fetal bovine serum (FBS, GIBCO™) and 0.05 mM 2-mercaptoethanol. The THP-1 cells were seeded at $1\times10^5$ cells/100 μL/well into 96-well culture plates, and treated with lipopolysaccharide (1 μg/ml), and serially diluted compound was then added. After an 18-hour incubation period at 37° C., supernatants were collected for the determination of the TNF-α level by ELISA, and the remaining cells were subjected to an MTT assay to determine the cytotoxic effects of compound.

Results

Compounds of Formula (I) exhibited useful pharmacological properties. As used herein, control used without the presence of an inhibitor indicates zero inhibition of TNF-α release.

In certain embodiments, compounds of Formula (I) exhibited a percentage inhibition of greater than 50 at 0.3 μM concentration in a SYK dependent manner (e.g., IgG stimulation). Specifically, at 0.3 μM concentration, Compounds 6 and 151 of the present invention exhibited a percentage inhibition greater than those exhibited by R406, a widely known kinase inhibitor, in SYK dependent TNF-α release assay (i.e., IgG stimulated release). Furthermore, Compound 6 of the present invention exhibited a percentage inhibition greater than or equal to those exhibited by dexamethasone, a well known inhibitor of TNF-α, in SYK independent TNF-α release assay (i.e., LPS stimulated release).

For example, Compound 152 of Formula (I), 2-(4-hydroxy-4-(hydroxymethyl)piperidin-1-yl)-4-(4-methoxy-3-(trifluoromethyl)phenylamino)pyrido[4,3-d]pyrimidin-5 (6H)-one (see table 3, Compound 151) exhibited a higher percentage inhibition of TNF-α release in a SYK dependent manner at a concentration of 0.3 μM. The percentage inhibition data of the representative compounds of Formula (I) is shown in Table 3.

TABLE 3

Inhibition of TNF-α Release

| Compound no. | IgG stimulation | | LPS stimulation | |
| --- | --- | --- | --- | --- |
| | At 0.3 μM | At 1 μM | At 0.3 μM | At 1 μM |
| 6 | 51.9 | 83.0 | 58.0 | 68.9 |
| 152 | 80.5 | 82.9 | n.d. | n.d. |
| R406 | 49.9 | 87.4 | n.d. | n.d. |
| Dexamethasone | n.d. | n.d. | n.d. | 68.4 |

* n.d.; not determined

3. Cell Viability Assay: RET Inhibition

Compounds of the invention are tested for their effects on cell viability in various human cancer cell lines such as MTC-TT to illustrate efficacy of the invention.

The RET proto-oncogene encodes a receptor tyrosine kinase for members of the glial cell line-derived neurotrophic factor family of extracellular signaling molecules. RET loss of function mutations are associated with the development of Hirschsprung's disease, while gain of function mutations are involved in the development of various types of human cancer, including medullary thyroid carcinoma, multiple endocrine neoplasias type 2A (MEN2A) and 2B (MEN2B), phaeochromocytoma and parathyroid hyperplasia.

Methods

In order to address RET dependent cell viability, the medullary thyroid carcinoma cell line, MTC-TT representing MEN2A was utilized to test compounds of the invention. MTC-TT were cultured at RPMI containing 15 bovine calf serum (Hyclon™ of Thermo™) and supplemented with 2 mM L-Glutamine. The cells were grown at a density of $5\times10^4$ cells/100 μL/well in duplicate in 96-well plates for one day and treated with different concentrations of test compound. Cell viability for MTC-TT two days after drug treatment was measured by Cell Titer 96 Aqueous One Solution Reagent (Promega™) according to the manufacture instructions. The IC50 value of test compound was calculated at Gradpad Prism 5 unless specified otherwise.

Results

As used herein, control used without the presence of an inhibitor indicates 50 inhibition concentration (IC50) of cell viability.

Compounds of Formula (I) exhibited an inhibition range greater than 100 nM at IC50 concentration. Specially, Compounds 8 and 136 of the present invention exhibited an inhibition level greater than those exhibited by Vandetinib and Sunitinib, a widely known kinase inhibitor, in RET induced cancer cell line.

For example, Compound 8 of Formula (I), (S)-2-(pyrrolidin-3-ylamino)-4-(4-(trifluoromethyl)phenylamino)pyrido[4,3-d]pyrimidin-5(6H)-one hydrochloride, (see table 4) exhibited 6 time higher inhibition in IC50 measurement than those appeared by Vandetanib (AstraZeneca™) and Sunitinib (Pfizer™), which are an antagonist of the vascular endothelial growth factor receptor (VEGFR) and the epidermal growth factor receptor (EGFR). The IC50 inhibition data of the representative compounds of Formula (I) of the present invention is shown in Table 4.

TABLE 4

Cell Viability by Inhibiting RET kinase

| Compound no. | MTC-TT (IC50 nM) |
| --- | --- |
| 8 | 14 |
| 136 | 33 |
| Vandetanib | 81.6 |
| Sunitinib | 116.7 |

4. Cell Viability Assay: Inhibition of FLT3-ITD-Positive Cells

Compounds of the invention are tested for their effects on inhibition of FLT3-ITD in human acute leukemia cell line (MV4-11). FLT3 is primarily expressed in immature hematopoietic progenitor as well as in mature myeloid cells. It belongs to type III receptor tyrosine kinase (RTK) family including KIT, FMS, and PDGFR. It is activated by binding to FL, which leads to increased kinase activity and activation of downstream signaling pathway including STAT5, Ras, and PI3Kinase.

The FLT3-ITD (Internal Tandem Duplication) mutations in the juxtamembrane domain are the most frequently observed molecular defect in acute myelogenous leukemia (AML). The FLT3-ITD induces ligand-independent dimerization, autophosphorylation and constitutive activation, and is able to transform hematopoietic cells. Clinically, FLT3-ITD is known to increased leukocytosis, increased blast count, increased relapse rate, decreased disease-free survival, and poor overall survival. Therefore, FLT3-ITD is an attractive molecular target for AML therapy.

Methods

Compounds of the invention were tested for cell viability effect on MV4-11 cells. For cell viability assay, MV4-11 cells expressing human FLT3-ITD were obtained from the American Type Culture Collection (ATCC, Manassas, Va.). This cell line was maintained with an Roswell Park Memorial Institute (RPMI) medium (HyClone™) containing 10 bovine calf serum (BCS; Hyclone™) supplemented iron. The MV4-11 cells were seeded at $2\times10^4$ cells in 96-well culture plates, and serially diluted compound was then added. After a 72-hour incubation period at 37° C., cell viability was measured using the ATPLite 1 step assay (Perkin-Elmer™) that is based on the quantification of ATP from viable cells. CellTiter Aqueous assay (Promega™) was also performed in parallel as an orthogonal assay. $IC_{50}$ values were calculated using nonlinear regression and defined as the concentration needed for a 50 reduction in luminescence or absorbance treated versus untreated control cells (Prism™ Software).

Results

Compounds of Formula (I) exhibited an inhibition of greater than 10 nM at IC50 concentration. Specially, Compounds 8 and 136 of the present invention exhibited an inhibition level greater than those exhibited by Vandetinib and Sunitinib in FLT3 ITD induced cancer cell line.

For example, Compound 8 of Formula (I), (S)-2-(pyrrolidin-3-ylamino)-4-(4-(trifluoromethyl)phenylamino)pyrido[4,3-d]pyrimidin-5(6H)-one hydrochloride, exhibited 10-30 time higher inhibition in IC50 than those appeared by Sunitinib (Pfizer) and PKC-412 (Novartis), widely known antagonists of the vascular endothelial growth factor receptor (VEGFR) and the epidermal growth factor receptor (EGFR). The IC50 inhibition data of the representative compounds of Formula (I) (e.g., Compound 6 and 136) are shown in Table 5.

TABLE 5

Cell Viability by FLT3-ITD Induced Cancer Cell Line

| Compound no. | MV-4-11 (IC50 nM) |
|---|---|
| 8 | 0.1 |
| 136 | 0.1 |
| Sunitinib | 3.8 |
| PKC-412 | 11.7 |

5. Cell Viability Assay: JAK2 Inhibition

Compounds of the invention are tested for their effects on JAK2 inhibition in human erythroleukemia cell line (HEL) to illustrate efficacy at the cellular level. The Janus-associated kinase (JAK) family, comprised of four different protein tyrosine kinases JAK1, JAK2, JAK3, and TYK2, plays an important role in cellular survival, proliferation, and differentiation. A unique mutation in the JAK2 gene encoding a valine-to-phenylalanine substitution, V617F, results in constitutive kinase activity and promotes deregulated hematopoiesis. JAK2 V617F is frequently detected in myeloproliferative disorders (MPDs), a group of clonal hematopoietic stem cell disorders that include polycythemia vera (PV), essential thrombocythemia (ET), and idiopathic myelofibrosis (IMF), all of which have the potential to transform to acute myeloid leukemia. JAK2 V617F is constitutively phosphorylated and able to activate downstream signaling in the absence of cytokine stimulation.

JAK2 is also a key mediator of signaling, downstream of a variety of cytokine and growth factor receptors. In particular, JAK2 phosphorylate the signal transducers and activators of transcription (STAT) family of proteins. Once phosphorylated, STATs dimerize and translocate to the nucleus where they bind DNA and regulate expression of target genes. JAK2/STAT signaling has been implicated in driving both cell cycle regulation and anti-apoptotic pathways.

Methods

Compounds of the invention were tested for cell viability effect on HEL cells. For cell viability assay, HEL cells expressing human JAK2 V617F were obtained from the American Type Culture Collection (ATCC, Manassas, Va.). This cell line was maintained with an Roswell Park Memorial Institute (RPMI) medium (HyClone™) containing 10 bovine calf serum (BCS; Hyclone™) supplemented iron. The HEL cells were seeded at $2\times10^4$ cells in 96 well culture plates, and serially diluted compound was then added. After a 72-hour incubation period at 37° C., Cell viability was measured using the ATPLite 1 step assay (Perkin-Elmer™) that is based on the quantification of ATP from viable cells. CellTiter Aqueous assay (Promega™) was also performed in parallel as an orthogonal assay. $IC_{50}$ values were calculated using nonlinear regression and defined as the concentration needed for a 50 reduction in luminescence or absorbance treated versus untreated control cells (Prism™ Software).

Results

Compounds of Formula (I) exhibited an inhibition of greater than 10 nM at IC50 concentration. Specially, compounds 137 and 139 of the present invention exhibited an inhibition level greater than those exhibited by Sorafenib (Bayer), a known kinase inhibitor of Raf, VEGFR and PDGFR in cancer cell line.

For example, Compound 139, 2-(4-(hydroxymethyl)piperidin-1-yl)-4-(4-morpholinophenylamino)pyrido[4,3-d]pyrimidin-5(6H)-one, (see table 6, compound 139) exhibited about 10 time higher inhibition in terms of IC50 measurement than those appeared by Sorafenib (Bayer). The IC50 inhibition data of the representative compounds of Formula (I) of the present invention is shown in Table 6.

TABLE 6

Cell Viability by Inhibiting JAK2 kinase

| Compound no. | HEL (IC50 nM) |
|---|---|
| 139 | 152 |
| 137 | 89 |
| Sorafenib | >1000 |

6. Neuroprotection from LRRK2-Mediated Dopaminergic Cell Death by Inhibition of LRRK2

Parkinson's disease (PD) is a progressive neurodegenerative disease occurring in about 1 of the population over 65 years old. The degeneration of dopaminergic neurons in the substantia nigra is a major PD pathologic phenotype, resulting in decreased dopamine secretion. During the last decade, more than ten PARK loci were mapped and several genes such as LRRK2, α-synuclein, PINK1, Parkin and DJ-1, have been identified as genes corresponding to these PARK loci.

LRRK2 has been recently identified as a PD causative gene corresponding to the PARK8 locus. LRRK2 is particularly important because symptoms of PD caused by LRRK2 mutations are the most similar to that of idiopathic PD cases. The protein is present largely in the cytoplasm, but also associates with the mitochondrial outer membrane. Expression of mutant LRRK2 induced apoptotic cell death in neuroblastoma cells and in mouse cortical neurons. Some mutations in LRRK2, such as G2019S, have been shown to be associated with PD.

Methods

SN4741, a murine dopaminergic cell line were cultured in DMEM containing 10 FBS at 37° C., respectively. SN4741 cells ($1.5 \times 10^4$/well) were seeded in 48 well plates 1 day before transient transfection with 1 μg of the pcDNA3.1 plasmids of either vector, LRRK wildtype cDNA, LRRK G2019S cDNA, by standard $CaCl_2$ precipitation. Two days after transfection, cells were treated with 100 μM hydrogen peroxide for 1 day and cell viability was measured by crystal violet assay. For compound treatment, the test compounds were added at 0.05 μM, 0.5 μM and 5 μM and the cells were incubated for 1 hour prior to the addition of hydrogen peroxide.

Results

SN4741 cells were transfected with plasmids containing the LRRK2 wild-type or G2019S and incubated them for 2 days followed by addition of 100 μM of hydrogen peroxide for 24 h to sensitize them to oxidative stress. Cell survival was assessed using the crystal violet. As shown in Table 7, after hydrogen peroxide treatment, about 49-51 of cell death in cells transfected with empty vector compared to cells not subjected to oxidative stress. Cells over-expressing LRRK2 wild-type and G2019S showed increased cell death by 35.7-40.4 and 29.1-30.8, respectively, consistent with the previous data that combination of either LRRK2 wild-type or G2019S expression with oxidative stress synergistically increased cell death, with the strongest effect being observed with G2019S.

As shown in Table 7, Compound 6 of Formula (I), which is 2-(4-hydroxypiperidin-1-yl)-4-(3-(trifluoromethyl)phenylamino)pyrido[4,3-d]pyrimidine-5(6H)-one, and Compound 102, which is 4-(3,5-bis(trifluoromethyl)phenylamino)-2-(4-hydroxypiperidin-1-yl)pyrido[4,3-d]pyrimidin-5(6H)-one, exhibited increased protective effects against LRRK2-associated cell death in SN4741 cells overexpressing either LRRK2 wild-type or LRRK2 G2019S at 0.05 uM and higher as compared with those observed with vector control, DMSO, or $H_2O_2$ controls.

TABLE 7

Percent Cell Death

|  |  | Compounds | |
| --- | --- | --- | --- |
|  | Concentration | 102 | 6 |
| Vector | DMSO | 49.0 | 51.7 |
|  | 0.05 uM | 50.0 | 54.2 |
|  | 0.5 uM | 54.4 | 57.5 |
|  | 5 uM | 50.5 | 42.5 |
| LRRK2 WT | DMSO | 40.4 | 35.7 |
|  | 0.05 uM | 49.9 | 62.2 |
|  | 0.5 uM | 55.3 | 62.2 |
|  | 5 uM | 46.5 | 49.7 |
| LRRK2 G2019S | DMSO | 29.4 | 29.1 |
|  | 0.05 uM | 54.9 | 53.5 |
|  | 0.5 uM | 56.0 | 56.9 |
|  | 5 uM | 44.0 | 45.8 |
| $H_2O_2$ Control | N.T |  | 51.3 |
|  | DMSO |  | 50.6 |

N.T; $H_2O_2$ treatment only without compound treatment

7. In Vitro Kinase Inhibition

Up to 518 different kinases have been identified in humans. They act on small molecules such as lipids, carbohydrates, amino acids, and nucleotides. To determine the scope of inhibitory effects of a representative compound of Formula (I) on known kinases, Compound 6 was tested against 104 commercially available kinases (Ambit Biosciences™) in vitro. 104 kinases included ABL1(E255K)-phosphorylated, ABL1(T315I)-phosphorylated, ABL1-phosphorylated, ACVR1B, ADCK3, AKT1, AKT2, ALK, AURKA, AURKB, AXL, BMPR2, BRAF, BRAF(V600E), BTK, CDK11, CDK2, CDK3, CDK7, CDK9, CHEK1, CSF1R, CSNK1D, CSNK1G2, DCAMKL1, DYRK1B, EGFR, EGFR(L858R), EPHA2, ERBB2, ERBB4, ERK1, FAK, FGFR2, FGFR3, FLT1, FLT3, FLT4, GSK3B, IGF1R, IKK-α, IKK-β, INSR, JAK2(JH1domain-catalytic), JAK3(JH1domain-catalytic), JNK1, JNK2, JNK3, KIT, KIT(D816V), KIT(V559D, T670I), LKB1, LRRK2, LRRK2(G2019S), MAP3K4, MAPKAPK2, MARK3, MEK1, MEK2, MET, MKNK1, MKNK2, MLK1, MTOR, p38-alpha, p38-beta, PAK1, PAK2, PAK4, PCTK1, PDGFRA, PDGFRB, PDPK1, PIK3C2B, PIK3CA, PIK3CG, PIM1, PIM2, PIM3, PKAC-alpha, PLK1, PLK3, PLK4, PRKCE, PYK2, RAFT, RET, RIOK2, ROCK2, RSK2, SNARK, SRC, SRPK3, SYK, TAK1, TGFBR1, TIE2, TRKA, TSSK1B, TYK2(JH1domain-catalytic), ULK2, VEGFR2, YANK3 and ZAP70.

Results

Inhibition activity of Compound 6 was reported as percent control where lower numbers indicate stronger activities. Table 8 summarizes 29 different kinases whose activity was significantly inhibited by the presence of Compound 6. Conventionally, the percent control of less than 35 is deemed to be significant inhibition of kinase activity as the numeric value 35 is frequently used as a threshold.

TABLE 8

Kinase Inhibition Profile of the Percent Control Less than 35

| Kinase | % inhibition |
| --- | --- |
| ALK | 29 |
| AURKA | 31 |
| AXL | 11 |
| BMPR2 | 0 |
| CSF1R | 5.2 |
| FAK | 34 |
| FLT3 | 28 |
| JAK2 | 3 |
| JAK3 | 4.4 |
| JNK1 | 4.8 |
| JNK2 | 25 |
| JNK3 | 7 |
| KIT | 11 |
| KIT(D816V) | 9.3 |
| LKB1 | 18 |
| LRRK2 | 2.2 |
| LRRK2(G2019S) | 2.2 |
| MLK1 | 2.8 |
| PAK4 | 21 |
| PDGFRB | 19 |
| PLK4 | 13 |
| PYK2 | 32 |
| RET | 16 |
| RSK2 | 18 |
| SNARK | 3.6 |
| SRPK3 | 2.6 |
| SYK | 8.4 |
| TAK1 | 1 |
| TYK2 | 16 |

8. Growth Inhibition of Cancer Cell Lines

The compounds of the invention exhibited potent inhibition of various cancer cell lines. The National Institute of Health (NIH) 60 cell lines (U.S. Department of Health & Human Services) were used to test the compounds. The tested cancer cell lines include, for example, CCRF-CEM, HL-60 (TB), K-562, MOLT-4, RPMI-8226, SR, A549/ATCC, EKVX, HOP-62, HOP-92, NCI-H226, NCI-H23, NCI- H322M, NCI-H460, NCI-H522, COLO 205, HCC-2998, HCT-116, HCT-15, HT29, KM12, SW-620, SF-268, SF-295, SF-539, SNB-19, SNB-75, U251, LOX IMVI, MALME-3M, M14, MDA-MB-435, SK-MEL-28, SK-MEL-5, UACC-257, UACC-62, OVCAR-3, OVCAR-4, OVCAR-5, OVCAR-8, NCI/ADR-RES, SK-OV-3, 786-0, A498, ACHN, CAKI-1, RXF 393, SN12C, TK-10, UO-31, PC-3, DU-145, MCF7, MDA-MB-231/ATCC, HS 578T, 8T-549, T-47D, and MDA-MB-468.

Results

Compound 6 was tested for its potency in growth inhibition (IC50) and cytotoxicity (LC50) toward listed NIH 60 cell lines. Compound 6 exhibited potency of nM to μM concentration range. As shown in Table 9, Compound 6 repressed proliferation of cell lines associated with leukemia, lung cancer, colon cancer, CNS cancer, melanoma, ovarian cancer, renal cancer, prostate cancer, and breast cancer.

TABLE 9

Cell Viability and Inhibition by Compound 6 (Molar Concentration)

| Cancer type | Cell line | GI50 | IC50 | LC50 | TGI |
|---|---|---|---|---|---|
| Leukemia | CCRF-CEM | 2.09E−06 | 4.07E−06 | 0.0001 | 0.0001 |
| Leukemia | HL-60(TB) | 8.71E−07 | 1.86E−06 | 0.0001 | 5.01E−06 |
| Leukemia | K-562 | 3.16E−06 | 3.98E−06 | 0.0001 | 0.0001 |
| Leukemia | MOLT-4 | 2.24E−06 | 3.63E−06 | 0.0001 | 7.76E−06 |
| Leukemia | RPMI-8226 | 2.95E−06 | 5.5E−06 | 0.0001 | 9.12E−05 |
| Leukemia | SR | 7.08E−07 | 2.51E−06 | 0.0001 | 2.69E−05 |
| NSCLC | A549/ATCC | 3.80E−06 | 6.31E−06 | 0.0001 | 0.0001 |
| NSCLC | EKVX | 2.88E−06 | 7.59E−06 | 0.0001 | 1.2E−05 |
| NSCLC | HOP-62 | 4.37E−06 | 8.91E−06 | 7.94E−05 | 1.86E−05 |
| NSCLC | HOP-92 | 1.00E−04 | 0.0001 | 0.0001 | 0.0001 |
| NSCLC | NCI-H226 | 3.24E−06 | 8.32E−06 | 0.0001 | 1.78E−05 |
| NSCLC | NCI-H23 | 3.24E−06 | 6.92E−06 | 5.01E−05 | 1.38E−05 |
| NSCLC | NCI-H322M | 2.29E−06 | 2.14E−05 | 0.0001 | 2.88E−05 |
| NSCLC | NCI-H460 | 1.62E−06 | 2.4E−06 | 6.46E−05 | 1.51E−05 |
| NSCLC | NCI-H522 | 2.34E−06 | 7.59E−06 | 3.47E−05 | 0.00001 |
| Colon Cancer | COLO 205 | 3.09E−06 | 5.25E−06 | 4.57E−05 | 1.45E−05 |
| Colon Cancer | HCC-2998 | 1.12E−05 | 2.51E−05 | 0.0001 | 3.8E−05 |
| Colon Cancer | HCT-116 | 8.71E−07 | 1.32E−06 | 7.59E−05 | 1.23E−05 |
| Colon Cancer | HCT-15 | 5.37E−07 | 7.59E−07 | 0.0001 | 3.16E−05 |
| Colon Cancer | HT29 | 3.89E−06 | 7.08E−06 | 0.0001 | 9.55E−05 |
| Colon Cancer | KM12 | 1.45E−06 | 2.69E−06 | 2.4E−05 | 5.37E−06 |
| Colon Cancer | SW-620 | 1.91E−06 | 2.82E−06 | 7.41E−05 | 1.29E−05 |
| CNS Cancer | SF-268 | 3.09E−06 | 1.29E−05 | 0.0001 | 3.55E−05 |
| CNS Cancer | SF-295 | 2.95E−06 | 6.76E−06 | 5.62E−05 | 7.76E−06 |
| CNS Cancer | SF-539 | 5.25E−06 | 1.35E−05 | 0.0001 | 3.89E−05 |
| CNS Cancer | SNB-19 | 1.82E−05 | 6.46E−05 | 0.0001 | 0.0001 |
| CNS Cancer | SNB-75 | 5.75E−06 | 7.76E−05 | 0.0001 | 8.13E−05 |
| CNS Cancer | U251 | 6.17E−06 | 1.17E−05 | 0.0001 | 0.0001 |
| Melanoma | LOX IMVI | 1.41E−06 | 2.63E−06 | 9.12E−05 | 1.66E−05 |
| Melanoma | MALME-3M | 2.63E−06 | 9.77E−06 | 3.24E−05 | 7.94E−06 |
| Melanoma | M14 | 1.55E−06 | 3.31E−06 | 3.24E−05 | 8.32E−06 |
| Melanoma | MDA-MB-435 | 1.29E−06 | 2.57E−06 | 9.77E−06 | 3.55E−06 |
| Melanoma | SK-MEL-28 | 4.68E−06 | 1.1E−05 | 5.01E−05 | 1.74E−05 |
| Melanoma | SK-MEL-5 | 1.23E−06 | 2.14E−06 | 5.13E−06 | 2.51E−06 |
| Melanoma | UACC-257 | 4.27E−06 | 8.71E−06 | 4.57E−05 | 1.29E−05 |
| Melanoma | UACC-62 | 1.82E−06 | 3.98E−06 | 2.75E−05 | 6.92E−06 |
| Ovarian Cancer | OVCAR-3 | 1.35E−06 | 3.63E−06 | 4.68E−05 | 3.98E−06 |
| Ovarian Cancer | OVCAR-4 | 1.74E−06 | 9.12E−06 | 0.0001 | 3.63E−05 |
| Ovarian Cancer | OVCAR-5 | 2.82E−05 | 7.41E−05 | 0.0001 | 9.33E−05 |
| Ovarian Cancer | OVCAR-8 | 3.31E−06 | 5.01E−06 | 0.0001 | 4.07E−05 |
| Ovarian Cancer | NCI/ADR-RES | 2.34E−06 | 4.37E−06 | 0.0001 | 7.41E−06 |
| Ovarian Cancer | SK-OV-3 | 4.90E−07 | 2E−05 | 0.0001 | 0.0001 |
| Renal Cancer | 786-0 | 2.04E−06 | 8.13E−06 | 0.0001 | 0.0001 |
| Renal Cancer | A498 | 2.51E−06 | 0.0001 | 0.0001 | 0.0001 |
| Renal Cancer | ACHN | 7.08E−07 | 2.24E−06 | 0.0001 | 8.51E−05 |
| Renal Cancer | CAKI-1 | 2.82E−07 | 1.29E−06 | 0.0001 | 6.31E−06 |
| Renal Cancer | RXF 393 | 1.45E−06 | 2.14E−05 | 0.0001 | 2.34E−05 |
| Renal Cancer | SN12C | 4.07E−06 | 1.29E−05 | 0.0001 | 0.0001 |
| Renal Cancer | TK-10 | 6.03E−06 | 3.63E−05 | 0.0001 | 4.47E−05 |
| Renal Cancer | UO-31 | 7.76E−07 | 1.62E−05 | 0.0001 | 2.29E−05 |
| Prostate Cancer | PC-3 | 2.29E−06 | 4.68E−06 | 9.33E−05 | 1.29E−05 |
| Prostate Cancer | DU-145 | 1.55E−06 | 6.03E−06 | 0.0001 | 1.95E−05 |
| Breast Cancer | MCF7 | 2.82E−06 | 4.07E−06 | 0.0001 | 1.26E−05 |
| Breast Cancer | MDA-MB-231/ATCC | 1.23E−05 | 0.0001 | 0.0001 | 0.0001 |
| Breast Cancer | HS 578T | 1.95E−06 | 4.37E−05 | 0.0001 | 1.41E−05 |
| Breast Cancer | BT-549 | 1.58E−06 | 4.57E−06 | 1.41E−05 | 4.37E−06 |
| Breast Cancer | T-47D | 3.09E−06 | 8.51E−06 | 0.0001 | 2.63E−05 |
| Breast Cancer | MDA-MB-468 | 1.78E−06 | 4.68E−06 | 0.0001 | 7.08E−06 |

*NSCLC: Non-Small Cell Lung Cancer;
GI, growth inhibition;
LC, lethal concentration;
TGI, total growth inhibition.

While this invention has been particularly shown and described to example embodiments thereof, it will be understood by those skilled in the art that various changes in form and details may be made therein without departing from the scope of the invention encompassed by the appended claims.

What is claimed is:

1. A compound of Formula (I):

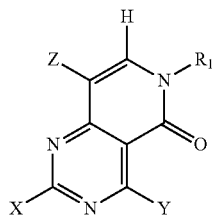

Formula (I)

wherein: (a) when $R^1$ is H and X is $NR^2R^3$ or $NR^4R^5$, then Y is $NHR^6$ and Z is selected from H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl or heteroaryl is optionally substituted with halo, alkyl, or cyano; wherein:
$R^2$ and $R^3$, taken together with the nitrogen atom to which they are bonded form:
   i) a 3-8 membered saturated or partially saturated monocyclic group having no heteroatom other than the nitrogen atom to which $R^2$ and $R^3$ are bonded, wherein said 3-8 membered saturated or partially saturated monocyclic group is independently substituted at one or more carbon atoms with 1-2 $R^7$ and optionally substituted at one or more carbon atoms with 0-4 $R^8$, wherein $R^7$ is hydroxy, heterocycloalkyl, or $NR^9R^9$ and $R^8$ is hydroxy($C_1$-$C_6$)alkyl, aryl, $COOR^9$, $(CH_2)_n NR^9R^9$, or $(CH_2)_n NR^9R^{10}$, wherein each n is independently 1, 2, or 3 and the aryl is optionally substituted with halo; or
   ii) an 8-10 membered bicyclic aryl group having 0-5 heteroatoms independently selected from nitrogen, oxygen, sulfur, sulfoxide, or sulfone;
each $R^9$ is independently selected from H, $C_1$-$C_6$ alkyl, $C_3$-$C_6$ alkynyl, $C_2$-$C_6$ alkyl cyano, $C_2$-$C_6$ alkyl sulfone, $C_3$-$C_6$ cycloalkyl sulfone, $C_2$-$C_6$ sulfonamide, $C_3$-$C_6$ cycloalkyl, $C_3$-$C_8$ heterocycloalkyl, aryl, aryl($C_1$-$C_6$) alkyl, or heteroaryl, wherein the alkyl, alkynyl, alkylcyano, alkylsulfone, sulfonamide, cycloalkyl, heterocycloalkyl, aryl, arylalkyl, or heteroaryl is optionally substituted with $R^{25}$;
$R^{10}$ is $C(O)R^9$, $COOR^9$, $C(O)NR^9R^9$, or $S(O)_n R^9$, wherein n is 1 or 2;
$R^4$ is selected from H, $C_1$-$C_6$ alkyl, or hydroxy($C_1$-$C_6$) alkyl;
$R^5$ is aryl($C_1$-$C_3$)alkyl, wherein the aryl group is independently substituted at one or more carbon atoms with 1-3 $R^{11}$, wherein $R^{11}$ is independently selected from $OR^9$, $NR^9R^9$, $NR^9COR^9$, or $NR^9S(O)_n R^9$, wherein n is 1 or 2;
$R^6$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, or heteroaryl, wherein the heterocycloalkyl, aryl, or heteroaryl is optionally substituted, wherein the heterocycloalkyl, aryl, or heteroaryl of $R^6$ is optionally substituted with an aryl selected from the group consisting of:
   i) a 5-6 membered monocyclic aryl group;
   ii) an 8-10 membered bicyclic aryl group having 0-5 heteroatoms independently selected from nitrogen, oxygen, sulfur, sulfoxide, or sulfone;
   iii) an 8-10 membered unsaturated or partially unsaturated bicyclic aryl group having 0-5 heteroatoms independently selected from nitrogen, oxygen, sulfur, sulfoxide, or sulfone; and
   iv) an 8-10 membered unsaturated or partially unsaturated bicyclic aryl group having a carbonyl, carboxamide, or sulfoxamide; or
the heterocycloalkyl, aryl, or heteroaryl of $R^6$ is optionally substituted at one or more carbon atoms with $R^{12}$, wherein each $R^{12}$ is independently selected from $C_1$-$C_6$ alkyl, $CF_3$, $OCF_3$, $S(O)_n(C_1$-$C_4)$alkyl, halo($C_1$-$C_4$) alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl ($C_1$-$C_6$)alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O)NR^{13}R^{13}$, $S(O)_n R^{13}$, $S(O)_n NR^{13}R^{13}$, or $NR^{15}R^{16}$, wherein each n is independently 1 or 2 and the alkyl, alkenyl, alkynyl, cycloalkyl, heterocycloalkyl, cycloalkenyl, aryl, arylalkyl, haloalkyl, or heteroaryl is optionally substituted with $R^{25}$, wherein the aryl and heteroaryl of $R^{12}$ is independently selected from:
   i) a 5-6 membered monocyclic aryl group;
   ii) an 8-10 membered bicyclic aryl group having 0-5 heteroatoms independently selected from nitrogen, oxygen, sulfur, sulfoxide or sulfone;
   iii) an 8-10 membered unsaturated or partially unsaturated bicyclic aryl group having 0-5 heteroatoms independently nitrogen, oxygen, sulfur, sulfoxide or sulfone; or
   iv) an 8-10 membered unsaturated or partially unsaturated bicyclic aryl group having a carbonyl, carboxamide, or sulfoxamide;
each $R^{13}$ is independently selected from H, $C_1$-$C_6$ alkyl, $C_2$-$C_6$ alkenyl, $C_3$-$C_6$ alkynyl, $C_2$-$C_6$ alkyl cyano, $C_2$-$C_6$ alkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl or heteroaryl, wherein the alkyl, alkenyl, alkynyl, alkyl cyano, alkyl sulfone, alkyl sulfonamide, cycloalkyl, heterocycloalkyl, cycloalkenyl, aryl, arylalkyl, haloalkyl, or heteroaryl is optionally substituted with $R^{25}$;
$R^{14}$ is $C(O)R^{13}$, $COOR^{13}$, $C(O)NR^{13}R^{13}$, $SO_2NR^{13}R^{13}$, or $S(O)_n R^{13}$, wherein n is 1 or 2;
$R^{15}$ and $R^{16}$, taken together with the nitrogen atom to which they are bonded, form:
   i) a 3-8 membered saturated or partially saturated monocyclic group, wherein the 3-8 membered saturated or partially saturated monocyclic group is optionally substituted with $R^{25}$;
   ii) an 8-12 membered saturated or partially saturated bicyclic group, wherein the 8-12 membered saturated or partially saturated bicyclic group is optionally substituted with $R^{25}$;
   iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or
   iv) a 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$;
(b) when $R^1$ is H and Y is $NHR^{17}$ or $R^{17}$, then X is $OR^{18}$, $NHR^{18}$, $NR^{15}R^{16}$, $NR^{18}R^{19}$, or $NR^{19}R^{20}$; and Z is H, halogen, $C_1$-$C_3$ alkyl, $C_2$-$C_4$ alkynyl, aryl, heteroaryl, or $C_3$-$C_8$ cycloalkyl, wherein the alkyl, alkynyl, cycloalkyl, aryl, or heteroaryl is optionally substituted with halo, alkyl, or cyano, wherein:
  $R^{17}$ is selected from aryl($C_1$-$C_6$)alkyl, aryl, or heteroaryl, wherein the aryl, or the heteroaryl is substituted at one or more carbon atoms with at least one $R^{21}$ and 0-2 $R^{22}$ and the aryl group of said aryl($C_1$-$C_6$)alkyl is optionally substituted with halo;
  $R^{21}$ is independently selected from OH, $CF_3$, $OCF_3$, O-aryl, or $NR^{15}R^{16}$;
  $R^{22}$ is independently H, $C_1$-$C_6$ alkyl, $CF_3$, $OCF_3$, $S(O)_n$ ($C_1$-$C_4$)alkyl, halo($C_1$-$C_4$)alkyl, $C_2$-$C_6$ alkenyl, $C_2$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, heteroaryl, halo, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O)NR^{13}R^{13}$, $S(O)_nR^{13}$, $S(O)_n$ $NR^{13}R^{13}$, $NR^{13}C(O)NR^{13}R^{13}$, $NR^{13}C(O)R^{13}$, $NR^{13}(COOR^{13})$, $NR^{13}S(O)_nR^{13}$, or $NR^{15}R^{16}$, wherein each n is independently 1 or 2 and wherein the alkyl, alkenyl, alkynyl, cycloalkyl, heterocycloalkyl, cycloalkenyl, aryl, arylalkyl, haloalkyl, or heteroaryl is optionally substituted with $R^{25}$;
  $R^{18}$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$) alkyl, hydroxy($C_2$-$C_6$)alkyl, amino($C_2$-$C_6$)alkyl, haloalkyl, or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$;
  each $R^{19}$ is independently selected from $C_1$-$C_6$ alkyl, $C_2$-$C_6$ alkenyl, $C_3$-$C_6$ alkynyl, hydroxy($C_2$-$C_6$) alkyl, amino($C_2$-$C_6$)alkyl, $C_2$-$C_6$ alkyl cyano, $C_2$-$C_6$ alkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl, or heteroaryl, wherein the alkyl, alkenyl, alkynyl, alkyl cyano, alkylsulfone, sulfonamide, cycloalkyl, heterocycloalkyl, cycloalkenyl, aryl, arylalkyl, haloalkyl, or heteroaryl is optionally substituted with $R^{25}$;
$R^{20}$ is $C(O)R^{19}COOR^{19}$, $C(O)NR^{19}R^{19}$ or $S(O)_nR^{19}$, wherein n is 1 or 2;
each $R^{25}$ is independently selected from hydroxy, hydroxy ($C_1$-$C_6$)alkyl, $C_1$-$C_6$ alkyl, $C_2$-$C_6$ alkenyl, $C_3$-$C_6$ alkynyl, $C_3$-$C_6$cycloalkyl, $C_3$-$C_8$ heterocycloalkyl, $C_4$-$C_6$ cycloalkenyl, aryl($C_1$-$C_6$)alkyl, aryl, halo, haloalkyl, oxo, oxime, $CF_3$, $SR^{13}$, $OCF_3$, $OR^{13}$, $OC(O)CH_2R^{13}$, $NR^{13}R^{13}$, $NR^{13}R^{14}$, $NHC(O)R^{13}$, $(CH_2)_nNR^{13}R^{13}$, $COOR^{13}$, CN, $C(O)R^{13}$, $C(O)CF_3$, $CONR^{15}R^{16}$, $CONH_2$, $S(O)_nR^{13}$, $S(O)_nNR^{13}R^{13}$, or $NR^{15}R^{16}$, wherein each n is independently 1 or 2 and the heterocycloalkyl is optionally substituted with $C_1$-$C_3$ alkyl; and
(c) when $R^1$ is $CH_3$, then
X is $NH_2$ or $NHR^6$,
Y is $NHR^6$ or $R^6$, and
Z is H, halogen, $C_1$-$C_3$ alkyl, $C_2$-$C_4$ alkynyl, aryl, heteroaryl, or $C_3$-$C_8$ cycloalkyl, wherein the alkyl, cycloalkyl, aryl, alkynyl, or heteroaryl is optionally substituted with halo, alkyl, or cyano, or
a pharmaceutically acceptable salt thereof;
wherein each heterocycloalkyl is independently a 3 to 8 membered ring having 1 to 3 heteroatoms in the ring selected from N, O, S, sulfone or sulfoxide.

2. The compound of claim 1, wherein $R^1$ is H and X is $NR^2R^3$.

3. The compound of claim 1, wherein $R^1$ is H and X is $NR^4R^5$.

4. The compound of claim 2, wherein $NR^2R^3$ is a 3-8 membered saturated or partially saturated monocyclic group having no heteroatom other than the nitrogen atom to which $R^2$ and $R^3$ are bonded, wherein said 3-8 membered saturated or partially saturated monocyclic group is independently substituted at one or more carbon atoms with 1-2 $R^7$ and optionally substituted at one or more carbon atoms with 0-4 $R^8$, wherein $R^7$ is hydroxy, heterocycloalkyl, or $NR^9R^9$ and $R^8$ is hydroxy($C_1$-$C_6$)alkyl, aryl, $COOR^9$, $(CH_2)_nNR^9R^9$, or $(CH_2)_n$ $NR^9R^{10}$, wherein each n is independently 1, 2, or 3 and the aryl is optionally substituted with halo.

5. The compound of claim 2, wherein $NR^2R^3$ is selected from an 8-10 membered bicyclic aryl group having 0-5 heteroatoms independently selected from nitrogen, oxygen, sulfur, sulfoxide, or sulfone.

6. The compound of claim 4, wherein the 3-8 membered saturated or partially saturated monocyclic group is substituted with hydroxy or amine.

7. The compound of claim 6, wherein the 3-8 membered saturated or partially saturated monocyclic group is azetidine, piperidine or pyrrolidine, wherein the azetidine, piperidine or pyrrolidine is independently substituted with 1-3 hydroxy or amino group and optionally and independently substituted with hydroxymethyl at the one or more carbon atoms.

8. The compound of claim 3, wherein $R^4$ is selected from H, $C_1$-$C_6$ alkyl, or hydroxy($C_1$-$C_6$)alkyl and $R^5$ is aryl($C_1$-$C_3$) alkyl, wherein the aryl group of aryl($C_1$-$C_3$)alkyl of $R^5$ is independently substituted at the one or more carbon atoms with 1-3 $R^{11}$, wherein $R^{11}$ is independently selected from $OR^9$, $NR^9R^9$, $NR^9COR^9$, or $NR^9S(O)_nR^9$, wherein n is 1 or 2.

9. The compound of claim 4, wherein $R^9$ is independently selected from H, $C_1$-$C_6$ alkyl, $C_2$-$C_6$ alkenyl, $C_3$-$C_6$ alkynyl, $C_2$-$C_6$ alkyl cyano, $C_2$-$C_6$ alkyl sulfone, $C_3$-$C_6$ alkyl sulfone, $C_3$-$C_6$ cycloalkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl, or heteroaryl, wherein the alkyl, alkenyl, alkynyl, alkyl cyano, alkyl sulfone, sulfonamide, cycloalkyl, heterocycloalkyl, cycloalkenyl, aryl, arylalkyl, haloalkyl, or heteroaryl is optionally substituted with $R^{25}$.

10. The compound of claim 2, wherein Y is $NHR^6$.

11. The compound of claim 10, wherein $R^6$ is selected from $C_1$-$C_6$ alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$.

12. The compound of claim 11, wherein the aryl of $R^6$ is an optionally substituted aryl selected from the group consisting of:
  i) a 5-6 membered monocyclic aryl group;
  ii) an 8-10 membered bicyclic aryl group having 0-5 heteroatoms independently selected from nitrogen, oxygen, sulfur, sulfoxide, or sulfone;
  iii) an 8-10 membered unsaturated or partially unsaturated bicyclic aryl group having 0-5 heteroatoms independently selected from nitrogen, oxygen, sulfur, sulfoxide or sulfone; and iv) an 8-10 membered unsaturated or partially unsaturated bicyclic aryl group having a carbonyl, carboxamide, or sulfoxamide.

13. The compound of claim 12, wherein the aryl of $R^6$ is optionally substituted at one or more carbon atoms with $R^{12}$, wherein each $R^{12}$ is independently selected from $C_1$-$C_6$ alkyl, $OCF_3$, $CF_3$, $S(O)_n(C_1$-$C_4)$alkyl, halo($C_1$-$C_4$)alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl $C_1$-$C_6$ alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O)NR^{13}R^{13}$, $S(O)_nR^{13}$, $S(O)_nNR^{13}R^{13}$, or $NR^{15}R^{16}$, wherein each n is independently 1 or 2; and wherein the alkyl, alkenyl, alkynyl, cycloalkyl, heterocycloalkyl, cycloalkenyl, aryl, arylalkyl, haloalkyl, or heteroaryl is optionally substituted with $R^{25}$.

14. The compound of claim 13, wherein $R^{12}$ is independently selected from $C_1$-$C_6$ alkyl, $CF_3$, $OCF_3$, $S(O)_n(C_1$-$C_4)$alkyl, halo($C_1$-$C_4$)alkyl, $C_2$-$C_6$ alkenyl, $C_2$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, heteroaryl, halo, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)NR^{13}R^{13}$, $S(O)_nR^{13}$, $S(O)_nNR^{13}R^{13}$, or $NR^{15}R^{16}$, wherein each n is independently 1 or 2.

15. The compound of claim 14, wherein $R^{12}$ is an aryl and the aryl is independently selected from:
   i) a 5-6 membered monocyclic aryl group;
   ii) an 8-10 membered bicyclic aryl group having 0-5 heteroatoms independently selected from nitrogen, oxygen, sulfur, sulfoxide, or sulfone;
   iii) an 8-10 membered unsaturated or partially unsaturated bicyclic aryl group having 0-5 heteroatoms independently nitrogen, oxygen, sulfur, sulfoxide, or sulfone; or
   iv) an 8-10 membered unsaturated or partially unsaturated bicyclic aryl group having a carboxamide, or sulfoxamide.

16. The compound of claim 14, wherein $R^{12}$ is $SR^{13}$, $OR^{13}$, $OC(O)R^{13}$, $NR^{13}R^{13}$, $NR^{13}R^{14}$, $COOR^{13}$, CN, $C(O)R^{13}$, $C(O)NR^{13}R^{13}$, $S(O)_nR^{13}$, $S(O)_nNR^{13}R^{13}$, or $NR^{15}R^{16}$, wherein each $R^{13}$ is independently selected from H, $C_1$-$C_6$ alkyl, $C_2$-$C_6$ alkenyl, $C_2$-$C_6$ alkynyl, $C_2$-$C_6$ alkylcyano, $C_2$-$C_6$ alkyl sulfone, $C_2$-$C_6$ sulfonamide, $C_3$-$C_6$ cycloalkyl, $C_3$-$C_8$ heterocycloalkyl, $C_4$-$C_6$ cycloalkenyl, aryl, alkoxy, aryl($C_1$-$C_6$)alkyl, haloalkyl, or heteroaryl and $R^{14}$ is $C(O)R^{13}$, $COOR^{13}$, $C(O)NR^{13}R^{13}$, $SO_2NR^{13}R^{13}$, or $S(O)_nR^{13}$, wherein n is 1 or 2 and the alkyl, alkenyl, alkynyl, alkyl cyano, alkyl sulfone, alkyl sulfonamide, cycloalkyl, heterocycloalkyl, cycloalkenyl, aryl, alkoxy, arylalkyl, haloalkyl, or heteroaryl is optionally substituted with $R^{25}$.

17. The compound claim 16, wherein $R^{12}$ is $NR^{15}R^{16}$.

18. The compound claim 17, wherein $R^{15}$ and $R^{16}$, taken together with the nitrogen atom to which they are bonded, form:
   i) a 3-8 membered saturated or partially saturated monocyclic group, wherein the 3-8 membered saturated or partially saturated monocyclic group is optionally substituted with $R^{25}$;
   ii) an 8-12 membered saturated or partially saturated bicyclic group, wherein the 8-12 membered saturated or partially saturated bicyclic group is optionally substituted with $R^{25}$;
   iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or
   iv) an 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$.

19. The compound of claim 11, wherein $R^6$ is the optionally substituted 5-6 membered monocyclic aryl group or 9-10 membered bicyclic aryl group.

20. The compound of claim 19, wherein the optionally substituted 5-6 membered monocyclic aryl group is phenyl and 9-10 membered bicyclic aryl group is naphtyl, quinolinyl, indazoyl, indolyl, or dihydrobenzodioxynyl.

21. The compound of claim 20, wherein the phenyl group is optionally substituted with 1-4 groups selected from the group consisting of methyl, methoxy, methylsulfone, amino, hydroxy, $CF_3$, $OCF_3$, halo, phenyl, phenoxy, piperazinyl, and morpholino.

22. The compound of claim 1, wherein Z is H, halo, $C_1$-$C_3$ alkyl, alkynyl or phenyl.

23. The compound of claim 1, wherein $R^1$ is H and Y is $NHR^{17}$ or $R^{17}$.

24. The compound of claim 23, wherein X is $NHR^{18}$ or $OR^{18}$.

25. The compound of claim 23, wherein X is $NR^{18}R^{19}$.

26. The compound of claim 23, wherein X is $NR^{19}R^{20}$.

27. The compound of claim 23, wherein X is $NR^{15}R^{16}$.

28. The compound of claim 23, wherein $R^{17}$ is aryl($C_1$-$C_6$) alkyl, aryl or heteroaryl, wherein the aryl or the heteroaryl of $R^{17}$ is substituted at two or more carbon atoms with at least one $R^{21}$ and 0-2 $R^{22}$, wherein $R^{21}$ is independently selected from OH, $CF_3$, $OCF_3$, O-aryl, or $NR^{15}R^{16}$ and $R^{22}$ is independently selected from H, $C_1$-$C_6$ alkyl, $CF_3$, $OCF_3$, $S(O)_n(C_1$-$C_4)$alkyl, halo($C_1$-$C_4$)alkyl, $C_2$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl $C_1$-$C_6$ alkyl, heteroaryl, halo, haloalkyl, $SR^{13}$, $OR^{13}$, $OC(O)R^{13}$, $NR^{13}R^{13}$, $NR^{13}R^{14}$, $COOR^{13}$, $NO_2$, CN, $C(O)R^{13}$, $C(O)C(O)R^{13}$, $C(O)NR^{13}R^{13}$, $S(O)_nR^{13}$, $S(O)_nNR^{13}R^{13}$, or $NR^{15}R^{16}$, wherein each n is independently 1 or 2; and wherein the alkyl, alkenyl, alkynyl, cycloalkyl, heterocycloalkyl, cycloalkenyl, aryl, arylalkyl, haloalkyl, heteroarylalkyl, or heteroaryl is optionally substituted with $R^{25}$; and wherein the aryl group of said aryl($C_1$-$C_6$)alkyl is optionally substituted with halo.

29. The compound of claim 28, wherein the aryl of O-aryl is independently selected from:
   i) a 5-6 membered monocyclic aryl group;
   ii) an 8-10 membered bicyclic aryl group having 0-5 heteroatoms independently selected from nitrogen, oxygen, sulfur, sulfoxide or sulfone;
   iii) an 8-10 membered unsaturated or partially unsaturated bicyclic aryl group having 0-5 heteroatoms independently nitrogen, oxygen, sulfur, sulfoxide or sulfone; or
   iv) an 8-10 membered unsaturated or partially unsaturated bicyclic aryl group having a carboxamide or sulfoxamide.

30. The compound of claim 28, wherein the aryl of $R^{17}$ is a 5-6 membered monocyclic aryl group substituted with at least one group selected from $CF_3$, $OCF_3$, O-aryl, or $NR^{15}R^{16}$ at the one or more carbon atoms.

31. The compound of claim 30, wherein the monocyclic aryl group is phenyl substituted with at least one group selected from $CF_3$, $OCF_3$, O-aryl, or $NR^{15}R^{16}$ at the one or more carbon atoms.

32. The compound of claim 27, wherein $NR^{15}R^{16}$ is morpholino, piperazinyl, homopiperazinyl, thiomorpholino, piperidinyl, or pyrrolidinyl, wherein the piperazinyl, homopiperazinyl, piperidinyl, or pyrrolidinyl is optionally substituted at one or more carbon atoms with 1, 2 or 3 $R^{25}$ or at one nitrogen atom with $R^{13}$ or $R^{14}$.

33. The compound of claim 24, wherein $R^{18}$ is selected from $C_1$-$C_6$ alkyl, $C_3$-$C_6$ alkenyl, $C_3$-$C_6$ alkynyl, $C_3$-$C_6$ cycloalkyl, $C_3$-$C_8$ heterocycloalkyl, $C_4$-$C_6$ cycloalkenyl, aryl, aryl($C_1$-$C_6$)alkyl, haloalkyl or heteroaryl, wherein the alkyl, alkenyl, alkynyl, cycloalkyl, heterocycloalkyl, cycloalkenyl, aryl, arylalkyl, haloalkyl, or heteroaryl is optionally substituted with $R^{25}$.

34. The compound of claim 33, wherein $R^{18}$ is $C_1$-$C_6$ alkyl optionally substituted with one or more aryl, alkyl, halo, $R^{23}$ or $R^{24}$, wherein each $R^{23}$ is independently $CF_3$, $OCF_3$, $SR^{13}$, $OR^{13}$, $NR^{13}R^{13}$, $S(O)_nNR^{13}R^{13}$, $S(O)_nR^{13}$, or $NR^{15}R^{16}$, each of n being independently 1 or 2 and wherein each $R^{24}$ is selected from a 5-8 membered monocyclic group having 1-3 heteroatoms, an 8-12 membered bicyclic group having 1-5 heteroatoms, or an 11-14 membered tricyclic group having 1-8 heteroatoms, wherein said heteroatoms of $R^{24}$ are independently oxygen, nitrogen, or sulfur, wherein $R^{24}$ is optionally substituted with $R^{13}$ or $R^{14}$.

35. The compound of claim 34, wherein zero, one, two, three or four atoms of $R^{24}$ are optionally and independently substituted with $R^{13}$.

36. The compound of claim 34, wherein the aryl is optionally and independently substituted at one or more carbon atoms with 1-3 $R^{11}$, wherein $R^{11}$ is independently selected from $OR^9$, $NR^9R^9$, $NR^9COR^9$, or $NR^9S(O)_nR^9$, wherein n is 1 or 2.

37. The compound of claim 34, wherein the $C_1$-$C_6$ alkyl is $C_2$-$C_4$ alkyl optionally substituted with 1-3 groups selected from the group consisting of amino, hydroxy, phenyl, benzyl, and morpholino.

38. The compound of claim 33, wherein $R^{18}$ is $C_3$-$C_6$ alkenyl optionally substituted with one or more, aryl, alkyl, halo, $R^{23}$, or $R^{24}$, wherein each $R^{23}$ is independently selected from $CF_3$, $OCF_3$, $SR^{13}$, $OR^{13}$, $NR^{13}R^{13}$, $S(O)_nNR^{13}R^{13}$, $S(O)_nR^{13}$, or $NR^{15}R^{16}$, wherein each n is independently 1 or 2, and wherein each $R^{24}$ is independently selected from: a 5-8 membered monocyclic group having 1-3 heteroatoms; an 8-12 membered bicyclic having 1-5 heteroatoms; or an 11-14 membered tricyclic group having 1-8 heteroatoms, wherein said heteroatoms of $R^{24}$ is independently selected from oxygen, nitrogen or sulfur, and wherein $R^{24}$ is optionally substituted with $R^{13}$ or $R^{14}$.

39. The compound of claim 38, wherein zero, one, two, three or four atoms of $R^{24}$ are optionally and independently substituted with $R^{13}$.

40. The compound of claim 33, wherein $R^{18}$ is $C_3$-$C_6$ cycloalkyl optionally substituted with one or more, aryl, alkyl, halo, $R^{23}$ or $R^{24}$; wherein each $R^{23}$ is independently selected from $CF_3$, $OCF_3$, $SR^{13}$, $OR^{13}$, $NR^{13}R^{13}$, $(CH_2)_n NR^{13}R^{13}$, $S(O)_nNR^{13}R^{13}$, $S(O)_nR^{13}$, or $NR^{15}R^{16}$, wherein each n is independently 1 or 2; and wherein each $R^{24}$ is independently selected from a 5-8 membered monocyclic group having 1-3 heteroatoms, an 8-12 membered bicyclic group having 1-5 heteroatoms, or an 11-14 membered tricyclic group having 1-8 heteroatoms, wherein said heteroatoms of $R^{24}$ is independently selected from oxygen, nitrogen or sulfur, and wherein $R^{24}$ is optionally substituted with $R^{13}$ or $R^{14}$.

41. The compound of claim 40, wherein zero, one, two, three or four atoms of $R^{24}$ are optionally and independently substituted with $R^{13}$.

42. The compound of claim 25, wherein $R^{18}$ is $C_3$-$C_6$ cycloalkyl optionally substituted with one or more aryl, alkyl, halo, $R^{23}$, or $R^{24}$.

43. The compound of claim 33, wherein $R^{18}$ is $C_3$-$C_8$ heterocycloalkyl, wherein the $C_3$-$C_8$ heterocycloalkyl is a 5-7 membered monocycle having a heteroatom, wherein said heteroatom is independently selected from oxygen, nitrogen, sulfur, or sulfone; wherein the nitrogen atom is optionally substituted with $R^{19}$.

44. The compound of claim 43, wherein the monocycle is optionally substituted morpholine, tetrahydrofuran, thiomorpholine, piperazine or homopiperazine.

45. The compound of claim 25, wherein $R^{19}$ is independently selected from $C_1$-$C_6$ alkyl, $C_2$-$C_6$ alkenyl, $C_3$-$C_6$ alkynyl, hydroxy($C_2$-$C_6$)alkyl, amino($C_2$-$C_6$)alkyl, $C_2$-$C_6$ alkyl cyano, $C_2$-$C_6$ alkyl sulfone, $C_2$-$C_6$ sulfonamide, $C_3$-$C_6$ cycloalkyl, $C_4$-$C_6$ heterocycloalkyl, $C_4$-$C_6$ cycloalkenyl, aryl, aryl($C_1$-$C_6$)alkyl, haloalkyl, or heteroaryl.

46. The compound of claim 26, wherein $R^{19}$ is independently selected from hydroxy($C_2$-$C_6$)alkyl, amino($C_2$-$C_6$) alkyl, $C_2$-$C_6$ alkyl cyano, $C_2$-$C_6$ alkyl sulfone, $C_2$-$C_6$ sulfonamide, $C_3$-$C_6$ cycloalkyl, or $C_4$-$C_8$ heterocycloalkyl.

47. The compound of claim 26, wherein $R^{20}$ is selected from $C(O)R^{19}$, $COOR^{19}$, $C(O)NR^{19}R^{19}$, or $S(O)_nR^{19}$, wherein n is 1 or 2.

48. The compound of claim 27, wherein $R^{15}$ and $R^{16}$ of $NR^{15}R^{16}$, taken together with the nitrogen atom to which they are bonded, form:
i) a 3-8 membered saturated or partially saturated monocyclic group, wherein the 3-8 membered saturated or partially saturated monocyclic group is optionally substituted with $R^{25}$;
ii) an 8-12 membered saturated or partially saturated bicyclic group, wherein the 8-12 membered saturated or partially saturated bicyclic group is optionally substituted with $R^{25}$;
iii) a 3-8 membered saturated or partially saturated monocyclic group having 1-3 heteroatoms selected from nitrogen, oxygen, sulfur, sulfone or sulfoxide, wherein the 3-8 membered saturated or partially saturated monocyclic group having 1-2 heteroatoms is optionally substituted with $R^{13}$ or $R^{14}$; or
iv) an 8-12 membered saturated or partially saturated bicyclic group having 1-3 heteroatoms selected from nitrogen, oxygen, sulfur, sulfone, sulfoxide, wherein the 8-12 membered saturated or partially saturated bicyclic group having 1-3 heteroatoms is optionally substituted with $R^{13}$ or $R^{14}$.

49. The compound of claim 48, wherein $NR^{15}R^{16}$ is the 4-6 membered saturated monocyclic group optionally and independently substituted at one or more carbon atoms with 1-4 $R^{25}$.

50. The compound of claim 49, wherein the aryl group of $R^{25}$ is selected from:
i) a 5-6 membered monocyclic aryl group;
ii) an 8-10 membered bicyclic aryl group having 0-5 heteroatoms independently selected from nitrogen, oxygen, sulfur, sulfoxide or sulfone;
iii) an 8-10 membered unsaturated or partially unsaturated bicyclic aryl group having 0-5 heteroatoms independently selected from nitrogen, oxygen, sulfur, sulfoxide, or sulfone; or
iv) an 8-10 membered unsaturated or partially unsaturated bicyclic aryl group having a carbonyl, carboxamide, or sulfoxamide.

51. The compound of claim 48, wherein $NR^{15}R^{16}$ is a 5-8 membered saturated heterocyclic group having 1-2 heteroatoms selected from nitrogen, oxygen, sulfur, sulfone, or sulfoxide, wherein said 5-8 membered saturated heterocyclic group is optionally substituted with hydroxy, amino, $C_1$-$C_6$ alkyl, or phenyl at one or more carbon atoms or nitrogen atoms.

52. The compound of claim 49, wherein the 4-6 membered saturated monocyclic group is selected from piperidine or pyrrolidine optionally substituted with 1-4 groups selected from hydroxy, amino, $C_1$-$C_6$ alkyl, hydroxy($C_1$-$C_6$)alkyl, amino($C_1$-$C_6$)alkyl, or phenyl.

53. The compound of claim 51, wherein the 5-8 membered saturated heterocyclic group is selected from morpholine, thiomorpholine, piperazine or homopiperazine optionally substituted with 1-4 groups selected from hydroxy, amino, $C_1$-$C_6$ alkyl and phenyl, wherein each $C_1$-$C_6$ alkyl is optionally substituted with one or more amino, or hydroxy.

54. The compound of claim 51, wherein the 1-2 heteroatoms are nitrogen and nitrogen atoms are independently substituted with $C_1$-$C_6$ alkyl, $C(O)C_1$-$C_3$ alkyl, or $S(O)_2C_1$-$C_3$ alkyl, wherein the alkyl is optionally and independently substituted with amino or hydroxy.

55. The compound of claim 1, wherein $R^1$ is methyl, X is selected from $NH_2$ or $NHR^6$, and Y is selected from $R^6$ or $NHR^6$.

56. A compound or salt of claim 1, wherein the compound or salt is selected from the group consisting of:
- 4-(3,5-dimethoxyphenylamino)-2-(4-hydroxypiperidin-1-yl)pyrido[4,3-d]pyrimidin-6(6H)-one;
- 4-(3,5-dimethoxyphenylamino)-2-(4-hydroxy-4-(hydroxymethyl)piperidin-1-yl)pyrido[4,3d]pyrimidin-5(6H)-one;
- 2-(4-aminopiperidin-1-yl)-4-(3,5-dimethoxyphenylamino)pyrido[4,3-d]pyrimidin-5(6H)-one hydrochloride;
- 4-(3,5-dimethoxyphenylamino)-2-(4-morpholinopiperidin-1-yl)pyrido[4,3-d]pyrimidin-5(6H)-one;
- methyl 1-(4-(3,5-dimethoxyphenyl amino)-5-oxo-5,6-dihydropyrido[4,3-d]pyrimidin-2-yl)-4-hydroxy piperidine-4-carboxylate;
- 2-(4-hydroxypiperidin-1-yl)-4-(3-(trifluoromethyl)phenylamino)pyrido[4,3-d]pyrimidine-5(6H)-one;
- (R)-2-(3-aminopyrrolidin-1-yl)-4-(3-(trifluoromethyl)phenylamino)pyrido[4,3-d]pyrimidin-5(6H)-one hydrochloride;
- (S)-2-(pyrrolidin-3-ylamino)-4-(4-trifluoromethylamino)pyrido[4,3-d]pyrimidin-5(6H)-one;
- 2-((1R,4R)-4-aminocyclohexyl amino)-4-(3-(trifluoromethyl)phenylamino)pyrido[4,3-d]pyrimidin-5(6H)-one;
- 2-(2-morpholinoethoxy)-4-(3-(trifluoro methyl)phenylamino)pyrido[4,3-d]pyrimidin-5(6H)-one;
- 2-(4-aminopiperidin-1-yl)-4-(3-(trifluoro methyl)phenylamino)pyrido[4,3-d]pyrimidin-5(6H)-one hydrochloride;
- 2-(4-methylpiperazin-1-yl)-4-(3-(trifluoro methyl)phenylamino)pyrido[4,3-d]pyrimidin-5(6H)-one;
- 2-(3,4-dihydroisoquinolin-2(1H)-yl)-4-(3-(trifluoromethyl)phenylamino)pyrido[4,3-d]pyrimidin-5(6H)-one;
- (R)-2-(3-hydroxypyrrolidin-1-yl)-4-(3-(trifluoromethyl)phenylamino)pyrido[4,3-d]pyrimidin-5(6H)-one;
- 2-(piperidin-1-yl)-4-(3-(trifluoromethyl)phenylamino)pyrido[4,3-d]pyrimidin-5(6H)-one;
- 2-(4-aminopiperidin-1-yl)-4-(3-(trifluoro methyl)phenylamino)pyrido[4,3-d]pyrimidin-5(6H)-one hydrochloride;
- 2-(4-hydroxypiperidin-1-yl)-4-(4-(trifluoromethyl)phenylamino)pyrido[4,3-d]pyrimidin-5(6H)-one;
- 2-(4-(2-hydroxyethyl)piperazin-1-yl)-4-(3-(trifluoromethyl)phenylamino)pyrido[4,3-d]pyrimidin-5(6H)-one;
- N-(2-((5-oxo-4-(3-(trifluoromethyl)phenylamino)-5,6-dihydropyrido[4,3-d]pyrimidin-2-ylamino)methyl)phenyl)methanesulfonamide;
- (S)-2-(3-hydroxypyrrolidin-1-yl)-4-(3-(trifluoromethyl)phenylamino)pyrido[4,3-d]pyrimidin-5(6H)-one;
- 2-(4-aminopiperidin-1-yl)-4-(4-(trifluoro methyl)phenylamino)pyrido[4,3-d]pyrimidin-5(6H)-one hydrochloride;
- N-(1-(5-oxo-4-(4-(trifluoromethyl)phenylamino)-5,6-dihydropyrido[4,3-d]pyrimidin-2-yl)piperidin-4-yl)cyclopropanesulfonamide;
- 2-(piperidin-4-ylamino)-4-(4-(trifluoromethyl)phenylamino)pyrido[4,3-d]pyrimidin-5(6H)-one hydrochloride;
- (S)-2-(3-aminopyrrolidin-1-yl)-4-(3-(trifluoromethyl)phenylamino)pyrido[4,3-d]pyrimidin-5(6H)-one hydrochloride;
- 2-morpholino-4-(4-(trifluoromethyl)phenylamino)pyrido[4,3-a]pyrimidin-5(6H)-one;
- 2-((1R,4R)-4-hydroxycyclohexylamino)-4-(3-(trifluoromethyl)phenylamino)pyrido[4,3-d]pyrimidin-5(6H)-one;
- 2-(4-oxopiperidin-1-yl)-4-(3-(trifluoromethyl)phenylamino)pyrido[4,3-d]pyrimidin-5(6H)-one;
- 2-(3,4-dihydroisoquinolin-2(1H)-yl)-4-(4-(trifluoromethyl)phenylamino)pyrido[4,3-d]pyrimidin-5(6H)-one;
- 2-(3-(3-(trifluoromethyl)phenyl)-6,7-dihydro-[1,2,3]triazolo[1,5-a]pyrazin-5(4H)-yl)-4-(4-(trifluoromethyl)phenylamino)pyrido[4,3-d]pyrimidin-5(6H)-one;
- 2-(cyclopropylamino)-4-(4-(trifluoromethyl)phenylamino)pyrido[4,3-d]pyrimidin-5(6H)-one;
- 2-(cyclopentylamino)-4-(4-(trifluoromethyl)phenylamino)pyrido[4,3-d]pyrimidin-5(6H)-one;
- (R)-2-(pyrrolidin-3-ylamino)-4-(4-(trifluoromethyl)phenylamino)pyrido[4,3-d]pyrimidin-5(6H)-one hydrochloride;
- 2-(3-(trifluoromethyl)-5,6-dihydro-[1,2,4]triazolo[4,3-a]pyrazin-7(8H)-yl)-4-(4-(trifluoromethyl)phenylamino)pyrido[4,3-d]pyrimidin-5(6H)-one;
- 2-(benzylamino)-4-(4-(trifluoromethyl)phenylamino)pyrido[4,3-d]pyrimidin-5(6H)-one;
- 2-(benzyl(methyl)amino)-4-(4-(trifluoromethyl)phenylamino)pyrido[4,3-d]pyrimidin-5(6H)-one;
- (S)-2-(1-(4-fluorophenyl)ethylamino)-4-(4-(trifluoromethyl)phenylamino)pyrido[4,3-d]pyrimidin-5(6H)-one;
- 2-((tetrahydro-2H-pyran-4-yl)methylamino)-4-(4-(trifluoromethyl)phenyl amino)pyrido[4,3-d]pyrimidin-5(6H)-one;
- 2-(4-fluorobenzylamino)-4-(4-(trifluoromethyl)phenylamino)pyrido[4,3-d]pyrimidin-5(6H)-one;
- 2-(piperidin-4-ylmethylamino)-4-(4-(trifluoromethyl)phenylamino)pyrido[4,3-d]pyrimidin-5(6H)-one hydrochloride;
- 2-(tetrahydro-2H-pyran-4-ylamino)-4-(4-(trifluoromethyl)phenylamino)pyrido[4,3-d]pyrimidin-5(6H)-one;
- 2-(1,4-diazepan-1-yl)-4-(4-(trifluoromethyl)phenylamino)pyrido[4,3-d]pyrimidin-5(6H)-one hydrochloride;
- 2-(thiazolidin-3-yl)-4-(4-(trifluoromethyl)phenylamino)pyrido[4,3-d]pyrimidin-5(6H)-one;
- N-(2-((5-oxo-4-(4-(trifluoromethyl)phenylamino)-5,6-dihydropyrido[4,3-d]pyrimidin-2-ylamino)methyl)phenyl)methanesulfonamide;
- (S)-2-(1-cyclohexylethylamino)-4-(4-(trifluoromethyl)phenylamino)pyrido[4,3-d]pyrimidin-5(6H)-one;
- 2-(cyclohexylamino)-4-(4-(trifluoromethyl)phenylamino)pyrido[4,3-d]pyrimidin-5(6H)-one;

(R)-2-(1-methylpyrrolidin-3-ylamino)-4-(4-(trifluoromethyl)phenylamino)pyrido[4,3-d]pyrimidin-5(6H)-one;

(R)-2-(1-isopropylpyrrolidin-3-ylamino)-4-(4-(trifluoromethyl)phenylamino)pyrido[4,3-d]pyrimidin-5(6H)-one;

2-((1-methylpiperidin-4-yl)methylamino)-4-(4-(trifluoromethyl)phenylamino) pyrido[4,3-d]pyrimidin-5(6H)-one;

2-((1-isopropylpiperidin-4-yl)methylamino)-4-(4-(trifluoromethyl)phenyl amino)pyrido[4,3-d]pyrimidin-5(6H)-one;

2-(4-((dimethylamino)methyl)piperidin-1-yl)-4-(4-(trifluoromethyl)phenylamino) pyrido[4,3-d]pyrimidin-5(6H)-one;

2-(4-methylthiazol-2-ylamino)-4-(4-(trifluoromethyl)phenylamino)pyrido[4,3-d]pyrimidin-5(6H)-one;

(S)-2-(1-(methylsulfonyl)pyrrolidin-3-ylamino)-4-(4-(trifluoromethyl)phenyl amino)pyrido[4,3-d]pyrimidin-5(6H)-one;

2-(4-(2-hydroxyethyl)piperazin-1-yl)-4-(4-(trifluoromethyl)phenylamino)pyrido[4,3-d]pyrimidin-5(6H)-one;

2-(4-(hydroxymethyl)piperidin-1-yl)-4-(4-(trifluoromethyl)phenylamino)pyrido[4,3-d]pyrimidin-5(6H)-one;

ethyl 1-(5-oxo-4-(4-(trifluoromethyl)phenylamino)-5,6-dihydropyrido[4,3-d]pyrimidin-2-yl)piperidine-4-carboxylate;

2-(4-(4-(2-hydroxyethyl)piperazine-1-carbonyl)piperidin-1-yl)-4-(4-(trifluoromethyl)phenylamino)pyrido[4,3-d]pyrimidin-5(6H)-one;

2-(4-(4-(hydroxymethyl)piperidine-1-carbonyl)piperidin-1-yl)-4-(4-(trifluoromethyl)phenylamino)pyrido[4,3-d]pyrimidin-5(6H)-one;

2-((1S,2R)-2-aminocyclohexylamino)-4-(3-(trifluoromethyl)phenylamino)pyrido[4,3-d]pyrimidin-5(6H)-one;

2-((1S,2S)-2-aminocyclohexylamino)-4-(3-(trifluoromethyl)phenylamino)pyrido[4,3-d]pyrimidin-5(6H)-one;

2-((1R,2S)-2-aminocyclohexylamino)-4-(2-(trifluoromethyl)phenylamino)pyrido[4,3-d]pyrimidin-5(6H)-one;

2-((1R,2R)-2-aminocyclohexylamino)-4-(2-(trifluoromethyl)phenylamino)pyrido[4,3-d]pyrimidin-5(6H)-one;

2-((1R,4R)-4-aminocyclohexylamino)-4-(2-(trifluoromethyl)phenylamino)pyrido[4,3-d]pyrimidin-5(6H)-one;

2-(4-ethylpiperazin-1-yl)-4-(3-(trifluoromethyl)phenylamino)pyrido[4,3-d]pyrimidin-5(6H)-one;

2-(2-morpholinoethylamino)-4-(3-(trifluoromethyl)phenylamino)pyrido[4,3-d]pyrimidin-5(6H)-one;

2-(3-aminocyclohexylamino)-4-(3-(trifluoromethyl)phenylamino)pyrido[4,3-d]pyrimidin-5(6H)-one;

2-(4-(methylsulfonyl)piperazin-1-yl)-4-(3-(trifluoromethyl)phenylamino)pyrido[4,3-d]pyrimidin-5(6H)-one;

2-(morpholinoamino)-4-(3-(trifluoromethyl)phenylamino)pyrido[4,3-d]pyrimidin-5(6H)-one;

2-(4-acetylpiperazin-1-yl)-4-(3-(trifluoro methyl)phenylamino)pyrido[4,3-d]pyrimidin-5(6H)-one;

(R)-2-(2-hydroxy-1-phenylethylamino)-4-(3-(trifluoromethyl)phenylaminopyrido[4,3-d]pyrimidin-5(6H)-one;

(S)-2-(2-hydroxy-1-phenylethylamino)-4-(3-(trifluoromethyl)phenylaminopyrido[4,3-d]pyrimidin-5(6H)-one;

(R)-2-(1-hydroxy-3-phenylpropan-2-ylamino)-4-(3-(trifluoromethyl)phenyl amino)pyrido[4,3-d]pyrimidin-5(6H)-one;

(S)-2-(1-hydroxy-3-phenylpropan-2-ylamino)-4-(3-(trifluoromethyl)phenyl amino)pyrido[4,3-d]pyrimidin-5(6H)-one;

1-(5-oxo-4-(3-(trifluoromethyl)phenyl amino)-5,6-dihydropyrido[4,3-d]pyrimidin-2-yl)piperidine-4-carboxamide;

(R)-2,2,2-trifluoro-N-(1-(5-oxo-4-(3-(trifluoromethyl)phenylamino)-5,6-dihydropyrido[4,3-d]pyrimidin-2-yl)pyrrolidin-3-yl)acetamide;

2-(4-(4-chlorophenyl)-4-hydroxy piperidin-1-yl)-4-(3-(trifluoromethyl)phenylamino)pyrido[4,3-d]pyrimidin-5(6H)-one;

2-((1S,2S)-2-(phenylsulfonyl)cyclohexylamino)-4-(3-(trifluoromethyl)phenyl amino)pyrido[4,3-d]pyrimidin-5(6H)-one;

2-((1S,2R)-2-aminocyclohexylamino)-4-(4-(trifluoromethyl)phenylamino)pyrido[4,3-d]pyrimidin-5(6H)-one;

2-thiomorpholino-4-(3-(trifluoromethyl)phenylamino)pyrido[4,3-d]pyrimidin-5(6H)-one;

2-(4-sulfonylpyrido)-4-(3-(trifluoro methyl)phenylamino)pyrido[4,3-d]pyrimidin-5(6H)-one;

2-(4-morpholinopiperidin-1-yl)-4-(3-(trifluoromethyl)phenylamino)pyrido[4,3-d]pyrimidin-5(6H)-one;

N-((1R,2S)-2-(5-oxo-4-(3-(trifluoro methyl)phenylamino)-5,6-dihydropyrido[4,3-d]pyrimidin-2-ylamino)cyclohexyl)acetamide;

N-((1R,4R)-4-(5-oxo-4-(3-(trifluoro methyl)phenylamino)-5,6-dihydropyrido[4,3-d]pyrimidin-2-ylamino)cyclohexyl)acetamide;

2-((1R,2R)-2-(dimethylamino)cyclohexyl amino)-4-(3-(trifluoromethyl)phenyl amino)pyrido[4,3-d]pyrimidin-5(6H)-one;

2-(4-aminopiperidin-1-yl)-4-(3-bromophenylamino)pyrido[4,3-d]pyrimidin-5(6H)-one hydrochloride;

4-(3-bromophenylamino)-2-(4-hydroxypiperidin-1-yl) pyrido[4,3-d]pyrimidin-5(6H)-one;

2-(4-aminopiperidin-1-yl)-4-(3-bromophenylamino)pyrido[4,3-d]pyrimidin-5(6H)-one hydrochloride;

4-(3-bromophenylamino)-2-(4-(dimethylamino)piperidin-1-yl)pyrido[4,3-d]pyrimidin-5(6H)-one;

(S)-4-(3-bromophenylamino)-2-(4-(1-hydroxypropan-2-ylamino)piperidin-1-yl)pyrido[4,3-d]pyrimidin-5(6H)-one;

(R)-2-(4-(3-aminopyrrolidin-1-yl)piperidin-1-yl)-4-(3-bromophenyl amino)pyrido[4,3-d]pyrimidin-5(6H)-one hydrochloride;

(R)-2-(3-aminopyrrolidin-1-yl)-4-(3-bromophenylamino)pyrido[4,3-d]pyrimidin-5(6H)-one hydrochloride;

4-(3-bromophenylamino)-2-(3-hydroxypiperidin-1-yl) pyrido[4,3-d]pyrimidin-5(6H)-one;

(R)-2-(3-aminopyrrolidin-1-yl)-4-(4-bromophenylamino)pyrido[4,3-d]pyrimidin-5(6H)-one hydrochloride;

(S)-2-(3-aminopyrrolidin-1-yl)-4-(4-bromophenylamino)pyrido[4,3-d]pyrimidin-5(6H)-one hydrochloride;

4-(4-bromophenylamino)-2-(4-hydroxypiperidin-1-yl) pyrido[4,3-d]pyrimidin-5(6H)-one;

2-(4-aminopiperidin-1-yl)-4-(4-bromophenylamino)pyrido[4,3-d]pyrimidin-5(6H)-one hydrochloride;

(S)-4-(3-bromophenylamino)-2-(4-(1-hydroxypropan-2-ylamino)piperidin-1-yl)pyrido[4,3-d]pyrimidin-5(6H)-one;

4-(3-bromophenylamino)-2-(4-(dimethylamino)piperidin-1-yl)pyrido[4,3-d]pyrimidin-5(6H)-one;

2-(4-aminopiperidin-1-yl)-4-(m-tolylamino)pyrido[4,3-d]pyrimidin-5(6H)-one hydrochloride;

2-(4-hydroxypiperidin-1-yl)-4-(m-tolyl amino)pyrido[4,3-d]pyrimidin-5(6H)-one;

2-((1R,2R)-2-aminocyclohexylamino)-4-(3,5-bis(trifluoromethyl)phenylamino) pyrido[4,3-d]pyrimidin-5(6H)-one;

(2-((1R,2S)-2-aminocyclohexylamino)-4-(3-(trifluoromethyl)phenylamino)pyrido[4,3-d]pyrimidin-5(6H)-one with (2-((1S,2R)-2-aminocyclohexylamino)-4-(3-(trifluoromethyl)phenylamino)pyrido[4,3-d]pyrimidin-5(6H)-one;
4-(3,5-bis(trifluoromethyl)phenylamino)-2-(4-hydroxypiperidin-1-yl)pyrido[4,3-d]pyrimidin-5(6H)-one;
4-(3,5-bis(trifluoromethyl)phenylamino)-2-morpholinopyrido[4,3-d]pyrimidin-5(6H)-one;
4-(3,5bis(trifluoromethyl)phenyl amino)-2-((1r,4r)-4-hydroxycyclohexyl amino)pyrido[4,3-d]pyrimidin-5(6H)-one;
2-(2-aminobenzylamino)-4-(3,5-bis(trifluoromethyl)phenylamino)pyrido[4,3-d]pyrimidin-5(6H)-one;
4-(3,5-bis(trifluoromethyl)phenylamino)-2-(4-methylpiperazin-1-yl)pyrido[4,3-d]pyrimidin-5(6H)-one;
2-(4-aminopiperidin-1-yl)-4-(3,5-bis(trifluoromethyl)phenylamino)pyrido[4,3-d]pyrimidin-5(6H)-one hydrochloride;
(S)-4-(3,5-bis(trifluoromethyl)phenylamino)-2-(pyrrolidin-3-ylamino)pyrido[4,3-d]pyrimidin-5(6H)-one hydrochloride;
4-(3,5-bis(trifluoromethyl)phenylamino)-2-(piperidin-4-ylamino)pyrido[4,3-d]pyrimidin-5(6H)-one hydrochloride;
4-(3,5-bis(trifluoromethyl)phenylamino)-2-(1-methylpiperidin-4-ylamino)pyrido[4,3-d]pyrimidin-5(6H)-one;
(S)-4-(3,5-bis(trifluoromethyl)phenyl amino)-2-(1-methylpyrrolidin-3-ylamino)pyrido[4,3-d]pyrimidin-5(6H)-one;
4-(3,5-bis(trifluoromethyl)phenylamino)-2-(4-(dimethylamino)piperidin-1-yl)pyrido[4,3-d]pyrimidin-5(6H)-one;
4-(3,5-bis(trifluoromethyl)phenylamino)-2-(4-(hydroxymethyl)piperidin-1-yl)pyrido[4,3-d]pyrimidin-5(6H)-one;
4-(3,5-bis(trifluoromethyl)phenylamino)-2-(4-(2-hydroxyethyl)piperazin-1-yl)pyrido[4,3-d]pyrimidin-5(6H)-one;
(R)-4-(3,5-bis(trifluoromethyl)phenyl amino)-2-(3-hydroxypyrrolidin-1-yl)pyrido[4,3-d]pyrimidin-5(6H)-one;
4-(3,5-bis(trifluoromethyl)phenylamino)-2-(3-hydroxyazetidin-1-yl)pyrido[4,3-d]pyrimidin-5(6H)-one;
4-(3,5-bis(trifluoromethyl)phenylamino)-2-(4-(2-hydroxyethyl)piperidin-1-yl)pyrido[4,3-d]pyrimidin-5(6H)-one;
N-((1r,4r)-4-(4-(3,5-bis(trifluoromethyl)phenylamino)-5-oxo-5,6-dihydropyrido[4,3-d]pyrimidin-2-ylamino)cyclohexyl)acetamide;
4-(3,5-bis(trifluoromethyl)phenylamino)-2-(3-oxopiperazin-1-yl)pyrido[4,3-d]pyrimidin-5(6H)-one;
4-(3,5-bis(trifluoromethyl)phenylamino)-2-(piperazin-1-yl)pyrido[4,3-d]pyrimidin-5(6H)-one hydrochloride;
methyl 1-(4-(3,5-bis(trifluoromethyl)phenylamino)-5-oxo-5,6-dihydropyrido[4,3-d]pyrimidin-2-yl)-4-hydroxy piperidine-4-carboxylate;
4-(3,5-bis(trifluoromethyl)phenylamino)-2-(4-hydroxy-4-(hydroxymethyl)piperidin-1-yl)pyrido[4,3-d]pyrimidin-5(6H)-one;
2-((1R,4R)-4-aminocyclohexylamino)-4-(3,5-bis(trifluoromethyl)phenylamino) pyrido[4,3-d]pyrimidin-5(6H)-one;
4-(3,5-bis(trifluoromethyl)phenylamino)-2-(4-(hydroxyimino)piperidin-1-yl)pyrido[4,3-d]pyrimidin-5(6H)-one;
(S)-4-(phenoxyphenylamino)-2-(pyrrolidin-3-ylamino)pyrido[4,3-d]pyrimidin-5(6H)-one hydrochloride;
2-(4-hydroxypiperidin-1-yl)-4(4-(methylsulfonyl)phenylamino)pyrido[4,3d]pyrimidin-5(6H)-one;
N-(2-((4-(4-(methylsulfonyl)phenylamino)-5-oxo-5,6-dihydropyrido[4,3-d]pyrimidin-2-ylamino)methyl)phenyl)methanesulfonamide;
2-(4-hydroxypiperidin-1-yl)-4-(4-(methyl sulfonyl)phenylamino)pyrido[4,3-d]pyrimidin-5(6H)-one;
4-(4-(methylsulfonyl)phenylamino)-2-(4-morpholinopiperidin-1-yl)pyrido[4,3-d]pyrimidin-5(6H)-one;
2-(4-hydroxypiperidin-1-yl)-4-(3-(methyl sulfonyl)phenylamino)pyrido[4,3-d]pyrimidin-5(6H)-one;
N-(2-((4-(4-(methylsulfonyl)phenylamino)-5-oxo-5,6-dihydropyrido[4,3-d]pyrimidin-2-yl amino)methyl)phenyl)cyclopropane sulfonamide;
N-methyl-N-(2-((4-(4-(methylsulfonyl)phenylamino)-5-oxo-5,6-dihydropyrido[4,3-d]pyrimidin-2-ylamino)methyl)phenyl)cyclopropanesulfonamide;
(S)-2-(3-aminopyrrolidin-1-yl)-4-(4-(methylsulfonyl)phenylamino)pyrido[4,3-d]pyrimidin-5(6H)-one;
2-(4-hydroxypiperidin-1-yl)-4-(4-morpholinophenylamino)pyrido[4,3-d]pyrimidin-5(6H)-one;
4-(4-(4-acetylpiperazin-1-yl)phenylamino)-2-(4-(hydroxymethyl)piperidin-1-yl)pyrido[4,3-d]pyrimidin-5(6H)-one;
(S)-4-(4-morpholinophenylamino)-2-(pyrrolidin-3-ylamino)pyrido[4,3-d]pyrimidin-5(6H)-one hydrochloride;
2-(4-(hydroxymethyl)piperidin-1-yl)-4-(4-sulfonylphenylamino)pyrido[4,3-d]pyrimidin-5(6H)-one;
4-(4-(4-acetylpiperazin-1-yl)phenylamino)-2-(4-(hydroxymethyl)piperidin-1-yl)pyrido[4,3-d]pyrimidin-5(6H)-one;
2-(4-(hydroxymethyl)piperidin-1-yl)-4-(4-morpholinophenylamino)pyrido[4,3-d]pyrimidin-5(6H)-one;
4-(4-(5-oxo-2-(piperidin-4-ylmethyl amino)-5,6-dihydropyrido[4,3-d]pyrimidin-4-ylamino)phenyl)morpholine 4-oxide hydrochloride;
4-(4-morpholinophenylamino)-2-(piperidin-4-ylmethylamino)pyrido[4,3-d]pyrimidin-5(6H)-one hydrochloride;
N-methyl-N-(2-((4-(4-morpholinophenylamino)-5-oxo-5,6-dihydropyrido[4,3-d]pyrimidin-2-ylamino)methyl)phenyl)cyclopropanesulfonamide;
N-(2-((4-(4-morpholinophenylamino)-5-oxo-5,6-dihydropyrido[4,3-d]pyrimidin-2-ylamino)methyl)phenyl)cyclopropanesulfonamide;
N-(2-((4-(4-morpholinophenylamino)-5-oxo-5,6-dihydropyrido[4,3-d]pyrimidin-2-ylamino)methyl)phenyl)methanesulfonamide;
2-(2-aminobenzylamino)-4-(4-morpholinophenylamino)pyrido[4,3-d]pyrimidin-5(6H)-one;
2-((1R,2R)-2-aminocyclohexylamino)-4-(4-morpholinophenylamino)pyrido[4,3-d]pyrimidin-5(6H)-one;
2-((1R,2S)-2-aminocyclohexylamino)-4-(4-morpholinophenylamino)pyrido[4,3-d]pyrimidin-5(6H)-one;
2-((1R,2R)-2-aminocyclohexylamino)-4-(benzo[d][1,3]dioxol-5-ylamino)pyrido[4,3-d]pyrimidin-5(6H)-one;
2-(4-hydroxypiperidin-1-yl)-4-(3,4,5-triemethoxyphenylamino)pyrido[4,3d]pyrimidin-5(6H)-one;
2-(4-hydroxypiperidin-1-yl)-4-(4-methoxy-3-(trifluoromethyl)phenylamino)pyrido[4,3d]pyrimidin-5(6H)-one;
2-(4-(hydroxymethyl)piperidin-1-yl)-4-(4-methoxy-3-(trifluoromethyl)phenylamino) pyrido[4,3d]pyrimidin-5(6H)-one;
2-(4-hydroxy-4-(hydroxymethyl)piperidin-1-yl)-4-(4-methoxy-3-(trifluoromethyl)phenylamino)pyrido[4,3d]pyrimidin-5(6H)-one;

2-(4-hydroxypiperidin-1-yl)-4-(3-methoxy-5-(trifluoromethyl)phenylamino)pyrido[4,3d]pyrimidin-5(6H)-one;
2-(4-(hydroxymethyl)piperidin-1-yl)-4-(3-methoxy-5-(trifluoromethyl)phenylamino) pyrido[4,3d]pyrimidin-5(6H)-one;
2-(4-hydroxy-4-(hydroxymethyl)piperidin-1-yl)-4-(3-methoxy-5-(trifluoromethyl)phenyl amino)pyrido[4,3d]pyrimidin-5(6H)-one;
2-(4-hydroxy-4-(hydroxymethyl)piperidin-1-yl)-4-(3,4,5-trimethoxyphenylamino)pyrido[4,3d]pyrimidin-5(6H)-one;
4-(3,5-dimethylphenylamino)-2-(4-hydroxy-4-(hydroxymethyl)piperidin-1-yl)pyrido[4,3-d]pyrimidin-5(6H)-one;
4-(4-chloro-3-methoxyphenylamino)-2-(4-hydroxypiperidin-1-yl)pyrido[4,3-d]pyrimidin-5(6H)-one;
2-(4-hydroxypiperidin-1-yl)-4-(3-methoxy-5-(trifluoromethyl)phenylamino)pyrido[4,3-d]pyrimidin-5(6H)-one;
2-(4-(hydroxymethyl)piperidin-1-yl)-4-(3-methoxy-5-(trifluoromethyl)phenylamino)pyrido[4,3-d]pyrimidin-5(6H)-one;
2-(4-hydroxy-4-(hydroxymethyl)piperidin-1-yl)-4-(3-methoxy-5-(trifluoromethyl)phenyl amino)pyrido[4,3-d]pyrimidin-5(6H)-one;
4-(4-chloro-3-(trifluoromethyl)phenylamino)-2-(4-hydroxypiperidin-1-yl)pyrido[4,3-d]pyrimidin-5(6H)-one;
4-(4-chloro-3-(trifluoromethyl)phenylamino)-2-(4-(hydroxymethyl)piperidin-1-yl)pyrido[4,3-d]pyrimidin-5(6H)-one;
4-(4-chloro-3-(trifluoromethyl)phenylamino)-2-(4-hydroxy-4-(hydroxymethyl)piperidin-1-yl)pyrido[4,3-d]pyrimidin-5(6H)-one
4-(3-chloro-5-(trifluoromethyl)phenylamino)-2-(4-hydroxy-4-(hydroxymethyl)piperidin-1-yl)pyrido[4,3-d]pyrimidin-5(6H)-one;
4-(3-bromo-5-(trifluoromethyl)phenylamino)-2-(4-hydroxy-4-(hydroxymethyl)piperidin-1-yl)pyrido[4,3-d]pyrimidin-5(6H)-one;
4-(4-chloro-3-(trifluoromethoxy)phenylamino)-2-(4-hydroxy-4-(hydroxymethyl)piperidin-1-yl)pyrido[4,3-d]pyrimidin-5(6H)-one;
2-(4-hydroxypiperidine-1-yl)-6-methyl-4-(3-(trifluoromethyl)phenylamino)pyrido[4,3-d]pyrimidin-5(6H)-one;
6-methyl-4-(phenylamino)-2-(3-(trifluoromethyl)phenylamino)pyrido[4,3-d]pyrimidin-5(6H)-one;
methyl 4-(6-methyl-2-morpholino-5-oxo-5,6-dihydropyrido[4,3-d]pyrimidin-4-ylamino)benzoate;
6-methyl-2-(methylamino)-4-(4-(piperazine-1-carbonyl)phenylamino)pyrido[4,3-d]pyrimidin-5(6H)-one hydrochloride;
methyl 4-(6-methyl-2-(methylamino)-5-oxo-5,6-dihydropyrido[4,3-d]pyrimidin-4-ylamino)benzoate;
2-amino-6-methyl-4-(phenylamino)pyrido[4,3-d]pyrimidin-5(6H)-one;
4-(4-fluorobenzylamino)-6-methyl-2-(methylamino)pyrido[4,3-d]pyrimidin-5(6H)-one;
6-methyl-2-(methylamino)-4-(phenylamino)pyrido[4,3-d]pyrimidin-5(6H)-one;
2-(4-methoxybenzylamino)-6-methyl-4-(phenyl amino) pyrido[4,3-d]pyrimidin-5(6H)-one;
2-(4-hydroxycyclohexylamino)-6-methyl-4-(phenylamino)pyrido[4,3-d]pyrimidin-5(6H)-one;
4-(4-methoxyphenyl)-6-methyl-2-(methylamino)pyrido[4,3-d]pyrimidin-5(6H)-one;
2-(4-(hydroxymethyl)piperidin-1-yl)-4-(4-methoxyphenyl)pyrido[4,3-d]pyrimidin-5(6H)-one;
4-(4-methoxyphenyl)-6-methyl-2-(methylamino)pyrido[4,3-d]pyrimidin-5(6H)-one;
4-(4-aminophenyl)-6-methyl-2-(methylamino)pyrido[4,3-d]pyrimidin-5(6H)-one hydrochloride;
1-(4-fluorophenyl)-3-(4-(6-methyl-2-(methylamino)-5-oxo-5,6-dihydropyrido[4,3-d]pyrimidin-4-yl)phenyl)urea;
8-bromo-2-(4-hydroxypiperidin-1-yl)-4-(3-(trifluoromethyl)phenylamino)pyrido[4,3-d]pyrimidin-5(6H)-one;
8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one;
8-chloro-2-(4-hydroxypiperidin-1-yl)-4-(3-(trifluoromethyl)phenylamino)pyrido[4,3-d]pyrimidin-5(6H)-one;
8-bromo-2-(4-hydroxy-4-(hydroxymethyl)piperidin-1-yl)-4-(3-(trifluoromethyl)phenyl amino)pyrido[4,3-d]pyrimidin-5(6H)-one;
(R)-2-(3-aminopyrrolidin-1-yl)-8-bromo-4-(3-(trifluoromethyl)phenylamino)pyrido[4,3-d]pyrimidin-5(6H)-one hydrochloride;
(R)-2-(3-aminopyrrolidin-1-yl)-8-bromo-4-(4-bromo-3-methylphenylamino)pyrido[4,3-d]pyrimidin-5(6H)-one hydrochloride;
8-bromo-2-(4-hydroxypiperidin-1-yl)-4-(3-(trifluoromethyl)phenylamino)pyrido[4,3-d]pyrimidin-5(6H)-one;
8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one;
8-chloro-2-(4-hydroxypiperidin-1-yl)-4-(3-(trifluoromethyl)phenylamino)pyrido[4,3-d]pyrimidin-5(6H)-one;
8-bromo-2-(4-hydroxy-4-(hydroxymethyl)piperidin-1-yl)-4-(3-(trifluoromethyl)phenyl amino)pyrido[4,3-d]pyrimidin-5(6H)-one;
(R)-2-(3-aminopyrrolidin-1-yl)-8-bromo-4-(3-(trifluoromethyl)phenylamino)pyrido[4,3-d]pyrimidin-5(6H)-one hydrochloride;
(R)-2-(3-aminopyrrolidin-1-yl)-8-bromo-4-(4-bromo-3-methylphenylamino)pyrido[4,3-d]pyrimidin-5(6H)-one hydrochloride;
8-bromo-2-(4-hydroxypiperidin-1-yl)-4-(3-(trifluoromethyl)phenylamino)pyrido[4,3-d]pyrimidin-5(6H)-one;
8-bromo-2-(4-hydroxy-4-(hydroxymethyl)piperidin-1-yl)-4-(4-methoxy-3-(trifluoromethyl)phenylamino)pyrido[4,3-d]pyrimidin-5(6H)-one;
8-chloro-2-(4-hydroxypiperidin-1-yl)-4-(3-(trifluoromethyl)phenylamino)pyrido[4,3-d]pyrimidin-5(6H)-one;
2-(4-hydroxypiperidin-1-yl)-4-(3-methoxy-5-(trifluoromethyl)phenylamino)pyrido[4,3-d]pyrimidin-5(6H)-one;
2-(4-(hydroxymethyl)piperidin-1-yl)-4-(3-methoxy-5-(trifluoromethyl)phenylamino) pyrido[4,3-d]pyrimidin-5(6H)-one;
4-(4-chloro-3-(trifluoromethyl)phenylamino)-2-(4-hydroxypiperidin-1-yl)pyrido[4,3-d]pyrimidin-5(6H)-one;
4-(4-chloro-3-(trifluoromethyl)phenylamino)-2-(4-(hydroxymethyl)piperidin-1-yl)pyrido[4,3-d]pyrimidin-5(6H)-one;
4-(4-chloro-3-methoxyphenylamino)-2-(4-hydroxy-4-(hydroxymethyl)piperidin-1-yl)pyrido[4,3-d]pyrimidin-5(6H)-one;
2-(4-hydroxy-4-(hydroxymethyl)piperidin-1-yl)-4-(3-methoxy-5-(trifluoromethyl)phenyl amino)pyrido[4,3-d]pyrimidin-5(6H)-one;
4-(4-chloro-3-(trifluoromethyl)phenylamino)-2-(4-hydroxy-4-(hydroxymethyl)piperidin-1-yl)pyrido[4,3-d]pyrimidin-5(6H)-one;

8-bromo-2-(4-hydroxy-4-(hydroxymethyl)piperidin-1-yl)-4-(3-(trifluoromethyl)phenyl amino)pyrido[4,3-d]pyrimidin-5(6H)-one;

4-(3,4-dimethoxyphenylamino)-2-(4-hydroxypiperidin-1-yl)pyrido[4,3-d]pyrimidin-5(6H)-one;

4-(3-bromo-4-methoxyphenylamino)-2-(4-hydroxypiperidin-1-yl)pyrido[4,3-d]pyrimidin-5(6H)-one;

(R)-2-(3-aminopyrrolidin-1-yl)-8-bromo-4-(4-phenoxyphenylamino)pyrido[4,3-d]pyrimidin-5(6H)-one hydrochloride;

8-bromo-2-(4-hydroxy-4-(hydroxymethyl)piperidin-1-yl)-4-(4-phenoxyphenyl amino)pyrido[4,3-d]pyrimidin-5(6H)-one;

4-(3,4-dimethoxyphenylamino)-2-(4-hydroxy-4-(hydroxymethyl)piperidin-1-yl)pyrido[4,3-d]pyrimidin-5(6H)-one;

4-(3-bromo-4-methoxyphenylamino)-2-(4-hydroxy-4-(hydroxymethyl)piperidin-1-yl)pyrido[4,3-d]pyrimidin-5(6H)-one;

2-(4-aminopiperidin-1-yl)-8-bromo-4-(4-phenoxyphenylamino)pyrido[4,3-d]pyrimidin-5(6H)-one hydrochloride;

(R)-2-(3-aminopyrrolidin-1-yl)-8-iodo-4-(4-phenoxyphenylamino)pyrido[4,3-d]pyrimidin-5(6H)-one hydrochloride;

4-(4-chloro-3-(trifluoromethyl)phenylamino)-2-(4-hydroxy-4-(hydroxymethyl)piperidin-1-yl)-8-iodopyrido[4,3-d]pyrimidin-5(6H)-one;

4-(4-chloro-3-(trifluoromethyl)phenylamino)-2-(4-hydroxypiperidin-1-yl)-8-iodopyrido[4,3-d]pyrimidin-5(6H)-one;

(R)-2-(3-aminopyrrolidin-1-yl)-8-bromo-4-(4-chloro-3-(trifluoromethyl)phenylamino)pyrido[4,3-d]pyrimidin-5(6H)-one hydrochloride;

2-(4-hydroxypiperidin-1-yl)-8-iodo-4-(4-(trifluoromethyl)phenylamino)pyrido[4,3-d]pyrimidin-5(6H)-one;

2-(4-hydroxypiperidin-1-yl)-4-(4-morpholino-3-(trifluoromethyl)phenylamino)pyrido[4,3-d]pyrimidin-5(6H)-one;

(R)-2-(3-aminopyrrolidin-1-yl)-8-bromo-4-(4-methoxy-3-(trifluoromethyl)phenylamino)pyrido[4,3-d]pyrimidin-5(6H)-one hydrochloride;

(R)-2-(3-aminopyrrolidin-1-yl)-8-bromo-4-(4-chloro-3-(trifluoromethoxy)phenylamino)pyrido[4,3-d]pyrimidin-5(6H)-one hydrochloride;

4-(4-chloro-3-(trifluoromethoxy)phenylamino)-2-(4-hydroxypiperidin-1-yl)pyrido[4,3-d]pyrimidin-5(6H)-one;

4-(3-bromo-5-(trifluoromethyl)phenylamino)-2-(4-hydroxypiperidin-1-yl)pyrido[4,3-d]pyrimidin-5(6H)-one;

(R)-6-(3-aminopyrrolidin-1-yl)-4-iodo-8-(4-(trifluoromethyl)phenylamino)isoquinolin-1(2H)-one hydrochloride;

(R)-6-(3-aminopyrrolidin-1-yl)-4-bromo-8-(4-(trifluoromethyl)phenylamino)isoquinolin-1(2H)-one hydrochloride;

(S)-6-(3-aminopyrrolidin-1-yl)-4-bromo-8-(4-(trifluoromethyl)phenylamino)isoquinolin-1(2H)-one hydrochloride;

4-(2,3-dihydrobenzo[b][1,4]dioxin-6-ylamino)-2-(4-hydroxypiperidin-1-yl)pyrido[4,3-d]pyrimidin-5(6H)-one;

2-(4-hydroxypiperidin-1-yl)-4-(naphthalen-2-ylamino)pyrido[4,3-d]pyrimidin-5(6H)-one;

2-(4-hydroxypiperidin-1-yl)-4-(quinolin-5-ylamino)pyrido[4,3-d]pyrimidin-5(6H)-one;

4-(3H-indol-2-ylamino)-2-(4-hydroxypiperidin-1-yl)pyrido[4,3-d]pyrimidin-5(6H)-one; and 2-(4-hydroxypiperidin-1-yl)-4-(4-phenoxyphenylamino)-8-phenylpyrido[4,3-d]pyrimidin-5(6H)-one;

or a pharmaceutically acceptable salt thereof.

57. A pharmaceutical formulation comprising a compound of claim 1, or a pharmaceutically acceptable salt thereof, in combination with a pharmaceutically acceptable carrier, diluent or excipient.

58. A method of treating a protein kinase-mediated disease in a subject in need thereof, comprising administering to said subject a therapeutically effective amount of a compound of claim 1 or a pharmaceutically acceptable salt thereof, wherein said protein kinase-mediated disease is selected from the group of consisting of rheumatoid arthritis, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, and gastrointestinal cancer.

59. The method of claim 58, wherein said compound or a pharmaceutically acceptable salt thereof is administered singly or in combination with one or more additional therapeutic agents.

60. The method of claim 59, wherein said compound of or a pharmaceutically acceptable salt thereof is administered via intravenous administration, subcutaneous administration, inhalation, oral administration, rectal administration, parenteral, intravitreal administration, intramuscular administration, intranasal administration, dermal administration, topical administration, otic administration, ophthalmic administration, buccal administration, tracheal administration, bronchial administration, or sublingual administration.

61. A method of inhibiting growth of cancer cells, comprising contacting the cancer cells with a compound of claim 1 or a pharmaceutically acceptable salt thereof, wherein the cancer cells are cells from a cancer selected from acute lymphoblastic leukemia, acute promyelocytic leukemia, acute myeloid leukemia, chronic myelogenous leukemia, lung cancer, colon cancer, brain cancer, melanoma, ovarian cancer, renal cancer, prostate cancer, or breast cancer.

62. A method of treating cancer in a subject in need thereof, comprising administering to the subject an effective amount of a compound of claim 1 or a pharmaceutically acceptable salt thereof, wherein said cancer is acute lymphoblastic leukemia, acute promyelocytic leukemia, chronic myelogenous leukemia, lung cancer, colon cancer, brain cancer, melanoma, ovarian cancer, renal cancer, prostate cancer, or breast cancer.

63. The method of claim 62, wherein said compound is selected from the group consisting of:
2-(4-hydroxypiperidin-1-yl)-4-(3-(trifluoromethyl)phenylamino)pyrido[4,3-d]pyrimidine-5(6H)-one;
(S)-2-(pyrrolidin-3-ylamino)-4-(4-trifluoromethylamino)pyrido[4,3-d]pyrimidin-5(6H)-one;
(S)-4-(4-morpholinophenylamino)-2-(pyrrolidin-3-ylamino)pyrido[4,3-d]pyrimidin-5(6H)-one hydrochloride;
2-(4-(hydroxymethyl)piperidin-1-yl)-4-(4-sulfonylphenylamino)pyrido[4,3-d]pyrimidin-5(6H)-one; and
2-(4-(hydroxymethyl)piperidin-1-yl)-4-(4-morpholinophenylamino)pyrido[4,3-d]pyrimidin-5(6H)-one.

* * * * *